US008501189B2

(12) United States Patent
Ben-Nun et al.

(10) Patent No.: US 8,501,189 B2
(45) Date of Patent: Aug. 6, 2013

(54) SYNTHETIC HUMAN GENES AND POLYPEPTIDES AND THEIR USE IN THE TREATMENT OF AUTOIMMUNE DISEASES

(76) Inventors: Avraham Ben-Nun, Yavne (IL); Nicole Kerlero De Rosbo, Rehovot (IL); Paul Gregor Sappler, Ammerbuch (DE)

( * ) Notice: Subject to any disclaimer, the term of this patent is extended or adjusted under 35 U.S.C. 154(b) by 0 days.

(21) Appl. No.: 13/340,187

(22) Filed: Dec. 29, 2011

(65) Prior Publication Data
US 2012/0172297 A1   Jul. 5, 2012

Related U.S. Application Data

(63) Continuation of application No. 10/111,713, filed as application No. PCT/IL00/00688 on Oct. 26, 2000, now Pat. No. 8,088,389.

(30) Foreign Application Priority Data

Oct. 27, 1999 (IL) .......................................... 132611

(51) Int. Cl.
| A61K 39/00 | (2006.01) |
| A61K 38/17 | (2006.01) |
| C07K 19/00 | (2006.01) |
| C07K 14/435 | (2006.01) |

(52) U.S. Cl.
USPC ...................... 424/185.1; 424/192.1; 530/350

(58) Field of Classification Search
None
See application file for complete search history.

(56) References Cited

U.S. PATENT DOCUMENTS

| 5,547,669 | A | * | 8/1996 | Rogers et al. ............... 424/185.1 |
| 5,683,695 | A | | 11/1997 | Shen et al. |
| 5,759,551 | A | | 6/1998 | Ladd et al. |
| 5,821,334 | A | * | 10/1998 | Powers .......................... 530/350 |
| 5,968,757 | A | | 10/1999 | Powers |
| 6,770,460 | B1 | * | 8/2004 | Hinkkanen .................. 435/69.7 |
| 7,030,098 | B2 | | 4/2006 | Steinman et al. |
| 2003/0035815 | A1 | | 2/2003 | Rogers et al. |
| 2005/0037422 | A1 | | 2/2005 | Ben-Nun et al. |

FOREIGN PATENT DOCUMENTS

| EP | 0 940 470 A2 | 9/1999 |
| WO | 93/08280 A1 | 4/1993 |
| WO | 95/25744 A1 | 9/1995 |
| WO | 96/34622 A1 | 11/1996 |
| WO | 97/00270 A1 | 1/1997 |
| WO | 97/40068 A1 | 10/1997 |
| WO | 97/45144 A1 | 12/1997 |
| WO | WO 98/31819 | * 7/1998 |
| WO | 99/32136 A1 | 7/1999 |

OTHER PUBLICATIONS

Wherrett et al., The Lancet 378: 319-327, Jul. 23, 2011.*
Anderton et al., J. Immunol. 161:3357-3364, 1998.*
Entrez Protein Database entry for Accession No. L18983 downloaded on Jul. 19, 2012.*
Entrez Protein Database entry for Accession No. M74826 downloaded on Jul. 19, 2012.*
Bach, J.-F., "The immunology of diabetes: Revolution of concepts over a decade." In Shoenfeld, Y. (Ed.) The decade of autoimmunity 1987-1997. Elsevier Science, Amsterdam, pp. 149-156 (1999).
Bronstein, J. M. et al., "Oligodendrocyte- specific protein (OSP) is a major component of CNS myelin" J. Neurosci. Res. 50, 713-20 (1997).
Gardinier, M. V. et al., "Myelin/oligodendrocyte glycoprotein is a unique member of the immunoglobulin superfamily" J. Neurosci. Res. 33, 177-187 (1992).
Kerlero de Rosbo, N., "Experimental autoimmune encephalomyelitis induced by various antigens of the central nervous system Overview and relevance to multiple sclerosis" in Shoenfeld, Y. (Ed.) The decade of autoimmunity 1987-1997. Elsevier Science, Amsterdam, pp. 169-177 (1999).
Kumar, V., "Determinant spreading during experimental autoimmune encephalomyelitis: is it potentiating, protecting or participating in the disease?" Immunol. Rev. 164:73-80 (1998).
Tuohy, V. K. et al., "The epitope spreading cascade during progression of experimental autoimmune encephalomyelitis and multiple sclerosis" Immunol. Rev. 164:93-100 (1998).
Tuohy, V. K., "Peptide determinants of myelin proteolipid protein (PLP) in autoimmune disease: A review" Neurochem. Res. 19:935-944 (1994).
Sant et al, "The relationship between immunodominance, OM editing, and the kinetic stability of MHG class II:peptide complexes," Immunol Rev 207:261-278 (2005).
He et al, "Structural snapshot of aberrant antigen presentation linked to autoimmunity: the immunodominant epitope of MBP complexed with I-Au," Immunity 17:83-94 (2002).
Meinl et al, "mmunopathogenesis of multiple sclerosis: MBP and beyond," Clin Exp Immunol, 128:395-397 (2002).
Kerlero De Rosbo et al, "Reactivity to myelin antigens in multiple sclerosis. Peripheral blood lymphocyles respond predominantly to myelin oligodendrocyte glycoprotein," J Clin Invest 92:2602-2608 (1993).
Wallstrom et al "Increased reactivity to myelin oligodendrocyte glycoprotein peptides and epitope mapping in HLA DR2(15)+ multiple sclerosis," Eur J Immunol28:3329-3335 (1998).
Linoert et al, "Multiple sclerosis: B- and T-cell responses to the extracellular domain of the myelin oligodendrocyle glycoprotein," Brain 122:2089-2100 (1999).
Jasinski et al, "Insulin as a primary autoantigen for type 1A diabetes," Clin Dev Immunol12:181-186 (2005).
Gorrigall et al, "Autoantigens and immune pathways in rheumatoid arthritis," Crit Rev Immunol22:281-293 (2002).
Gaspi RR, "Regulation, counter-regulation, and immunotherapy of autoimmune responses to immunologically privileged retinal antigens," Immunol Res 27:149-160 (2003).

(Continued)

*Primary Examiner* — Phuong Huynh
(74) *Attorney, Agent, or Firm* — Browdy and Neimark, PLLC

(57) ABSTRACT

Synthetic human target autoantigen genes comprising sequences coding for at least two immunogenic epitopic clusters (hereinafter IEC) of autoantigen(s) related to a specific autoimmune disease, wherein said at least two IECs may be derived from a sole autoantigen or from at least two different autoantigens related to said autoimmune disease, and polypeptides encoded thereby, can be used for the treatment and the diagnosis of autoimmune diseases such as multiple sclerosis (MS), insulin-dependent diabetes mellitus (IDDM), rheumatoid arthritis (RA), myasthenia gravis (MG) and uveitis.

13 Claims, 97 Drawing Sheets

OTHER PUBLICATIONS

Rayner et al, "Thyroglobulin as autoantigen and tolerogen," Immunol Ser 59:359-376 (1993).

Critchfield et al., "T cell deletion in high antigen dose therapy of autoimmune encephalomyelitis," Science 263:1139-1143 (1994).

Pedotti et al, "An unexpected version of horror autotoxicus: anaphylactic shock to a self-peptide," Nat Immunol 2:216-222 (2001).

Altmann et al, "The T cell response of HLA-DR transgenic mice to human myelin basic protein and other antigens in the presence and absence of human CD4," J Exp Med 181:867-875 (1995).

Ellmerich et al, "Disease-related epitope spread in a humanized T cell receptor transgenic model of multiple sclerosis," Eur J Immunol 34: 1839-1848 (2004).

Altmann et al, "HLA transgenic models of autoimmune disease," in Infection and Immunity, Friedland et al, eds, Harwood Academic Publishers, Reading, UK, Chapter 1 (2004).

Madsen et al, "A humanized model for multiple sclerosis using HLA-DR2 and a human T-cell receptor," Nat Genet 23:343-347 (1999).

Sireci et al, "A human leucocyte antigen-DR1 transgene confers susceptibility to experimental allergic encephalomyelitis elicited by an epitope of myelin basic protein," Scand J Immunol 58:188-194 (2003).

Ito et al, "HLA-DR4-IE chimeric class II transgenic, murine class II-deficient mice are susceptible to experimental allergic encephalomyelitis," J Exp Med 183:2635-2644 (1996).

Das et al, "Complementation between specific HLA-DR and HLA-DQ genes in transgenic mice determines susceptibility to experimental autoimmune encephalomyelitis," Hum Immunol 61 :279-289 (2000).

Kawamura et al, "HLA-DR2-restricted responses to proteolipid protein 95-116 peptide cause autoimmune encephalitis in transgenic mice," J Clin Invest 105:977-984 (2000).

Forsthuber et al, "T cell epitopes of human myelin oligodendrocyte glycoprotein identified in HLA-DR4 (DRB1*0401) transgenic mice are encephalitogenic and are presented by human B cells," J Immunol 167:7119-7125 (2001.

Khare et al, "HLA class II transgenic mice authenticate restriction of myelin oligodendrocyte glycoproteinspecific immune response implicated in multiple sclerosis pathogenesis," Int Immunol 15:535-546 (2003).

Rich et al, "Myelin oligodendrocyte glycoprotein-35-55 peptide induces severe chronic experimental autoimmune encephalomyelitis in HLA-DR2-transgenic mice," Eur J Immunol 34:1251-1261 (2004).

Sette et al, "Structural characteristics of an antigen required for its interaction with la and recognition by T cells," Nature 328:395-399 (1987).

Gautam et al, "Inhibition of experimental autoimmune encephalomyelitis by a nonimmunogenic non-self peptide that binds to I-Au," J Immunol 148:3049-3054 (1992).

Gautam et al, "A polyalanine peptide with only five native myelin basic protein residues induces autoimmune encephalomyelitis," J Exp Med 176:605-609 (1992).

Liu et al, "Alternate interactions define the binding of peptides to the MHC molecule IA(b)," Proc Natl Acad Sci USA 99:8820-8825 (2002).

Rothbard et al, "Interactions between immunogenic peptides and MHC proteins," Annu Rev Immunol, 9:527- 565(1991).

Gauthier et al, "Expression and crystallization of the complex of HLA-DR2 (DRA, DRB1'1501) and an immunodominant peptide of human myelin basic protein," Proc Natl Acad Sci USA 95:11828-11833 (1998).

Wucherpfennig et al, "Recognition of the immunodominant myelin basic protein peptide by autoantibodies and HLA-DR2-restricted T cell clones from multiple sclerosis patients. Identity of key contact residues in the Bcell and T-cell epitopes," J Clin Invest 100:1114-1122 (1997).

Wucherpfennig et al, "Structure of human T-cell receptors specific for an immunodominant myelin basic protein peptide: positioning of T-ceil receptors on HLA-DR2/peptide complexes," Proc Natl Acad Sci USA 92:8896-8900 (1995).

Wucherpfennig et al, "Structural requirements for binding of an immunodominant myelin basic protein peptide to DR2 isotypes and for its recognition by human T cell clones," J Exp Med 179:279-290 (1994).

Wucherpfennig et al, "Selective binding of self peptides to disease-associated major histocompatibility complex (MHC) molecules: a mechanism for MHC-linked susceptibility to human autoimmune diseases," J Exp Med 181:1597-1601 (1995).

Sloan-Lancaster et al, "Altered peptide ligand-induced partial T cell activation: molecular mechanisms and role in T cell biology," Annu Rev Immunol 14:1-27 (1996).

Ben-Nun et al, "Anatomy of T cell autoimmunity to myelin oligodendrocyte glycoprotein (MOG): prime role of MOG44F in selection and control of MOG-reactive T cells in H-2b mice," Eur J Immunol 36:478-493 (2006).

Sloan-Lancaster et al, "Induction of T-cell anergy by altered T-cell-receptor ligand on live antigen-presenting cells," Nature 363:156-159 (1993).

Ausubel et al, "Changes in cytokine secretion induced by altered peptide ligands of myelin basic protein peptide 85-99" J Immunol 159:2502-2512 (1997).

Nicholson et al, "An altered peptide ligand mediates immune deviation and prevents autoimmune encephalomyelitis," Immunity 3:397-405 (1995).

Vergelli et al, "Differential activation of human autoreactive T cell clones by altered peptide ligands derived from myelin basic protein peptide (87-99)," Eur J Immunol 26:2624-2634 (1996).

Windhagen et al, "Modulation of cytokine patterns of human autoreactive T cell clones by a single amino acid substitution of their peptide ligand," Immunity 2:373-380 (1995).

Gaur et al, "Amelioration of relapsing experimental autoimmune encephalomyelitis with altered myelin basic protein peptides involves different cellular mechanisms," J Neuroimmunol 74:149-158 (1997).

Wraith et al, "Cross-reactive antigen recognition by an encephalitogenic T cell receptor. Implications for T cell biology and autoimmunity," J Immunol 149:3765-3770 (1992).

Franco et al, "T cell receptor antagonist peptides are highly effective inhibitors of experimental allergic encephalomyelitis," Eur J Immunol 24:940-946 (1994).

Kuchroo et al, "A single TCR antagonist peptide inhibits experimental allergic encephalomyelitis mediated by a diverse T cell repertoire," J Immunol 153:3326-3336 (1994).

Nicholson et al, "A T cell receptor antagonist peptide induces T cells that mediate bystander suppression and prevent autoimmune encephalomyelitis induced with multiple myelin antigens," Proc Natl Acad Sci USA, 94:9279-9284 (1997).

McRae et al, "Degenerate antigen recognition by CD4+ effector T cells in experimental autoimmune encephalomyelitis," J Neuroimmunol 75:156-162 (1997).

Prakken et al, "Inhibition of adjuvant-induced arthritis by interleukin-10-driven regulatory cells induced via nasal administration of a peptide analog of an arthritis-related heat-shock protein 60 T cell epitope," Arthritis Rheum 46:1937-1946 (2002).

Bielekova et al, "Antigen-specific immunomodulation via altered peptide ligands," J Mol Med 79:552-565 (2001 ).

Blum et al, "Antigen-presenting cells and the selection of immunodominant epitopes," Crit Rev Immunol 17:411-417 (1997).

Li et al, "Structural basis for the binding of an immunodominant peptide from myelin basic protein in different registers by two HLA-DR2 proteins," J Mol Bioi 304:177-188 (2000).

Smith et al, "Crystal structure of HLA-DR2 (DRA'0101, DRB1'1501) complexed with a peptide from human myelin basic protein," J Exp Med 188:1511-1520 (1998).

Mastico et al., "Multiple presentation of foreign peptides on the surface of an RNA-free spherical bacteriophage capsid" J. Gen. Viral. 74(4):541-548) (1993).

Anderton et al., "Fine Specificity of the Myelin-Reactive T Cell Repertoire: Implications for TCR Antagonism in Autoimmunity" J. Immunol. 161:3357-3364 (1998).

Entrez Protein Database entry for Accession No. AAA59565, http://www.ncbi.nlm.nih.gov/entrezlviewer.fcgi?db=protein&id=187417, downloaded Oct. 12, 2007.

Entrez Protein Database entry for Accession No. AAC41944, http://www.ncbi.nlm:nih.gov/entrezlviewer.fcgi?db=protein&id=1162922, downloaded Oct. 12, 2007.
Elliott et al. "Treatment of Experimental Encephalomyelitis with a Novel Chimeric Fusion Protein of Myelin Basic Protein and Proteolipid Protein" J Neuroimmunol. 79: 1-11 (1997).
McFarland et al. "Determinant Spreading Associated with Demyelination in a Nonhuman Primate Model of Multiple Sclerosis" J. Immunol. 162:2384-2390 (1999).
Arnon R. et al., "Immunomodulation by the Copolymer Glatiramer Acetate", J. Mol. Recognit., 16:412-421 (2003).
Chen L. N. et al., "Immunization With a Synthetic Mutliepitope Antigen Induces Humoral and Cellular Immune Responses to Hepatitis C Virus in Mice", Viral Immunology, 20:170-179 (2007).
GenBank NP_005593., www.ncbi.nlm.nih.gov/entrezlviewer.fcgi?5031967:0LD02:500634, (Jun. 19, 1999).
GenBank NP_005593., www.ncbi.nlm.nih.gov/entrezlviewer.fcgi?10938016:0LD04:135066, (Oct. 20, 2000).
Hirahara K. et al., "Preclinical evaluation of an immunotherapeutic peptide comprising 7 T-cell determinants of Cry j 1 and Cry j 2, the major Japanese cedar pollen allergens", J Allergy Clin Immunol, 108:94-100 (2001).
Johnson K. P. et al., "Copolymer 1 Reduces Relapse Rate and Improves Disability in Relapsing-Remitting Multiple Sclerosis: Results of a Phage III Multicenter, Double-Blind, Placebo-controlled Trial", Neurology, 45:1268-1276 (1995).
Kappos, L. et al., "Induction of a non-encephalitogenic type 2 T helper-cell autoimmune response in multiple sclerosis after administration of an altered peptide ligand in a placebo-controlled, randomized phase II trial", Nature America, D 6:1176-1182 (2000).
Bayhill Therapeutics to Present Positive Data From a Phase lib Trial of BHT-3009 in Multiple Sclerosis: Preparations for a Phase III Trial Underway, http://www.businesswire.com/portal/site/google/index.jsp? DndmViewId=news_view&newsId=20071 004005332 &newsLang=en, Oct. 4, 2007.
Pedotii R., et al., "An unexpected version of horror autotoxicus: anaphylactic shock to a self-peptide", Nat Immunol. 2:216-222 (2001).
Pedotii R., et al., "Severe anaphylactic reactions to glutamic acid decarboxylase (GAD) self peptides in NOD mice that spontaneously develop autoimmune type 1 diabetes mellitus", BMC Immunol. 4:2 (2003).
Shi, Y. P., et al., "Development, Expression, and Murine Testing of a Multistage Plasmodiun Falciparum Malaria Vaccine Candidate", Vaccine 18:2902 (2000).
Thomson, S. A., et al., Minimal epitopes expressed in a recombinant polyepitope protein are processed and presented to C08+ cy1otoxic T cells: Implications for vaccine design, Proc. Natl. Acad. Sci. USA 92:5845 (1995).
Warren, K. G., et al., "Intravenous synthetic peptide MBP8298 delayed disease progression in an HLA Class 11-13 defined cohort of patients with progressive multiple sclerosis: results of a 24-month double-blind placebo-controlled clinical trial and 5 years of follow-up treatment", Eur J Neurol. Aug:13:887-95 (2006).
Kuerten et al. "MP4- and MOG:35-55-induced EAE in C57BL/6 mice differentially targets brain, spinal cord and cerebellum" J Neuroimmunology 189: 31-40, 2007.
Albani et al, "The Susceptibility Sequence to Rheumatoid Arthritis is a Cross-reactive B Cell Epitope Shared by the Escherichia coli Heat Shock Protein dnaJ and the Histocompatibility Leukocyte Antigen DRB10401 Molecule", Rapid Publication, 89:327-331 (1992).
Arden et al, "'imogen 38: A Novel 38-kD Islet Mitochondrial Autoantigen Recognized by T Cells from a Newly A Diagnosed Type 1 Diabetic Patient", J. of Clin. Invest, 97(2): 551-561 (1996).
Bell et al, "Sequence of the Human Insulin Gene", Macmillan Journals Ltd., 284: 26-32 (1980).
Bronstein et al, "Isolation and Characterization of a Novel Oligodendrocyte-Specific Protein", Amer. Acad. of Neuro., 47: 772-778 (1996).
Bronstein et al, "A Humoral Response to Oligodendrocyte-Specific Protein in MS (A potential Molecular Mimic)", Amer. Acad. of Neuro., 53: 154-161 (1999).

Bu et ai, "Two Human Glutamate Decarboxylases, 65-kDa GAD and 67-kDa GAD, are each Encoded by a Single Gene", Proc. Natl. Acad. Sci. USA (Medical Sciences), 89: 2115-2119 (1992).
Cope et ai, "Evaluating Candidate Autoantigens in Rheumatoid Arthritis", Springer Sem. in Immuno., 20: 23-39 (1998).
Diehl et al, "Individual Exons Encode the Integral Membrane Domains of Human Nyelin Proteolipid Protein", Proc. Natl. Acad. Sci. USA (Neurobiology), 83: 9807-9811 (1986).
Doege et al, "Complete Coding Sequence and Deduced Primary Structure of the Human Cartilage Large Aggregating Proteoglycan, Aggrecan", J. of Bio. Chem., 266(2): 894-902 (1991).
Dudhia et al, "The Primary Structure of Human Cartilage Link Protein", Nucleic Acids Res., 18(5): (1990).
Elliott et al, "Treatment of Experimental Encephalomyelitis with a Novel Chimeric Fusion Protein of Myelin J Basic Protein and Proteolipid Protein", J. of Clin. Inyest, 98(7): 1602-1612 (1996).
Elliott et al, "Immune Tolerance Mediated by Recombinant Proteolipid Protein Prevents Experimental Autoimmune Encephalomyelitis", J. of Neuroimmunology, 79: 1-11 (1997).
Gregerson et al, "Identification of T Cell Recognition Sites in S-Antigen: Dissociation of Proliferative and Pathogenic Sites", Cell. Immun , 123: 427-440 (1989).
Guerassimov et al, "Immunity to Cartilage Link Protein in Patients with Juvenile Rheumatoid Arthritis", Rheumatol, 24: 959-964 (1997).
Hakala et al, "Human Cartilage gp-39, a Major Secretory Product of Articular Chondrocytes and Synovial Cells, is a Mammalian Member of a Chitinase Protein Family", J. of Bio. Chern, 268(34): 25803-25810 (1993).
Handley et al, "Purification of Recombinant Human Hsp60: Use of a GroEL-free Preparation to Assess Autoimmunity in Rheumatoid Arthritis", J. of Autoimmunitv, 8: 659-673 (1995).
Kamholz et al, "Identification of Three Forms of Human Myelin Basic Protein by cDNA Cloning", Proc. Natl. Acad. Sci. USA (Neurobiology), 83: 4962-4966 (1986).
Katz-Lew et al. "A Peptide Composed of Tandem Analogs of Two Myasthenogenic T Cell Epitopes Interferes with Specific Autoimmune Responses", Proc. Natl. Acad. Sci USA (Immunology>, 94: 3200-3205 (1997).
Kerlero de Rosbo et al, "Predominance of the Autoimmune Response to Myelin Oligodendrocyte Glycoprotein (MOG) in Multiple Sclerosis: Reactivity to the Extracellular Domain of MOG is Directed Againstt Three Main Regions", Eur. J.I of Immun., 27: 3059-3069 (1997).
Lan et al, "Molecular Cloning and Identification of a Receptor-Type Protein Tyrosine Phosphatase, IA-2, from Human Insulinoma", DNA and Cell Bio, 13(5): 505-514 (1994).
Ohki et al, "Nucleotide Sequence of the Escherichia coli dnaJ Gene and Purification of the Gene Product", J. of Bio. Chem., 261(4): 1778-1781 (1986).
Pharn-Dinh et al, "Characterization and Expression of the cDNA Coding for the Human Myelin/Oligodendrocyte Glycoprotein", J of Neurochemistrv. 63: 2353-2356 (1994).
Pietropaolo et al, "Molecular Cloning and Characterization of a Novel Diabetes-Associated Autoantigen", J. of Clin. Invest., 92: 359-371 (1993).
Roep B, "Perspectives in Diabetes, T-Cell Responses to Autoantigens in IDDM, The Search for the Holy Grail", Diabetes, 45: 1147-1156 (1996).
Sato et al, "cDNA Cloning and Amino Acid Sequence for Human Myelin-Associated Glycoprotein", Bio. and .Biophysical Res. Comm., 163(3): 1473-1480 (1989).
Su et al, "Nucleotide Sequence of the Full Length cDNA Encoding for Human Type II Procollagen", Nucleic Acids Res., 17(22): 9473 (1989).
Venner et al, "Nucleotide Sequences and Novel Structural Features of Human and Chinese Hamster hsp60 (Chaperonin) Gene Families", DNA and Cell Bio., 9(8): 545-552 (1990).
Worthington et al, "Monoclonal Antibody Epitopes of Mycobacterial 65-kD Heat-shock Protein Defined by Epitope Scanning", Clin. Exp. Immun , 89: 115-119 (1992).

Yamaki et al, "The Sequence of Human Retinal S-Antigen Reveals Similarities with a-transducin", Fed. of Eur. Biochem. Soc., 234(1): 39-43 (1988).

Yamamoto et al, "Cloning and Expression of Myelin-Associated Oligodendrocytic Basic Protein", J of Bio. Chem., 269(50): 31725-31730 (1994).

Hart et al. "The Major Histocompatibility Complex Influences the Ethiopathogenesis of MS-Like Disease in Primates at Multiple LevelsHuman Imm" ; 62: 1371-81. (2001).

Weathington et al. Rational design of peptide vaccines for autoimmune disease: harnessing molecular recognition to fix a broken networkExper. Rev. Vaccines, 2:61-73. (2003).

Steinman, L. "Immune Therapy for Autoimmune Diseases" Science. 305:212-16 (2004).

Robinson et al. "Protein arrays for autoantibody profiling and fine-specificity mapping" Proteomics, 3:2077-84 (2003).

Robinson et al. "Protein microarrays guide tolerizing DNA vaccine treatment of autoimmune encephalomyelitis";Nat. Biotech. 21: 1033-39. (2003).

Monji et al. "Exogenously Provided Peptides Fail to Complex with Intracellular Class II Molecules for Presentation by Antigen-Presenting Cells" J. Immun. 158:3155-3164. (1997).

Mendel et al. "A myelin oligodendrocyte glycoprotein peptide induces typical chronic experimental autoimmune encephalomyelitis in H-2Beta mice: fine specificity and T cell receptor VBeta expression of encephalitogenic T cells". Eur. J. Immun. 25:1951-59. (1995).

McDevitt, H. "Specific antigen vaccination to treat autoimmune disease" Proc. Natl. Acad. Sci. 2004; 101(Supp. 2):14627-30.

Hohlfeld et al. "Autoimmune concepts of multiple sclerosis as a basis for selective immunotherapy: From pipe dreams to (therapeutic) pipelines" Proc. Natl. Acad. Sci. 101:14599-606. (2004).

Elliott et al. "Treatment of Experimental Encephalomyelitis with a Novel Chimeric Fusion Protein of Myelin Basic Protein and Proteolipid Protein" J. Clin. Invest. 98:1602-12. (1996).

Ben-Nun et al, "Vaccination against autoimmune encephalomyelitis (EAE): attenuated autoimmune T lymphocytes confer resistance to induction of active EAE but not to EAE mediated by the intact T lymphocyte line," Eur J Immunol11 :949-952 (1981).

Daniel et al, "Epitope specificity, cytokine production profile and diabetogenic activity of insulin-specific T cell clones isolated from NOD mice," Eur J Immunol25:1056-1062 (1995).

Doncarli et al, "A recurrent valpha17lvbeta10 TCR-expressing T cell clone is involved in the pathogenicity of collagen-induced arthritis in DBA/1 mice," Eur J Immunol29:3636-3642 (1999).

Van Eden et al, "Arthritis induced by a T-lymphocyte clone that responds to *Mycobacterium tuberculosis* and to cartilage proteoglycans," Proc Natl Acad Sci USA 82:5117-5120 (1985).

Akkaraju et al, "A range of CD4 T cell tolerance: partial inactivation to organ-specific antigen allows nondestructive thyroiditis or insulitis," Immunity 7:255-271 (1997).

Dipaolo et al, "The level of peptide-MHC complex determines the susceptibility to autoimmune diabetes: studies in HEL transgenic mice," Eur J Immunol 31 :3453-3459 (2001).

Schwartz RH, "T cell anergy," Annu Rev Immunol 21 :305-334 (2003).

Ufret-Vincenty et al, "In vivo survival of viral antigen-specific T cells that induce experimental autoimmune encephalomyelitis," J Exp Med 188:1725-1738 (1998).

Wucherpfennig et al, "Molecular mimicry in T cell-mediated autoimmunity: viral peptides activate human T cell clones specific for myelin basic protein," Cell 80:695-705 (1995).

Kotzin et al, "Superantigens and their potential role in human disease," Adv Immunol 54:99-166 (1993).

Hohlfeld R, "Biotechnological agents for the immunotherapy of multiple sclerosis. Principles, problems and perspectives," Brain 120(Pt 5):865-916 (1997).

Kroczek et al, "Emerging paradigms of T-cell co-stimulation," Curr Opin 16:321-327 (2004).

Monaco et al, T-cell-mediated signalling in immune, inflammatory and angiogenic processes: the cascade of events leading to inflammatory diseases, Curr Drug Targets Inflamm Allergy 3:35-42, Mar. 2004.

Rizvi et al, "Other therapy options and future strategies for treating patients with multiple sclerosis," Neurology 63:S47-54 (2004).

Farrell et al, "Emerging therapies in multiple sclerosis," Expert Opin Emerg Drugs 10:797-816 (2005).

Hohlfeld et al, "Autoimmune concepts of multiple sclerosis as a basis for selective immunotherapy: from pipe dreams to (therapeutic) pipelines," Proc Natl Acad Sci USA 101 Suppl2:14599-14606 (2004).

Vandenbark et al, "TCR peptide therapy in human autoimmune diseases," Neurochem Res 26:713-730 (2001 ).

Clayton et al, "Peptide-specific prevention of experimental allergic encephalomyelitis. Neonatal tolerance induced to the dominant T cell determinant of myelin basic protein," J Exp Med 169:1681-1691 (1989).

Bercovici et al, "Systemic administration of agonist peptide blocks the progression of spontaneous CD8-mediated autoimmune diabetes in transgenic mice without bystander damage," J Immunol165:202-210 (2000).

Nussenblatt R, "Orally and nasally induced tolerance studies in ocular inflammatory disease: guidance for future interventions," Ann NY Acad Sci 1029:278-285 (2004).

Wooley PH, "Immunotherapy in collagen-induced arthritis: past, present, and future," Am J Med Sci 327:217-226 (2004).

Al-Sabbagh et al, "Antigen-driven peripheral immune tolerance: suppression of experimental autoimmune encephalomyelitis and collagen-induced arthritis by aerosol administration of myelin basic protein or type II collagen," CeliImmunol171:111-119 (1996).

Garcia et al "Suppression of collagen-induced arthritis by oral or nasal administration of type II collagen," .J Autoimmun 13:315-324 (1999).

Chen et al, "Oral tolerance in myelin basic protein T-cell receptor transgenic mice: suppression of autoimmune encephalomyelitis and dose-dependent induction of regulatory cells," Proc Natl Acad Sci USA 93:388-391 (1996).

Al-Sabbagh et al, "Antigen-driven tissue-specific suppression following oral tolerance: orally administered myelin basic protein suppresses proteolipid protein-induced experimental autoimmune encephalomyelitis in the SJL mouse," Eur J Immunol24:21 04-2109 (1994).

Faria et al, "Oral tolerance," Immunol Rev 206:232-259 (2005).

Maron et al, "Oral administration of insulin to neonates suppresses spontaneous and cyclophosphamide induced diabetes in the NOD mouse," J Autoimmun 16:21-28 (2001).

Toussirot EA, "Oral tolerance in the treatment of rheumatoid arthritis," Curr Drug Targets Inflamm Allergy 1:45-52 (2002).

Rudolph et al, "The specificity of TCR/pMHC interaction," Curr Opin Immunol 14:52-65 (2002).

Evavold et al, "Tickling the TCR: selective T-cell functions stimulated by altered peptide ligands," Immunol Today 14:602-609 (1993).

Kappos et al, "Induction of a non-encephalitogenic type 2 T helper-cell autoimmune response in multiple sclerosis after administration of an altered peptide ligand in a placebo-controlled, randomized phase II trial," Nature Med 6:1176-1182 (2000).

Bielekova et al, "Encephalitogenic potential of the myelin basic protein peptide(amino acids 83-99) in multiple sclerosis: Results of a phase II clinical trial with an altered peptide ligand," Nature Med 6:1167-1175 (2000).

Kerlero De Rosbo et al, "The Myelin-Associated Oligodendrocytic Basic Protein Region MOBP15-36 Encompasses the Immunodominant Major Encephalitogenic Epitope(s) for SJLIJ Mice and Predicted Epitope(s) for Multiple Sclerosis-Associated HLA-DRB1'1501," J Immunol 173:1426-1435 (2004).

Kerlero De Rosbo et al, T-ceil responses to myelin antigens in multiple sclerosis; relevance of the predominant autoimmune reactivity to myelin oligodendrocyte glycoprotein, J Autoimmun 11 :287-299 (1998).

Holz et al, "Myelin-associated oligodendrocytic basic protein: identification of an encephalitogenic epitope and association with multiple sclerosis," J Immunol 164:1103-1109 (2000).

Bronstein et al, "A humoral response to oligodendrocyte-specific protein in MS: A potential molecular mimic," Neurology 53:154-161 (1999).

Vu et al,"T-cell responses to oligodendrocyte-specific protein in multiple sclerosis," J Neurosci Res 66:506-509 (2001 ).

Gaur et al, "Amelioration of autoimmune encephalomyelitis by myelin basic protein synthetic peptide-induced anergy," Science 258:1491-1494 (1992).

Elliott et al, "Treatment of experimental encephalomyelitis with a novel chimeric fusion protein of myelin basic protein and proteolipid protein," J Clin Invest 98:1602-1612 (1996).

Leadbetter et al, "Experimental autoimmune encephalomyelitis induced with a combination of myelin basic protein and myelin oligodendrocyte glycoprotein is ameliorated by administration of a single myelin basic protein peptide," J Immunol161:504-512 (1998).

Zhong et al, Multiantigen/multiepitope-directed immune-specific suppression of "complex autoimmune encephalomyelitis" by a novel protein product of a synthetic gene. J Clin Invest 110:81-90 (2002).

Mendel et al, "A myelin oligodendrocyte glycoprotein peptide induces typical chronic experimental autoimmune encephalomyelitis in H-2b mice: fine specificity and T cell receptor V beta expression of encephalitogenic T cells," Eur J Immunol, 25:1951-1959 (1995).

Morris-Downes et al, "Encephalitogenic and immunogenic potential of myelin-associated glycoprotein (MAG), oligodendrocyte-specific glycoprotein (OSP) and 2',3'-cyclic nucleotide 3'-phosphodiesterase (CNPase) in ABH and SJL mice," J Neuroimmunol122:20-33 (2002).

Kaye et al, "The central nervous system-specific myelin oligodendrocytic basic protein (MOBP) is encephalitogenic and a potential target antigen in multiple sclerosis (MS)," J Neuroimmunol 102:189-198 (2000).

Maatta et al, "Encephalitogenicity of myelin-associated oligodendrocytic basic protein and 2',3'-cyclic nucleotide 3'-phosphodiesterase for BALBIc and SJL mice," Immunology 95:383-388 (1998).

Stevens et al, "Oligodendrocyte-Specific Protein Peptides Induce Experimental Autoimmune Encephalomyelitis in SJLIJ Mice," J Immunol162:7501-7509 (1999).

Zhong et al, T-cells specific for soluble recombinant oligodendrocyte-specific protein induce severe clinical experimental autoimmune encephalomyelitis in H-2(b) and H-2(s) mice, J Neuroimmunol105:39-45 (2000).

Johnson et al, "Cell-mediated immunity to myelin-associated glycoprotein, proteolipid protein, and myelin basic protein in multiple sclerosis," J Neuroimmunol13:99-108 (1986).

Lehman et al, "Spreading of T-cell autoimmunity to cryptic determinants of an autoantigen," Nature 358:155-157 (1992).

\* cited by examiner

```
    GCTAGCGGGCAGTTCAGAGTGATAGGACCAAGACACCCTATCCGGGCTCTGGTCGGGGAT
1   ------------+-----------+-----------+-----------+-----------+-----------+  60
    CGATCGCCCGTCAAGTCTCACTATCCTGGTTCTGTGGGATAGGCCCGAGACCAGCCCCTA

A  S  G  Q  F  R  V  I  G  P  R  H  P  I  R  A  L  V  G  D  -

GAAGTGGAATTGCCATGTCGCGCTACAGGCATGGAGGTGGGGTGGTACCGCCCCCCCTTC
61  ------------+-----------+-----------+-----------+-----------+-----------+ 120
    CTTCACCTTAACGGTACAGCGCGATGTCCGTACCTCCACCCCACCATGGCGGGGGGGAAG

E  V  E  L  P  C  R  A  T  G  M  E  V  G  W  Y  R  P  P  F  -

TCTAGGGTGGTTCATCTCTACAGAAATGGCAAGGACCAAGATCCTGAATATCGGGGCCGG
121 ------------+-----------+-----------+-----------+-----------+-----------+ 180
    AGATCCCACCAAGTAGAGATGTCTTTACCGTTCCTGGTTCTAGGACTTATAGCCCCGGCC

S  R  V  V  H  L  Y  R  N  G  K  D  Q  D  P  E  Y  R  G  R  -

ACAGAGCTGCTGAAAGATGCTATTGGTGAGGGAAAGGTGACTCTCAGGATCCGGAATGTA
181 ------------+-----------+-----------+-----------+-----------+-----------+ 240
    TGTCTCGACGACTTTCTACGATAACCACTCCCTTTCCACTGAGAGTCCTAGGCCTTACAT

T  E  L  L  K  D  A  I  G  E  G  K  V  T  L  R  I  R  N  V  -

AGGTTCTCAGATGAAGGAGGTTTCACCAGATCTTAGAAGCTT
241 ------------+-----------+-----------+---- 282
    TCCAAGAGTCTACTTCCTCCAAAGTGGTCTAGAATCTTCGAA

```
  1  GCTAGCAGATCTTCCCAGAGGCACGGATCCAAGTACCTGGCCACAGCAAGTACCATGGAC   60
     CGATCGTCTAGAAGGGTCTCCGTGCCTAGGTTCATGGACCGGTGTCGTTCATGGTACCTG

A  S  R  S  S  Q  R  H  G  S  K  Y  L  A  T  A  S  T  M  D  -

CATGCCAGGCATGGCTTCCTCCCAAGGCACAGAGACACGGGCATCCTTGACTCCATCGGG
 61  ------------------------------------------------------------  120
     GTACGGTCCGTACCGAAGGAGGGTTCCGTGTCTCTGTGCCCGTAGGAACTGAGGTAGCCC

H  A  R  H  G  F  L  P  R  H  R  D  T  G  I  L  D  S  I  G  -

CGCTTCTTTGGCGGTGACAGGGGTGAAAACCCCGTAGTCCACTTCTTCAAGAACATTGTG
121  ------------------------------------------------------------  180
     GCGAAGAAACCGCCACTGTCCCCACTTTTGGGGCATCAGGTGAAGAAGTTCTTGTAACAC

R  F  F  G  G  D  R  G  E  N  P  V  V  H  F  F  K  N  I  V  -

ACGCCTCGCACACCACCCCCGTCGCAGGGAAAGGGGAAGGGAGTCGATGCCCAGGGCACG
181  ------------------------------------------------------------  240
     TGCGGAGCGTGTGGTGGGGGCAGCGTCCCTTTCCCCTTCCCTCAGCTACGGGTCCCGTGC

T  P  R  T  P  P  S  Q  G  K  G  K  G  V  D  A  Q  G  T  -

CTTTCCAAAATTTTTAAGCTGGGAGGAAGAGATAGTCGCTCTGGATCACCCATGCTCGAG
241  ------------------------------------------------------------  300
     GAAAGGTTTTAAAAATTCGACCCTCCTTCTCTATCAGCGAGACCTAGTGGGTACGAGCTC

L  S  K  I  F  K  L  G  G  R  D  S  R  S  G  S  P  M  L  E  -

TAGAAGCTT
301  ---------  309
     ATCTTCGAA

```
      GCTAGCCTCGAGCTGTTCTGTGGCTGTGGACATGAAGCCCTCACTGGCACAGAAAAGCTA
  1   ------------+---------+---------+---------+---------+---------+  60
      CGATCGGAGCTCGACAAGACACCGACACCTGTACTTCGGGAGTGACCGTGTCTTTTCGAT

A  S  L  E  L  F  C  G  C  G  H  E  A  L  T  G  T  E  K  L  -

ATTGAGACCTATTTCTCCAAAAACTACCAAGACTATGAGTATCTCCTCCTGCTGGCTGAG
  61  ------------+---------+---------+---------+---------+---------+  120
      TAACTCTGGATAAAGAGGTTTTTGATGGTTCTGATACTCATAGAGGAGGACGACCGACTC

I  E  T  Y  F  S  K  N  Y  Q  D  Y  E  Y  L  L  L  L  A  E  -

GGCTTCTACACCACCGGCGCAGTCAGGCAGATATTTGGCGACTACAAGACCACCATCTGC
  121 ------------+---------+---------+---------+---------+---------+  180
      CCGAAGATGTGGTGGCCGCGTCAGTCCGTCTATAAACCGCTGATGTTCTGGTGGTAGACG

G  F  Y  T  T  G  A  V  R  Q  I  F  G  D  Y  K  T  T  I  C  -

GGCAAGGGCCTGAGCGCAACGGTACATTGTTTGGGAAAATGGCTAGGACATCCCGACAAG
  181 ------------+---------+---------+---------+---------+---------+  240
      CCGTTCCCGGACTCGCGTTGCCATGTAACAAACCCTTTTACCGATCCTGTAGGGCTGTTC

G  K  G  L  S  A  T  V  H  C  L  G  K  W  L  G  H  P  D  K  -

TTTGTGGGCATCACCGAATTCTAGAAGCTT
  241 ------------+---------+------+  270
      AAACACCCGTAGTGGCTTAAGATCTTCGAA

```
      GCTAGCGAATTCAGTCAGAAACCGGCCAAGGAGGGTCCCAGACTCTCCAAGAACCAGAAG
1     ------------+---------+---------+---------+---------+---------+ 60
      CGATCGCTTAAGTCAGTCTTTGGCCGGTTCCTCCCAGGGTCTGAGAGGTTCTTGGTCTTC

A  S  E  F  S  Q  K  P  A  K  E  G  P  R  L  S  K  N  Q  K   -

TACTCCGAACACTTCAGCATAACCTTCCTCAATTCCAAGAAGGAGATAGTGGATCGGAAA
61    ------------+---------+---------+---------+---------+---------+ 120
      ATGAGGCTTGTGAAGTCGTATTGGAAGGAGTTAAGGTTCTTCCTCTATCACCTAGCCTTT

Y  S  E  H  F  S  I  T  F  L  N  S  K  K  E  I  V  D  R  K   -

TACAGCATCAGTAAGAGCGGCCAGAAGACCAGAACCAGCCGCCGTGCCAAGTCCCCTCAG
121   ------------+---------+---------+---------+---------+---------+ 180
      ATGTCGTAGTCATTCTCGCCGGTCTTCTGGTCTTGGTCGGCGGCACGGTTCAGGGGAGTC

Y  S  I  S  K  S  G  Q  K  T  R  T  S  R  R  A  K  S  P  Q   -

AGGCCCAAGCAACAGCCAGCTGCGCCTCCAGCGGTGGTCTAGAAGCTT
181   ------------+---------+---------+---------+-------- 228
      TCCGGGTTCGTTGTCGGTCGACGCGGAGGTCGCCACCAGATCTTCGAA

```
1   GCTAGCGGGCAGTTCAGAGTGATAGGACCAAGACACCCTATCCGGGCTCTGGTCGGGGAT   60
    CGATCGCCCGTCAAGTCTCACTATCCTGGTTCTGTGGGATAGGCCCGAGACCAGCCCCTA

A  S  G  Q  F  R  V  I  G  P  R  H  P  I  R  A  L  V  G  D  -

61  GAAGTGGAATTGCCATGTCGCGCTACAGGCATGGAGGTGGGGTGGTACCGCCCCCCCTTC  120
    CTTCACCTTAACGGTACAGCGCGATGTCCGTACCTCCACCCCACCATGGCGGGGGGGAAG

E  V  E  L  P  C  R  A  T  G  M  E  V  G  W  Y  R  P  P  F  -

121 TCTAGGGTGGTTCATCTCTACAGAAATGGCAAGGACCAAGATCCTGAATATCGGGGCCGG  180
    AGATCCCACCAAGTAGAGATGTCTTTACCGTTCCTGGTTCTAGGACTTATAGCCCCGGCC

S  R  V  V  H  L  Y  R  N  G  K  D  Q  D  P  E  Y  R  G  R  -

181 ACAGAGCTGCTGAAAGATGCTATTGGTGAGGGAAAGGTGACTCTCAGGATCCGGAATGTA  240
    TGTCTCGACGACTTTCTACGATAACCACTCCCTTTCCACTGAGAGTCCTAGGCCTTACAT

T  E  L  L  K  D  A  I  G  E  G  K  V  T  L  R  I  R  N  V  -

241 AGGTTCTCAGATGAAGGAGGTTTCACCAGATCTTCCCAGAGGCACGGATCCAAGTACCTG  300
    TCCAAGAGTCTACTTCCTCCAAAGTGGTCTAGAAGGGTCTCCGTGCCTAGGTTCATGGAC

R  F  S  D  E  G  G  F  T  R  S  S  Q  R  H  G  S  K  Y  L  -

301 GCCACAGCAAGTACCATGGACCATGCCAGGCATGGCTTCCTCCCCAAGGCACAGAGACACG  360
    CGGTGTCGTTCATGGTACCTGGTACGGTCCGTACCGAAGGAGGGTTCCGTGTCTCTGTGC

A  T  A  S  T  M  D  H  A  R  H  G  F  L  P  R  H  R  D  T  -

361 GGCATCCTTGACTCCATCGGGCGCTTCTTTGGCGGTGACAGGGGTGAAAACCCCGTAGTC  420
    CCGTAGGAACTGAGGTAGCCCGCGAAGAAACCGCCACTGTCCCCACTTTTGGGGCATCAG

G  I  L  D  S  I  G  R  F  F  G  G  D  R  G  E  N  P  V  V  -

421 CACTTCTTCAAGAACATTGTGACGCCTCGCACACCACCCCCGTCGCAGGGAAAGGGGAAG  480
    GTGAAGAAGTTCTTGTAACACTGCGGAGCGTGTGGTGGGGGCAGCGTCCCTTTCCCCTTC

H  F  F  K  N  I  V  T  P  R  T  P  P  P  S  Q  G  K  G  K  -

481 GGAGTCGATGCCCAGGGCACGCTTTCCAAAATTTTTAAGCTGGGAGGAAGAGATAGTCGC  540
    CCTCAGCTACGGGTCCCGTGCGAAAGGTTTTAAAAATTCGACCCTCCTTCTCTATCAGCG

```
      TCTGGATCACCCATGCTCGAGCTGTTCTGTGGCTGTGGACATGAAGCCCTCACTGGCACA
541   ------------+---------+---------+---------+---------+---------+ 600
      AGACCTAGTGGGTACGAGCTCGACAAGACACCGACACCTGTACTTCGGGAGTGACCGTGT

S  G  S  P  M  L  E  L  F  C  G  C  G  H  E  A  L  T  G  T  -

GAAAAGCTAATTGAGACCTATTTCTCCAAAAACTACCAAGACTATGAGTATCTCCTCCTG
601   ------------+---------+---------+---------+---------+---------+ 660
      CTTTTCGATTAACTCTGGATAAAGAGGTTTTTGATGGTTCTGATACTCATAGAGGAGGAC

E  K  L  I  E  T  Y  F  S  K  N  Y  Q  D  Y  E  Y  L  L  L  -

CTGGCTGAGGGCTTCTACACCACCGGCGCAGTCAGGCAGATATTTGGCGACTACAAGACC
661   ------------+---------+---------+---------+---------+---------+ 720
      GACCGACTCCCGAAGATGTGGTGGCCGCGTCAGTCCGTCTATAAACCGCTGATGTTCTGG

L  A  E  G  F  Y  T  T  G  A  V  R  Q  I  F  G  D  Y  K  T  -

ACCATCTGCGGCAAGGGCCTGAGCGCAACGGTACATTGTTTGGGAAAATGGCTAGGACAT
721   ------------+---------+---------+---------+---------+---------+ 780
      TGGTAGACGCCGTTCCCGGACTCGCGTTGCCATGTAACAAACCCTTTTACCGATCCTGTA

T  I  C  G  K  G  L  S  A  T  V  H  C  L  G  K  W  L  G  H  -

CCCGACAAGTTTGTGGGCATCACCGAATTCTAGAAGCTT
781   ------------+---------+---------+------ 819
      GGGCTGTTCAAACACCCGTAGTGGCTTAAGATCTTCGAA

Y-MSPa     Y-MSPb

Fig. 13

```
  1  GCTAGCGGGCAGTTCAGAGTGATAGGACCAAGACACCCTATCCGGGCTCTGGTCGGGGAT   60
     CGATCGCCCGTCAAGTCTCACTATCCTGGTTCTGTGGGATAGGCCCGAGACCAGCCCCTA
     A  S  G  Q  F  R  V  I  G  P  R  H  P  I  R  A  L  V  G  D  -

61  GAAGTGGAATTGCCATGTCGCGCTACAGGCATGGAGGTGGGGTGGTACCGCCCCCCCTTC  120
     CTTCACCTTAACGGTACAGCGCGATGTCCGTACCTCCACCCCACCATGGCGGGGGGGAAG
     E  V  E  L  P  C  R  A  T  G  M  E  V  G  W  Y  R  P  P  F  -

121  TCTAGGGTGGTTCATCTCTACAGAAATGGCAAGGACCAAGATCCTGAATATCGGGGCCGG  180
     AGATCCCACCAAGTAGAGATGTCTTTACCGTTCCTGGTTCTAGGACTTATAGCCCCGGCC
     S  R  V  V  H  L  Y  R  N  G  K  D  Q  D  P  E  Y  R  G  R  -

181  ACAGAGCTGCTGAAAGATGCTATTGGTGAGGGAAAGGTGACTCTCAGGATCCGGAATGTA  240
     TGTCTCGACGACTTTCTACGATAACCACTCCCTTTCCACTGAGAGTCCTAGGCCTTACAT
     T  E  L  L  K  D  A  I  G  E  G  K  V  T  L  R  I  R  N  V  -

241  AGGTTCTCAGATGAAGGAGGTTTCACCAGATCTTCCCAGAGGCACGGATCCAAGTACCTG  300
     TCCAAGAGTCTACTTCCTCCAAAGTGGTCTAGAAGGGTCTCCGTGCCTAGGTTCATGGAC
     R  F  S  D  E  G  G  F  T  R  S  S  Q  R  H  G  S  K  Y  L  -

301  GCCACAGCAAGTACCATGGACCATGCCAGGCATGGCTTCCTCCCAAGGCACAGAGACACG  360
     CGGTGTCGTTCATGGTACCTGGTACGGTCCGTACCGAAGGAGGGTTCCGTGTCTCTGTGC
     A  T  A  S  T  M  D  H  A  R  H  G  F  L  P  R  H  R  D  T  -

361  GGCATCCTTGACTCCATCGGGCGCTTCTTTGGCGGTGACAGGGGTGAAAACCCCGTAGTC  420
     CCGTAGGAACTGAGGTAGCCCGCGAAGAAACCGCCACTGTCCCCACTTTTGGGGCATCAG
     G  I  L  D  S  I  G  R  F  F  G  G  D  R  G  E  N  P  V  V  -

421  CACTTCTTCAAGAACATTGTGACGCCTCGCACACCACCCCCGTCGCAGGGAAAGGGGAAG  480
     GTGAAGAAGTTCTTGTAACACTGCGGAGCGTGTGGTGGGGGCAGCGTCCCTTTCCCCTTC
     H  F  F  K  N  I  V  T  P  R  T  P  P  P  S  Q  G  K  G  K  -

481  GGAGTCGATGCCCAGGGCACGCTTTCCAAAATTTTTAAGCTGGGAGGAAGAGATAGTCGC  540
     CCTCAGCTACGGGTCCCGTGCGAAAGGTTTTAAAAATTCGACCCTCCTTCTCTATCAGCG
     G  V  D  A  Q  G  T  L  S  K  I  F  K  L  G  G  R  D  S  R  -
```

Fig. 15

```
541 TCTGGATCACCCATGCTCGAGCTGTTCTGTGGCTGTGGACATGAAGCCCTCACTGGCACA 600
    AGACCTAGTGGGTACGAGCTCGACAAGACACCGACACCTGTACTTCGGGAGTGACCGTGT
     S  G  S  P  M  L  E  L  F  C  G  C  G  H  E  A  L  T  G  T  -

601 GAAAAGCTAATTGAGACCTATTTCTCCAAAAACTACCAAGACTATGAGTATCTCCTCCTG 660
    CTTTTCGATTAACTCTGGATAAAGAGGTTTTTGATGGTTCTGATACTCATAGAGGAGGAC
     E  K  L  I  E  T  Y  F  S  K  N  Y  Q  D  Y  E  Y  L  L  L  -

661 CTGGCTGAGGGCTTCTACACCACCGGCGCAGTCAGGCAGATATTTGGCGACTACAAGACC 720
    GACCGACTCCCGAAGATGTGGTGGCCGCGTCAGTCCGTCTATAAACCGCTGATGTTCTGG
     L  A  E  G  F  Y  T  T  G  A  V  R  Q  I  F  G  D  Y  K  T  -

721 ACCATCTGCGGCAAGGGCCTGAGCGCAACGGTACATTGTTTGGGAAAATGGCTAGGACAT 780
    TGGTAGACGCCGTTCCCGGACTCGCGTTGCCATGTAACAAACCCTTTTACCGATCCTGTA
     T  I  C  G  K  G  L  S  A  T  V  H  C  L  G  K  W  L  G  H  -

781 CCCGACAAGTTTGTGGGCATCACCGAATTCAGTCAGAAACCGGCCAAGGAGGGTCCCAGA 840
    GGGCTGTTCAAACACCCGTAGTGGCTTAAGTCAGTCTTTGGCCGGTTCCTCCCAGGGTCT
     P  D  K  F  V  G  I  T  E  F  S  Q  K  P  A  K  E  G  P  R  -

841 CTCTCCAAGAACCAGAAGTACTCCGAACACTTCAGCATAACCTTCCTCAATTCCAAGAAG 900
    GAGAGGTTCTTGGTCTTCATGAGGCTTGTGAAGTCGTATTGGAAGGAGTTAAGGTTCTTC
     L  S  K  N  Q  K  Y  S  E  H  F  S  I  T  F  L  N  S  K  K  -

901 GAGATAGTGGATCGGAAATACAGCATCAGTAAGAGCGGCCAGAAGACCAGAACCAGCCGC 960
    CTCTATCACCTAGCCTTTATGTCGTAGTCATTCTCGCCGGTCTTCTGGTCTTGGTCGGCG
     E  I  V  D  R  K  Y  S  I  S  K  S  G  Q  K  T  R  T  S  R  -

961 CGTGCCAAGTCCCCTCAGAGGCCCAAGCAACAGCCAGCTGCGCCTCCAGCGGTGGTCTAG 1020
    GCACGGTTCAGGGGAGTCTCCGGGTTCGTTGTCGGTCGACGCGGAGGTCGCCACCAGATC
     R  A  K  S  P  Q  R  P  K  Q  Q  P  A  A  P  A  V  V  *   -

1021 AAGCTT 1026
     TTCGAA
      K  L  -
```

Fig. 15 (cont.)

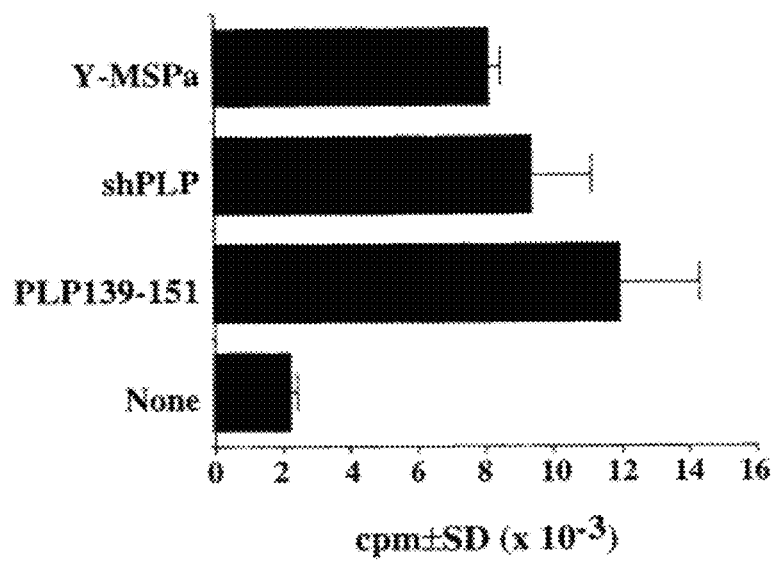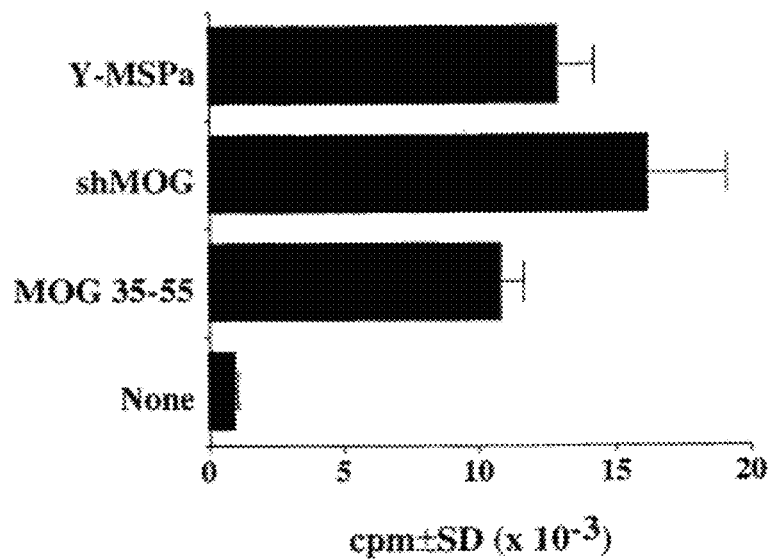
Fig. 16

```
    GAATTCGCTAGCGGCATGGAGGTGGGGTGGTATCGCCCACCATTCTCTAGGGTGGTTCAT
1   ------------+------------+------------+------------+------------+------------+  60
    CTTAAGCGATCGCCGTACCTCCACCCCACCATAGCGGGTGGTAAGAGATCCCACCAAGTA

E  P  A  S  G  M  E  V  G  W  Y  R  P  P  F  S  R  V  V  H   -

CTCTACCGTAATGGCAAGGACGGCCGTACAGAGCTGCTGAAAGATGCTATTGGTGAGGGA
61  ------------+------------+------------+------------+------------+------------+  120
    GAGATGGCATTACCGTTCCTGCCGGCATGTCTCGACGACTTTCTACGATAACCACTCCCT

L  Y  R  N  G  K  D  G  R  T  E  L  L  K  D  A  I  G  E  G   -

AAGGTGACTCTCAGGATTCGGAATGTACGCTTCTCTGATGAAGGAGGTTTCACCAGCTTC
121 ------------+------------+------------+------------+------------+------------+  180
    TTCCACTGAGAGTCCTAAGCCTTACATGCGAAGAGACTACTTCCTCCAAAGTGGTCGAAG

K  V  T  L  R  I  R  N  V  R  F  S  D  E  G  G  F  T  S  F   -

TTCCGTGACCATTCTTACCAAGAGGAGGCAGCAATGGAATTGAAAAGATCTTTCAGAGTG
181 ------------+------------+------------+------------+------------+------------+  240
    AAGGCACTGGTAAGAATGGTTCTCCTCCGTCGTTACCTTAACTTTTCTAGAAAGTCTCAC

F  R  D  H  S  Y  Q  E  E  A  A  M  E  L  K  R  S  F  R  V   -

ATAGGACCAAGACACCCAATCCGTGCTCTGGTCGGGGATGAAGTGGAATTGCCATCTCGC
241 ------------+------------+------------+------------+------------+------------+  300
    TATCCTGGTTCTGTGGGTTAGGCACGAGACCAGCCCCTACTTCACCTTAACGGTAGAGCG

I  G  P  R  H  P  I  R  A  L  V  G  D  E  V  E  L  P  S  R   -

ATATCGAGACTTGCAGGGCAATTCCTTGAAGAGCTGCGTGGATCCTGAAAGCTT
301 ------------+------------+------------+------------+---- 354
    TATAGCTCTGAACGTCCCGTTAAGGAACTTCTCGACGCACCTAGGACTTTCGAA

```
     GAATTCGCTAGCGGATCCAACCCAGTAGTCCACTTCTTCAAGAACATTGTGACGCCACGC
1    ------------+-----------+-----------+-----------+-----------+-----------+  60
     CTTAAGCGATCGCCTAGGTTGGGTCATCAGGTGAAGAAGTTCTTGTAACACTGCGGTGCG

E  F  A  S  G  S  N  P  V  V  H  F  F  K  N  I  V  T  P  R   -

ACACCACCACCGTCGCAGGGAAAGGGGAGAGGACTGTCCCTGTTCAAGGGAGTCGATGCC
61   ------------+-----------+-----------+-----------+-----------+-----------+  120
     TGTGGTGGTGGCAGCGTCCCTTTCCCCTCTCCTGACAGGGACAAGTTCCCTCAGCTACGG

T  P  P  P  S  Q  G  K  G  R  G  L  S  L  F  K  G  V  D  A   -

CAGGGCACGCTTTCCAAAATTTTTTAAGCTGGGAGGACGTGATAGTCGCTCTGGATCTCCG
121  ------------+-----------+-----------+-----------+-----------+-----------+  180
     GTCCCGTGCGAAAGGTTTTAAAAATTCGACCCTCCTGCACTATCAGCGAGACCTAGAGGC

Q  G  T  L  S  K  I  F  K  L  G  G  R  D  S  R  S  G  S  P   -

ATGGCTTCTAGATCCAAGTACCTGGCCACAGCAAGTACGATGGATCATGCCCGTCATGGC
181  ------------+-----------+-----------+-----------+-----------+-----------+  240
     TACCGAAGATCTAGGTTCATGGACCGGTGTCGTTCATGCTACCTAGTACGGGCAGTACCG

M  A  S  R  S  K  Y  L  A  T  A  S  T  M  D  H  A  R  H  G   -

TTCCTCCCACGTCACCGCGACACGGGCATCCTTGACTCCATCGGGACTAGTTGAAAGCTT
241  ------------+-----------+-----------+-----------+-----------+-----------+  300
     AAGGAGGGTGCAGTGGCGCTGTGCCCGTAGGAACTGAGGTAGCCCTGATCAACTTTCGAA

```
  1  GAATTCGCTAGCCTCGAGTACAAGACCACCATCAGCGGCAAGGGCCTGAGCGCAACGKTA  60
     ----------+---------+---------+---------+---------+---------+
     CTTAAGCGATCGGAGCTCATGTTCTGGTGGTAGTCGCCGTTCCCGGACTCGCGTTGCCAT

E  F  A  S  L  E  Y  K  T  T  I  S  G  K  G  L  S  A  T  V  -

ACAGGGGGCCAGAAGGGGCGTGGTTCCAGAGGTCAACATCAAGCTCATTCTTTGGAGCGT
 61  ----------+---------+---------+---------+---------+---------+ 120
     TGTCCCCCGGTCTTCCCCGCACCAAGGTCTCCGGTTGTAGTTCGAGTAAGAAACCTCGCA

T  G  G  Q  K  G  R  G  S  R  G  Q  H  Q  A  H  S  L  E  R  -

GTGAGCCATTCTTTGGGAAAATGGTTAGGACATCCGGACAAGTTCAACACCTGGACCACC
121  ----------+---------+---------+---------+---------+---------+ 180
     CACTCGGTAAGAAACCCTTTTACCAATCCTGTAGGCCTGTTCAAGTTGTGGACCTGGTGG

V  S  H  S  L  G  K  W  L  G  H  P  D  K  F  N  T  W  T  T  -

AGCCAGTCTATTGCCTTCCCAAGCAAGACCTCTGCCAGTATAGGCAGTCTCTCTGCTGAC
181  ----------+---------+---------+---------+---------+---------+ 240
     TCGGTCAGATAACGGAAGGGTTCGTTCTGGAGACGGTCATATCCGTCAGAGAGACGACTG

S  Q  S  I  A  F  P  S  K  T  S  A  S  I  G  S  L  S  A  D  -

GCCGTTTCTGGCTCCAACCTTCTGTCCATCAGCAAAACAGCAGAGTTCCAAATGACCTTC
241  ----------+---------+---------+---------+---------+---------+ 300
     CGGCAAAGACCGAGGTTGGAAGACAGGTAGTCGTTTTGTCGTCTCAAGGTTTACTGGAAG

A  V  S  G  S  N  L  L  S  I  S  K  T  A  E  F  Q  N  T  F  -

CACCTGTTTATTGGATCCGCCCTCACTGGCACAGAAAAGCTGATTGAGACCTATTTCTCC
301  ----------+---------+---------+---------+---------+---------+ 360
     GTGGACAAATAACCTAGGCGGGAGTGACCGTGTCTTTTCGACTAACTCTGGATAAAGAGG

H  L  F  I  G  S  A  L  T  G  T  E  K  L  I  E  T  Y  F  S  -

AAATTTGCCGTCCTTAAACTCATGGGCCGTGGCACCAAGTTCTGATCATGAGCGGCCCCA
361  ----------+---------+---------+---------+---------+---------+ 420
     TTTAAACGGCAGGAATTTGAGTACCCGGCACCGTGGTTCAAGACTAGTACTCGCCGGGGT

K  F  A  V  L  K  L  M  G  R  G  T  K  F  *  S  *  A  A

AGCTTA
421  ------ 426
     TCGAAT

```
      GAATTCGCTAGCCTGCAGCAGAAGTATTCCGAACACTTCAGCATACACAGCAGCCCACCG
 1    ------------+---------+---------+---------+---------+---------+ 60
      CTTAAGCGATCGGACGTCGTCTTCATAAGGCTTGTGAAGTCGTATGTGTCGTCGGGTGGC

E  F  A  S  L  Q  Q  K  Y  S  E  H  F  S  I  H  S  S  P   -

TTCACCTTCCTCAATAAAGAGGAGGACTGGATCAGCTCTGCCAGCCAGAAGACCCGTACC
 61   ------------+---------+---------+---------+---------+---------+ 120
      AAGTGGAAGGAGTTATTTCTCCTCCTGACCTAGTCGAGACGGTCGGTCTTCTGGGCATGG

F  T  F  L  N  K  E  E  D  W  I  S  S  A  S  Q  K  T  R  T  -

AGCCGCCGTGCCAAGTCCCCACAGCGTCCGAAGCAACAGCCAGCTGCCGCCGCCAGCCGTG
 121  ------------+---------+---------+---------+---------+---------+ 180
      TCGGCGGCACGGTTCAGGGGTGTCGCAGGCTTCGTTGTCGGTCGACGGCGGCGGTCGGCAC

S  R  R  A  K  S  P  Q  R  P  K  Q  Q  P  A  A  P  P  A  V  -

GTCGTCGACAAGCAACAGCCCCGCAGCAGCCCGCTCCGTGGGCCAGGTGCCAGCCGTGGG
 181  ------------+---------+---------+---------+---------+---------+ 240
      CAGCAGCTGTTCGTTGTCGGGGCGTCGTCGGGCGAGGCACCCGGTCCACGGTCGGCACCC

V  V  D  K  Q  Q  P  R  S  S  P  L  R  G  P  G  A  S  R  G  -

CTCGAGTGAAAGCTT
 241  ------------+--- 255
      GAGCTCACTTTCGAA

```
       GAATTCACTAGTAAGCTGGATGAGCTGGGCTCCAAGGGGCTGTGGGCCGACAGCGTCATG
  1    ------------+---------+---------+---------+---------+---------+  60
       CTTAAGTGATCATTCGACCTACTCGACCCGAGGTTCCCCGACACCCGGCTGTCGCAGTAC

E  F  T  S  K  L  D  E  L  G  S  K  G  L  W  A  D  S  V  M  -

GCAACGGGGCTGTACCACAGCAAGCCACTGGTGGACATCCTCATCCTGCTGCTGACTGTT
 61    ------------+---------+---------+---------+---------+---------+ 120
       CGTTGCCCCGACATGGTGTCGTTCGGTGACCACCTGTAGGAGTAGGACGACGACTGACAA

A  T  G  L  Y  H  S  K  P  L  V  D  I  L  I  L  L  L  T  V  -

CTTCCGTCTATCCGTATGGGCCAGCAGGCATTTGGTGAAAACGTTTCTACTACACTGCGT
121    ------------+---------+---------+---------+---------+---------+ 180
       GAAGGCAGATAGGCATACCCGGTCGTCCGTAAACCACTTTTGCAAAGATGATGTGACGCA

L  P  S  I  R  M  G  Q  Q  A  F  G  E  N  V  S  T  T  L  R  -

GCTCTGGCTCCGCGTCTCATGCGAAGAATGCATGTCATCGTGACCACCTCCACCAATGAC
181    ------------+---------+---------+---------+---------+---------+ 240
       CGAGACCGAGGCGCAGAGTACGCTTCTTACGTACAGTAGCACTGGTGGAGGTGGTTACTG

A  L  A  P  R  L  M  R  R  M  H  V  I  V  T  T  S  T  N  D  -

TGGGTGGTGACCAGCCTGGCTCTCAGCGCCCTTGTTGCCACCATCTGGTTCCCAGTGAGC
241    ------------+---------+---------+---------+---------+---------+ 300
       ACCCACCACTGGTCGGACCGAGAGTCGCGGGAACAACGGTGGTAGACCAAGGGTCACTCG

W  V  V  T  S  L  A  L  S  A  L  V  A  T  I  W  F  P  V  S  -

GCCCACCTGCAGTGAAAGCTT
301    ------------+---------+-- 321
       CGGGTGGACGTCACTTTCGAA

```
  1  GAATTCGCTAGCGGCATGGAGGTGGGGTGGTATCGCCCACCATTCTCTAGGGTGGTTCAT   60
     ------------+------------+------------+------------+------------+------------+
     CTTAAGCGATCGCCGTACCTCCACCCCACCATAGCGGGTGGTAAGAGATCCCACCAAGTA

E  F  A  S  G  M  E  V  G  W  Y  R  P  P  F  S  R  V  V  H  -

61 CTCTACCGTAATGGCAAGGACGGCCGTACAGAGCTGCTGAAAGATGCTATTGGTGAGGGA  120
     ------------+------------+------------+------------+------------+------------+
     GAGATGGCATTACCGTTCCTGCCGGCATGTCTCGACGACTTTCTACGATAACCACTCCCT

L  Y  R  N  G  K  D  G  R  T  E  L  L  K  D  A  I  G  E  G  -

121 AAGGTGACTCTCAGGATTCGGAATGTACGCTTCTCTGATGAAGGAGGTTTCACCAGCTTC  180
     ------------+------------+------------+------------+------------+------------+
     TTCCACTGAGAGTCCTAAGCCTTACATGCGAAGAGACTACTTCCTCCAAAGTGGTCGAAG

K  V  T  L  R  I  R  N  V  R  F  S  D  E  G  G  F  T  S  F  -

181 TTCCGTGACCATTCTTACCAAGAGGAGGCAGCAATGGAATTGAAAAGATCTTTCAGAGTG  240
     ------------+------------+------------+------------+------------+------------+
     AAGGCACTGGTAAGAATGGTTCTCCTCCGTCGTTACCTTAACTTTTCTAGAAAGTCTCAC

F  R  D  H  S  Y  Q  E  E  A  A  M  E  L  K  R  S  F  R  V  -

241 ATAGGACCAAGACACCCAATCCGTGCTCTGGTCGGGGATGAAGTGGAATTGCCATCTCGC  300
     ------------+------------+------------+------------+------------+------------+
     TATCCTGGTTCTGTGGGTTAGGCACGAGACCAGCCCCTACTTCACCTTAACGGTAGAGCG

I  G  P  R  H  P  I  R  A  L  V  G  D  E  V  E  L  P  S  R  -

301 ATATCGAGACTTGCAGGGCAATTCCTTGAAGAGCTGCGTGGATCCAACCCAGTAGTCCAC  360
     ------------+------------+------------+------------+------------+------------+
     TATAGCTCTGAACGTCCCGTTAAGGAACTTCTCGACGCACCTAGGTTGGGTCATCAGGTG

I  S  R  L  A  G  Q  F  L  E  E  L  R  G  S  N  P  V  V  H  -

361 TTCTTCAAGAACATTGTGACGCCACGCACACCACCACCGTCGCAGGGAAAGGGGAGAGGA  420
     ------------+------------+------------+------------+------------+------------+
     AAGAAGTTCTTGTAACACTGCGGTGCGTGTGGTGGTGGCAGCGTCCCTTTCCCCTCTCCT

F  F  K  N  I  V  T  P  R  T  P  P  P  S  Q  G  K  G  R  G  -

421 CTGTCCCTGTTCAAGGGAGTCGATGCCCAGGGCACGCTTTCCAAAATTTTTAAGCTGGGA  480
     ------------+------------+------------+------------+------------+------------+
     GACAGGGACAAGTTCCCTCAGCTACGGGTCCCGTGCGAAAGGTTTTAAAAATTCGACCCT

```
481 GGACGTGATAGTCGCTCTGGATCTCCGATGGCTTCTAGATCCAAGTACCTGGCCACAGCA 540
    CCTGCACTATCAGCGAGACCTAGAGGCTACCGAAGATCTAGGTTCATGGACCGGTGTCGT
     G  R  D  S  R  S  G  S  P  M  A  S  R  S  K  Y  L  A  T  A  -

541 AGTACGATGGATCATGCCCGTCATGGCTTCCTCCCACGTCACCGCGACACGGGCATCCTT 600
    TCATGCTACCTAGTACGGGCAGTACCGAAGGAGGGTGCAGTGGCGCTGTGCCCGTAGGAA
     S  T  M  D  H  A  R  H  G  F  L  P  R  H  R  D  T  G  I  L  -

601 GACTCCATCGGGACTAGTAAGCTGGATGAGCTGGGCTCCAAGGGGCTGTGGGCCGACAGC 660
    CTGAGGTAGCCCTGATCATTCGACCTACTCGACCCGAGGTTCCCCGACACCCGGCTGTCG
     D  S  I  G  T  S  K  L  D  E  L  G  S  K  G  L  W  A  D  S  -

661 GTCATGGCAACGGGGCTGTACCACAGCAAGCCACTGGTGGACATCCTCATCCTGCTGCTG 720
    CAGTACCGTTGCCCCGACATGGTGTCGTTCGGTGACCACCTGTAGGAGTAGGACGACGAC
     V  M  A  T  G  L  Y  H  S  K  P  L  V  D  I  L  I  L  L  L  -

721 ACTGTTCTTCCGTCTATCCGTATGGGCCAGCAGGCATTTGGTGAAAACGTTTCTACTACA 780
    TGACAAGAAGGCAGATAGGCATACCCGGTCGTCCGTAAACCACTTTTGCAAAGATGATGT
     T  V  L  P  S  I  R  M  G  Q  Q  A  F  G  E  N  V  S  T  T  -

781 CTGCGTGCTCTGGCTCCGCGTCTCATGCGAAGAATGCATGTCATCGTGACCACCTCCACC 840
    GACGCACGAGACCGAGGCGCAGAGTACGCTTCTTACGTACAGTAGCACTGGTGGAGGTGG
     L  R  A  L  A  P  R  L  M  R  R  M  H  V  I  V  T  T  S  T  -

841 AATGACTGGGTGGTGACCAGCCTGGCTCTCAGCGCCCTTGTTGCCACCATCTGGTTCCCA 900
    TTACTGACCCACCACTGGTCGGACCGAGAGTCGCGGGAACAACGGTGGTAGACCAAGGGT
     N  D  W  V  V  T  S  L  A  L  S  A  L  V  A  T  I  W  F  P  -

901 GTGAGCGCCCACCTGCAGCAGAAGTATTCCGAACACTTCAGCATACACAGCAGCCCACCG 960
    CACTCGCGGGTGGACGTCGTCTTCATAAGGCTTGTGAAGTCGTATGTGTCGTCGGGTGGC
     V  S  A  H  L  Q  Q  K  Y  S  E  H  F  S  I  H  S  S  P  P  -
```

Fig. 31 (cont.)

```
961  TTCACCTTCCTCAATAAAGAGGAGGACTGGATCAGCTCTGCCAGCCAGAAGACCCGTACC  1020
     AAGTGGAAGGAGTTATTTCTCCTCCTGACCTAGTCGAGACGGTCGGTCTTCTGGGCATGG
       F  T  F  L  N  K  E  D  W  I  S  S  A  S  Q  K  T  R  T  -

1021 AGCCGCCGTGCCAAGTCCCCACAGCGTCCGAAGCAACAGCCAGCTGCCGCCGCCAGCGGTG  1080
     TCGGCGGCACGGTTCAGGGGTGTCGCAGGCTTCGTTGTCGGTCGACGGCGGCGGTCGCCAC
       S  R  R  A  K  S  P  Q  R  P  K  Q  Q  P  A  A  P  A  V  -

1081 GTCGTCGACAAGCAACAGCCGCGCAGCAGCCCGCTCCGTGGGCCAGGTGCCAGCCGTGGG  1140
     CAGCAGCTGTTCGTTGTCGGCGCGTCGTCGGGCGAGGCACCCGGTCCACGGTCGGCACCC
       V  V  D  K  Q  Q  P  R  S  S  P  L  R  G  P  G  A  S  R  G  -

1141 CTCGAGTACAAGACCACCATCAGCGGCAAGGGCCTGAGCGCAACGGTAACAGGGGGCCAG  1200
     GAGCTCATGTTCTGGTGGTAGTCGCCGTTCCCGGACTCGCGTTGCCATTGTCCCCGGGTC
       L  E  Y  K  T  T  I  S  G  K  G  L  S  A  T  V  T  G  G  Q  -

1201 AAGGGGCGTGGTTCCAGAGGCCAACATCAAGCTCATTCTTTGGAGCGTGTGAGCCATTCT  1260
     TTCCCCGCACCAAGGTCTCCGGTTGTAGTTCGAGTAAGAAACCTCGCACACTCGGTAAGA
       K  G  R  G  S  R  G  Q  H  Q  A  H  S  L  E  R  V  S  H  S  -

1261 TTGGGAAAATGGTTAGGACATCCGGACAAGTTCAACACCTGGACCACCAGCCAGTCTATT  1320
     AACCCTTTTACCAATCCTGTAGGCCTGTTCAAGTTGTGGACCTGGTGGTCGGTCAGATAA
       L  G  K  W  L  G  H  P  D  K  F  N  T  W  T  T  S  Q  S  I  -

1321 GCCTTCCCAAGCAAGACCTCTGCCAGTATAGGCAGTCTCTCTGCTGACGCCGTTTCTGGC  1380
     CGGAAGGGTTCGTTCTGGAGACGGTCATATCCGTCAGAGAGACGACTGCGGCAAAGACCG
       A  F  P  S  K  T  S  A  S  I  G  S  L  S  A  D  A  V  S  G  -

1381 TCCAACCTTCTGTCCATCAGCAAAACAGCAGAGTTCCAAATGACCTTCCACCTGTTTATT  1440
     AGGTTGGAAGACAGGTAGTCGTTTTGTCGTCTCAAGGTTTACTGGAAGGTGGACAAATAA
       S  N  L  L  S  I  S  K  T  A  E  F  Q  M  T  F  H  L  F  I  -
```

Fig. 31 (cont.)

```
      GGATCCGCCCTCACTGGCACAGAAAAGCTGATTGAGACCTATTTCTCCAAATTTGCCGTC
1441  ------------+---------+---------+---------+---------+---------+ 1500
      CCTAGGCGGGAGTGACCGTGTCTTTTCGACTAACTCTGGATAAAGAGGTTTAAACGGCAG

G  S  A  L  T  G  T  E  K  L  I  E  T  Y  F  S  K  F  A  V   -

CTTAAACTCATGGGCCGTGGCACCAAGTTCTGATCATGAGCGGCCGCAAGCTTA
1501  ------------+---------+---------+---------+---------+---  1554
      GAATTTGAGTACCCGGCACCGTGGTTCAAGACTAGTACTCGCCGGCGTTCGAAT

```
     GAATTCGCTAGCGGCATGGAGGTGGGGTGGTATCGCCCACCATTCTCTAGGGTGGTTCAT
1    ------------+---------+---------+---------+---------+---------+  60
     CTTAAGCGATCGCCGTACCTCCACCCCACCATAGCGGGTGGTAAGAGATCCCACCAAGTA

E  F  A  S  G  M  E  V  G  W  Y  R  P  P  F  S  R  V  V  H  -

CTCTACCGTAATGGCAAGGACGGCCGTACAGAGCTGCTGAAAGATGCTATTGGTGAGGGA
61   ------------+---------+---------+---------+---------+---------+  120
     GAGATGGCATTACCGTTCCTGCCGGCATGTCTCGACGACTTTCTACGATAACCACTCCCT

L  Y  R  N  G  K  D  G  R  T  E  L  L  K  D  A  I  G  E  G  -

AAGGTGACTCTCAGGATTCGGAATGTACGCTTCTCTGATGAAGGAGGTTTCACCAGCTTC
121  ------------+---------+---------+---------+---------+---------+  180
     TTCCACTGAGAGTCCTAAGCCTTACATGCGAAGAGACTACTTCCTCCAAAGTGGTCGAAG

K  V  T  L  R  I  R  N  V  R  F  S  D  E  G  G  F  T  S  F  -

TTCCGTGACCATTCTTACCAAGAGGAGGCAGCAATGGAATTGAAAAGATCCAACCCAGTA
181  ------------+---------+---------+---------+---------+---------+  240
     AAGGCACTGGTAAGAATGGTTCTCCTCCGTCGTTACCTTAACTTTTCTAGGTTGGGTCAT

F  R  D  H  S  Y  Q  E  E  A  A  M  E  L  K  R  S  N  P  V  -

GTCCACTTCTTCAAGAACATTGTGACGCCACGCACACCACCACCCGTCGCAGGGAAAGGG
241  ------------+---------+---------+---------+---------+---------+  300
     CAGGTGAAGAAGTTCTTGTAACACTGCGGTGCGTGTGGTGGTGGGCAGCGTCCCTTTCCC

V  H  F  F  K  N  I  V  T  P  R  T  P  P  P  S  Q  G  K  G  -

AGAGGACTGTCCCTGTTCAAGGGAGTCGATGCCCAGGGCACGCTTTCCAAAATTTTTAAG
301  ------------+---------+---------+---------+---------+---------+  360
     TCTCCTGACAGGGACAAGTTCCCTCAGCTACGGGTCCCGTGCGAAAGGTTTTAAAAATTC

R  G  L  S  L  F  K  G  V  D  A  Q  G  T  L  S  K  I  F  K  -

CTGGGAGGACGTGATAGTCGCTCTGGATCTCCGATGGCTTCTAGTAAGCTGGATGAGCTG
361  ------------+---------+---------+---------+---------+---------+  420
     GACCCTCCTGCACTATCAGCGAGACCTAGAGGCTACCGAAGATCATTCGACCTACTCGAC

L  G  G  R  D  S  R  S  G  S  P  M  A  S  S  K  L  D  E  L  -

GGCTCCAAGGGGCTGTGGGCCGACAGCGTCATGGCAACGGGGCTGTACCACAGCAAGCCA
421  ------------+---------+---------+---------+---------+---------+  480
     CCGAGGTTCCCCGACACCCGGCTGTCGCAGTACCGTTGCCCCGACATGGTGTCGTTCGGT

```
481  CTGGTGGACATCCTCATCCTGCTGCTGACTGTTCTTCCGTCTATCCGTATGGGCCAGCAG  540
     GACCACCTGTAGGAGTAGGACGACGACTGACAAGAAGGCAGATAGGCATACCCGGTCGTC

L  V  D  I  L  I  L  L  L  T  V  L  P  S  I  R  M  G  Q  Q

541  GCATTTGGTGAAAACGTTTCTACTACACTGCGTGCTCTGGCTCCGCGTCTCATGCGAAGA  600
     CGTAAACCACTTTTGCAAAGATGATGTGACGCACGAGACCGAGGCGCAGAGTACGCTTCT

A  F  G  E  N  V  S  T  T  L  R  A  L  A  P  R  L  M  R  R

601  ATGCAGCAGAAGTATTCCGAACACTTCAGCATACACAGCAGCCCACCGTTCACCTTCCTC  660
     TACGTCGTCTTCATAAGGCTTGTGAAGTCGTATGTGTCGTCGGGTGGCAAGTGGAAGGAG

M  Q  Q  K  Y  S  E  H  F  S  I  H  S  S  P  P  F  T  F  L

661  AATAAAGAGGAGGACTGGATCAGCTCTGCCAGCCAGAAGACCCGTACCAGCCGCCGTGCC  720
     TTATTTCTCCTCCTGACCTAGTCGAGACGGTCGGTCTTCTGGGCATGGTCGGCGGCACGG

N  K  E  E  D  W  I  S  S  A  S  Q  K  T  R  T  S  R  R  A

721  AAGTCCCCACAGCGTCCGAAGCAACAGCCAGCTGCGCCGCCAGCGGTGGTCGTCGAGTAC  780
     TTCAGGGGTGTCGCAGGCTTCGTTGTCGGTCGACGCGGCGGTCGCCACCAGCAGCTCATG

K  S  P  Q  R  P  K  Q  Q  P  A  A  P  P  A  V  V  V  E  Y

781  AAGACCACCATCAGCGGCAAGGGCCTGAGCGCAACGGTAACAGGGGGCCAGAAGGGGCGT  840
     TTCTGGTGGTAGTCGCCGTTCCCGGACTCGCGTTGCCATTGTCCCCCGGTCTTCCCCGCA

K  T  T  I  S  G  K  G  L  S  A  T  V  T  G  G  Q  K  G  R

841  GGTTCCAGAGGCCAACATCAAGCTCATTCTTTGGAGCGTGTGAGCCATTCTTTGGGAAAA  900
     CCAAGGTCTCCGGTTGTAGTTCGAGTAAGAAACCTCGCACACTCGGTAAGAAACCCTTTT

G  S  R  G  Q  H  Q  A  H  S  L  E  R  V  S  H  S  L  G  K

901  TGGTTAGGACATCCGGACAAGTTCAACACCTGGACCACCAGCCAGTCTATTGCCTTCCCA  960
     ACCAATCCTGTAGGCCTGTTCAAGTTGTGGACCTGGTGGTCGGTCAGATAACGGAAGGGT

```
      AGCAAGACCTCTGCCAGTATAGGCAGTCTCTCTGCTGACGCCGTTTCTGGCTCCAACCTT
961   ------------+-----------+-----------+-----------+-----------+-----------+   1020
      TCGTTCTGGAGACGGTCATATCCGTCAGAGAGACGACTGCGGCAAAGACCGAGGTTGGAA

S  K  T  S  A  S  I  G  S  L  S  A  D  A  V  S  G  S  N  L
      CTGTCCATCAGCAAAACAGCAGAGTTCCAAATGACCTTCCACCTGTTTATTGGATCCTGA
1021  ------------+-----------+-----------+-----------+-----------+-----------+   1080
      GACAGGTAGTCGTTTTGTCGTCTCAAGGTTTACTGGAAGGTGGACAAATAACCTAGGACT

L  S  I  S  K  T  A  E  F  Q  M  T  F  H  L  F  I  G  *

GCGGCCGCAAGCTTA
1081  ------------+---   1095
      CGCCGGCGTTCGAAT

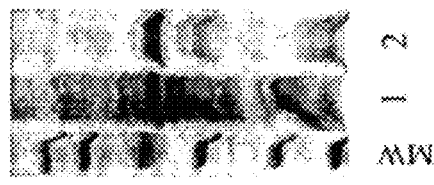
Fig. 33a

```
  1  ATGGCTAGCATGCGCCTCCTGCCGCTGCTGGCGCTGCTGGCCCTCTGGGGACCTGACCCA  60
     TACCGATCGTACGCGGAGGACGGCGACGACCGCGACGACCGGGAGACCCCTGGACTGGGT

M  A  S  M  R  L  L  P  L  L  A  L  L  A  L  W  G  P  D  P  -

61  GCCGCATCACACCTGGTGGAAGCTCTCTACCTGGTGAGCGGGGAACGTGGCTTCTTCTAC  120
     CGGCGTAGTGTGGACCACCTTCGAGAGATGGACCACTCGCCCCTTGCACCGAAGAAGATG

A  A  S  H  L  V  E  A  L  Y  L  V  S  G  E  R  G  F  F  Y  -

122  ACACCGAAGACCCGCATTGAGGCAGAGGCCGGTGCAGGCAGCCTGCAACCGTTGGCCCTG  180
     TGTGGCTTCTGGGCGTAACTCCGTCTCCGGCCACGTCCGTCGGACGTTGGCAACCGGGAC

T  P  K  T  R  I  E  A  E  A  G  A  G  S  L  Q  P  L  A  L  -

181  GAGGGGTCCCTGCAAAAGATACTAGTCGATACCTGGAGCGGCGTGGCACATGGAAGCACC  240
     CTCCCCAGGGACGTTTTCTATGATCAGCTATGGACCTCGCCGCACCGTGTACCTTCGTGG

E  G  S  L  Q  K  I  L  V  D  T  W  S  G  V  A  H  G  S  T  -

241  CGTAAACTGGGGCTCAAGATCAGCGGCTTCTTGCAACGTACCAACAGCCTGGAAGAGAAG  300
     GCATTTGACCCCGAGTTCTAGTCGCCGAAGAACGTTGCATGGTTGTCGGACCTTCTCTTC

R  K  L  G  L  K  I  S  G  F  L  Q  R  T  N  S  L  E  E  K  -

301  GCCGTGGACATACTCCTCAACTATGTCCGCAAGACATTTGATAGATCTTAGCTCGAGGCG  360
     CGGCACCTGTATGAGGAGTTGATACAGGCGTTCTGTAAACTATCTAGAATCGAGCTCCGC

```
     GATAGATCTGCGACCTATGAAATTGCTCCAGTATTTGTGCTTTTGGAATATGTCACACTG
1    ------------+---------+---------+---------+---------+---------+  60
     CTATCTAGACGCTGGATACTTTAACGAGGTCATAAACACGAAAACCTTATACAGTGTGAC

D  R  S  A  T  Y  E  I  A  P  V  F  V  L  L  E  Y  V  T  L   -

AAGAAAATGCGTGAAATCATTGGCTGGCCAGGGGGCTCTGGCGATGCGAACATGTATGCC
61   ------------+---------+---------+---------+---------+---------+  120
     TTCTTTTACGCACTTTAGTAACCGACCGGTCCCCCGAGACCGCTACGCTTGTACATACGG

K  K  M  R  E  I  I  G  W  P  G  G  S  G  D  A  N  M  Y  A   -

ATGATGATCGCACGCTTTGAAGATGTTCCCAGAAGTCAAGGAGAAAGGAATGGCTGCTCTT
121  ------------+---------+---------+---------+---------+---------+  180
     TACTACTAGCGTGCGAAATTCTACAAGGGTCTTCAGTTCCTCTTTCCTTACCGACGAGAA

M  M  I  A  R  F  E  M  F  P  E  V  K  E  G  M  A  A  L   -

CCGCGTCTCATTGCCTTCACGTCTGAACATAGTCATGCGAATGTCAGCTTCTGGTACATT
181  ------------+---------+---------+---------+---------+---------+  240
     GGCGCAGAGTAACGGAAGTGCAGACTTGTATCAGTACGCTTACAGTCGAAGACCATGTAA

P  R  L  I  A  F  T  S  E  H  S  H  A  N  V  S  F  W  Y  I   -

CCGCCGAGCTTGCGTACTCTGGAAGACAATGAAGAGCGCATGAGTCGCCTCTCGAAGGTG
241  ------------+---------+---------+---------+---------+---------+  300
     GGCGGCTCGAACGCATGAGACCTTCTGTTACTTCTCGCGTACTCAGCGGAGAGCTTCCAC

P  P  S  L  R  T  L  E  D  N  E  E  R  M  S  R  L  S  K  V   -

GCTCCAGTGATTAAAGCCCGTATGATGGAGTATGGAACCACAATGGTCGCGAAGGTCAAT
301  ------------+---------+---------+---------+---------+---------+  360
     CGAGGTCACTAATTTCGGGCATACTACCTCATACCTTGGTGTTACCAGCGCTTCCAGTTA

A  P  V  I  K  A  R  M  M  E  Y  G  T  T  M  V  A  K  V  N   -

TTCTTCCGCATGGTCATCTCAAACCCAGCGGCAACTCACCAAGACATTGACCCTAGGTAG
361  ------------+---------+---------+---------+---------+---------+  420
     AAGAAGGCGTACCAGTAGAGTTTGGGTCGCCGTTGAGTGGTTCTGTAACTGGGATCCATC

F  F  R  M  V  I  S  N  P  A  A  T  H  Q  D  I  D  P  R  *   -

GGATCCGCG
421  ---------  439
     CCTAGGCGC

```
       GATCCTAGGAAGCAGGCGTTTATTAAAGCCACAGGGAAGAAGGAAGATGAACATGTTGCG
  1    ------------+---------+---------+---------+---------+---------+  60
       CTAGGATCCTTCGTCCGCAAATAATTTCGGTGTCCCTTCTTCCTTCTACTTGTACAACGC

D  P  R  K  Q  A  F  I  K  A  T  G  K  K  E  D  E  H  V  A   -

CGCCTTGCAAAGAAGAACTTTGACAAATTGAAGATGGATGTGAGCCAAGCGATGAAATCT
  61   ------------+---------+---------+---------+---------+---------+  120
       GCGGAACGTTTCTTCTTGAAACTGTTTAACTTCTACCTACACTCGGTTCGCTACTTTAGA

R  L  A  K  K  N  F  D  K  L  K  M  D  V  S  Q  A  M  K  S   -

GAGGAAGGTGCAAGCCTGGGACCGGTGGCAGGGACCGCGCATACCATCGCAGACTTCTGG
  121  ------------+---------+---------+---------+---------+---------+  180
       CTCCTTCCACGTTCGGACCCTGGCCACCGTCCCTGGCGCGTATGGTAGCGTCTGAAGACC

E  E  G  A  S  L  G  P  V  A  G  T  A  H  T  I  A  D  F  W   -

CAGATGGTGTGGGAGAGCGGCTCTACCGTCATCGTCATGCTGACTCCGCTGGTGGAGGAT
  181  ------------+---------+---------+---------+---------+---------+  240
       GTCTACCACACCCTCTCGCCGAGATGGCAGTAGCAGTACGACTGAGGCGACCACCTCCTA

Q  M  V  W  E  S  G  S  T  V  I  V  M  L  T  P  L  V  E  D   -

GGTGTCAAGCAGGCGGTGAGCGAGCACATCTGGAGCGAGGACTTTCTGGTGCGTAGCTTC
  241  ------------+---------+---------+---------+---------+---------+  300
       CCACAGTTCGTCCGCCACTCGCTCGTGTAGACCTCGCTCCTGAAAGACCACGCATCGAAG

G  V  K  Q  A  V  S  E  H  I  W  S  E  D  F  L  V  R  S  F   -

TACCTGAAGAACGTGCAGACCCAGGAGACGCGTACGCTGACGCAGTTCCACTTCCTGAGC
  301  ------------+---------+---------+---------+---------+---------+  360
       ATGGACTTCTTGCACGTCTGGGTCCTCTGCGCATGCGACTGCGTCAAGGTGAAGGACTCG

Y  L  K  N  V  Q  T  Q  E  T  R  T  L  T  Q  F  H  F  L  S   -

GCGAGCCCGTCTCTGTGGGAGATAGAGTTTGCTAAGCAGTTAGCCAGCGTATCTAGATAG
  361  ------------+---------+---------+---------+---------+---------+  420
       CGCTCGGGCAGAGACACCCTCTATCTCAAACGATTCGTCAATCGGTCGCATAGATCTATC

A  S  P  S  L  W  E  I  E  F  A  K  Q  L  A  S  V  S  R  *   -

GAATTCGCG
  421  ---------  429
       CTTAAGCGC

```
     TCTAGATTGGGAGGAGGTTCTGCCCTGCTTCGTAGCATTCCGGCCTGGACTCTTTGACT
1    ------------+---------+---------+---------+---------+---------+ 60
     AGATCTAACCCTCCTCCAAGACGGGACGAAGCATCGTAAGGCCGGACCTGAGAAACTGA

S  R  L  G  G  G  S  A  L  L  R  S  I  P  A  L  D  S  L  T  -

CCGGCTAATGAAGATGCGAAACGTACACTGAAAATTCCGGCAATGACCATTGCTAAGAAT
61   ------------+---------+---------+---------+---------+---------+ 120
     GGCCGATTACTTCTACGCTTTGCATGTGACTTTTAAGGCCGTTACTGGTAACGATTCTTA

P  A  N  E  D  A  K  R  T  L  K  I  P  A  M  T  I  A  K  N  -

GCAGGTGTTTCTAGATAGGAATTCGCG
121  ------------+---------+------ 147
     CGTCCACAAAGATCTATCCTTAAGCGC

```
     ATGCCTAGGCGCCTCCTGCCGCTGCTGGCGCTGCTGGCCCTCTGGGGACCTGACCCAGCC
  1  ------------+------------+------------+------------+------------+------------+  60
     TACGGATCCGCGGAGGACGGCGACGACCGCGACGACCGGGAGACCCCTGGACTGGGTCGG

M  P  R  R  L  L  P  L  L  A  L  L  A  L  W  G  P  D  P  A  -

GCATCACACCTGGTGGAAGCTCTCTACCTGGTGAGCGGGGAACGTTGGCTTCTTCTACACA
 61  ------------+------------+------------+------------+------------+------------+  120
     CGTAGTGTGGACCACCTTCGAGAGATGGACCACTCGCCCCTTGCACCGAAGAAGATGTGT

A  S  H  L  V  E  A  L  Y  L  V  S  G  E  R  G  F  F  Y  T  -

CCGAAGACCCGCATTGAGGCAGAGGCTGGTGCAGGCAGCCTGCAACCGTTGGCCCTGGAG
121  ------------+------------+------------+------------+------------+------------+  180
     GGCTTCTGGGCGTAACTCCGTCTCCGACCACGTCCGTCGGACGTTGGCAACCGGGACCTC

P  K  T  R  I  E  A  E  A  G  A  G  S  L  Q  P  L  A  L  E  -

GGGTCCCTGCAAAAGATACCTAGGTAGGAATTCGCG
181  ------------+------------+------------  217
     CCCAGGGACGTTTTCTATGGATCCATCCTTAAGCGC

```
1    ATGGCTAGCGATACCTGGAGCGGCGTGGCACATGGAAGCACCCGTAAACTGGGGCTCAAG
     ------+---------+---------+---------+---------+---------+    60
     TACCGATCGCTATGGACCTCGCCGCACCGTGTACCTTCGTGGGCATTTGACCCCGAGTTC
     M  A  S  D  T  W  S  G  V  A  H  G  S  T  R  K  L  G  L  K  -

61   ATCAGCGGCTTCTTGCAACGTACCAACAGCCTGGAAGAGAAGGCGGTGGACATACTCCTC
     ------+---------+---------+---------+---------+---------+    120
     TAGTCGCCGAAGAACGTTGCATGGTTGTCGGACCTTCTCTTCCGCCACCTGTATGAGGAG
     I  S  G  F  L  Q  R  T  N  S  L  E  E  K  A  V  D  I  L  L  -

121  AACTATGTCCGCAAGACATTTGATAGATCTGCGACCTATGAAATTGCTCCAGTATTTGTG
     ------+---------+---------+---------+---------+---------+    180
     TTGATACAGGCGTTCTGTAAACTATCTAGACGCTGGATACTTTAACGAGGTCATAAACAC
     N  Y  V  R  K  T  F  D  R  S  A  T  Y  E  I  A  P  V  F  V  -

181  CTTTTGGAATATGTCACACTGAAGAAAATGCGTGAAATCATTGGCTGGCCAGGGGGCTCT
     ------+---------+---------+---------+---------+---------+    240
     GAAAACCTTATACAGTGTGACTTCTTTTACGCACTTTAGTAACCGACCGGTCCCCCGAGA
     L  L  E  Y  V  T  L  K  K  N  R  E  I  I  G  W  P  G  G  S  -

241  GGCGATGCGAACATGTATGCCATGATGATCGCACGCTTTAAGATGTTCCCAGAAGTCAAG
     ------+---------+---------+---------+---------+---------+    300
     CCGCTACGCTTGTACATACGGTACTACTAGCGTGCGAAATTCTACAAGGGTCTTCAGTTC
     G  D  A  N  M  Y  A  M  M  I  A  R  F  K  M  F  P  E  V  K  -

301  GAGAAAGGAATGGCTGCTCTTCCGCGTCTCATTGCCTTCACGTCTGAACATAGTCATGCG
     ------+---------+---------+---------+---------+---------+    360
     CTCTTTCCTTACCGACGAGAAGGCGCAGAGTAACGGAAGTGCAGACTTGTATCAGTACGC
     E  K  G  M  A  A  L  P  R  L  I  A  F  T  S  E  H  S  H  A  -

361  AATGTCAGCTTCTGGTACATTCCGCCGAGCTTGCGTACTCTGGAAGACAATGAAGAGCGC
     ------+---------+---------+---------+---------+---------+    420
     TTACAGTCGAAGACCATGTAAGGCGGCTCGAACGCATGAGACCTTCTGTTACTTCTCGCG
     N  V  S  F  W  Y  I  P  P  S  L  R  T  L  E  D  N  E  E  R  -

421  ATGAGTCGCCTCTCGAAGGTGGCTCCAGTGATAAAGCCCGTATGATGGAGTATGGAACC
     ------+---------+---------+---------+---------+---------+    480
     TACTCAGCGGAGAGCTTCCACCGAGGTCACTAATTTCGGGCATACTACCTCATACCTTGG
     M  S  R  L  S  K  V  A  P  V  I  K  A  R  M  M  E  Y  G  T  -

481  ACAATGGTCGCGAAGGTCAATTTCTTCCGCATGGTCATCTCAAACCCAGCGGCAACTCAC
     ------+---------+---------+---------+---------+---------+    540
     TGTTACCAGCGCTTCCAGTTAAAGAAGGCGTACCAGTAGAGTTTGGGTCGCCGTTGAGTG
     T  M  V  A  K  V  N  F  F  R  M  V  I  S  N  P  A  A  T  H  -
```

Fig. 42c

```
     CAAGACATTGACCCTAGGCGCCTCCTGCCGCTGCTGGCGCTGCTGGCCCTCTGGGGACCT
541  ------------+---------+---------+---------+---------+---------+  600
     GTTCTGTAACTGGGATCCGCGGAGGACGGCGACGACCGCGACGACCGGGAGACCCCTGGA

Q  D  I  D  P  R  R  L  L  P  L  L  A  L  L  A  L  W  G  P  -

GACCCAGCCGCATCACACCTGGTGGAAGCTCTCTACCTGGTGAGCGGGGAACGTGGCTTC
601  ------------+---------+---------+---------+---------+---------+  660
     CTGGGTCGGCGTAGTGTGGACCACCTTCGAGAGATGGACCACTCGCCCCTTGCACCGAAG

D  P  A  A  S  H  L  V  E  A  L  Y  L  V  S  G  E  R  G  F  -

TTCTACACACCGAAGACCCGCATTGAGGCAGAGGCCGGGTGCAGGCAGCCTGCAACCGTTG
671  ------------+---------+---------+---------+---------+---------+  720
     AAGATGTGTGGCTTCTGGGCGTAACTCCGTCTCCGCCCACGTCCGTCGGACGTTGGCAAC

F  Y  T  P  K  T  R  I  E  A  E  A  G  A  G  S  L  Q  P  L  -

GCCCTGGAGGGGTCCCTGCAAAAGATACCTAGGTAGGAATTCGCG
721  ------------+---------+---------+---------+-----  765
     CGGGACCTCCCCAGGGACGTTTTCTATGGATCCATCCTTAAGCGC

```
     ATGGCTAGCGATACCTGGAGCGGCGTGGCACATGGAAGCACCCGTAAACTGGGGCTCAAG
1    ------------+------------+------------+------------+------------+------------+ 60
     TACCGATCGCTATGGACCTCGCCGCACCGTGTACCTTCGTGGGCATTTGACCCCGAGTTC

M  A  S  D  T  W  S  G  V  A  H  G  S  T  R  K  L  G  L  K  -

ATCAGCGGCTTCTTGCAACGTACCAACAGCCTGGAAGAGAAGGCCGTGGACATACTCCTC
61   ------------+------------+------------+------------+------------+------------+ 120
     TAGTCGCCGAAGAACGTTGCATGGTTGTCGGACCTTCTCTTCCGCCACCTGTATGAGGAG

I  S  G  F  L  Q  R  T  N  S  L  E  E  K  A  V  D  I  L  L  -

AACTATGTCCGCAAGACATTTGATAGATCTGCGACCTATGAAATTGCTCCAGTATTTGTG
121  ------------+------------+------------+------------+------------+------------+ 180
     TTGATACAGGCGTTCTGTAAACTATCTAGACGCTGGATACTTTAACGAGGTCATAAACAC

N  Y  V  R  K  T  F  D  R  S  A  T  Y  E  I  A  P  V  F  V  -

CTTTTGGAATATGTCACACTGAAGAAAATGCGTGAAATCATTGGCTGGCCAGGGGGGCTCT
181  ------------+------------+------------+------------+------------+------------+ 240
     GAAAACCTTATACAGTGTGACTTCTTTTACGCACTTTAGTAACCGACCGGTCCCCCGAGA

L  L  E  Y  V  T  L  K  K  M  R  E  I  I  G  W  P  G  G  S  -

GGCGATGCAACATGTATGCCATGATGATCGCACGCTTTAAGATGTTCCCAGAAGTCAAG
241  ------------+------------+------------+------------+------------+------------+ 300
     CCGCTACGCTTGTACATACGGTACTACTAGCGTGCGAAATTCTACAAGGGTCTTCAGTTC

G  D  A  N  M  Y  A  M  M  I  A  R  F  K  M  F  P  E  V  K  -

GAGAAAGGAATGGCTGCTCTTCCGCGTCTCATTGCCTTCACGTCTGAACATAGTCATGCG
301  ------------+------------+------------+------------+------------+------------+ 360
     CTCTTTCCTTACCGACGAGAAGGCGCAGAGTAACGGAAGTGCAGACTTGTATCAGTACGC

E  K  G  M  A  A  L  P  R  L  I  A  F  T  S  E  H  S  H  A  -

AATGTCAGCTTCTGGTACATTCCGCCGAGCTTGCGTACTCTGGAAGACAATGAAGAGCGC
361  ------------+------------+------------+------------+------------+------------+ 420
     TTACAGTCGAAGACCATGTAAGGCGGCTCGAACGCATGAGACCTTCTGTTACTTCTCGCG

N  V  S  F  W  Y  I  P  P  S  L  R  T  L  E  D  N  E  E  R  -

ATGAGTCGCCTCTCGAAGGTGGCTCCAGTGATTAAAGCCCGTATGATGGAGTATGGAACC
421  ------------+------------+------------+------------+------------+------------+ 480
     TACTCAGCGGAGAGCTTCCACCGAGGTCACTAATTTCGGGCATACTACCTCATACCTTGG

M  S  R  L  S  K  V  A  P  V  I  K  A  R  M  M  E  Y  G  T  -

ACAATGGTCGCGAAGGTCAATTTCTTCCGCATGGTCATCTCAAACCCAGCGGCAACTCAC
481  ------------+------------+------------+------------+------------+------------+ 540
     TGTTACCAGCGCTTCCAGTTAAAGAAGGCGTACCAGTAGAGTTTGGGTCGCCGTTGAGTG

```
      CAAGACATTGACCCTAGGCGCCTCCTGCCGCTGCTGGCGCTGCTGGCCCTCTGGGGACCT
541   ------------+-----------+-----------+-----------+-----------+-----------+ 600
      GTTCTGTAACTGGGATCCGCGGAGGACGGCGACGACCGCGACGACCGGGAGACCCCTGGA

Q  D  I  D  P  R  R  L  L  P  L  L  A  L  L  A  L  W  G  P  -

GACCCAGCCGCATCACACCTGGTGGAAGCTCTCTACCTGGTGAGCGGGGAACGTGGCTTC
601   ------------+-----------+-----------+-----------+-----------+-----------+ 660
      CTGGGTCGGCGTAGTGTGGACCACCTTCGAGAGATGGACCACTCGCCCCTTGCACCGAAG

D  P  A  A  S  H  L  V  E  A  L  Y  L  V  S  G  E  R  G  F  -

TTCTACACACCGAAGACCCGCATTGAGGCAGAGGCGGGTGCAGGCAGCCTGCAACCGTTG
671   ------------+-----------+-----------+-----------+-----------+-----------+ 720
      AAGATGTGTGGCTTCTGGGCGTAACTCCGTCTCCGCCCACGTCCGTCGGACGTTGGCAAC

F  Y  T  P  K  T  R  I  E  A  E  A  G  A  G  S  L  Q  P  L  -

GCCCTGGAGGGGTCCCTGCAAAAGATACCTAGGTAGGAATTCGCG
721   ------------+-----------+-----------+-----------+----          765
      CGGGACCTCCCCAGGGACGTTTTCTATGGATCCATCCTTAAGCGC

```
  1   ATGGCTAGCATGCGCCTCCTGCCGCTGCTGGCGCTGCTGGCCCTCTGGGGACCTGACCCA   60
      TACCGATCGTACGCGGAGGACGGCGACGACCGCGACGACCGGGAGACCCCTGGACTGGGT
      M   A   S   M   R   L   L   P   L   L   A   L   L   A   L   W   G   P   D   P   -

61   GCCGCATCACACCTGGTGGAAGCTCTCTACCTGGTGAGCGGGGAACGTGGCTTCTTCTAC  120
      CGGCGTAGTGTGGACCACCTTCGAGAGATGGACCACTCGCCCCTTGCACCGAAGAAGATG
      A   A   S   H   L   V   E   A   L   Y   L   V   S   G   E   R   G   F   F   Y   -

121   ACACCGAAGACCCGCATTGAGGCAGAGGCGGGTGCAGGCAGCCTGCAACCGTTGGCCCTG  180
      TGTGGCTTCTGGGCGTAACTCCGTCTCCGCCCACGTCCGTCGGACGTTGGCAACCGGGAC
      T   P   K   T   R   I   E   A   E   A   G   A   G   S   L   Q   P   L   A   L   -

181   GAGGGGTCCCTGCAAAAGATACTAGTCGATACCTGGAGCGGCGTGGCACATGGAAGCACC  240
      CTCCCCAGGGACGTTTTCTATGATCAGCTATGGACCTCGCCGCACCGTGTACCTTCGTGG
      E   G   S   L   Q   K   I   L   V   D   T   W   S   G   V   A   H   G   S   T   -

241   CGTAAACTGGGCTCAAGATCAGCGGCTTCTTGCAACGTACCAACAGCCTGGAAGAGAAG   300
      GCATTTGACCCGAGTTCTAGTCGCCGAAGAACGTTGCATGGTTGTCGGACCTTCTCTTC
      R   K   L   G   L   K   I   S   G   F   L   Q   R   T   N   S   L   E   E   K   -

301   GCGGTGGACATACTCCTCAACTATGTCCGCAAGACATTTGATAGATCTGCGACCTATGAA  360
      CGCCACCTGTATGAGGAGTTGATACAGGCGTTCTGTAAACTATCTAGACGCTGGATACTT
      A   V   D   I   L   L   N   Y   V   R   K   T   F   D   R   S   A   T   Y   E   -

361   ATTGCTCCAGTATTTGTGCTTTTGGAATATGTCACACTGAAGAAAATGCGTGAAATCATT  420
      TAACGAGGTCATAAACACGAAAACCTTATACAGTGTGACTTCTTTTACGCACTTTAGTAA
      I   A   P   V   F   V   L   L   E   Y   V   T   L   K   K   M   R   E   I   I   -

421   GGCTGGCCAGGGGGCTCTGGCGATGCGAACATGTATGCCATGATGATCGCACGCTTTAAG  480
      CCGACCGGTCCCCCGAGACCGCTACGCTTGTACATACGGTACTACTAGCGTGCGAAATTC
      G   W   P   G   G   S   G   D   A   N   M   Y   A   M   M   I   A   R   F   K   -
```

Fig. 43

```
481  ATGTTCCCAGAAGTCAAGGAGAAAGGAATGGCTGCTCTTCCGCGTCTCATTGCCTTCACG  540
     TACAAGGGTCTTCAGTTCCTCTTTCCTTACCGACGAGAAGGCGCAGAGTAACGGAAGTGC

M  F  P  E  V  K  E  K  G  M  A  A  L  P  R  L  I  A  F  T  -

541  TCTGAACATAGTCATGCGAATGTCAGCTTCTGGTACATTCCGCCGAGCTTGCGTACTCTG  600
     AGACTTGTATCAGTACGCTTACAGTCGAAGACCATGTAAGGCGGCTCGAACGCATGAGAC

S  E  H  S  H  A  N  V  S  F  W  Y  I  P  P  S  L  R  T  L  -

601  GAAGACAATGAAGAGCGCATGAGTCGCCTCTCGAAGGTGGCTCCAGTGATTAAAGCCCGT  660
     CTTCTGTTACTTCTCGCGTACTCAGCGGAGAGCTTCCACCGAGGTCACTAATTTCGGGCA

E  D  N  E  E  R  M  S  R  L  S  K  V  A  P  V  I  K  A  R  -

661  ATGATGGAGTATGGAACCACAATGGTCGCGAAGGTCAATTTCTTCCGCATGGTCATCTCA  720
     TACTACCTCATACCTTGGTGTTACCAGCGCTTCCAGTTAAAGAAGGCGTACCAGTAGAGT

M  M  E  Y  G  T  T  M  V  A  K  V  N  F  F  R  M  V  I  S  -

721  AACCCAGCGGCAACTCACCAAGACATTGACCCTAGGAAGCAGGCGTTTATTAAAGCCACA  780
     TTGGGTCGCCGTTGAGTGGTTCTGTAACTGGGATCCTTCGTCCGCAAATAATTTCGGTGT

N  P  A  A  T  H  Q  D  I  D  P  R  K  Q  A  F  I  K  A  T  -

781  GGGAAGAAGGAAGATGAACATGTTGCGCGCCTTGCAAAGAAGAACTTTGACAAATTGAAG  840
     CCCTTCTTCCTTCTACTTGTACAACGCGCGGAACGTTTCTTCTTGAAACTGTTTAACTTC

G  K  K  E  D  E  H  V  A  R  L  A  K  K  N  F  D  K  L  K  -

841  ATGGATGTGAGCCAAGCGATGAAATCTGAGGAAGGTGCAAGCCTGGGACCGGTGGCAGGG  900
     TACCTACACTCGGTTCGCTACTTTAGACTCCTTCCACGTTCGGACCCTGGCCACCGTCCC

M  D  V  S  Q  A  M  K  S  E  E  G  A  S  L  G  P  V  A  G  -

901  ACCGCGCATACCATCGCAGACTTCTGGCAGATGGTGTGGGAGAGCGGCTCTACCGTCATC  960
     TGGCGCGTATGGTAGCGTCTGAAGACCGTCTACCACACCCTCTCGCCGAGATGGCAGTAG

```
961  GTCATGCTGACTCCGCTGGTGGAGGATGGTGTCAAGCAGGCGGTGAGCGAGCACATCTGG  1020
     CAGTACGACTGAGGCGACCACCTCCTACCACAGTTCGTCCGCCACTCGCTCGTGTAGACC

V  M  L  T  P  L  V  E  D  G  V  K  Q  A  V  S  E  H  I  W  -

1021 AGCGAGGACTTTCTGGTGCGTAGCTTCTACCTGAAGAACGTGCAGACCCAGGAGACGCGT  1080
     TCGCTCCTGAAAGACCACGCATCGAAGATGGACTTCTTGCACGTCTGGGTCCTCTGCGCA

S  E  D  F  L  V  R  S  F  Y  L  K  N  V  Q  T  Q  E  T  R  -

1081 ACGCTGACGCAGTTCCACTTCCTGAGCGCGAGCCCGTCTCTGTGGGAGATAGAGTTTGCT  1140
     TGCGACTGCGTCAAGGTGAAGGACTCGCGCTCGGGCAGAGACACCCTCTATCTCAAACGA

T  L  T  Q  F  H  F  L  S  A  S  P  S  L  W  E  I  E  F  A  -

1141 AAGCAGTTAGCCAGCGTATCTAGATAGGAATTCGCG  1176
     TTCGTCAATCGGTCGCATAGATCTATCCTTAAGCGC

```
  1  ATGGCTAGCGATACCTGGAGCGGCGTGGCACATGGAAGCACCCGTAAACTGGGGCTCAAG   60
     ------------+-----------+-----------+-----------+-----------+
     TACCGATCGCTATGGACCTCGCCGCACCGTGTACCTTCGTGGGCATTTGACCCCGAGTTC

M  A  S  D  T  W  S  G  V  A  H  G  S  T  R  K  L  G  L  K  -

61  ATCAGCGGCTTCTTGCAACGTACCAACAGCCTGGAAGAGAAGGCGGTGGACATACTCCTC  120
     ------------+-----------+-----------+-----------+-----------+
     TAGTCGCCGAAGAACGTTGCATGGTTGTCGGACCTTCTCTTCCGCCACCTGTATGAGGAG

I  S  G  F  L  Q  R  T  N  S  L  E  E  K  A  V  D  I  L  L  -

121  AACTATGTCCGCAAGACATTTGATAGATCTGCGACCTATGAAATTGCTCCAGTATTTGTG  180
     ------------+-----------+-----------+-----------+-----------+
     TTGATACAGGCGTTCTGTAAACTATCTAGACGCTGGATACTTTAACGAGGTCATAAACAC

N  Y  V  R  K  T  F  D  R  S  A  T  Y  E  I  A  P  V  F  V  -

181  CTTTTTGGAATATGTCACACTGAAGAAAATGCGTGAAATCATTGGCTGGCCAGGGGGCTCT  240
     ------------+-----------+-----------+-----------+-----------+
     GAAAACCTTATACAGTGTGACTTCTTTTACGCACTTTAGTAACCGACCGGTCCCCCGAGA

L  L  E  Y  V  T  L  K  K  M  R  E  I  I  G  W  P  G  G  S  -

241  GGCGATGCGAACATGTATGCCATGATGATCGCACGCTTTAAGATGTTCCCAGAAGTCAAG  300
     ------------+-----------+-----------+-----------+-----------+
     CCGCTACGCTTGTACATACGGTACTACTAGCGTGCGAAATTCTACAAGGGTCTTCAGTTC

G  D  A  N  M  Y  A  M  M  I  A  R  F  K  M  F  P  E  V  K  -

301  GAGAAAGGAATGGCTGCTCTTCCGCGTCTCATTGCCTTCACGTCTGAACATAGTCATGCG  360
     ------------+-----------+-----------+-----------+-----------+
     CTCTTTCCTTACCGACGAGAAGGCGCAGAGTAACGGAAGTGCAGACTTGTATCAGTACGC

E  K  G  M  A  A  L  P  R  L  I  A  F  T  S  E  H  S  H  A  -

361  AATGTCAGCTTCTGGTACATTCCGCCGAGCTTGCGTACTCTGGAAGACAATGAAGAGCGC  420
     ------------+-----------+-----------+-----------+-----------+
     TTACAGTCGAAGACCATGTAAGGCGGCTCGAACGCATGAGACCTTCTGTTACTTCTCGCG

N  V  S  F  W  Y  I  P  P  S  L  R  T  L  E  D  N  E  E  R  -

421  ATGAGTCGCCTCTCGAAGGTGGCTCCAGTGATTAAAGCCCGTATGATGGAGTATGGAACC  480
     ------------+-----------+-----------+-----------+-----------+
     TACTCAGCGGAGAGCTTCCACCGAGGTCACTAATTTCGGGCATACTACCTCATACCTTGG

```
481  ACAATGGTCGCGAAGGTCAATTTCTTCCGCATGGTCATCTCAAACCCAGCGGCAACTCAC  540
     ----------+---------+---------+---------+---------+---------+
     TGTTACCAGCGCTTCCAGTTAAAGAAGGCGTACCAGTAGAGTTTGGGTCGCCGTTGAGTG

T  M  V  A  K  V  N  F  F  R  M  V  I  S  N  P  A  A  T  H   -

541  CAAGACATTGACCCTAGGCGCCTCCTGCCGCTGCTGGCGCTGCTGGCCCTCTGGGGACCT  600
     ----------+---------+---------+---------+---------+---------+
     GTTCTGTAACTGGGATCCGCGGAGGACGGCGACGACCGCGACGACCGGGAGACCCCTGGA

Q  D  I  D  P  R  R  L  L  P  L  L  A  L  L  A  L  W  G  P   -

601  GACCCAGCCGCATCACACCTGGTGGAAGCTCTCTACCTGGTGAGCGGGGAACGTGGCTTC  660
     ----------+---------+---------+---------+---------+---------+
     CTGGGTCGGCGTAGTGTGGACCACCTTCGAGAGATGGACCACTCGCCCCTTGCACCGAAG

D  P  A  A  S  H  L  V  E  A  L  Y  L  V  S  G  E  R  G  F   -

661  TTCTACACACCGAAGACCCGCATTGAGGCAGAGGCGGGTGCAGGCAGCCTGCAACCGTTG  720
     ----------+---------+---------+---------+---------+---------+
     AAGATGTGTGGCTTCTGGGCGTAACTCCGTCTCCGCCCACGTCCGTCGGACGTTGGCAAC

F  Y  T  P  K  T  R  I  E  A  E  A  G  A  G  S  L  Q  P  L   -

721  GCCCTGGAGGGGTCCCTGCAAAAGATACCTAGGAAGCAGGCGTTTATTAAAGCCACAGGG  780
     ----------+---------+---------+---------+---------+---------+
     CGGGACCTCCCCAGGGACGTTTTCTATGGATCCTTCGTCCGCAAATAATTTCGGTGTCCC

A  L  E  G  S  L  Q  K  I  P  R  K  Q  A  F  I  K  A  T  G   -

781  AAGAAGGAAGATGAACATGTTGCGCGCCTTGCAAAGAAGAACTTTGACAAATTGAAGATG  840
     ----------+---------+---------+---------+---------+---------+
     TTCTTCCTTCTACTTGTACAACGCGCGGAACGTTTCTTCTTGAAACTGTTTAACTTCTAC

K  K  E  D  E  H  V  A  R  L  A  K  K  N  F  D  K  L  K  M   -

841  GATGTGAGCCAAGCGATGAAATCTGAGGAAGGTGCAAGCCTGGGACCGGTGGCAGGGACC  900
     ----------+---------+---------+---------+---------+---------+
     CTACACTCGGTTCGCTACTTTAGACTCCTTCCACGTTCGGACCCTGGCCACCGTCCCTGG

D  V  S  Q  A  M  K  S  E  E  G  A  S  L  G  P  V  A  G  T   -

901  GCGCATACCATCGCAGACTTCTGGCAGATGGTGTGGGAGAGCGGCTCTACCGTCATCGTC  960
     ----------+---------+---------+---------+---------+---------+
     CGCGTATGGTAGCGTCTGAAGACCGTCTACCACACCCTCTCGCCGAGATGGCAGTAGCAG

```
       ATGCTGACTCCGCTGGTGGAGGATGGTGTCAAGCAGGCGGTGAGCGAGCACATCTGGAGC
961    ------------+-----------+-----------+-----------+-----------+-----------+ 1020
       TACGACTGAGGCGACCACCTCCTACCACAGTTCGTCCGCCACTCGCTCGTGTAGACCTCG

M  L  T  P  L  V  E  D  G  V  K  Q  A  V  S  E  H  I  W  S  -

GAGGACTTTCTGGTGCGTAGCTTCTACCTGAAGAACGTGCAGACCCAGGAGACGCGTACG
1021   ------------+-----------+-----------+-----------+-----------+-----------+ 1080
       CTCCTGAAAGACCACGCATCGAAGATGGACTTCTTGCACGTCTGGGTCCTCTGCGCATGC

E  D  F  L  V  R  S  F  Y  L  K  N  V  Q  T  Q  E  T  R  T  -

CTGACGCAGTTCCACTTCCTGAGCGCGAGCCCGTCTCTGTGGGAGATAGAGTTTGCTAAG
1081   ------------+-----------+-----------+-----------+-----------+-----------+ 1140
       GACTGCGTCAAGGTGAAGGACTCGCGCTCGGGCAGAGACACCCTCTATCTCAAACGATTC

L  T  Q  F  H  F  L  S  A  S  P  S  L  W  E  I  E  F  A  K  -

CAGTTAGCCAGCGTATCTAGATAGGAATTCGCG
1141   ------------+-----------+-----------+---- 1173
       GTCAATCGGTCGCATAGATCTATCCTTAAGCGC

```
  1   ATGGCTAGCATGCGCCTCCTGCCGCTGCTGGCGCTGCTGGCCCTCTGGGGACCTGACCCA   60
      ----+----+----+----+----+----+----+----+----+----+----+----+
      TACCGATCGTACGCGGAGGACGGCGACGACCGCGACGACCGGGAGACCCCTGGACTGGGT

M  A  S  M  R  L  L  P  L  L  A  L  L  A  L  W  G  P  D  P  -

61   GCCGCATCACACCTGGTGGAAGCTCTCTACCTGGTGAGCGGGGAACGTGGCTTCTTCTAC  120
      ----+----+----+----+----+----+----+----+----+----+----+----+
      CGGCGTAGTGTGGACCACCTTCGAGAGATGGACCACTCGCCCCTTGCACCGAAGAAGATG

A  A  S  H  L  V  E  A  L  Y  L  V  S  G  E  R  G  F  F  Y  -

121   ACACCGAAGACCCGCATTGAGGCAGAGGCGGGTGCAGGCAGCCTGCAACCGTTGGCCCTG  180
      ----+----+----+----+----+----+----+----+----+----+----+----+
      TGTGGCTTCTGGGCGTAACTCCGTCTCCGCCCACGTCCGTCGGACGTTGGCAACCGGGAC

T  P  K  T  R  I  E  A  E  A  G  A  G  S  L  Q  P  L  A  L  -

181   GAGGGGTCCCTGCAAAAGATACTAGTCGATACCTGGAGCGGCGTGGCACATGGAAGCACC  240
      ----+----+----+----+----+----+----+----+----+----+----+----+
      CTCCCCAGGGACGTTTTCTATGATCAGCTATGGACCTCGCCGCACCGTGTACCTTCGTGG

E  G  S  L  Q  K  I  L  V  D  T  W  S  G  V  A  H  G  S  T  -

241   CGTAAACTGGGGCTCAAGATCAGCGGCTTCTTGCAACGTACCAACAGCCTGGAAGAGAAG  300
      ----+----+----+----+----+----+----+----+----+----+----+----+
      GCATTTGACCCCGAGTTCTAGTCGCCGAAGAACGTTGCATGGTTGTCGGACCTTCTCTTC

R  K  L  G  L  K  I  S  G  F  L  Q  R  T  N  S  L  E  E  K  -

301   GCGGTGGACATACTCCTCAACTATGTCCGCAAGACATTTGATAGATCTGCGACCTATGAA  360
      ----+----+----+----+----+----+----+----+----+----+----+----+
      CGCCACCTGTATGAGGAGTTGATACAGGCGTTCTGTAAACTATCTAGACGCTGGATACTT

A  V  D  I  L  L  N  Y  V  R  K  T  F  D  R  S  A  T  Y  E  -

361   ATTGCTCCAGTATTTGTGCTTTTGGAATATGTCACACTGAAGAAAATGCGTGAAATCATT  420
      ----+----+----+----+----+----+----+----+----+----+----+----+
      TAACGAGGTCATAAACACGAAAACCTTATACAGTGTGACTTCTTTTACGCACTTTAGTAA

I  A  P  V  F  V  L  L  E  Y  V  T  L  K  K  M  R  E  I  I  -

421   GGCTGGCCAGGGGGCTCTGGCGATGCGAACATGTATGCCATGATGATCGCACGCTTTAAG  480
      ----+----+----+----+----+----+----+----+----+----+----+----+
      CCGACCGGTCCCCCGAGACCGCTACGCTTGTACATACGGTACTACTAGCGTGCGAAATTC

```
481  ATGTTCCCAGAAGTCAAGGAGAAAGGAATGGCTGCTCTTCCGCGTCTCATTGCCTTCACG  540
     ----+----+----+----+----+----+----+----+----+----+----+----+
     TACAAGGGTCTTCAGTTCCTCTTTCCTTACCGACGAGAAGGCGCAGAGTAACGGAAGTGC
     M  F  P  E  V  K  E  K  G  M  A  A  L  P  R  L  I  A  F  T  -

541  TCTGAACATAGTCATGCGAATGTCAGCTTCTGGTACATTCCGCCGAGCTTGCGTACTCTG  600
     ----+----+----+----+----+----+----+----+----+----+----+----+
     AGACTTGTATCAGTACGCTTACAGTCGAAGACCATGTAAGGCGGCTCGAACGCATGAGAC
     S  E  H  S  H  A  N  V  S  F  W  Y  I  P  P  S  L  R  T  L  -

601  GAAGACAATGAAGAGCGCATGAGTCGCCTCTCGAAGGTGGCTCCAGTGATTAAAGCCCGT  660
     ----+----+----+----+----+----+----+----+----+----+----+----+
     CTTCTGTTACTTCTCGCGTACTCAGCGGAGAGCTTCCACCGAGGTCACTAATTTCGGGCA
     E  D  N  E  E  R  M  S  R  L  S  K  V  A  P  V  I  K  A  R  -

661  ATGATGGAGTATGGAACCACAATGGTCGCGAAGGTCAATTTCTTCCGCATGGTCATCTCA  720
     ----+----+----+----+----+----+----+----+----+----+----+----+
     TACTACCTCATACCTTGGTGTTACCAGCGCTTCCAGTTAAAGAAGGCGTACCAGTAGAGT
     M  M  E  Y  G  T  T  M  V  A  K  V  N  F  F  R  M  V  I  S  -

721  AACCCAGCGGCAACTCACCAAGACATTGACCCTAGGAAGCAGGCGTTTATTAAAGCCACA  780
     ----+----+----+----+----+----+----+----+----+----+----+----+
     TTGGGTCGCCGTTGAGTGGTTCTGTAACTGGGATCCTTCGTCCGCAAATAATTTCGGTGT
     N  P  A  A  T  H  Q  D  I  D  P  R  K  Q  A  F  I  K  A  T  -

781  GGGAAGAAGGAAGATGAACATGTTGCGCGCCTTGCAAAGAAGAACTTTGACAAATTGAAG  840
     ----+----+----+----+----+----+----+----+----+----+----+----+
     CCCTTCTTCCTTCTACTTGTACAACGCGCGGAACGTTTCTTCTTGAAACTGTTTAACTTC
     G  K  K  E  D  E  H  V  A  R  L  A  K  K  N  F  D  K  L  K  -

841  ATGGATGTGAGCCAAGCGATGAAATCTGAGGAAGGTGCAAGCCTGGGACCGGTGGCAGGG  900
     ----+----+----+----+----+----+----+----+----+----+----+----+
     TACCTACACTCGGTTCGCTACTTTAGACTCCTTCCACGTTCGGACCCTGGCCACCGTCCC
     M  D  V  S  Q  A  M  K  S  E  E  G  A  S  L  G  P  V  A  G  -

901  ACCGCGCATACCATCGCAGACTTCTGGCAGATGGTGTGGGAGAGCGGCTCTACCGTCATC  960
     ----+----+----+----+----+----+----+----+----+----+----+----+
     TGGCGCGTATGGTAGCGTCTGAAGACCGTCTACCACACCCTCTCGCCGAGATGGCAGTAG
     T  A  H  T  I  A  D  F  W  Q  M  V  W  E  S  G  S  T  V  I  -
```

Fig. 45 (cont.)

```
      GTCATGCTGACTCCCCTGGTGGAGGATGGTGTCAAGCAGGCGGTGAGCGAGCACATCTGG
961   ------------+---------+---------+---------+---------+---------+ 1020
      CAGTACGACTGAGGCGACCACCTCCTACCACAGTTCGTCCGCCACTCGCTCGTGTAGACC

V  M  L  T  P  L  V  E  D  G  V  K  Q  A  V  S  E  H  I  W   -

AGCGAGGACTTTCTGGTGCGTAGCTTCTACCTGAAGAACGTGCAGACCCAGGAGACGCGT
1021  ------------+---------+---------+---------+---------+---------+ 1080
      TCGCTCCTGAAAGACCACGCATCGAAGATGGACTTCTTGCACGTCTGGGTCCTCTGCGCA

S  E  D  F  L  V  R  S  F  Y  L  K  N  V  Q  T  Q  E  T  R   -

ACGCTGACGCAGTTCCACTTCCTGAGCGCGAGCCCGTCTCTGTGGGAGATAGAGTTTGCT
1081  ------------+---------+---------+---------+---------+---------+ 1140
      TGCGACTGCGTCAAGGTGAAGGACTCGCGCTCGGGCAGAGACACCCTCTATCTCAAACGA

T  L  T  Q  F  H  F  L  S  A  S  P  S  L  W  E  I  E  F  A   -

AAGCAGTTAGCCAGCGTATCTAGATTGGGAGGAGGTTCTGCCCTGCTTCGTAGCATTCCG
1141  ------------+---------+---------+---------+---------+---------+ 1200
      TTCGTCAATCGGTCGCATAGATCTAACCCTCCTCCAAGACGGGACGAAGCATCGTAAGGC

K  Q  L  A  S  V  S  R  L  G  G  G  S  A  L  L  R  S  I  P   -

GCCTTGGACTCTTTGACTCCGGCTAATGAAGATGCGAAACGTACACTGAAAATTCCGGCA
1201  ------------+---------+---------+---------+---------+---------+ 1260
      CGGAACCTGAGAAACTGAGGCCGATTACTTCTACGCTTTGCATGTGACTTTTAAGGCCGT

A  L  D  S  L  T  P  A  N  E  D  A  K  R  T  L  K  I  P  A   -

ATGACCATTGCTAAGAATGCAGGTGTTTCTAGATAGGAATTCGCG
1261  ------------+---------+---------+---------+----- 1305
      TACTGGTAACGATTCTTACGTCCACAAAGATCTATCCTTAAGCGC

```
1    ATGGCTAGCGATACCTGGAGCGGCGTGGCACATGGAAGCACCCGTAAACTGGGGCTCAAG   60
     ------+---------+---------+---------+---------+---------+
     TACCGATCGCTATGGACCTCGCCGCACCGTGTACCTTCGTGGGCATTTGACCCCGAGTTC

M  A  S  D  T  W  S  G  V  A  H  G  S  T  R  K  L  G  L  K  -

61   ATCAGCGGCTTCTTGCAACGTACCAACAGCCTGGAAGAGAAGGCGGTGGACATACTCCTC   120
     ------+---------+---------+---------+---------+---------+
     TAGTCGCCGAAGAACGTTGCATGGTTGTCGGACCTTCTCTTCCGCCACCTGTATGAGGAG

I  S  G  F  L  Q  R  T  N  S  L  E  E  K  A  V  D  I  L  L  -

121  AACTATGTCCGCAAGACATTTGATAGATCTGCGACCTATGAAATTGCTCCAGTATTTGTG   180
     ------+---------+---------+---------+---------+---------+
     TTGATACAGGCGTTCTGTAAACTATCTAGACGCTGGATACTTTAACGAGGTCATAAACAC

N  Y  V  R  K  T  F  D  R  S  A  T  Y  E  I  A  P  V  F  V  -

181  CTTTTGGAATATGTCACACTGAAGAAAATGCGTGAAATCATTGGCTGGCCAGGGGGCTCT   240
     ------+---------+---------+---------+---------+---------+
     GAAAACCTTATACAGTGTGACTTCTTTTACGCACTTTAGTAACCGACCGGTCCCCCGAGA

L  L  E  Y  V  T  L  K  K  M  R  E  I  I  G  W  P  G  G  S  -

241  GGCGATGCAACATGTATGCCATGATGATCGCACGCTTTAAGATGTTCCCAGAAGTCAAG   300
     ------+---------+---------+---------+---------+---------+
     CCGCTACGCTTGTACATACGGTACTACTAGCGTGCGAAATTCTACAAGGGTCTTCAGTTC

G  D  A  N  M  Y  A  M  M  I  A  R  F  K  M  F  P  E  V  K  -

301  GAGAAAGGAATGGCTGCTCTTCCGCGTCTCATTGCCTTCACGTCTGAACATAGTCATGCG   360
     ------+---------+---------+---------+---------+---------+
     CTCTTTCCTTACCGACGAGAAGGCGCAGAGTAACGGAAGTGCAGACTTGTATCAGTACGC

E  K  G  M  A  A  L  P  R  L  I  A  F  T  S  E  H  S  H  A  -

361  AATGTCAGCTTCTGGTACATTCCGCCGAGCTTGCGTACTCTGGAAGACAATGAAGAGCGC   420
     ------+---------+---------+---------+---------+---------+
     TTACAGTCGAAGACCATGTAAGGCGGCTCGAACGCATGAGACCTTCTGTTACTTCTCGCG

N  V  S  F  W  Y  I  P  P  S  L  R  T  L  E  D  N  E  E  R  -

421  ATGAGTCGCCTCTCGAAGGTGGCTCCAGTGATTAAAGCCCGTATGATGGAGTATGGAACC   480
     ------+---------+---------+---------+---------+---------+
     TACTCAGCGGAGAGCTTCCACCGAGGTCACTAATTTCGGGCATACTACCTCATACCTTGG

```
481 ACAATGGTCGCGAAGGTCAATTTCTTCCGCATGGTCATCTCAAACCCAGCGGCAACTCAC 540
    TGTTACCAGCGCTTCCAGTTAAAGAAGGCGTACCAGTAGAGTTTGGGTCGCCGTTGAGTG
     T  M  V  A  K  V  N  F  F  R  M  V  I  S  N  P  A  A  T  H  -

541 CAAGACATTGACCCTAGGCGCCTCCTGCCGCTGCTGGCGCTGCTGGCCCTCTGGGGACCT 600
    GTTCTGTAACTGGGATCCGCGGAGGACGGCGACGACCGCGACGACCGGGAGACCCCTGGA
     Q  D  I  D  P  R  R  L  L  P  L  L  A  L  L  A  L  W  G  P  -

601 GACCCAGCCGCATCACACCTGGTGGAAGCTCTCTACCTGGTGAGCGGGGAACGTGGCTTC 660
    CTGGGTCGGCGTAGTGTGGACCACCTTCGAGAGATGGACCACTCGCCCCTTGCACCGAAG
     D  P  A  A  S  H  L  V  E  A  L  Y  L  V  S  G  E  R  G  F  -

661 TTCTACACACCGAAGACCCGCATTGAGGCAGAGGCGGGTGCAGGCAGCCTGCAACCGTTG 720
    AAGATGTGTGGCTTCTGGGCGTAACTCCGTCTCCGCCCACGTCCGTCGGACGTTGGCAAC
     F  Y  T  P  K  T  R  I  E  A  E  A  G  A  G  S  L  Q  P  L  -

721 GCCCTGGAGGGGTCCCTGCAAAAGATACCTAGGAAGCAGGCGTTTATTAAAGCCACAGGG 780
    CGGGACCTCCCCAGGGACGTTTTCTATGGATCCTTCGTCCGCAAATAATTTCGGTGTCCC
     A  L  E  G  S  L  Q  K  I  P  R  K  Q  A  F  I  K  A  T  G  -

781 AAGAAGGAAGATGAACATGTTGCGCGCCTTGCAAAGAAGAACTTTGACAAATTGAAGATG 840
    TTCTTCCTTCTACTTGTACAACGCGCGGAACGTTTCTTCTTGAAACTGTTTAACTTCTAC
     K  K  E  D  E  H  V  A  R  L  A  K  K  N  F  D  K  L  K  M  -

841 GATGTGAGCCAAGCGATGAAATCTGAGGAAGGTGCAAGCCTGGGACCGGTGGCAGGGACC 900
    CTACACTCGGTTCGCTACTTTAGACTCCTTCCACGTTCGGACCCTGGCCACCGTCCCTGG
     D  V  S  Q  A  M  K  S  E  E  G  A  S  L  G  P  V  A  G  T  -

901 GCGCATACCATCGCAGACTTCTGGCAGATGGTGTGGGAGAGCGGCTCTACCGTCATCGTC 960
    CGCGTATGGTAGCGTCTGAAGACCGTCTACCACACCCTCTCGCCGAGATGGCAGTAGCAG
     A  H  T  I  A  D  F  W  Q  M  V  W  E  S  G  S  T  V  I  V  -
```

Fig. 45a (cont.)

```
961  ATGCTGACTCCGCTGGTGGAGGATGGTGTCAAGCAGGCGGTGAGCGAGCACATCTGGAGC  1020
     TACGACTGAGGCGACCACCTCCTACCACAGTTCGTCCGCCACTCGCTCGTGTAGACCTCG
      M  L  T  P  L  V  E  D  G  V  K  Q  A  V  S  E  H  I  W  S  -

1021 GAGGACTTTCTGGTGCGTAGCTTCTACCTGAAGAACGTGCAGACCCAGGAGACGCGTACG  1080
     CTCCTGAAAGACCACGCATCGAAGATGGACTTCTTGCACGTCTGGGTCCTCTGCGCATGC
      E  D  F  L  V  R  S  F  Y  L  K  N  V  Q  T  Q  E  T  R  T  -

1081 CTGACGCAGTTCCACTTCCTGAGCGCGAGCCCGTCTCTGTGGGAGATAGAGTTTGCTAAG  1140
     GACTGCGTCAAGGTGAAGGACTCGCGCTCGGGCAGAGACACCCTCTATCTCAAACGATTC
      L  T  Q  F  H  F  L  S  A  S  P  S  L  W  E  I  E  F  A  K  -

1141 CAGTTAGCCAGCGTATCTAGATTGGGAGGAGGTTCTGCCCTGCTTCGTAGCATTCCGGCC  1200
     GTCAATCGGTCGCATAGATCTAACCCTCCTCCAAGACGGGACGAAGCATCGTAAGGCCGG
      Q  L  A  S  V  S  R  L  G  G  G  S  A  L  L  R  S  I  P  A  -

1201 TTGGACTCTTTGACTCCGGCTAATGAAGATGCGAAACGTACACTGAAAATTCCGGCAATG  1260
     AACCTGAGAAACTGAGGCCGATTACTTCTACGCTTTGCATGTGACTTTTAAGGCCGTTAC
      L  D  S  L  T  P  A  N  E  D  A  K  R  T  L  K  I  P  A  M  -

1261 ACCATTGCTAAGAATGCAGGTGTTTCTAGATAGGAATTCGCG  1302
     TGGTAACGATTCTTACGTCCACAAAGATCTATCCTTAAGCGC
      T  I  A  K  N  A  G  V  S  R  *  E  F  A  -
```

Fig. 45a (cont.)

```
  1  GAATTCGCTAGCGGTGCTCGTGGTTTCCCAGGAACCCCAGGTCTTCCGGGTGTCAAAGGT  60
     ------------+---------+---------+---------+---------+---------+
     CTTAAGCGATCGCCACGAGCACCAAAGGGTCCTTGGGGTCCAGAAGGCCCACAGTTTCCA

E  F  A  S  G  A  R  G  F  P  G  T  P  G  L  P  G  V  K  G  -

61  CACCGTGGTTATCCGGGCCTGGACGGTGCTGGTCAGACGGGTAAACCAGGTATTGCTGGC  120
     ------------+---------+---------+---------+---------+---------+
     GTGGCACCAATAGGCCCGGACCTGCCACGACCAGTCTGCCCATTTGGTCCATAACGACCG

H  R  G  Y  P  G  L  D  G  A  G  Q  T  G  K  P  G  I  A  G  -

121  TTCAAAGGTGAACAAGGCCCGAAGGGAGAACCCGGCCCAGCAGGTGAAGAAGGCAAGCGT  180
     ------------+---------+---------+---------+---------+---------+
     AAGTTTCCACTTGTTCCGGGCTTCCCTCTTGGGCCGGGTCGTCCACTTCTTCCGTTCGCA

F  K  G  E  Q  G  P  K  G  E  P  G  P  A  G  E  E  G  K  R  -

181  GGTGCCCGTGGAGAGCCGGGTGGCGTTGGGCCGATCAGATCTGGCCCACCAGGCCCGGCT  240
     ------------+---------+---------+---------+---------+---------+
     CCACGGGCACCTCTCGGCCCACCGCAACCCGGCTAGTCTAGACCGGGTGGTCCGGGCCGA

G  A  R  G  E  P  G  G  V  G  P  I  R  S  G  P  P  G  P  A  -

241  GGACCAGCTGGTGAACGTGGCGAGCAGGCGGTTGGACCGCCAGGTCCGGCAGGAAGCGCT  300
     ------------+---------+---------+---------+---------+---------+
     CCTGGTCGACCACTTGCACCGCTCGTCCGCCAACCTGGCGGTCCAGGCCGTCCTTCGCGA

G  P  A  G  E  R  G  E  Q  A  V  G  P  P  G  P  A  G  S  A  -

301  GGTGCTCGTGGCGCTCCGGGTGCGCCAGGCGAGCGTGGCCTGAAGGGACACCGTGGCTTC  360
     ------------+---------+---------+---------+---------+---------+
     CCACGAGCACCGCGAGGCCCACGCGGTCCGCTCGCACCGGACTTCCCTGTGGCACCGAAG

G  A  R  G  A  P  G  A  P  G  E  R  G  L  K  G  H  R  G  F  -

361  ACTGGTCTGCAAGGTCTGCCAGGCGGATCCTAGAAGCTT  399
     ------------+---------+---------+-------
     TGACCAGACGTTCCAGACGGTCCGCCTAGGATCTTCGAA

```
     GAATTCCTAGGATCCGCCACTGAAGGGCGCGTCCGTGTCAACAGCCCCTATCAGGACAAG
1    ------------+---------+---------+---------+---------+---------+  60
     CTTAAGGATCCTAGGCGGTGACTTCCCGCGCACGCACAGTTGTCGGGGATAGTCCTGTTC

E  F  L  G  S  A  T  E  G  R  V  R  V  N  S  A  Y  Q  D  K   -

GCGTCTGGAGAAGTTCTGGAGACCACTGCCCCAGGAGTAGAGGACATCAGCGGGCTTCCG
61   ------------+---------+---------+---------+---------+---------+  120
     CGCAGACCTCTTCAAGACCTCTGGTGACGGGGTCCTCATCTCCTGTAGTCGCCCGAAGGC

A  S  G  E  V  L  E  T  T  A  P  G  V  E  D  I  S  G  L  P   -

TCTGGAGAAGTTCTGGAGACCGCTGCCCCAGGAGTAGAGGACATCAGCGGGCTTCCGTCT
121  ------------+---------+---------+---------+---------+---------+  180
     AGACCTCTTCAAGACCTCTGGCGACGGGGTCCTCATCTCCTGTAGTCGCCCGAAGGCAGA

S  G  E  V  L  E  T  A  A  P  G  V  E  D  I  S  G  L  P  S   -

GGAGCCGGCTGGCTGGCTGACCAGACTGTCCGTTACCCGATCAGCGCCGGCTGGCTGGCC
181  ------------+---------+---------+---------+---------+---------+  240
     CCTCGGCCGACCGACCGACTGGTCTGACAGGCAATGGGCTAGTCGCGGCCGACCGACCGG

G  A  G  W  L  A  D  Q  T  V  R  Y  P  I  S  A  G  W  L  A   -

GACCGCAGCGTGCGCTACCCGATCTCTTCTAGAGCCGGCTGGCTGGCCGACGGCAGCCTG
241  ------------+---------+---------+---------+---------+---------+  300
     CTGGCGTCGCACGCGATGGGCTAGAGAAGATCTCGGCCGACCGACCGGCTGCCGTCGGAC

D  R  S  V  R  Y  P  I  S  S  R  A  G  W  L  A  D  G  S  L   -

CGCTACCCGATCGCGTCTGGAGCATATTATGGCAGCGGAACTCCGTCTAGCTTCCCGACG
301  ------------+---------+---------+---------+---------+---------+  360
     GCGATGGGCTAGCGCAGACCTCGTATAATACCGTCGCCTTGAGGCAGATCGAAGGGCTGC

R  Y  P  I  A  S  G  A  Y  Y  G  S  G  T  P  S  S  F  P  T   -

GTCTCTACTAGTTAGAAGCTT
361  ------------+---------+  381
     CAGAGATGATCAATCTTCGAA

```
      GAATTCACTAGTAACTTTGGGTCTCAACGCTTTTCTAAGATAGCCTCCAACACCCAGAGC
  1   ------------+---------+---------+---------+---------+---------+  60
      CTTAAGTGATCATTGAAACCCAGAGTTGCGAAAAGATTCTATCGGAGGTTGTGGGTCTCG

E  F  T  S  N  F  G  S  Q  R  F  S  K  I  A  S  N  T  Q  S  -

CCGCCGGGCATCCCGACCTTCGGGCGTAGCTTCACTCTGGCTTCTTCTGAGACTGGTGTT
 61   ------------+---------+---------+---------+---------+---------+ 120
      GCGGCGCCCGTAGGGCTGGAAGCCCGCATCGAAGTGAGACCGAAGAAGACTCTGACCACAA

R  A  G  I  P  T  F  G  R  S  F  T  L  A  S  S  E  T  G  V  -

GGAGCGCAGTGGGTAGGATACGACGACCAGGAAAGCGTCAAAAGCAAGGTGCAGTACGTC
131   ------------+---------+---------+---------+---------+---------+ 180
      CCTCGCGTCACCCATCCTATGCTGCTGGTCCTTTCGCAGTTTTCGTTCCACGTCATGCAG

G  A  Q  W  V  G  Y  D  D  Q  E  S  V  K  S  K  V  Q  Y  V  -

GACGCCGGCTGGCTGAGCGATGGCTCTGTGCAATATCCGATTGCGAATGATGGTGCTCAG
181   ------------+---------+---------+---------+---------+---------+ 240
      CTGCGGCCGACCGACTCGCTACCGAGACACGTTATAGGCTAACGCTTACTACCACGAGTC

D  A  G  W  L  S  D  G  S  V  Q  Y  P  I  A  N  D  G  A  Q  -

ATTGCAAAAGTGGGCCAGATATTTGCTGCCTGGAAAATTCTGGGATATGACCGCTCTGAT
241   ------------+---------+---------+---------+---------+---------+ 300
      TAACGTTTTCACCCGGTCTATAAACGACGGACCTTTTAAGACCCTATACTGGCGAGACTA

I  A  K  V  G  Q  I  F  A  A  W  K  I  L  G  Y  D  R  S  D  -

CTCGAGTAGAAGCTT
301   ------------+-- 315
      GAGCTCATCTTCGAA

```
  1  GAATTCGCTAGCCTCGAGGCTCACCGTAAGCCGTTGGTCATAATCGCTGAAGATGTTGAT   60
     ------------+------------+------------+------------+------------+------------+
     CTTAAGCGATCGGAGCTCCGAGTGGCATTCGGCAACCAGTATTAGCGACTTCTACAACTA

E  F  A  S  L  E  A  H  R  K  P  L  V  I  I  A  E  D  V  D  -

61  GGAGAAGCTCTGAGCACACTGGTCTTGAATCGTCTTAAGGTTGGTCTTCAGGTTGTGGCA  120
     ------------+------------+------------+------------+------------+------------+
     CCTCTTCGAGACTCGTGTGACCAGAACTTAGCAGAATTCCAACCAGAAGTCCAACACCGT

G  E  A  L  S  T  L  V  L  N  R  L  K  V  G  L  Q  V  V  A  -

121  GTCAAGGCTCCAGGGTTTGGTGACAATGCGATGGCCAAGACAATTGCGTACGACGAAGAG  180
     ------------+------------+------------+------------+------------+------------+
     CAGTTCCGAGGTCCCAAACCACTGTTACGCTACCGGTTCTGTTAACGCATGCTGCTTCTC

V  K  A  P  G  F  G  D  N  A  M  A  K  T  I  A  Y  D  E  E  -

181  GCCCGTCGCGGCCTCGGATCCGGTGTCATCACAGTAAAGGATGGAAAAACACTGAATGAT  240
     ------------+------------+------------+------------+------------+------------+
     CGGGCAGCGCCGGAGCCTAGGCCACAGTAGTGTCATTTCCTACCTTTTTGTGACTTACTA

A  R  R  G  L  G  S  G  V  I  T  V  K  D  G  K  T  L  N  D  -

241  GAATTAGAAATTATTGAAGGCATGAAGTTTGATCGTGGCTATATTTCTGCGTCTCAAAAA  300
     ------------+------------+------------+------------+------------+------------+
     CTTAATCTTTAATAACTTCCGTACTTCAAACTAGCACCGATATAAAGACGCAGAGTTTTT

E  L  E  I  I  E  G  M  K  F  D  R  G  Y  I  S  A  S  Q  K  -

301  CGTGCGGCATACGATCAGTATGGTCATGCTGCGTTTGAGTGATCATAGAAGCTT         354
     ------------+------------+------------+------------+--------
     GCACGCCGTATGCTAGTCATACCAGTACGACGCAAACTCACTAGTATCTTCGAA

```
  1 GAATTCGCTAGCGGTGCTCGTGGTTTCCCAGGAACCCCAGGTCTTCCGGGTGTCAAAGGT  60
    ------+---------+---------+---------+---------+---------+
    CTTAAGCGATCGCCACGAGCACCAAAGGGTCCTTGGGGTCCAGAAGGCCCACAGTTTCCA

E  F  A  S  G  A  R  G  F  P  G  T  P  G  L  P  G  V  K  G   -

61 CACCGTGGTTATCCGGGCCTGGACGGTGCTGGTCAGACGGGTAAACCAGGTATTGCTGGC 120
    ------+---------+---------+---------+---------+---------+
    GTGGCACCAATAGGCCCGGACCTGCCACGACCAGTCTGCCCATTTGGTCCATAACGACCG

H  R  G  Y  P  G  L  D  G  A  G  Q  T  G  K  P  G  I  A  G   -

121 TTCAAAGGTGAACAAGGCCCCGAAGGGAGAACCGGGCCCAGCAGGTGAAGAAGGCAAGCGT 180
    ------+---------+---------+---------+---------+---------+
    AAGTTTCCACTTGTTCCGGGGCTTCCCTCTTGGCCCGGGTCGTCCACTTCTTCCGTTCGCA

F  K  G  E  Q  G  P  E  G  E  P  G  P  S  R  W  R  R  Q  A   -
```

(Note: amino acid row reads: F K G E Q G P K G E P G P A G E E G K R)

```
181 GGTGCCCGTGGAGAGCCCGGTGGCGTTGGGCCGATCAGATCTGGCCCACCAGGCCCGGCT 240
    ------+---------+---------+---------+---------+---------+
    CCACGGGCACCTCTCGGGCCACCGCAACCCGGCTAGTCTAGACCGGGTGGTCCGGGCCGA

G  A  R  G  E  P  G  G  V  G  P  I  R  S  G  P  P  G  P  A   -

241 GGACCAGCTGGTGAACGTGGCGAGCAGGCGGTTGGACCGCCAGGTCCGGCAGGAAGCGCT 300
    ------+---------+---------+---------+---------+---------+
    CCTGGTCGACCACTTGCACCGCTCGTCCGCCAACCTGGCGGTCCAGGCCGTCCTTCGCGA

G  P  A  G  E  R  G  E  Q  A  V  G  P  P  G  P  A  G  S  A   -

301 GGTGCTCGTGGCGCTCCGGGTGCGCCAGGCGAGCGTGGCCTGAAGGGACACCGTGGCTTC 360
    ------+---------+---------+---------+---------+---------+
    CCACGAGCACCGCGAGGCCCACGCGGTCCGCTCGCACCGGACTTCCCTGTGGCACCGAAG

G  A  R  G  A  P  G  A  P  G  E  R  G  L  K  G  H  R  G  F   -

361 ACTGGTCTGCAAGGTCTGCCAGGCGGATCCGCCACTGAAGGGCGCGTGCGTGTCAACAGC 420
    ------+---------+---------+---------+---------+---------+
    TGACCAGACGTTCCAGACGGTCCGCCTAGGCGGTGACTTCCCGCGCACGCACAGTTGTCG

T  G  L  Q  G  L  P  G  G  S  A  T  E  G  R  V  R  V  N  S   -

421 GCCTATCAGGACAAGGCGTCTGGAGAAGTTCTGGAGACCACTGCCCCAGGAGTAGAGGAC 480
    ------+---------+---------+---------+---------+---------+
    CGGATAGTCCTGTTCCGCAGACCTCTTCAAGACCTCTGGTGACGGGGTCCTCATCTCCTG

```
       ATCAGCGGGCTTCCGTCTGGAGAAGTTCTGGAGACCGCTGCCCCAGGAGTAGAGGACATC
481    ------------+-----------+-----------+-----------+-----------+-----------+  540
       TAGTCGCCCGAAGGCAGACCTCTTCAAGACCTCTGGCGACGGGGTCCTCATCTCCTGTAG

I  S  G  L  P  S  G  E  V  L  E  T  A  A  P  G  V  E  D  I   -

AGCGGGCTTCCGTCTGGAGCCGGCTGGCTGGCTGACCAGACTGTCCGTTACCCGATCAGC
541    ------------+-----------+-----------+-----------+-----------+-----------+  600
       TCGCCCGAAGGCAGACCTCGGCCGACCGACCGACTGGTCTGACAGGCAATGGGCTAGTCG

S  G  L  P  S  G  A  G  W  L  A  D  Q  T  V  R  Y  P  I  S   -

GCCGGCTGGCTGGCCGACCGCAGCGTGCGCTACCCGATCTCTTCTAGAGCCGGCTGGCTG
601    ------------+-----------+-----------+-----------+-----------+-----------+  660
       CGGCCGACCGACCGGCTGGCGTCGCACGCGATGGGCTAGAGAAGATCTCGGCCGACCGAC

A  G  W  L  A  D  R  S  V  R  Y  P  I  S  S  R  A  G  W  L   -

GCCGACGGCAGCCTGCGCTACCCGATTGCGTCTGGAGCATATTATGGCAGCGGAACTCCG
661    ------------+-----------+-----------+-----------+-----------+-----------+  720
       CGGCTGCCGTCGGACGCGATGGGCTAACGCAGACCTCGTATAATACCGTCGCCTTGAGGC

A  D  G  S  L  R  Y  P  I  A  S  G  A  Y  Y  G  S  G  T  P   -

TCTAGCTTCCCGACGGTCTCTACTAGTAACTTTGGGTCTCAACGCTTTTCTAAGATAGCC
721    ------------+-----------+-----------+-----------+-----------+-----------+  780
       AGATCGAAGGGCTGCCAGAGATGATCATTGAAACCCAGAGTTGCGAAAAGATTCTATCGG

S  S  F  P  T  V  S  T  S  N  F  G  S  Q  R  F  S  K  I  A   -

TCCAACACCCAGAGCCGCGCGGGCATCCCGACCTTCGGGCGTAGCTTCACTCTGGCTTCT
781    ------------+-----------+-----------+-----------+-----------+-----------+  840
       AGGTTGTGGGTCTCGGCGCGCCCGTAGGGCTGGAAGCCCGCATCGAAGTGAGACCGAAGA

S  N  T  Q  S  R  A  G  I  P  T  F  G  R  S  F  T  L  A  S   -

TCTGAGACTGGTGTTGGAGCGCAGTGGGTAGGATACGACGACCAGGAAAGCGTCAAAAGC
841    ------------+-----------+-----------+-----------+-----------+-----------+  900
       AGACTCTGACCACAACCTCGCGTCACCCATCCTATGCTGCTGGTCCTTTCGCAGTTTTCG

S  E  T  G  V  G  A  Q  W  V  G  Y  D  D  Q  E  S  V  K  S   -

AAGGTGCAGTACGTCGACGCCGGCTGGCTGAGCGATGGCTCTGTGCAATATCCGATTGCG
901    ------------+-----------+-----------+-----------+-----------+-----------+  960
       TTCCACGTCATGCAGCTGCGGCCGACCGACTCGCTACCGAGACACGTTATAGGCTAACGC

```
       AATGATGGTGCTCAGATTGCAAAAGTGGGCCAGATATTTGCTGCCTGGAAAATTCTGGGA
961    ------------+---------+---------+---------+---------+--------  1020
       TTACTACCACGAGTCTAACGTTTTCACCCGGTCTATAAACGACGGACCTTTTAAGACCCT

N  D  G  A  Q  I  A  K  V  G  Q  I  F  A  A  W  K  I  L  G  -

TATGACCGCTCTGATCTCGAGTAGAAGCTT
1021   ------------+---------+-------+  1050
       ATACTGGCGAGACTAGAGCTCATCTTCGAA

```
  1  GAATTCGCTAGCGGTGCTCGTGGTTTCCCAGGAACCCCAGGTCTTCCGGGTGTCAAAGGT
     ------------+---------+---------+---------+---------+---------+  60
     CTTAAGCGATCGCCACGAGCACCAAAGGGTCCTTGGGGTCCAGAAGGCCCACAGTTTCCA

E  F  A  S  G  A  R  G  F  P  G  T  P  G  L  P  G  V  K  G  -

61  CACCGTGGTTATCCGGGCCTGGACGGTGCTGGTCAGACGGGTAAACCAGGTATTGCTGGC
     ------------+---------+---------+---------+---------+---------+ 120
     GTGGCACCAATAGGCCCGGACCTGCCACGACCAGTCTGCCCATTTGGTCCATAACGACCG

H  R  G  Y  P  G  L  D  G  A  G  Q  T  G  K  P  G  I  A  G  -

121  TTCAAAGGTGAACAAGGCCCGAAGGGAGAACCGGGCCCAGCAGGTGAAGAAGGCAAGCGT
     ------------+---------+---------+---------+---------+---------+ 180
     AAGTTTCCACTTGTTCCGGGCTTCCCTCTTGGCCCGGGTCGTCCACTTCTTCCGTTCGCA

F  K  G  E  Q  G  P  K  G  E  P  G  P  A  G  E  E  G  K  R  -

181  GGTGCCCGTGGAGAGCCGGGTGGCGTTGGGCCGATCAGATCTGGCCCACCAGGCCCCGGCT
     ------------+---------+---------+---------+---------+---------+ 240
     CCACGGGCACCTCTCGGCCCACCGCAACCCGGCTAGTCTAGACCGGGTGGTCCGGGCCGA

G  A  R  G  E  P  G  G  V  G  P  I  R  S  G  P  P  G  P  A  -

241  GGACCAGCTGGTGAACGTGGCGAGCAGGCGGTTGGACCGCCAGGTCCGGCAGGAAGCGCT
     ------------+---------+---------+---------+---------+---------+ 300
     CCTGGTCGACCACTTGCACCGCTCGTCCGCCAACCTGGCGGTCCAGGCCGTCCTTCGCGA

G  P  A  G  E  R  G  E  Q  A  V  G  P  P  G  P  A  G  S  A  -

301  GGTGCTCGTGGCGCTCCGGGTGCGCCAGGCGAGCGTGGCCTGAAGGGACACCGTGGCTTC
     ------------+---------+---------+---------+---------+---------+ 360
     CCACGAGCACCGCGAGGCCCACGCGGTCCGCTCGCACCGGACTTCCCTGTGGCACCGAAG

G  A  R  G  A  P  G  A  P  G  E  R  G  L  K  G  H  R  G  F  -

361  ACTGGTCTGCAAGGTCTGCCAGGCGGATCCGCCACTGAAGGGCGCGTGCGTGTCAACAGC
     ------------+---------+---------+---------+---------+---------+ 420
     TGACCAGACGTTCCAGACGGTCCGCCTAGGCGGTGACTTCCCGCGCACGCACAGTTGTCG

T  G  L  Q  G  L  P  G  G  S  A  T  E  G  R  V  R  V  N  S  -

421  GCCTATCAGGACAAGGCGTCTGGAGAAGTTCTGGAGACCACTGCCCCAGGAGTAGAGGAC
     ------------+---------+---------+---------+---------+---------+ 480
     CGGATAGTCCTGTTCCGCAGACCTCTTCAAGACCTCTGGTGACGGGGTCCTCATCTCCTG

```
     ATCAGCGGGCTTCCGTCTGGAGAAGTTCTGGAGACCGCTGCCCAGGAGTAGAGGACATC
481  ------------+---------+---------+---------+---------+---------+ 540
     TAGTCGCCCGAAGGCAGACCTCTTCAAGACCTCTGGCGACGGGTCCTCATCTCCTGTAG

I  S  G  L  P  S  G  E  V  L  E  T  A  A  P  G  V  E  D  I  -
     AGCGGGCTTCCGTCTGGAGCCGGCTGGCTGGCTGACCAGACTGTCCGTTACCCGATCAGC
541  ------------+---------+---------+---------+---------+---------+ 600
     TCGCCCGAAGGCAGACCTCGGCCGACCGACCGACTGGTCTGACAGGCAATGGGCTAGTCG

S  G  L  P  S  G  A  G  W  L  A  D  Q  T  V  R  Y  P  I  S  -
     GCCGGCTGGCTGGCCGACCGCAGCGTGCGCTACCCGATCTCTTCTAGAGCCGGCTGGCTG
601  ------------+---------+---------+---------+---------+---------+ 660
     CGGCCGACCGACCGGCTGGCGTCGCACGCGATGGGCTAGAGAAGATCTCGGCCGACCGAC

A  G  W  L  A  D  R  S  V  R  Y  P  I  S  S  R  A  G  W  L  -
     GCCGACGGCAGCCTGCGCTACCCGATTGCGTCTGGAGCATATTATGGCAGCGGAACTCCG
661  ------------+---------+---------+---------+---------+---------+ 720
     CGGCTGCCGTCGGACGCGATGGGCTAACGCAGACCTCGTATAATACCGTCGCCTTGAGGC

A  D  G  S  L  R  Y  P  I  A  S  G  A  Y  Y  G  S  G  T  P  -
     TCTAGCTTCCCCGACGGTCTCTACTAGTAACTTTGGGTCTCAACGCTTTTCTAAGATAGCC
721  ------------+---------+---------+---------+---------+---------+ 780
     AGATCGAAGGGCTGCCAGAGATGATCATTGAAACCCAGAGTTGCGAAAAGATTCTATCGG

S  S  F  P  T  V  S  T  S  N  F  G  S  Q  R  F  S  K  I  A  -
     TCCAACACCCAGAGCCGCGCGGGCATCCCGACCTTCGGGCGTAGCTTCACTCTGGCTTCT
781  ------------+---------+---------+---------+---------+---------+ 840
     AGGTTGTGGGTCTCGGCGCGCCCGTAGGGCTGGAAGCCCGCATCGAAGTGAGACCGAAGA

S  N  T  Q  S  R  A  G  I  P  T  F  G  R  S  F  T  L  A  S  -
     TCTGAGACTGGTGTTGGAGCGCAGTGGGTAGGATACGACGACCAGGAAAGCGTCAAAAGC
841  ------------+---------+---------+---------+---------+---------+ 900
     AGACTCTGACCACAACCTCGCGTCACCCATCCTATGCTGCTGGTCCTTTCGCAGTTTTCG

S  E  T  G  V  G  A  Q  W  V  G  Y  D  D  Q  E  S  V  K  S  -
     AAGGTGCAGTACGTCGACGCCGGCTGGCTGAGCGATGGCTCTGTGCAATATCCGATTGCG
901  ------------+---------+---------+---------+---------+---------+ 960
     TTCCACGTCATGCAGCTGCGGCCGACCGACTCGCTACCGAGACACGTTATAGGCTAACGC

K  V  Q  Y  V  D  A  G  W  L  S  D  G  S  V  Q  Y  P  I  A  -
     AATGATGGTGCTCAGATTGCAAAAGTGGGCCAGATATTTGCTGCCTGGAAAATTCTGGGA
961  ------------+---------+---------+---------+---------+---------+ 1020
     TTACTACCACGAGTCTAACGTTTTCACCCGGTCTATAAACGACGGACCTTTTAAGACCCT

```
1021 TATGACCGCTCTGATCTCGAGGCTCACCGTAAGCCGTTGGTCATAATCGCTGAAGATGTT 1080
     ATACTGGCGAGACTAGAGCTCCGAGTGGCATTCGGCAACCAGTATTAGCGACTTCTACAA
      Y  D  R  S  D  L  E  A  R  R  K  P  L  V  I  I  A  E  D  V  -

1081 GATGGAGAAGCTCTGAGCACACTGGTCTTGAATCGTCTTAAGGTTGGTCTTCAGGTTGTG 1140
     CTACCTCTTCGAGACTCGTGTGACCAGAACTTAGCAGAATTCCAACCAGAAGTCCAACAC
      D  G  E  A  L  S  T  L  V  L  N  R  L  K  V  G  L  Q  V  V  -

1141 GCAGTCAAGGCTCCAGGGTTTGGTGACAATGCGATGGCCAAGACAATTGCGTACGACGAA 1200
     CGTCAGTTCCGAGGTCCCAAACCACTGTTACGCTACCGGTTCTGTTAACGCATGCTGCTT
      A  V  K  A  P  G  F  G  D  N  A  M  A  K  T  I  A  Y  D  E  -

1201 GAGGCCCGTCGCGGCCTCGGATCCGGTGTCATCACAGTAAAGGATGGAAAAACACTGAAT 1260
     CTCCGGGCAGCGCCGGAGCCTAGGCCACAGTAGTGTCATTTCCTACCTTTTTGTGACTTA
      E  A  R  R  G  L  G  S  G  V  I  T  V  K  D  G  E  T  L  N  -

1261 GATGAATTAGAAATTATTGAAGGCATGAAGTTTGATCGTGGCTATATTTCTGCGTCTCAA 1320
     CTACTTAATCTTTAATAACTTCCGTACTTCAAACTAGCACCGATATAAAGACGCAGAGTT
      D  E  L  E  I  I  E  G  M  K  F  D  R  G  Y  I  S  A  S  Q  -

1321 AAACGTGCGGCATACGATCAGTATGGTCATGCTGCGTTTGAGTGATCATAGAAGCTT    1377
     TTTGCACGCCGTATGCTAGTCATACCAGTACGACGCAAACTCACTAGTATCTTCGAA
      K  R  A  A  Y  D  Q  Y  G  H  A  A  F  E  *  S  *  K  L  -
```

Fig. 57 (cont.)

```
1   GAATTCGCTAGCGGTGCTCGTGGTTTCCCAGGAACCCCAGGTCTTCCGGGTGTCAAAGGT   60
    ------------+------------+------------+------------+------------+------------+
    CTTAAGCGATCGCCACGAGCACCAAAGGGTCCTTGGGGTCCAGAAGGCCCACAGTTTCCA

E  F  A  S  G  A  R  G  F  P  G  T  P  G  L  P  G  V  K  G  -

61  CACCGTGGTTATCCGGGCCTGGACGGTGCTGGTCAGACGGGTAAACCAGGTATTGCTGGC  120
    ------------+------------+------------+------------+------------+------------+
    GTGGCACCAATAGGCCCGGACCTGCCACGACCAGTCTGCCCATTTGGTCCATAACGACCG

H  R  G  Y  P  G  L  D  G  A  G  Q  T  G  K  P  G  I  A  G  -

121 TTCAAAGGTGAACAAGGCCCCAAAGGAGAACCGGGCCCAGCAGGTGAAGAAGGCAAGCGT  180
    ------------+------------+------------+------------+------------+------------+
    AAGTTTCCACTTGTTCCGGGGCTTTCCCTCTTGGCCCGGGTCGTCCACTTCTTCCGTTCGCA

F  K  G  E  Q  G  P  K  G  E  P  G  P  A  G  E  E  G  K  R  -

181 GGTGCCCGTGGAGAGCCGGGTGGCGTTGGGCCGATCAGATCCGCCACTGAAGGGCGCGTG  240
    ------------+------------+------------+------------+------------+------------+
    CCACGGGCACCTCTCGGCCCACCGCAACCCGGCTAGTCTAGGCGGTGACTTCCCGCGCAC

G  A  R  G  E  P  G  G  V  G  P  I  R  S  A  T  E  G  R  V  -

241 CGTGTCAACAGCGCCTATCAGGACAAGGCGTCTGGAGAAGTTCTGGAGACCACTGCCCCA  300
    ------------+------------+------------+------------+------------+------------+
    GCACAGTTGTCGCGGATAGTCCTGTTCCGCAGACCTCTTCAAGACCTCTGGTGACGGGGT

R  V  N  S  A  Y  Q  D  K  A  S  G  E  V  L  E  T  T  A  P  -

301 GGAGTAGAGGACATCAGCGGGCTTCCGTCTGGAGAAGTTCTGGAGACCGCTGCCCCAGGA  360
    ------------+------------+------------+------------+------------+------------+
    CCTCATCTCCTGTAGTCGCCCGAAGGCAGACCTCTTCAAGACCTCTGGCGACGGGGTCCT

G  V  E  D  I  S  G  L  P  S  G  E  V  L  E  T  A  A  P  G  -

361 GTAGAGGACATCAGCGGGCTTCCGTCTGGAGCCGGCTGGCTGGCTGACCAGACTGTCCGT  420
    ------------+------------+------------+------------+------------+------------+
    CATCTCCTGTAGTCGCCCGAAGGCAGACCTCGGCCGACCGACCGACTGGTCTGACAGGCA

V  E  D  I  S  G  L  P  S  G  A  G  W  L  A  D  Q  T  V  R  -

421 TACCCGATCAGCGCCGGCTGGCTGGCCGACCGCAGCGTGCGCTACCCGATCTCTTCTAGT  480
    ------------+------------+------------+------------+------------+------------+
    ATGGGCTAGTCGCGGCCGACCGACCGGCTGGCGTCGCACGCGATGGGCTAGAGAAGATCA

Y  P  I  S  A  G  W  L  A  D  R  S  V  R  Y  P  I  S  S  S  -

481 AACTTTGGGTCTCAACGCTTTTCTAAGATAGCCTCCAACACCCAGAGCCGCCGGGCATC   540
    ------------+------------+------------+------------+------------+------------+
    TTGAAACCCAGAGTTGCGAAAAGATTCTATCGGAGGTTGTGGGTCTCGGCGGCCCGTAG

```
     CCGACCTTCGGGCGTAGCTTCACTCTGGCTTCTTCTGAGACTGGTGTTGGAGCGCAGTGG
541  ------------+------------+------------+------------+------------+------------+ 600
     GGCTGGAAGCCCGCATCGAAGTGAGACCGAAGAAGACTCTGACCACAACCTCGCGTCACC

P  T  F  G  R  S  F  T  L  A  S  S  E  T  G  V  G  A  Q  W  -

GTAGGATACGACGACCAGGAAAGCGTCAAAAGCAAGGTGCAGTACGTCGAGTAGAAGCTT
601  ------------+------------+------------+------------+------------+------------+ 660
     CATCCTATGCTGCTGGTCCTTTCGCAGTTTTCGTTCCACGTCATGCAGCTGATCTTCGAA

```
  1 GAATTCGCTAGCGGTGCTCGTGGTTTCCCAGGAACCCCAGGTCTTCCGGGTGTCAAAGGT 60
    CTTAAGCGATCGCCACGAGCACCAAAGGGTCCTTGGGGTCCAGAAGGCCCACAGTTTCCA

E  F  A  S  G  A  R  G  F  P  G  T  P  G  L  P  G  V  K  G  -

61 CACCGTGGTTATCCGGGCCTGGACGGTGCTGGTCAGACGGGTAAACCAGGTATTGCTGGC 120
    GTGGCACCAATAGGCCCGGACCTGCCACGACCAGTCTGCCCATTTGGTCCATAACGACCG

H  R  G  Y  P  G  L  D  G  A  G  Q  T  G  K  P  G  I  A  G  -

121 TTCAAAGGTGAACAAGGCCCGAAGGGAGAACCCGGCCCAGCAGGTGAAGAAGGCAAGCGT 180
    AAGTTTCCACTTGTTCCGGGCTTCCCTCTTGGGCCGGGTCGTCCACTTCTTCCGTTCGCA

F  K  G  E  Q  G  P  K  G  E  P  G  P  A  G  E  E  G  K  R  -

181 GGTGCCCGTGGAGAGCCGGGTGGCGTTGGGCCGATCAGATCCGCCACTGAAGGGCGCGTG 240
    CCACGGGCACCTCTCGGCCCACCGCAACCCGGCTAGTCTAGGCGGTGACTTCCCGCGCAC

G  A  R  G  E  P  G  G  V  G  P  I  R  S  A  T  E  G  R  V  -

241 CGTGTCAACAGCGCCTATCAGGACAAGGCGTCTGGAGAAGTTCTGGAGACCACTGCCCCA 300
    GCACAGTTGTCGCGGATAGTCCTGTTCCGCAGACCTCTTCAAGACCTCTGGTGACGGGGT

R  V  N  S  A  Y  Q  D  K  A  S  G  E  V  L  E  T  T  A  P  -

301 GGAGTAGAGGACATCAGCGGGCTTCCGTCTGGAGAAGTTCTGGAGACCGCTGCCCCAGGA 360
    CCTCATCTCCTGTAGTCGCCCGAAGGCAGACCTCTTCAAGACCTCTGGCGACGGGGTCCT

G  V  E  D  I  S  G  L  P  S  G  E  V  L  E  T  A  A  P  G  -

361 GTAGAGGACATCAGCGGGCTTCCGTCTGGAGCCGGCTGGCTGGCTGACCAGACTGTCCGT 420
    CATCTCCTGTAGTCGCCCGAAGGCAGACCTCGGCCGACCGACCGACTGGTCTGACAGGCA

V  E  D  I  S  G  L  P  S  G  A  G  W  L  A  D  Q  T  V  R  -

421 TACCCGATCAGCGCCGGCTGGCTGGCCGACCGCAGCGTGCGCTACCCGATCTCTTCTAGT 480
    ATGGGCTAGTCGCGGCCGACCGACCGGCTGGCGTCGCACGCGATGGGCTAGAGAAGATCA

```
      AACTTTGGGTCTCAACGCTTTTCTAAGATAGCCTCCAACACCCAGAGCCGCGCGGGCATC
481   ------------------------------------------------------------  540
      TTGAAACCCAGAGTTGCGAAAAGATTCTATCGGAGGTTGTGGGTCTCGGCGCGCCCCGTAG

N  F  G  S  Q  R  F  S  K  I  A  S  N  T  Q  S  R  A  G  I  -

CCGACCTTCGGGCGTAGCTTCACTCTGGCTTCTTCTGAGACTGGTGTTGGAGCGCAGTGG
541   ------------------------------------------------------------  600
      GGCTGGAAGCCCGCATCGAAGTGAGACCGAAGAAGACTCTGACCACAACCTCGCGTCACC

P  T  F  G  R  S  F  T  L  A  S  S  E  T  G  V  G  A  Q  W  -

GTAGGATACGACGACCACGAAAGCGTCAAAAGCAAGGTGCAGTACGTCGAGGCTCACCGT
601   ------------------------------------------------------------  660
      CATCCTATGCTGCTGGTGCTTTCGCAGTTTTCGTTCCACGTCATGCAGCTCCGAGTGGCA

V  G  Y  D  D  Q  E  S  V  K  S  K  V  Q  Y  V  E  A  H  R  -

AAGCCGTTGGTCATAATCGCTGAAGATGTTGATGGAGAAGCTCTGAGCACACTGGTCTTG
661   ------------------------------------------------------------  720
      TTCGGCAACCAGTATTAGCGACTTCTACAACTACCTCTTCGAGACTCGTGTGACCAGAAC

K  P  L  V  I  I  A  E  D  V  D  G  E  A  L  S  T  L  V  L  -

AATCGTCTTAAGGTTGGTCTTCAGGTTGTGGCAGTCAAGGCTCCAGGGTTTGGTGACAAT
721   ------------------------------------------------------------  780
      TTAGCAGAATTCCAACCAGAAGTCCAACACCGTCAGTTCCGAGGTCCCAAACCACTGTTA

N  R  L  K  V  G  L  Q  V  V  A  V  K  A  P  G  F  G  D  N  -

GCGATGGCCAAGACAATTGCGTACGACGAAGAGGCCCGTCGCGGCCTCGGATCATAGAAG
781   ------------------------------------------------------------  840
      CGCTACCGGTTCTGTTAACGCATGCTGCTTCTCCGGGCAGCGCCGGAGCCTAGTATCTTC

A  M  A  K  T  I  A  Y  D  E  E  A  R  R  G  L  G  S  *  K  -

CTT
841   ---  843
      GAA

… # SYNTHETIC HUMAN GENES AND POLYPEPTIDES AND THEIR USE IN THE TREATMENT OF AUTOIMMUNE DISEASES

FIELD OF THE INVENTION

The present invention relates to synthetic human genes and polypeptides expressed thereby useful for the treatment of autoimmune diseases, as well as for diagnostic purposes.

ABBREVIATIONS

CNS: central nervous system; EAE: experimental autoimmune encephalomyelitis; EcoDNAJ: *Escherichia coli* DNAJ protein; Gad65: 65 kDa glutamic acid decarboxylase Gad67: 67 kDa glutamic acid decarboxylase; HCgP-39: human chondrocyte glycoprotein 69; Hsp60: human 60 kDa heat shock protein; hsp65: *Mycobacterium tuberculosis* 65 kDa heat shock protein; IA-2: tyrosine phosphatase islet antigen 2; ICA69: islet cell antigen p69; IDDM: insulin-dependent diabetes mellitus; IEC: immunogenic epitopic cluster; MAG: myelin-associated glycoprotein; MBP: myelin basic protein; MOBP: myelin-oligodendrocytic basic protein; MOG: myelin oligodendrocyte glycoprotein; MS: multiple sclerosis; OSP: oligodendrocyte-specific protein; PBL: peripheral blood lymphocytes; PLP: proteolipid protein; PNS: peripheral nervous system; PPI: preproinsulin; RA: rheumatoid arthritis; shMultiPEP: synthetic human multitarget autoantigen polypeptide; shMultiPEPG/DM: synthetic human multitarget autoantigen polypeptide related to IDDM; shMultiPEP/MS: synthetic human multitarget autoantigen polypeptide related to MS; shMultiPEP/RA: synthetic human multitarget autoantigen polypeptide related to RA; shMultiTAG: synthetic human multitarget autoantigen gene; shMultiTAG/DM: synthetic human multitarget autoantigen gene related to IDDM; shMultiTAG/MS: synthetic human multitarget autoantigen gene related to MS; shMultiTAG/RA: synthetic human multitarget autoantigen gene related to RA; shPEP: synthetic human target autoantigen polypeptide; shPEP/DM: synthetic human target autoantigen polypeptide related to IDDM; shPEP/MS: synthetic human target autoantigen polypeptide related to MS; shPEP/RA: synthetic human target autoantigen polypeptide related to RA; shTAG: synthetic human target autoantigen gene; shTAG/DM: synthetic human target autoantigen gene related to IDDM; shTAG/MS: synthetic human target autoantigen gene related to MS; shTAG/RA: synthetic human target autoantigen gene related to RA.

BACKGROUND TO THE INVENTION

Autoimmune diseases result from the immune system's failure to maintain self-tolerance to antigen(s) in the affected organ. Over 40 systemic and organ-specific autoimmune diseases have been observed. Among the organ-specific autoimmune diseases are multiple sclerosis, myasthenia gravis, thyroiditis, insulin-dependent diabetes mellitus, rheumatoid arthritis and others. In spite of major and significant advances in molecular and cellular immunology in the last two decades, the molecular basis for self-tolerance and the mechanisms regulating it are still a major challenge in immunology, and autoimmune diseases remain a major medical problem. The immune-specific approaches to therapy of the disease, expected to be the most effective, have not yet yielded an effective therapy for any of the autoimmune diseases.

Accordingly, many other approaches have been investigated, some of which resulted in a limited success in decreasing the progression of the disease, such as the use of β-interferon and Copolymer 1 for treatment of multiple sclerosis, yet none of them cure the disease. Apparently, the major difficulty in devising immune specific approaches to therapy lies in the complexity of the autoimmune diseases, particularly with regard to the multiplicity of target antigens and because of the possibility that the primary target antigen(s) may be different in different patients, the difficulty in determining which of the possible target antigens is the primary target antigen for each patient, and against which of the possible epitopes on that protein the pathogenic autoimmune response is primarily directed. This is further complicated by the likely "spread of autoimmunity" as disease develops.

By way of example, multiple sclerosis (MS), an inflammatory disease of the central nervous system (CNS) characterized by primary demyelination, is believed to result from an autoimmune reactivity to myelin components. Extensive efforts were made by many laboratories to define the primary target myelin antigen(s) towards which the deleterious autoimmune response is directed. Myelin basic protein (MBP) and proteolipid protein (PLP), the major proteins of CNS myelin, have long been regarded as the primary candidate target antigens in MS, particularly in view of their abundancy and their ability to induce experimental autoimmune encephalomyelitis (EAE), a well-accepted animal model for MS. Activated CD4+ T cells specific for MBP or PLP are sufficient to cause EAE upon their transfer into naive syngeneic recipients, and potentially pathogenic T cells reactive against MBP or PLP have been demonstrated in MS (reviewed in Tuohy, 1994); however, comparable T cell responses to MBP or PLP were also detected in healthy individuals (reviewed in Tuohy, 1994). Thus, although specific responses to these myelin antigens are likely to be of importance in the course of the disease, they may not represent the primordial pathogenic response in MS. Consequently, in the search for antigenic specificities associated with MS, other myelin-specific, and also more recently non myelin-specific CNS antigens, have been investigated for their encephalitogenicity and/or for the presence of autoreactivity to these antigens in MS. Thus, low levels of T cell response to myelin-associated glycoprotein (MAG) and S100b, found in CNS and PNS tissues, have been observed both in MS patients and control individuals and reactivity to non nervous system-specific antigens such as heat shock proteins, transaldolase, and, to a lesser extent, 2',3'-cyclic nucleotide 3'-phosphodiesterase, has been reported in MS (reviewed in Kerlero de Rosbo and Ben-Nun, 1998). However, none of these antigens have so far been demonstrated to be encephalitogenic, albeit T cells specific for MAG and S100b can cause CNS and PNS inflammation upon passive transfer into syngeneic mice with no clinical manifestations.

In view of the restricted localization of MS lesions to the CNS white matter, it is more likely that a primary target antigen in MS is CNS myelin-specific. Myelin proteins such as myelin oligodendrocyte glycoprotein (MOG), myelin-oligodendrocyte-specific protein, myelin-oligodendrocytic basic protein (MOBP) and oligodendrocyte-specific protein (OSP) are believed to be specific components of CNS myelin (Gardiner et al., 1992; Yamamoto et al., 1994; Bronstein et al., 1997). Our studies on the reactivity to MOG by PBL (peripheral blood lymphocytes) from patients with MS in the context of their reactivity to MBP, PLP and MAG have shown that a high proportion (50%) of MS patients react predominantly to MOG (Kerlero de Rosbo et al., 1997). Most importantly, reactivity to MOG by PBL from control individuals occurs far less frequently (Kerlero de Rosbo et al., 1997). These data, together with the demonstration of the encephalitogenic potential of MOG, strongly suggest that autoimmune reactivity to this CNS myelin-specific antigen plays an important role in the pathogenesis of MS.

Another important point emerged from our investigation of the reactivity by MS PBL to the different myelin antigens, MBP, PLP, MAG and MOG, concomitantly: 40% of the MS patients tested showed no reactivity to any of these myelin antigens. Among the several explanations which could account for this observation, one likely possibility is the involvement of autoimmune reactivity to myelin-specific antigen(s) other than MBP, PLP or MOG. In this context, we have studied the autoreactivity to MOBP, a recently uncovered CNS myelin-specific protein, which is apparently relatively abundant in CNS myelin. Our data yielded from two separate studies of the proliferative response to MOBP by PBL from MS patients and controls indicated that, out of the twenty-two patients tested overall, eleven reacted to one or several MOBP peptides whilst only four out of twenty controls tested overall reacted [Kaye et al., 2000]. The demonstration by us and another laboratory that MOBP is also encephalitogenic provides unequivocal evidence that the autoimmune reactivity observed in MS patients is potentially pathogenic and may play an important role in the pathogenesis of MS. We (Zhong et al., 2000) and another laboratory (Stevens et al., 1999) also recently demonstrated the strong encephalitogenic activity of another CNS myelin-specific protein, OSP, indicating that OSP may also be a potential target antigen for autoimmune demyelinating diseases such as MS.

A potential primary target antigen in MS could be defined as a CNS antigen which has an encephalitogenic potential, i.e. can cause EAE, and against which autoimmune reactivity can be detected in MS patients. In this context, MBP, PLP, MOG and now also MOBP can be considered potential primary target antigens, as autoreactivity against one of these antigens may play an important role in the initiation/progression of MS. In view of its high encephalitogenicity, the potential role of autoimmune responses to OSP in the pathogenesis of MS should also be considered. In contrast, autoimmune responses to other nonencephalitogenic CNS components, myelin-specific or non myelin-specific, which can be detected in MS, are more likely to represent secondary events resulting from "autoimmune spread" as a result of inflammation within CNS with ongoing disease. The multiplicity of potential primary target antigens in MS points to the complexity of the disease with regard to possible pathogenic processes involved, possible etiology of the disease, and most importantly, it imposes major difficulties in devising immune-specific therapeutic approaches to MS.

Thus, the major problems that must be addressed by immune-specific therapies for a given autoimmune disease include the multiplicity of potential primary target antigens with the possibility that the primary target antigens differ in different patients, and the recently acknowledged "spreading of autoimmunity" as disease develops. This phenomenon is described as the observation of variation in the active immunogenic epitopes with the progression of the disease. This results in the evolution of the primary T cell response focused on a particular self-antigen, towards the recruitment of T cells to multiple antigenic determinants on this or other potential target autoantigens within the affected organ (Tuohy et al., 1998; Kumar, 1998).

The present invention addresses these problems as a whole, allowing immune-specific modulation of multiple sclerosis and other autoimmune diseases, irrespective of the antigenic primacy of the autoimmune response.

SUMMARY OF THE INVENTION

In a first aspect, the present invention relates to a synthetic human target autoantigen gene that comprises sequences coding for at least two immunogenic epitopic clusters (hereinafter IEC) of autoantigen(s) related to a specific autoimmune disease, said synthetic gene being selected from:

(i) a synthetic human target autoantigen gene (hereinafter shTAG) comprising nucleotide sequences coding for at least two IEC of a sole autoantigen related to said autoimmune disease; and (ii) a synthetic human multitarget autoantigen gene (hereinafter shMultiTAG) comprising nucleotide sequences coding for at least one IEC of at least two different autoantigens related to said autoimmune disease.

In this aspect, the invention further includes nucleotide sequences homologous to the synthetic genes to the extent discussed below, provided that the expressed polypeptide retains its immunogenic, and more preferably, its immunomodulatory activity.

A second aspect of the invention relates to a synthetic polypeptide that comprises amino acid sequences of at least two immunogenic epitopic clusters (hereinafter IEC) of autoantigens related to a specific autoimmune disease, said synthetic polypeptide being selected from:

(i) a synthetic human polypeptide (hereinafter shPEP) comprising amino acid sequences of at least two IEC of a sole autoantigen related to said autoimmune disease; and (ii) a synthetic human multitarget polypeptide (hereinafter shMultiPEP) comprising amino acid sequences of at least one IEC of at least two different autoantigens related to said autoimmune disease, and analogs, variants, mimetics and derivatives of said polypeptides of (i) or (ii), provided that they retain the immunogenic and, more preferably, the immunomodulatory activity of the parent polypeptide.

In a third aspect, the present invention relates to pharmaceutical compositions comprising at least one of said synthetic genes or at least one of said polypeptides, for the treatment of autoimmune diseases, in particular, multiple sclerosis (MS), insulin-dependent diabetes mellitus (IDDM), rheumatoid arthritis (RA), myasthenia gravis (MG) or uveitis. In this aspect, the invention further relates to a mixture of at least two synthetic peptides, each comprising at least one IEC of a sole autoantigen or at least one IEC of at least two different autoantigens, the immune response against which is implicated in a specific autoimmune disease.

In a fourth aspect, the present invention relates to diagnostic compositions comprising at least one of said synthetic genes or at least one of said polypeptides, for the diagnosis and/or monitoring of the progression of an autoimmune disease.

BRIEF DESCRIPTION OF THE DRAWINGS

FIG. 3 depicts the DNA sequence (SEQ ID NO:1) of the shMOG/E gene and the amino acid sequence (SEQ ID NO:2) of the polypeptide encoded thereby.

FIG. 6 depicts the DNA sequence (SEQ ID NO:7) of the shMBP/E gene and the amino acid sequence (SEQ ID NO:8) of the polypeptide encoded thereby.

FIG. 8 depicts the DNA sequence (SEQ ID NO:14) of the shPLP/E gene and the amino acid sequence (SEQ ID NO:15) of the polypeptide encoded thereby.

FIG. 10 depicts the DNA sequence (SEQ ID NO:20) of the shMOBP/E gene and the amino acid (SEQ ID NO:21) sequence of the polypeptide encoded thereby.

FIG. 12 depicts the DNA sequence (SEQ ID NO:26) of the Y-MSPa gene and the amino acid sequence (SEQ ID NO:27) of the polypeptide encoded thereby.

FIG. 13 are Coomassie Blue-stained SDS-PAGE pictures showing bacterial expression and purified polypeptide products expressed by the Y-MSPa (left) and Y-MSPb (right) genes.

FIG. 15 depicts the DNA sequence (SEQ ID NO:28) of the Y-MSPb gene and the amino acid sequence (SEQ ID NO:29) of the polypeptide encoded thereby.

FIGS. 16A-B show that Y-MSPa can stimulate lines of T-cells specific for synthetic peptides of the sequences PLP 139-151 (FIG. 16A) or MOG 35-55 (FIG. 16B) to the same extent as their specific epitopes.

FIG. 21 depicts the DNA sequence (SEQ ID NO:30) of the shMOG/MS gene and the amino acid (SEQ ID NO:31) sequence of the polypeptide encoded thereby.

FIG. 23 depicts the DNA sequence (SEQ ID NO:36) of the shMBP/MS gene and the amino acid sequence (SEQ ID NO:37) of the polypeptide encoded thereby.

(SEQ ID NO:158) are presented at the top. The arrows below indicate the position and orientation of the oligonucleotides listed, which are used to generate and to amplify the DNA template. The oligonucleotides for template synthesis and PCR amplification are shown below the gene construct as follows: shPLP 1a (nucleotides 1-21 of SEQ ID NO:41), shPLP 1 (nucleotides 1-69 of SEQ ID NO:41), shPLP 2 (3'reverse) (SEQ ID NO:43), shPLP 3 (nucleotides 103-168 of SEQ ID NO:41), shPLP 4 (3'reverse) (SEQ ID NO:44), shPLP 5 (nucleotides 199-267 SEQ ID NO:41), shPLP 6 (3'reverse) (SEQ ID NO:45), shPLP 7 (nucleotides 298-366 of SEQ ID NO:41), shPLP 8 (3'reverse) (SEQ ID NO:46) and shPLP 8a (3'reverse) (SEQ ID NO:47).

FIG. 25 depicts the DNA sequence (SEQ ID NO:41) of the shPLP/MS gene and the amino acid sequence (SEQ ID NO:42) of the polypeptide encoded thereby.

Figure 26:
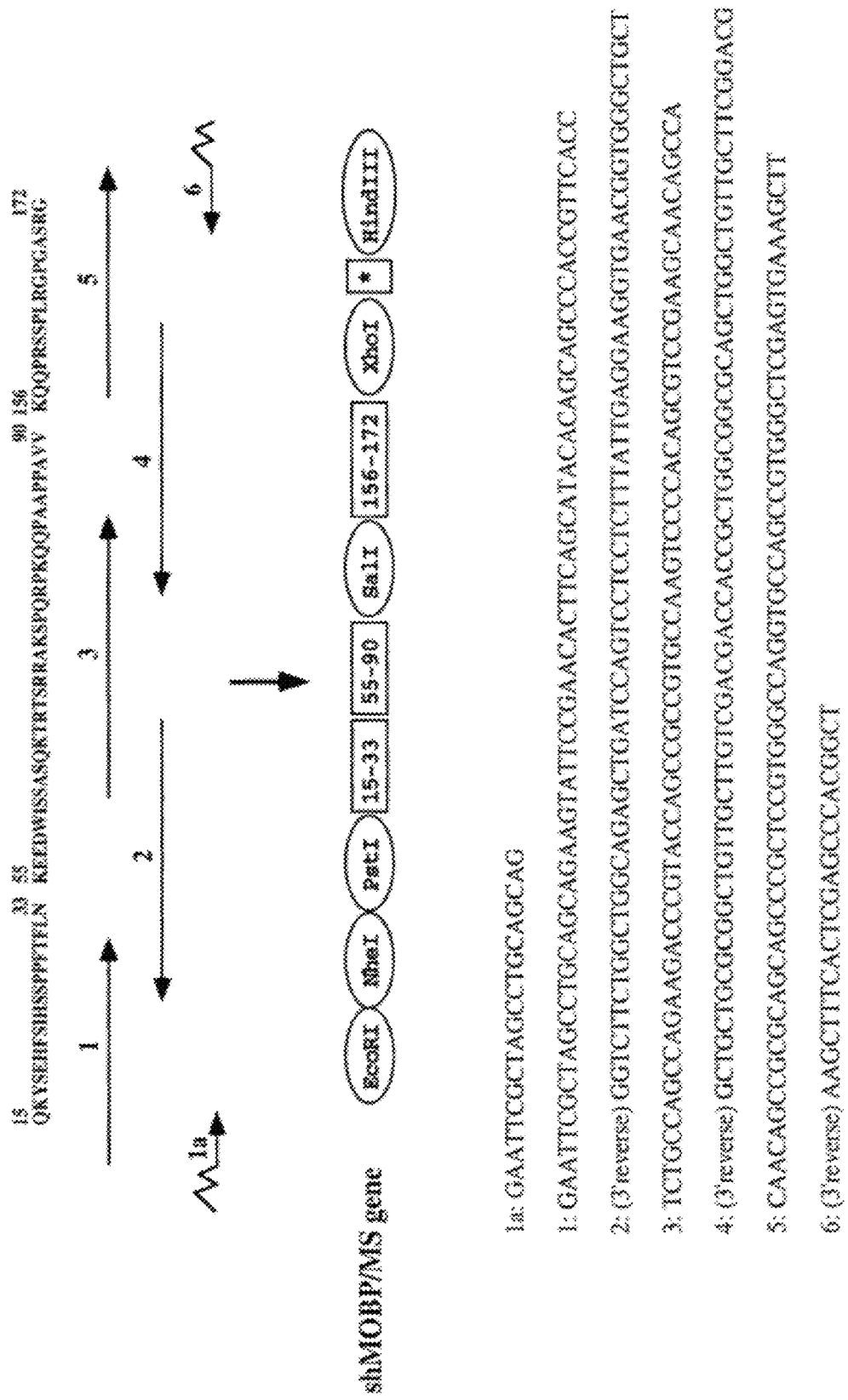

FIG. 26 depicts a scheme for construction of the shTAG/MS herein designated shMOBP/MS gene. The MOBP peptides 15-33 (SEQ ID NO:159), 55-90 (SEQ ID NO:160) and 156-172 (SEQ ID NO:161) are presented at the top. The arrows below indicate the position and orientation of the oligonucleotides listed, which are used to generate and to amplify the DNA template. The oligonucleotides for template synthesis and PCR amplification are shown below the gene construct as follows: shMOBP 1a (nucleotides 1-21 of SEQ ID NO:48), shMOBP 1 (nucleotides 1-66 of SEQ ID NO:48), shMOBP 2 (3'reverse) (SEQ ID NO:50), shMOBP 3 (nucleotides 97-162 of SEQ ID NO:48), shMOBP 4 (3'reverse) (SEQ ID NO:51), shMOBP 5 (nucleotides 193-255 of SEQ ID NO:48) and shMOB 6 (SEQ ID NO:52).

FIG. 27 depicts the DNA sequence (SEQ ID NO:48) of the shMOBP/MS gene and the amino acid sequence (SEQ ID NO:49) of the polypeptide encoded thereby.

Figure 28:
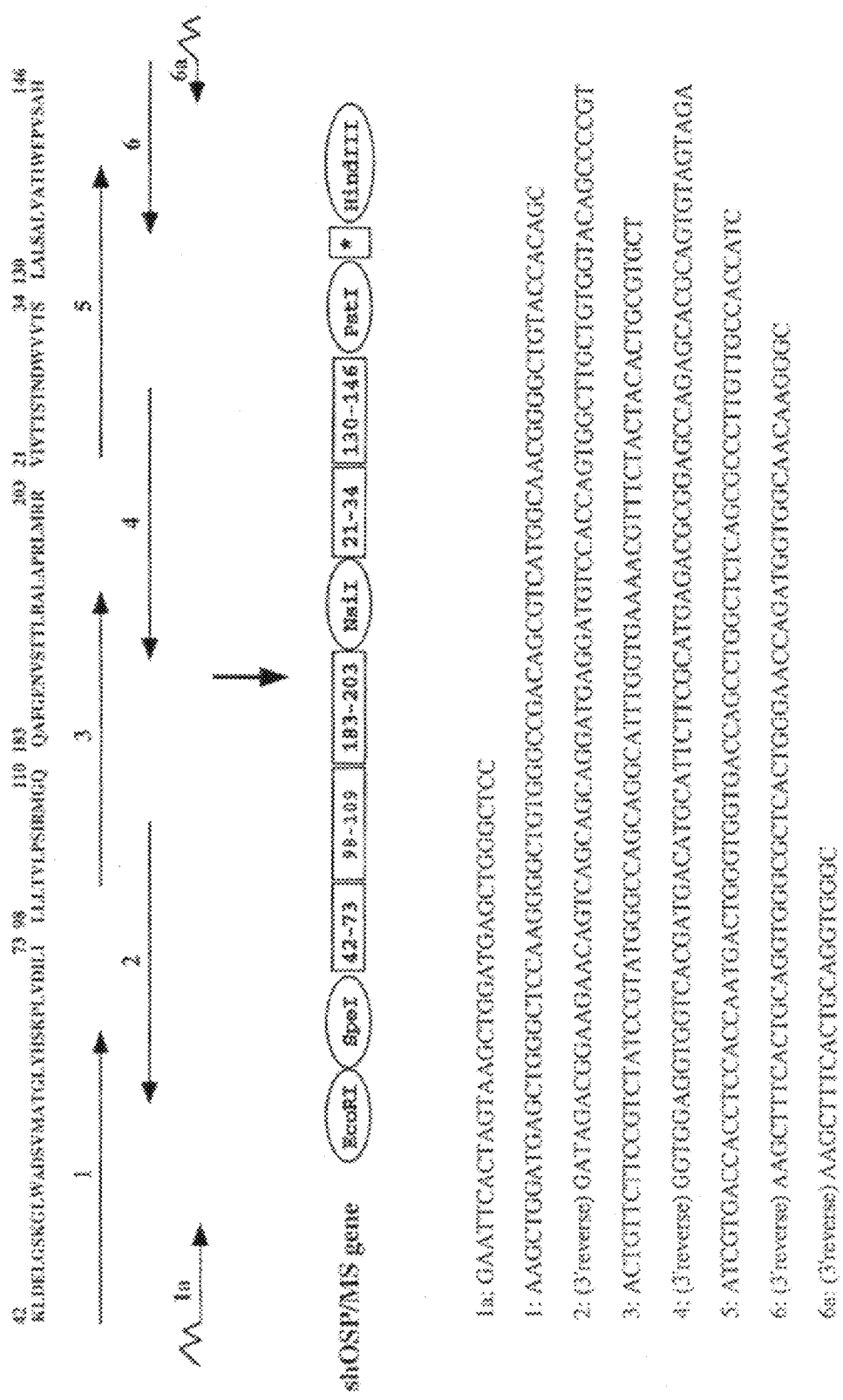

FIG. 28 depicts a scheme for construction of the shTAG/MS herein designated shOSP/MS gene. The OSP peptides 42-73 (SEQ ID NO:162), 98-110 (SEQ ID NO:163), 183-203 (SEQ ID NO:164), 21-34 (SEQ ID NO:165), and 130-146 (SEQ ID NO:166) are presented at the top. The arrows below indicate the position and orientation of the oligonucleotides listed, which are used to generate and to amplify the DNA template. The oligonucleotides for template synthesis and PCR amplification are shown below the gene construct as follows: shOSP 1a (nucleotides 1-33 of SEQ ID NO:53), shOSP 1 (nucleotides 13-81 of SEQ ID NO:53), shOSP 2 (3'reverse) (SEQ ID NO:55), shOSP 3 (nucleotides 115-183 of SEQ ID NO:53), shOSP 4 (3'reverse) (SEQ ID NO:56), shOSP 5 (nucleotides 217-285 of SEQ ID NO:53), shOSP 6 (3'reverse) (SEQ ID NO:57) and shOSP 6a (3'reverse) (SEQ ID NO:58).

FIG. 29 depicts the DNA sequence (SEQ ID NO:53) of the shOSP/MS gene and the amino acid sequence (SEQ ID NO:54) of the polypeptide encoded thereby.

Figure 30:
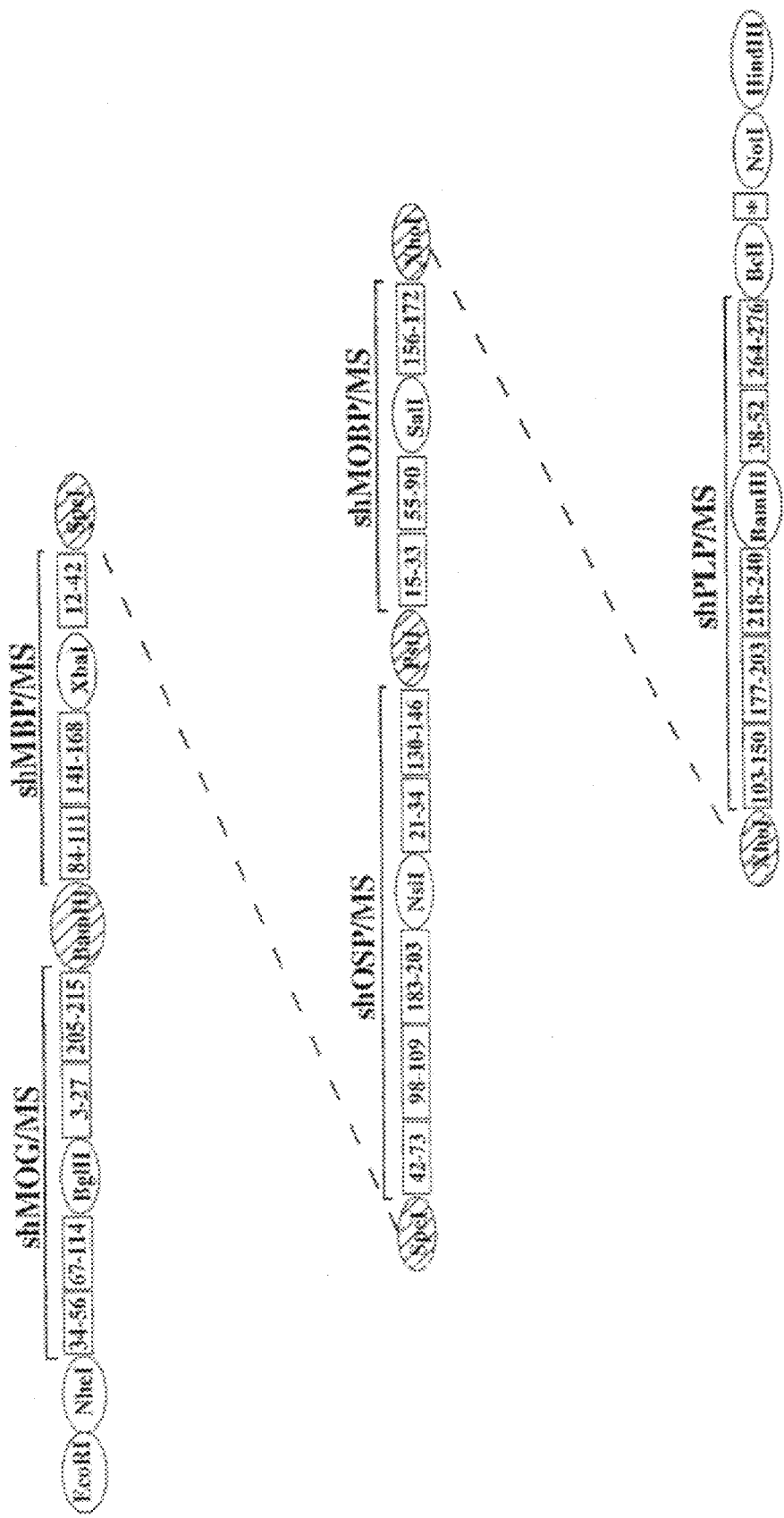

FIG. 30 depicts the construct of the shMultiTAG/MS herein designated Y-MSPc gene containing the shMOG/MS, shMBP/MS, shOSP/MS, shMOBP/MS and shPLP/MS genes.

FIG. 31 depicts the DNA sequence (SEQ ID NO:59) of the Y-MSPc gene and the amino acid sequence (SEQ ID NO:60) of the polypeptide encoded thereby.

Figure 31A:
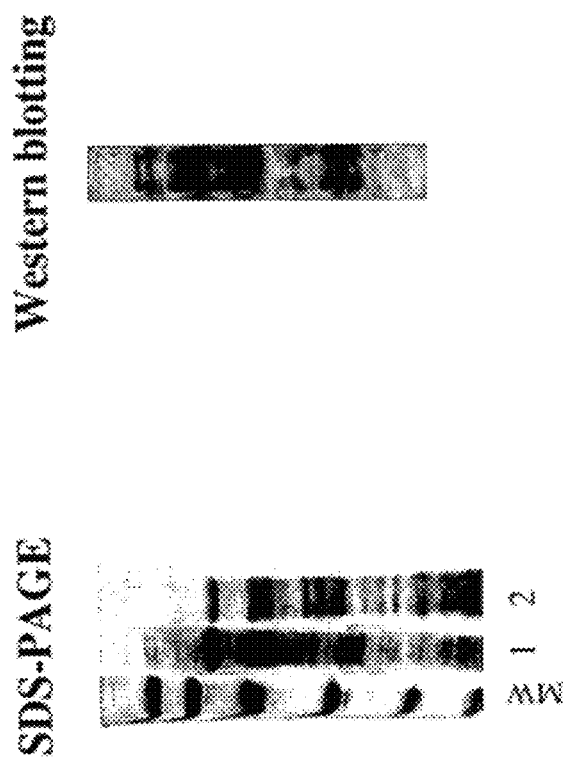

FIG. 31a are pictures of Coomassie Blue-stained SDS-PAGE (left) showing bacterial expression (lane 1) and purified protein product (lane 2) expressed by the Y-MSPc gene, and of Western blotting analysis of the purified protein product with anti-MOG 35-55 antibody.

Figure 31B:
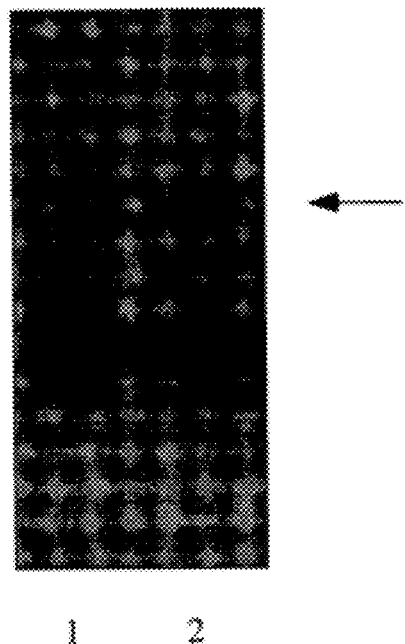

FIG. 31b is a picture of Western blotting analysis showing expression of the pcDNA 3.1/Y-MSPc transfected into mammalian cells. Lane 1, untransfected NIH3T3 mouse fibroblast lysate; lane 2, pcDNA3.1/Y-MSPc-transfected NIH3T3 mouse fibroblast lysate. The arrow indicates the anti-MOG 35-55 antibody-reactive protein band of expected molecular weight in the pcDNA3.1/Y-MSPc-transfected NIH3T3 mouse fibroblast lysate, which is not detectable in the control untransfected NIH3T3 mouse fibroblast lysate.

Figure 32:
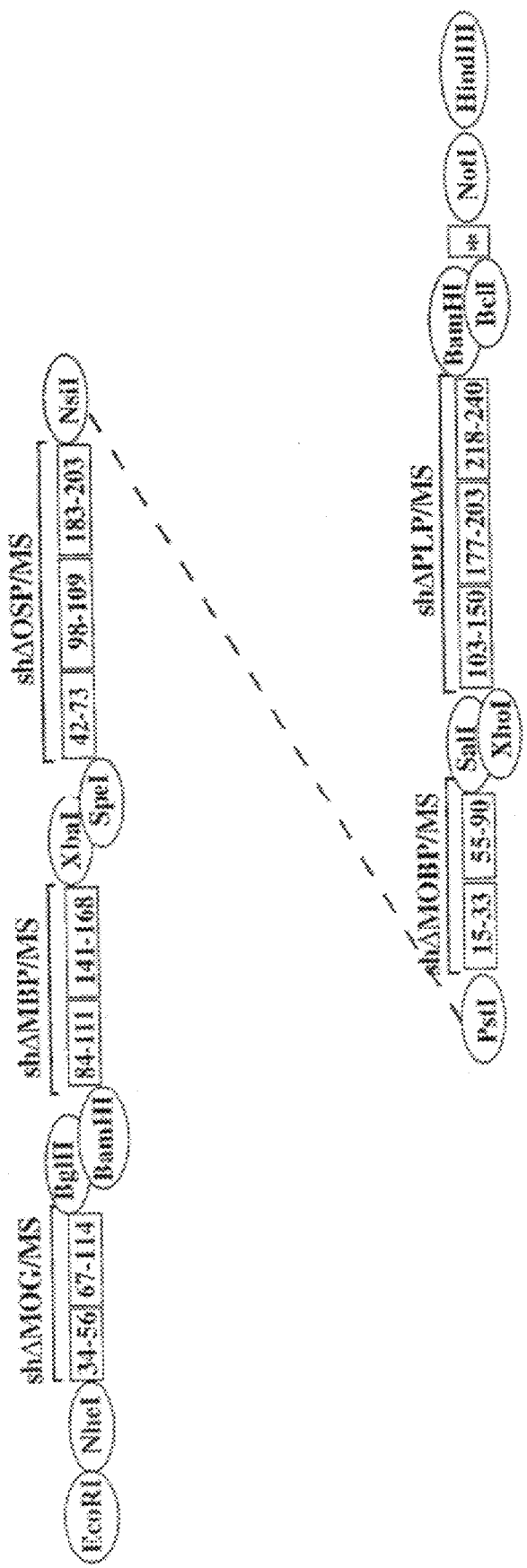

FIG. 32 depicts the construct of the shMultiTAG/MS herein designated Y-MSPd gene containing the truncated shΔMOG/MS, shΔMBP/MS, shΔOSP/MS, shΔMOBP/MS and shΔPLP/MS genes.

FIG. 33 depicts the DNA sequence (SEQ ID NO:61) of the Y-MSPd gene and the amino acid sequence (SEQ ID NO:62) of the polypeptide encoded thereby.

FIG. 33a are pictures of Coomassie Blue-stained SDS-PAGE (left) showing bacterial expression (lane 1) and purified protein product (lane 2) expressed by the Y-MSPd gene, and of Western blotting analysis (right) of the purified protein product with anti-MOG 35-55 antibody.

Figure 34:
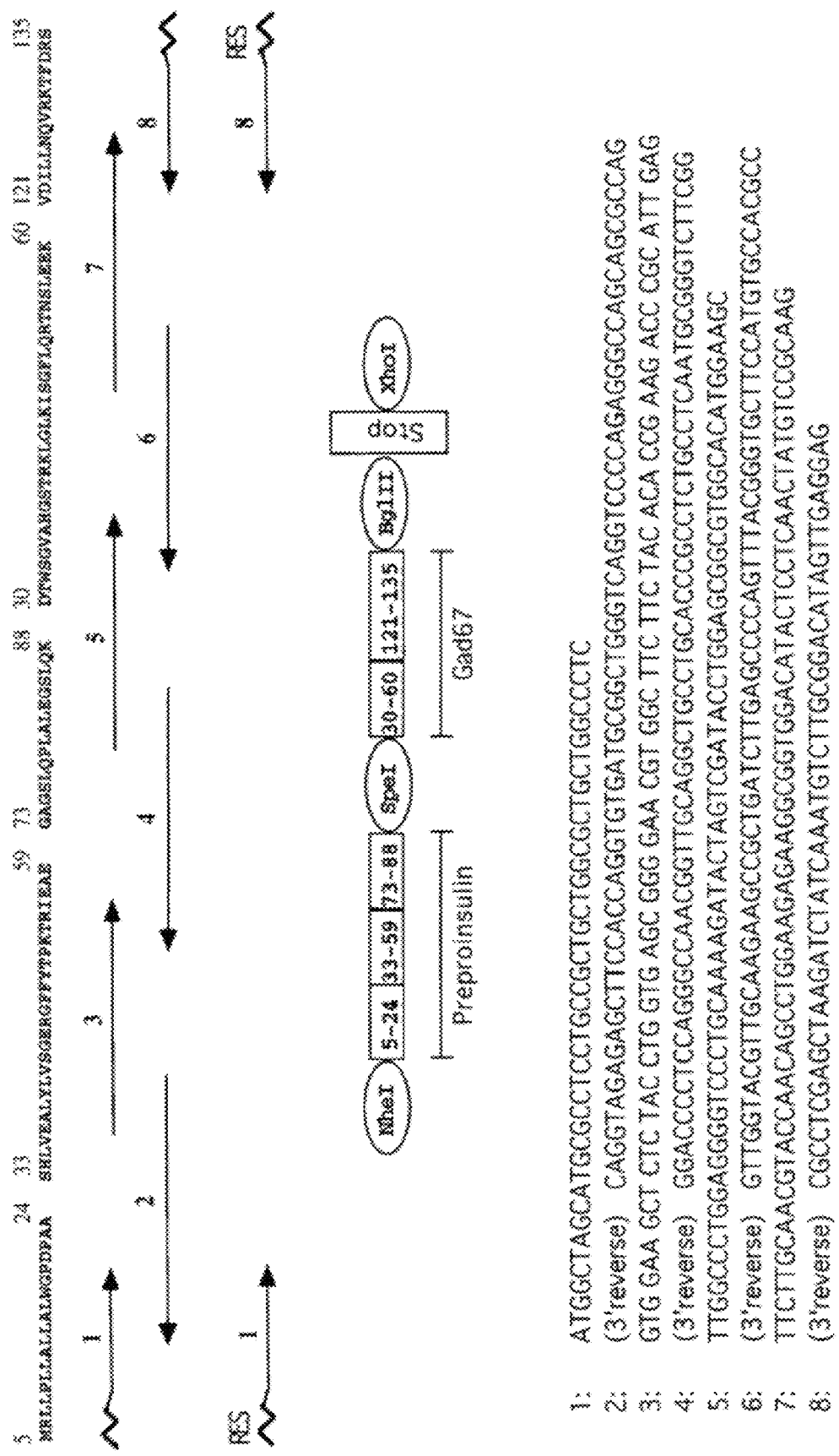

FIG. 34 depicts a scheme for construction of the shMultiTAG/DM (shMultiTAG related to IDDM) herein designated shPPIG/DM gene. The preproinsulin peptides 5-24 (SEQ ID NO:167), 33-59 (SEQ ID NO:168) and 73-88 (SEQ ID NO:169) and the Gad67 peptides 30-60 (SEQ ID NO:170) and 121-135 (SEQ ID NO:171) are presented at the top. The arrows below indicate the position and orientation of the oligonucleotides listed, which are used to generate and to amplify the DNA template. The oligonucleotides for template synthesis and PCR amplification are shown below the gene construct as follows: 1 (nucleotides 1-45 of SEQ ID NO:63), 2 (3'reverse) (SEQ ID NO:65), 3 (nucleotides 76-141 of SEQ ID NO:63), 4 (3'reverse) (SEQ ID NO:66), 5 (nucleotides 172-237 of SEQ ID NO:63), 6 (3'reverse) (SEQ ID NO:67), 7 (nucleotides 268-333 of SEQ ID NO:63) and 8 (3'reverse) (SEQ ID NO:68).

FIG. 35 depicts the DNA sequence (SEQ ID NO:63) of the shPPIG/DM gene and the amino acid sequence (SEQ ID NO:64) of the polypeptide encoded thereby.

Figure 36:
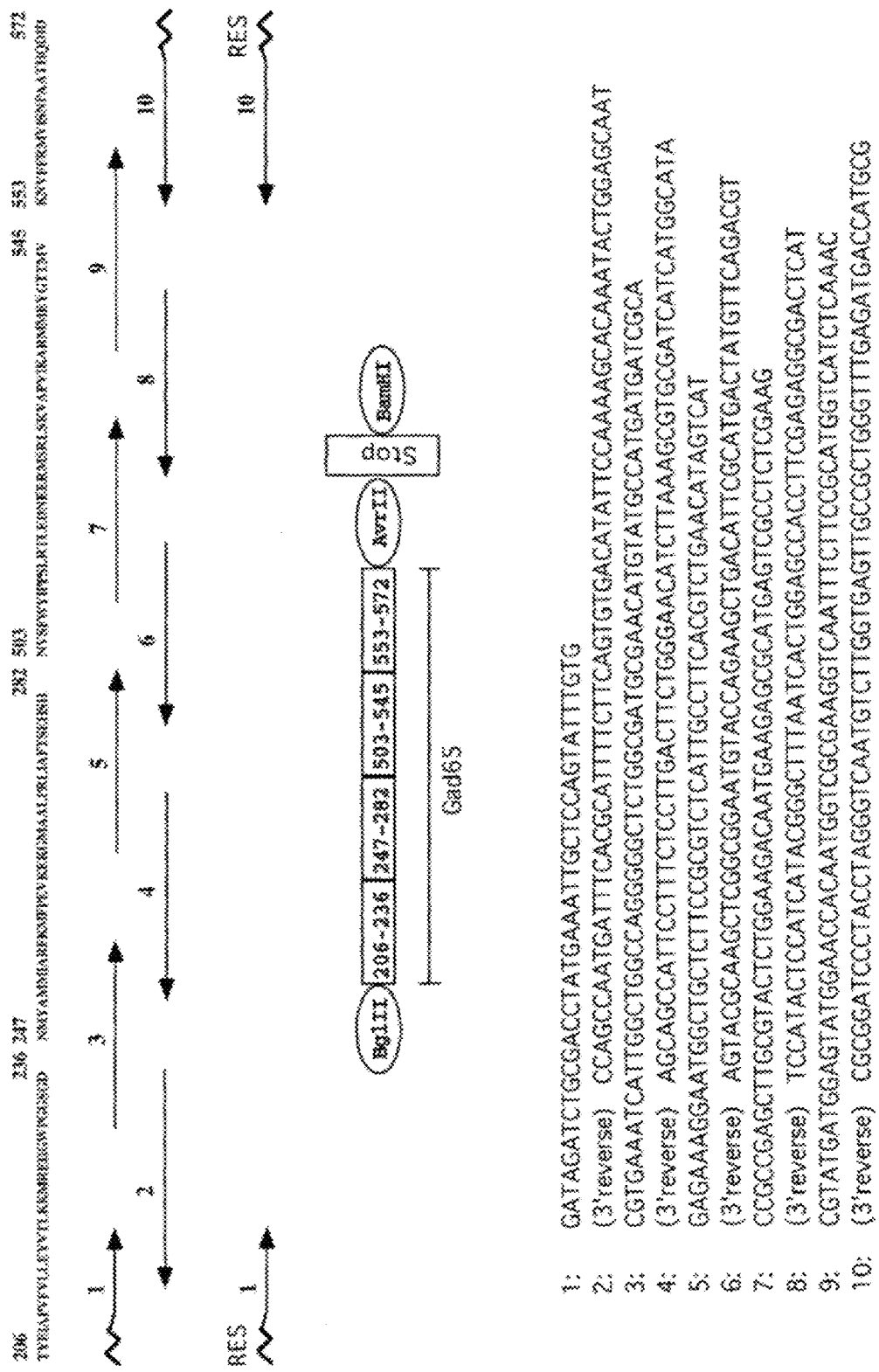

FIG. 36 depicts a scheme for construction of the shTAG/DM herein designated shGad65/DM gene. The shGad65 peptides 206-236 (SEQ ID NO:172), 247-282 (SEQ ID NO:173), 503-545 (SEQ ID NO:174) and 553-572 (SEQ ID NO:175) are presented at the top. The arrows below indicate the position and orientation of the oligonucleotides listed, which are used to generate and to amplify the DNA template. The oligonucleotides for template synthesis and PCR amplification are shown below the gene construct as follows: shGad65 1 (nucleotides 1-39 of SEQ ID NO:69), shGad65 2 (3'reverse) (SEQ ID NO:71), shGad65 3 (nucleotides 70-132 of SEQ ID NO:69), shGad65 4 (3'reverse) (SEQ ID NO:72), shGad65 5 (nucleotides 160-216 of SEQ ID NO:69), shGad65 6 (3'reverse) (SEQ ID NO:73), shGad65 7 (nucleotides 241-297 (SEQ ID NO:69), shGad65 8 (3'reverse) (SEQ ID NO:74), shGad65 9 (nucleotides 319-384 of SEQ ID NO:69) and shGad65 10 (SEQ ID NO:75).

FIG. 37 depicts the DNA sequence (SEQ ID NO:69) of the shGad65/DM gene and the amino acid sequence (SEQ ID NO:70) of the polypeptide encoded thereby.

Figure 38:
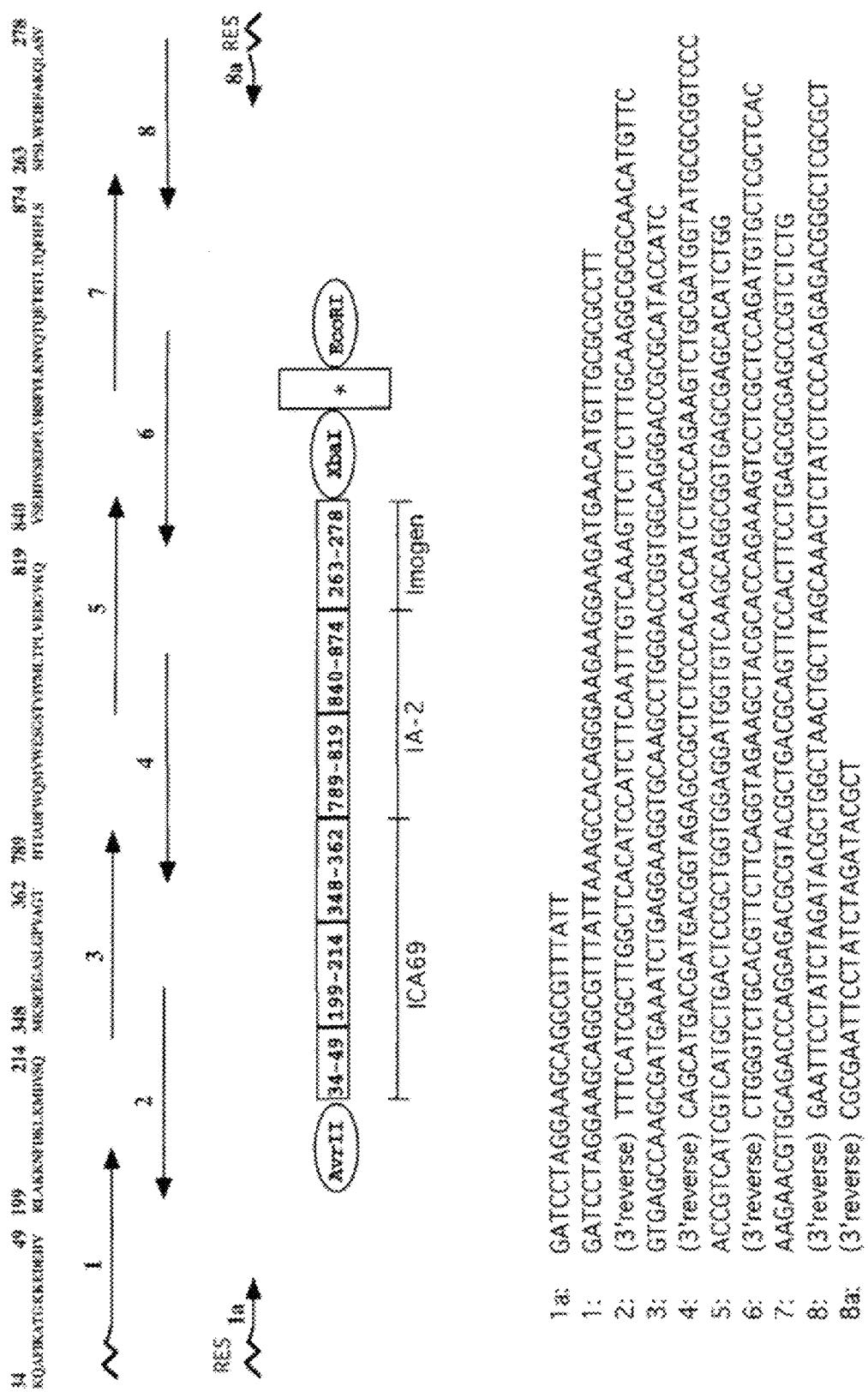

FIG. 38 depicts a scheme for construction of the shMultiTAG/DM herein designated shI3/DM gene. The ICA69 peptides 34-49 (SEQ ID NO:176), 199-214 (SEQ ID NO:177), 348-362 (SEQ ID NO:178), the IA-2 peptides 789-819 (SEQ ID NO:179), 840-874 (SEQ ID NO:180) and imogen peptide 263-278 (SEQ ID NO:181) are presented at the top. The arrows below indicate the position and orientation of the oligonucleotides listed, which are used to generate and to amplify the DNA template. The oligonucleotides for template synthesis and PCR amplification are shown below the gene construct as follows: 1a (nucleotides 1-24 of SEQ ID NO:76), 1 (nucleotides 1-66 of SEQ ID NO:76), 2 (3'reverse) (SEQ ID NO:78), 3 (3'reverse) (nucleotides 100-168 of SEQ ID NO:76), 4 (SEQ ID NO:79), (nucleotides 205-273 of SEQ ID NO:76), 6 (SEQ ID NO:80), 7 (nucleotides 307-375 of SEQ ID NO:76), 8 (3'reverse) (SEQ ID NO:81) and 8a (3'reverse) (SEQ ID NO:82).

FIG. 39 depicts the DNA sequence (SEQ ID NO:76) of the shI3/DM gene and the amino acid sequence (SEQ ID NO:77) of the polypeptide encoded thereby.

Figure 40:
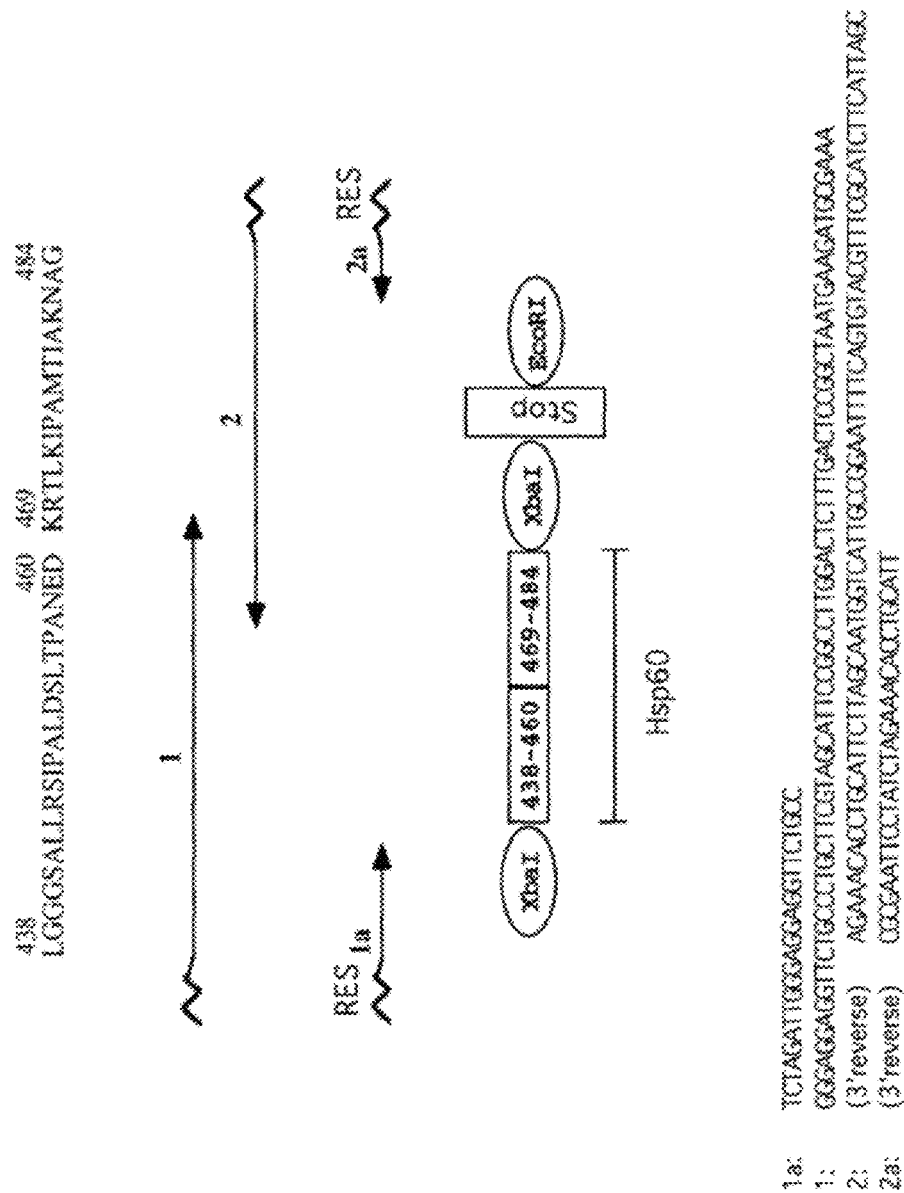

FIG. 40 depicts a scheme for construction of the shTAG/DM herein designated shHSP/DM gene. The shHSP60 peptides 438-460 (SEQ ID NO:182) and 469-484 (SEQ ID NO:183) are presented at the top. The arrows below indicate the position and orientation of the oligonucleotides listed, which are used to generate and to amplify the DNA template. The oligonucleotides for template synthesis and PCR amplification are shown below the gene construct as follows: 1a (nucleotides 1-24 of SEQ ID NO:83), 1 (nucleotides 9-81 of SEQ ID NO:83), 2 (3'reverse) (SEQ ID NO:85) and 2a (3'reverse) (SEQ ID NO:86).

FIG. 41 depicts the DNA sequence (SEQ ID NO:83) of the shHSP/DM gene and the amino acid sequence (SEQ ID NO:84) of the polypeptide encoded thereby.

Figure 42:
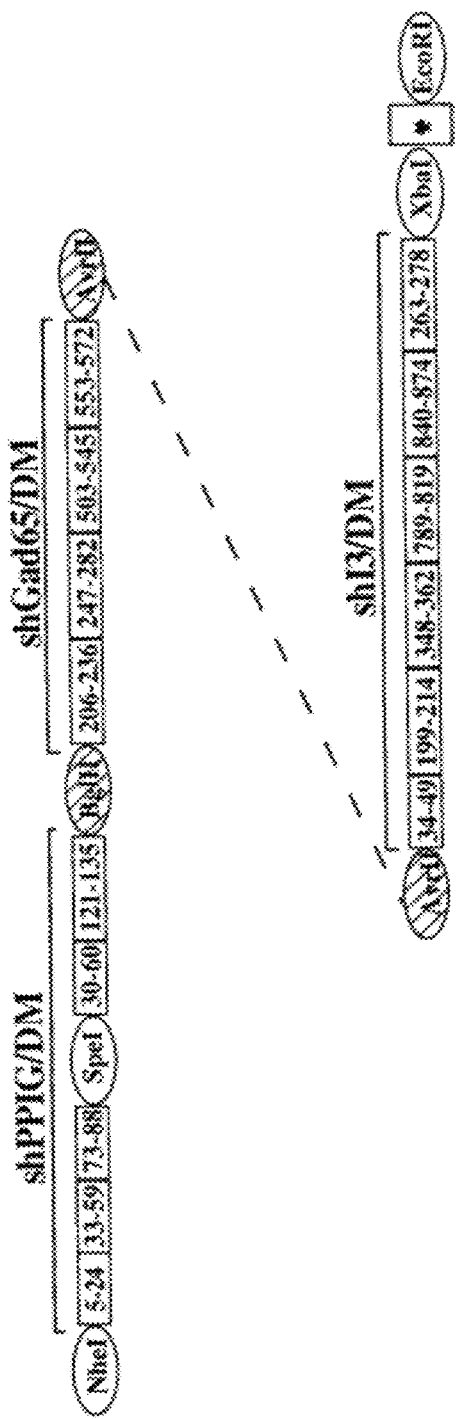

FIG. 42 depicts the construct of the shMultiTAG/DM herein designated Y-DMPa gene containing the shPPIG/DM, shGad65/DM and shI3/DM genes.

Figure 42A:
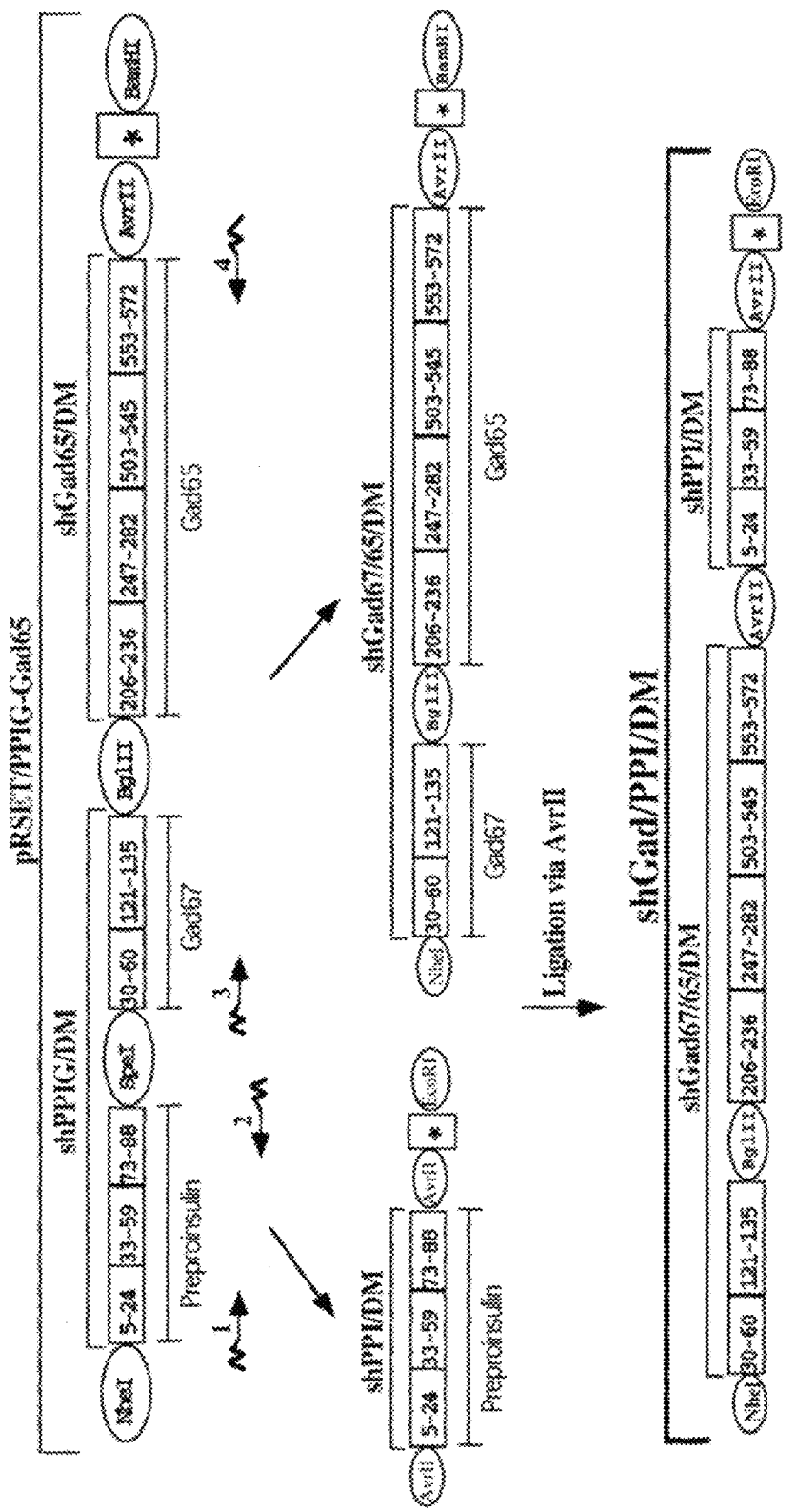

FIG. 42a depicts the scheme for construction of the shMultiTAG/DM herein designated shGad/PPI/DM gene containing the shPPI/DM and the shGad67/65/DM genes that were obtained by PCR from the pRSET/PPIG-Gad65 using the oligonucleotides shown (oligo 1: nucleotides 1-30 of SEQ ID NO:87; oligo 2 (3'reverse): SEQ ID NO:89; oligo 3: nucleotides 1-27 of SEQ ID NO:95; and oligo 4: SEQ ID NOs: 75 and 90), and ligated to form the shGad/PPI/DM gene.

FIG. 42b depicts the DNA sequence (SEQ ID NO:87) of the shPPI/DM gene and the amino acid sequence (SEQ ID NO:88) of the polypeptide encoded thereby.

FIG. 42c depicts the DNA sequence (SEQ ID NO:91) of the shGad67/65/DM gene and the amino acid sequence (SEQ ID NO:92) of the polypeptide encoded thereby.

FIG. 42d depicts the DNA sequence (SEQ ID NO:91) of the shGad/PPI/DM gene and the amino acid sequence (SEQ ID NO:92) of the polypeptide encoded thereby.

Figure 42E:
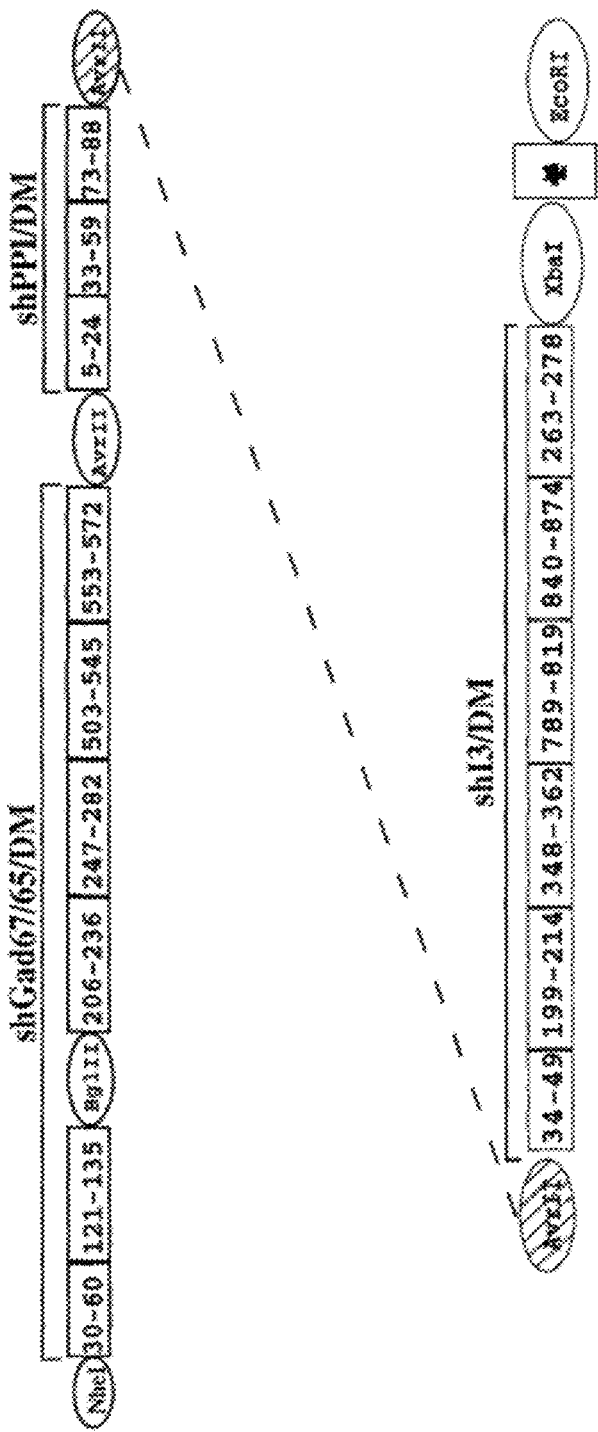

FIG. 42e depicts the construct of another shMultiTAG/DM herein designated Y-DMPc gene containing the shGad67/65/DM, the shPPI/DM and shI3/DM genes.

FIG. 43 depicts the DNA sequence (SEQ ID NO:93) of the Y-DMPa gene and the amino acid sequence (SEQ ID NO:94) of the polypeptide encoded thereby.

FIG. 43a depicts the DNA sequence (SEQ ID NO:95) of the Y-DMPc gene constructed according to the scheme presented in FIG. 42e, and the amino acid sequence (SEQ ID NO:96) of the polypeptide encoded thereby.

Figure 43B:
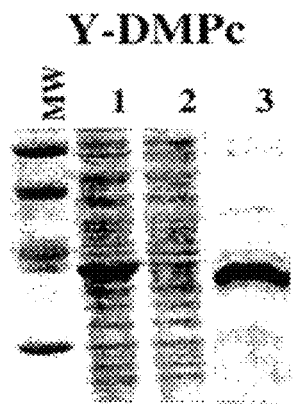

FIG. 43b is a Coomassie Blue-stained SDS-PAGE picture showing bacterial expression (lane 1) and purified protein product (lane 3) expressed by the Y-DMPc gene; lane 2 is the lysate of the pRSET/Y-DMPc-transformed bacteria prior to induction of protein expression with IPTG.

Figure 44:
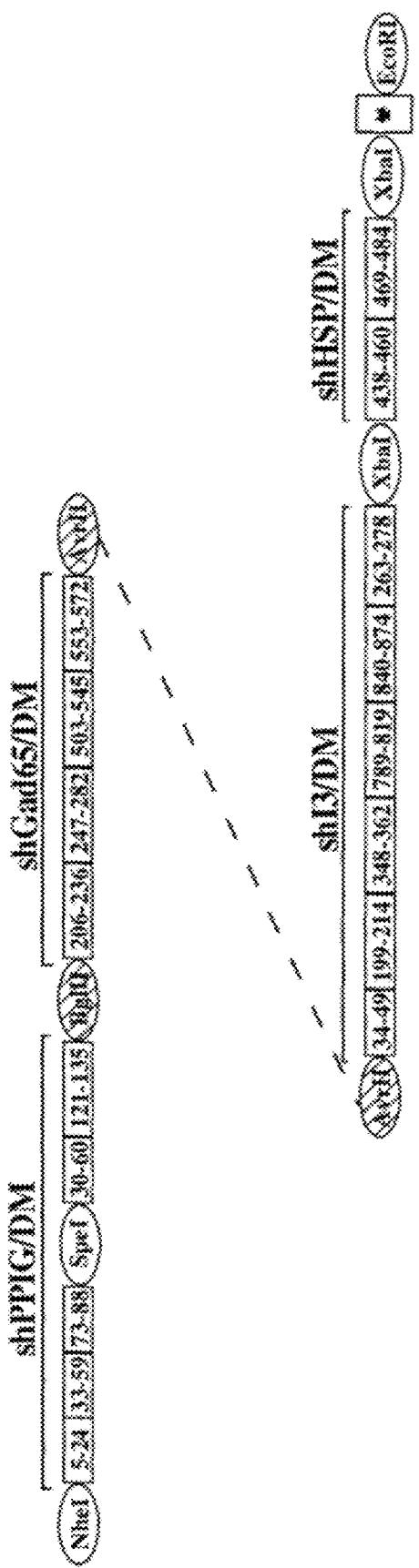

FIG. 44 depicts the construct of the shMultiTAG/DM herein designated Y-DMPb gene containing the shPPIG/DM, the shGad65/DM, the shI3/DM and the shHSP/DM genes.

Figure 44A:
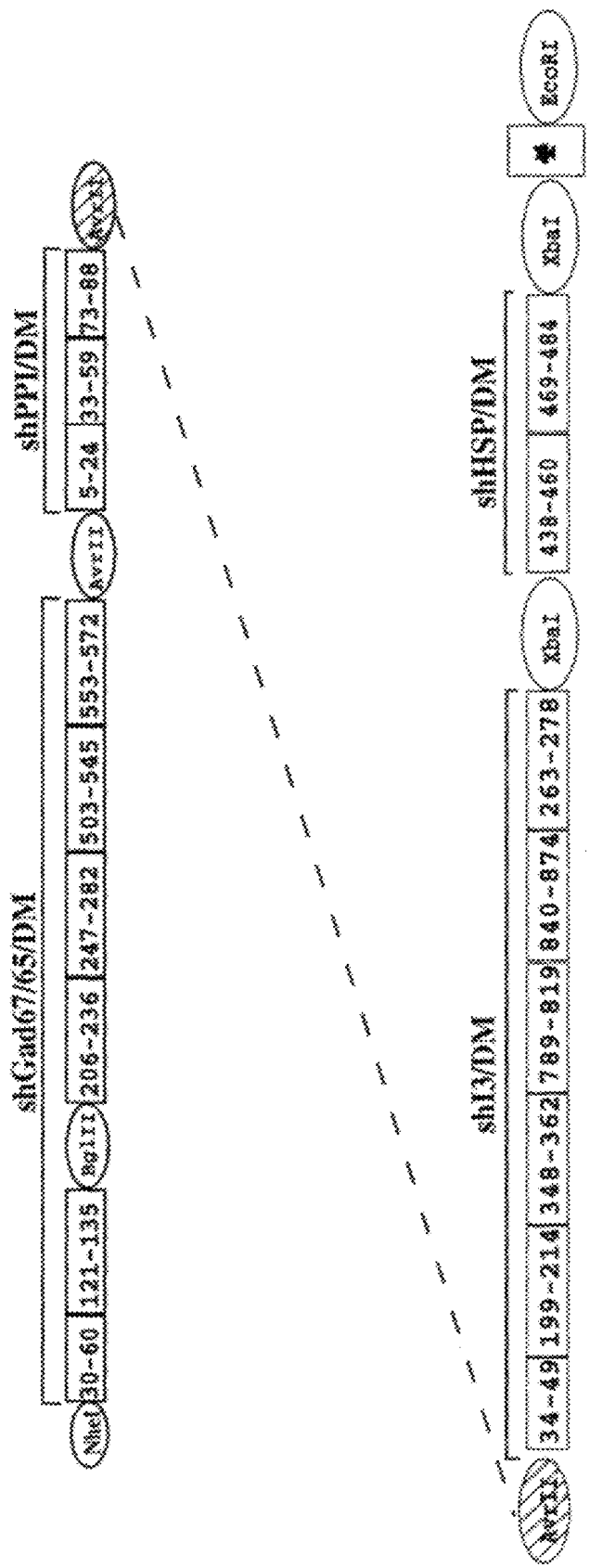

FIG. 44a depicts the construct of another shMultiTAG/DM herein designated Y-DMPd gene containing the shGad67/65/DM, the shPPI/DM, the shI3/DM and the shHSP/DM genes.

FIG. 45 depicts the DNA sequence (SEQ ID NO:97) of the Y-DMPb gene and the amino acid sequence (SEQ ID NO:98) of the polypeptide encoded thereby.

FIG. 45a depicts the DNA sequence (SEQ ID NO:99) of the Y-DMPd gene constructed according to the scheme presented in FIG. 44a, and the amino acid sequence (SEQ ID NO:100) of the polypeptide encoded thereby.

Figure 45B:
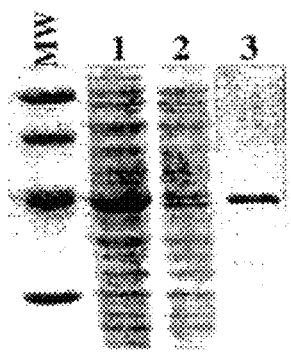

FIG. 45b is a Coomassie Blue-stained SDS-PAGE picture showing bacterial expression (lane 1) and purified protein product (lane 3) expressed by the Y-DMPd gene; lane 2 is the lysate of the pRSET/Y-DMPd-transformed bacteria prior to induction of protein expression with IPTG.

Figure 46:
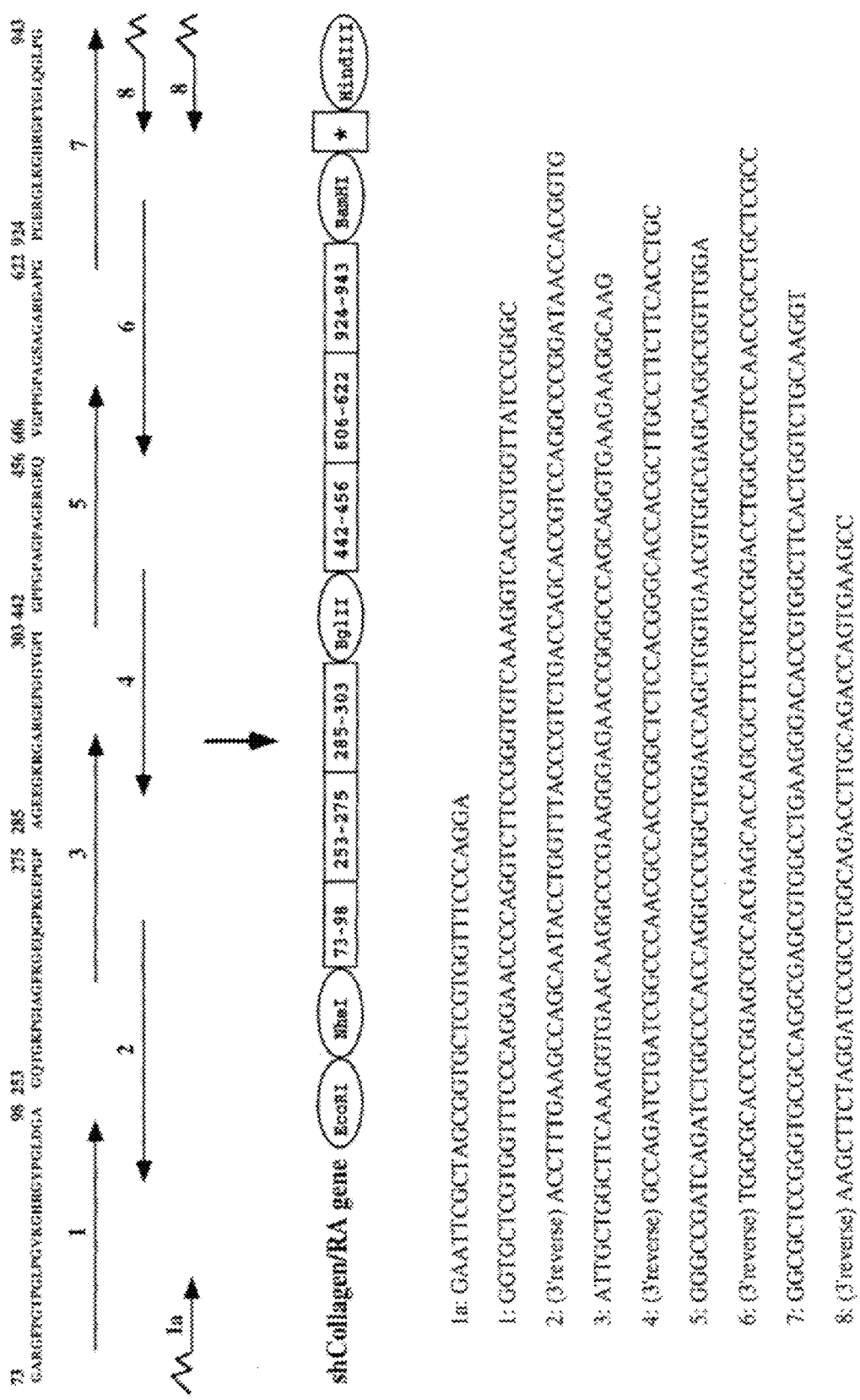

FIG. 46 depicts a scheme for construction of the shTAG/RA (shTAG related to rheumatoid arthritis) herein designated shCollagen/RA gene. The Collagen peptides 73-98 (SEQ ID NO:184), 253-275 (SEQ ID NO:185), 285-303 (SEQ ID NO:186), 442-456 (SEQ ID NO:187), 606-622 (SEQ ID NO:188) and 924-943 (SEQ ID NO:189) are presented at the top. The arrows below indicate the position and orientation of the oligonucleotides listed, which are used to generate and to amplify the DNA template. The oligonucleotides for template synthesis and PCR amplification are shown below the gene construct as follows: 1a (nucleotides 1-33 of SEQ ID NO:101), 1 (nucleotide 13-78 of SEQ ID NO:101), 2 (3'reverse) (SEQ ID NO:103), 3 (nucleotide 112-177 of SEQ ID NO:101), 4 (3'reverse) (SEQ ID NO:104), 5 (nucleotides 208-276 of SEQ ID NO:101), 6 (3'reverse) (SEQ ID NO:105), 7 (nucleotides 310-375 of SEQ ID NO:101) and 8 (3'reverse) (SEQ ID NO:106).

FIG. 47 depicts the DNA sequence (SEQ ID NO:101) of the shCollagen/RA gene and the amino acid sequence (SEQ ID NO:102) of the polypeptide encoded thereby.

Figure 48:
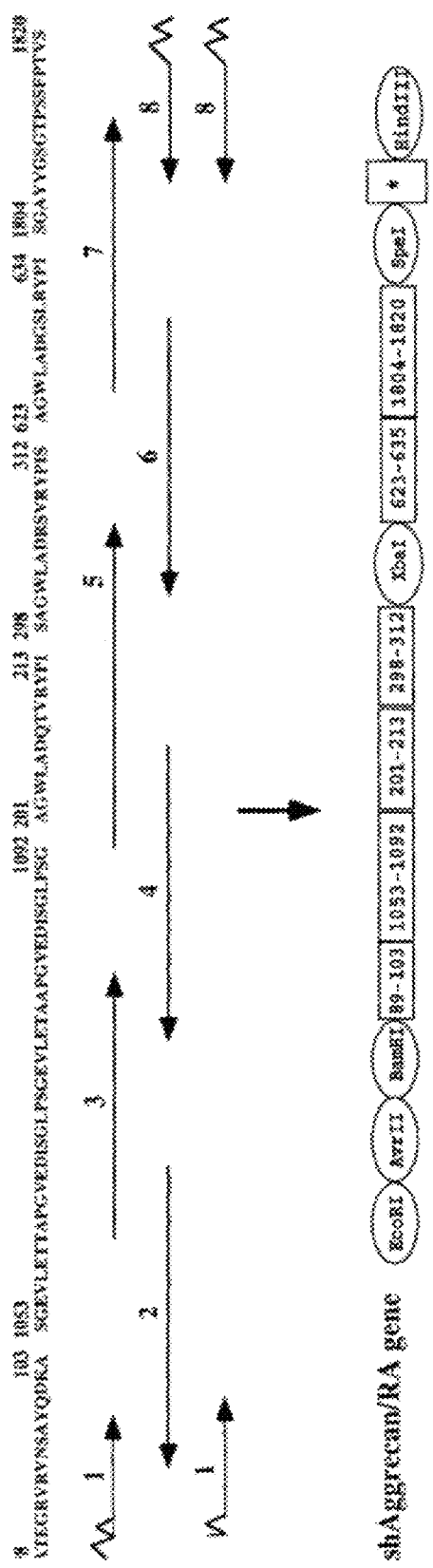

FIG. 48 depicts a scheme for construction of the shTAG/RA herein designated shAggrecan/RA gene. The Aggrecan peptides 89-103 (SEQ ID NO:190), 1053-1092 (SEQ ID NO:191), 201-213 (SEQ ID NO:192), 298-312 (SEQ ID NO:193), 623-635 (SEQ ID NO:194), and 1804-1820 (SEQ ID NO:195) are presented at the top. The arrows below indicate the position and orientation of the oligonucleotides listed, which are used to generate and to amplify the DNA template. The oligonucleotides for template synthesis and PCR amplification are shown below the gene construct as follows: 1 (nucleotides 1-45 of SEQ ID NO:107), 2 (3'reverse) (SEQ ID NO:109), 3 (nucleotides 79-147 of SEQ ID NO:107), 4 (3'reverse) (SEQ ID NO:110), 5 (nucleotides 181-249 of SEQ ID NO:107), 6 (SEQ ID NO:111), 7 (nucleotides 283-351 of SEQ ID NO:107) and 8 (SEQ ID NO:112).

FIG. 49 depicts the DNA sequence (SEQ ID NO:107) of the shAggrecan/RA gene and the amino acid sequence (SEQ ID NO:108) of the polypeptide encoded thereby.

Figure 50:
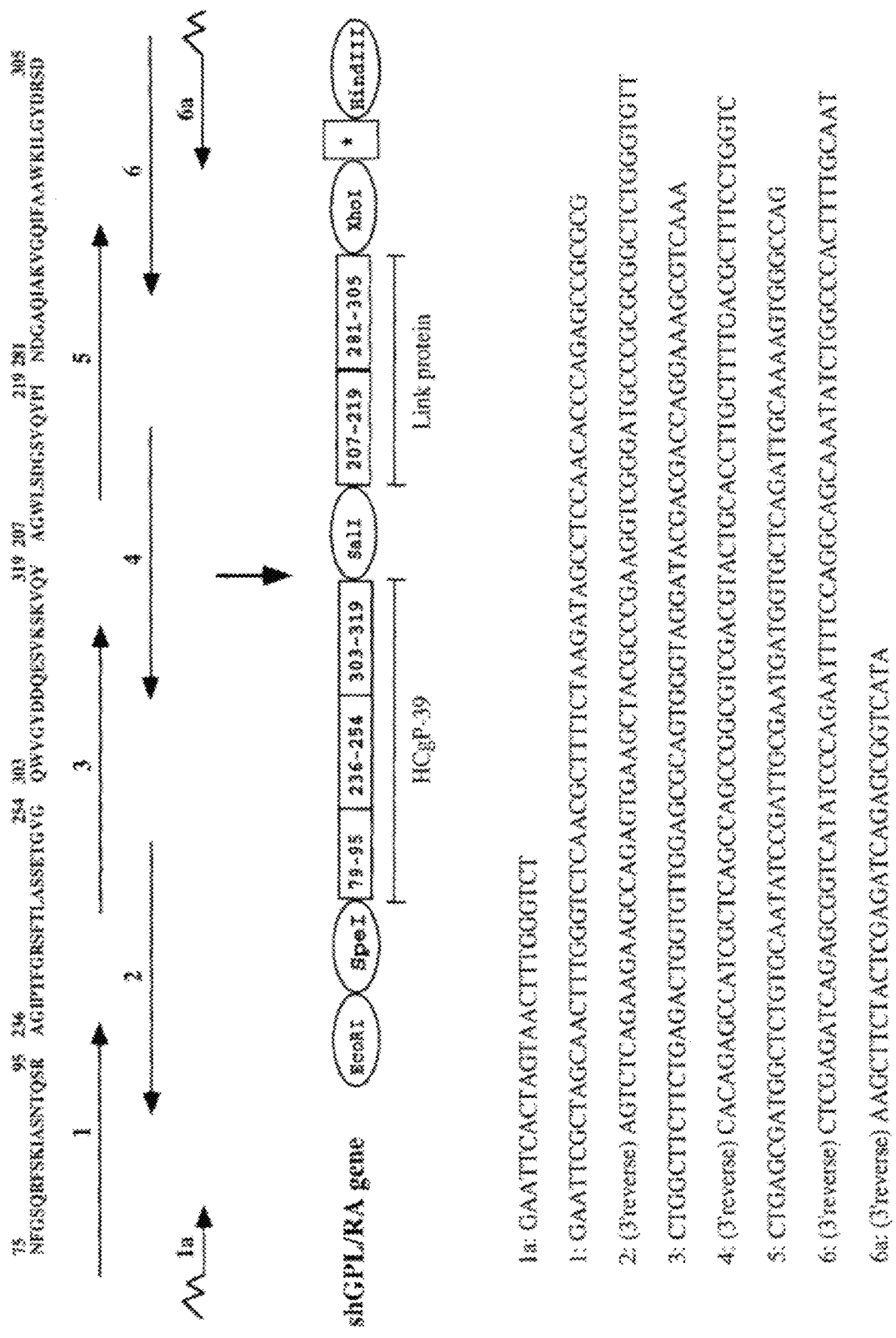

FIG. 50 depicts a scheme for construction of the shMultiTAG/RA herein designated shGPL/RA gene. The HCgP-39 peptides 79-95 (SEQ ID NO:196), 236-254 (SEQ ID NO:197), 303-319 (SEQ ID NO:198), and the Link protein peptides 207-219 (SEQ ID NO:199) and 281-305 (SEQ ID NO:200) are presented at the top. The arrows below indicate the position and orientation of the oligonucleotides listed, which are used to generate and to amplify the DNA template. The oligonucleotides for template synthesis and PCR amplification are shown below the gene construct as follows: 1a (nucleotides 1-24 of SEQ ID NO:113), 1 (nucleotide 1-66 of SEQ ID NO:113), 2 (3'reverse) (SEQ ID NO:115), 3 (nucleotides 97-162 of SEQ ID NO:113), 4 (3'reverse) (SEQ ID NO:116), 5 (nucleotide 193-258 of SEQ ID NO:113), 6 (3'reverse) (SEQ ID NO:117) and 6a (3'reverse) (SEQ ID NO:118).

FIG. 51 depicts the DNA sequence (SEQ ID NO:113) of the shGPL/RA gene and the amino acid sequence (SEQ ID NO:114) of the polypeptide encoded thereby.

Figure 52:
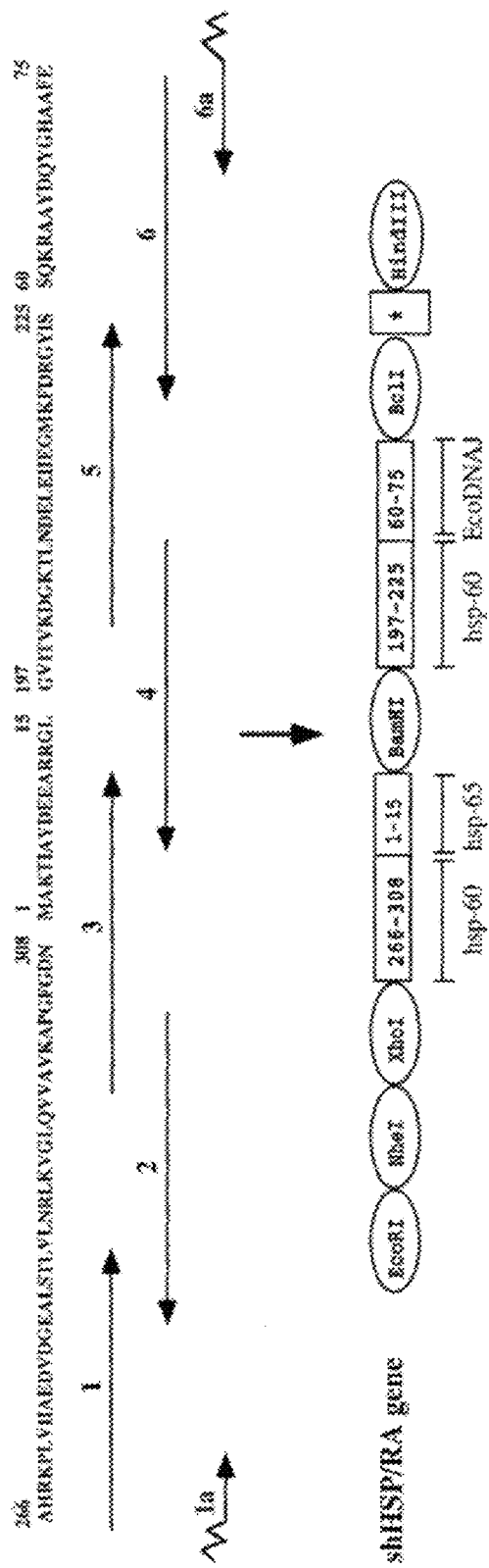

FIG. 52 depicts a scheme for construction of the shMultiTAG/RA herein designated shHSP/RA gene. The Hsp60 peptide 266-308 (SEQ ID NO:201), Hsp65 peptide 1-15 (SEQ ID NO:202), Hsp60 peptide 197-225 (SEQ ID NO:203), and EcoDNAJ peptide 60-75 (SEQ ID NO:204) are presented at the top. The arrows below indicate the position and orientation of the oligonucleotides listed, which are used to generate and to amplify the DNA template. The oligonucleotides for template synthesis and PCR amplification are shown below the gene construct as follows: 1a (nucleotides 1-33 of SEQ ID NO:119), 1 (nucleotides 13-81 of SEQ ID NO:119), 2 (3'reverse) (SEQ ID NO:121), 3 (nucleotides 115-183 of SEQ ID NO:119), 4 (3'reverse) (SEQ ID NO:122), 5 (nucleotides 217-285 of SEQ ID NO:119), 6 (3'reverse) (SEQ ID NO:123) and 6a (3'reverse) (SEQ ID NO:124).

FIG. 53 depicts the DNA sequence (SEQ ID NO:119) of the shHSP/RA gene and the amino acid sequence (SEQ ID NO:120) of the polypeptide encoded thereby.

Figure 54:
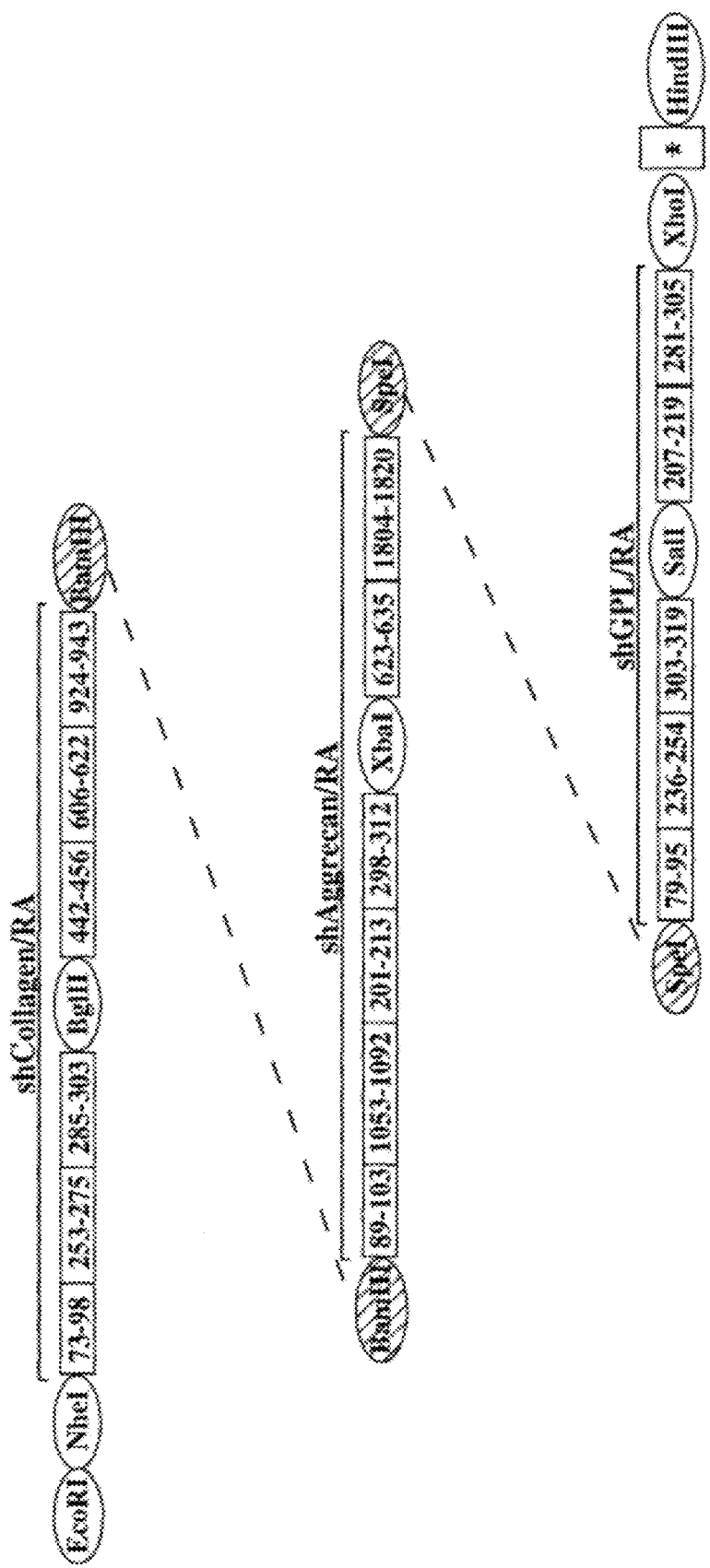

FIG. 54 depicts the construct of the shMultiTAG/RA herein designated Y-RAPa gene containing the shCollagen/RA, shAggrecan/RA and the shGPL/RA genes.

FIG. 55 depicts the DNA sequence (SEQ ID NO:125) of the Y-RAPa gene and the amino acid sequence (SEQ ID NO:126) of the polypeptide encoded thereby.

Figure 56:
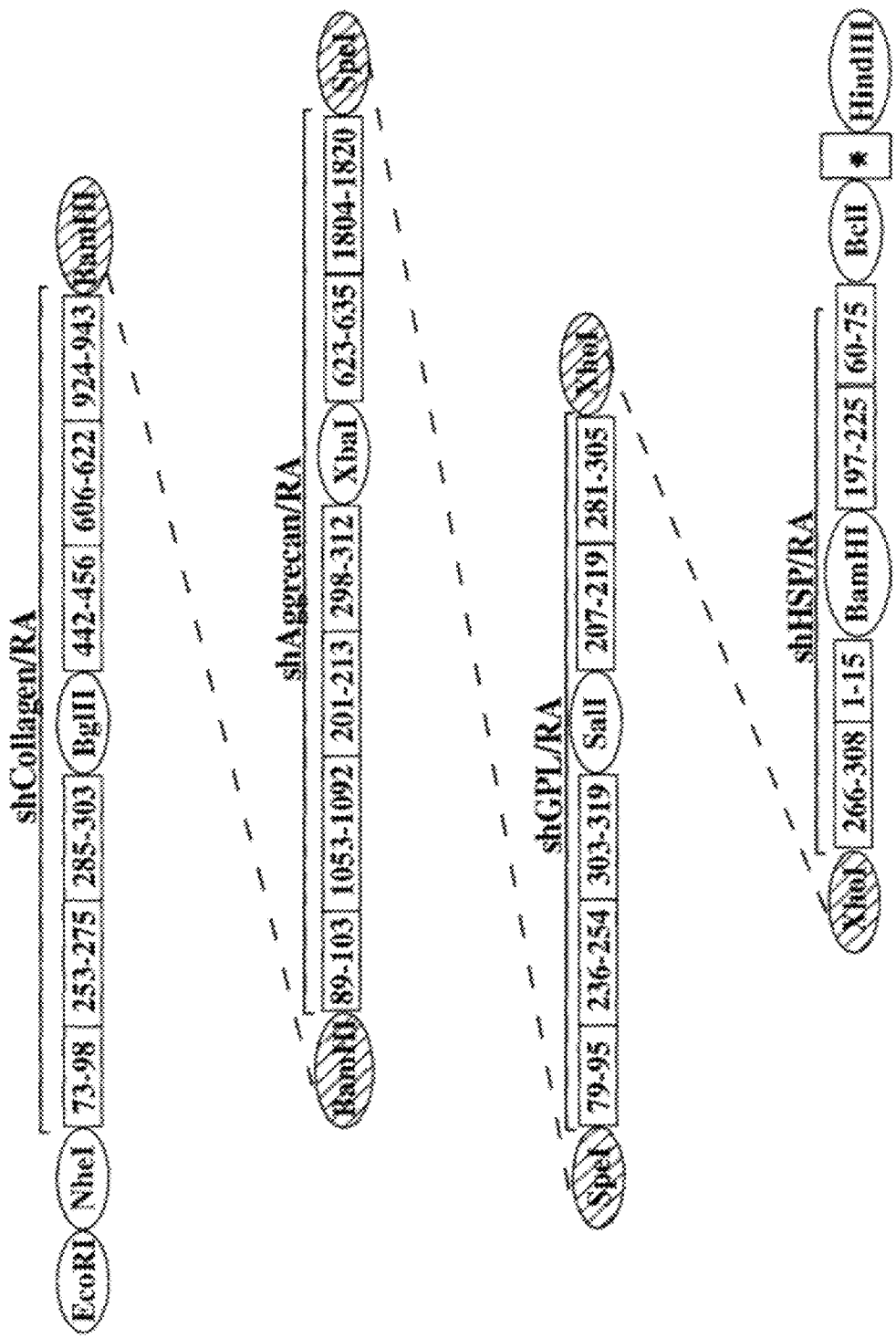

FIG. 56 depicts the construct of the shMultiTAG/RA herein designated Y-RAPb gene containing the shCollagen/RA, shAggrecan/RA, the shGPL/RA and the shHSP/RA genes.

FIG. 57 depicts the DNA sequence (SEQ ID NO:127) of the Y-RAPb gene and the amino acid sequence (SEQ ID NO:128) of the polypeptide encoded thereby.

Figure 58:
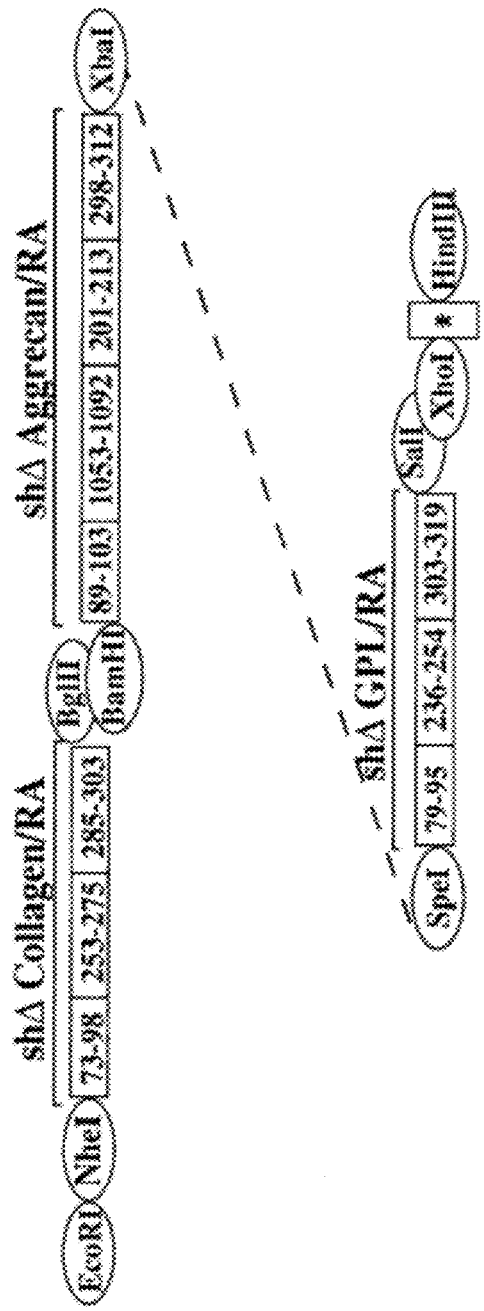

FIG. 58 depicts the construct of the shMultiTAG/RA herein designated Y-RAPc gene containing the truncated shΔ-Collagen/RA, shΔAggrecan/RA and the shΔGPL/RA genes.

FIG. 59 depicts the DNA sequence (SEQ ID NO:129) of the Y-RAPc gene and the amino acid sequence (SEQ ID NO:130) of the polypeptide encoded thereby.

Figure 60:
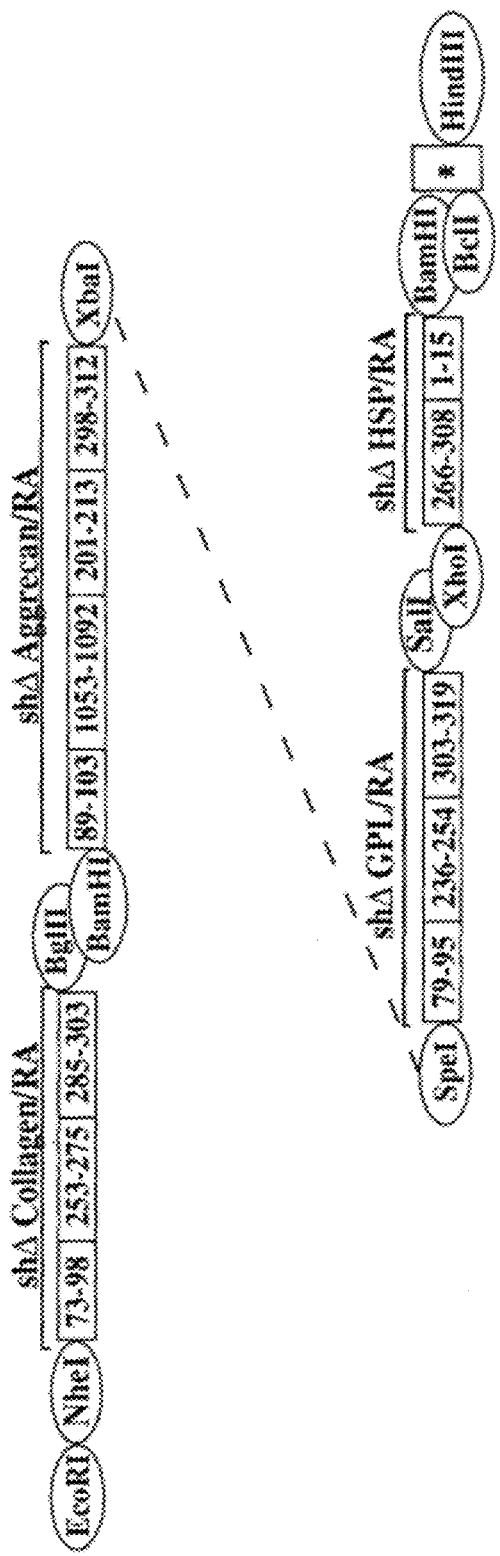

FIG. 60 depicts the construct of the shMultiTAG/RA herein designated Y-RAPd gene containing the truncated shΔCollagen/RA, shΔAggrecan/RA, the shΔGPL/RA and the shΔHSP/RA genes.

FIG. 61 depicts the DNA sequence (SEQ ID NO:131) of the Y-RAPd gene and the amino acid sequence (SEQ ID NO:132) of the polypeptide encoded thereby.

DETAILED DESCRIPTION OF THE INVENTION

A. Definitions

Within the context of the specification the following definitions will be used: "Autoantigen" refers to the self molecules (proteins) recognized as potential target antigens in an autoimmune disease. "Epitope" refers to an antigenic determinant of the autoantigen. "Immunogenic epitopic clusters (IEC's)" is used herein to refer to an epitope or collection of epitopes within a region of an autoantigen. The cluster may include one or more flanking, overlapping epitopes or such epitopes in tandem with one another. "Immunogenic (epitopic) cluster coding region" is used to refer to the nucleotide sequence that encodes for an IEC. "Immunogenic" is used herein to refer to the ability of an epitope to initiate an immune response. "Immunomodulatory" is used to refer to the ability of an IEC to modulate, regulate, control or antagonize an autoantigenic induction of an immune response in an appropriate animal model.

B. The Autoimmune Diseases

The spectrum of autoimmune disorders ranges from organ specific diseases such as thyroiditis, insulitis, insulin-dependent diabetes mellitus, multiple sclerosis, iridocyclitis, uveitis, orchitis, hepatitis, Addison's disease, and myasthenia gravis, to systemic illnesses such as rheumatoid arthritis or systemic lupus erythematosus. Other disorders include immune hyper-reactivity, such as allergic reactions. The synthetic genes of the present invention are primarily of interest in the class of autoimmune diseases involving T cell exposure to autoantigens. However, it may also be possible to address autoimmune diseases primarily involving B cell exposure utilizing the present invention.

The autoimmune diseases encompassed by the present invention are organ-specific autoimmune diseases including, but not being limited to, multiple sclerosis, insulin-dependent diabetes mellitus, autoimmune hepatitis, thyroiditis, insulitis, uveitis, orchitis, myasthenia gravis, idiopathic thrombocytopenic purpura, and inflammatory bowel diseases (Crohn's disease, ulcerative colitis), and systemic autoimmune diseases including, but not being limited to, rheumatoid arthritis and juvenile arthritis. In preferred embodiments the autoimmune disease is selected from multiple sclerosis (MS), insulin-dependent diabetes mellitus (IDDM), rheumatoid arthritis (RA), myasthenia gravis and uveitis. For some of these diseases, several autoantigens have been identified.

C. The autoantigens for MS, IDDM and RA

For most well studied autoimmune diseases several autoantigens have been proposed as being potential targets for the primary autoimmune attack.

Thus, for multiple sclerosis (MS), as discussed above, several antigens including MBP, PLP, MAG, MOG, MOBP and OSP have been proposed as being potential primary target autoantigens, by an assessment of PBLs of MS patients (Kerlero de Rosbo and Ben-Nun, 1998; Kaye et al., 2000) and/or by their ability to invoke a disease related immunogenic response in the relevant animal model (Kerlero de Rosbo and Ben-Nun, 1999; Maatta et al., 1998; Kaye et al., 2000; Stevens et al., 1999; Zhong et al., 2000). In the embodiment of the invention wherein the autoimmune disease is multiple sclerosis (MS), the IECs are related to the above autoantigens.

A similar approach may be adopted for other autoimmune diseases. Reactivity of PBLs from patients may be analyzed to identify which autoantigens are most frequently recognized. Alternatively, antigens can be identified as potential target autoantigens by their ability to actively (immunization) or passively (transfer of specific immune cells) induce, in an appropriate animal model, the autoimmune pathogenic effect characteristic of the disease.

Thus, for insulin-dependent diabetes mellitus (IDDM), preproinsulin (PPI), 67 kDa glutamic acid decarboxylase (Gad67), 65 kDa glutamic acid decarboxylase (Gad65), islet cell antigen p69 (ICA69), tyrosine phosphatase islet antigen 2 (IA-2), imogen and 60 kDa human heat shock protein (Hsp60) have been identified as autoantigens (reviewed in Roep, 1996, and in Bach, 1999). In the embodiment of the invention wherein the autoimmune disease is IDDM, the IECs are related to said autoantigens.

For rheumatoid arthritis (RA), collagen type II, aggrecan, human chondrocyte glycoprotein 69 (HCgP-39), cartilage link protein, 60 kDa human heat shock protein (Hsp60), 65 kDa Mycobacterium tuberculosis heat shock protein (hsp65) and Escherichia coli DNAJ protein (EcoDNAJ) have been identified as autoantigens (Cope and Sonderstrup, 1998; Guerassimov et al., 1997), and in the embodiment of the invention wherein the autoimmune disease is RA, the IECs are related to said autoantigens.

D. The immunogenic Epitopic Clusters (IECs) of the Autoantigens

The selection of the IECs of the identified potential target autoantigens related to each specific autoimmune disease is based on experimental identification of the epitopes most frequently recognized in patients, as assayed by reactivity to overlapping peptides of the relevant autoantigen, and/or on determination of the preferred binding mode of regions of the molecule to HLA associated with the disease as predicted by computer modelling, preferably confirmed by binding assays and/or experimental data obtained in HLA-transgenic mice. The following Table 1 summarizes IECs which have been experimentally identified or predicted to be potential epitopes for the autoimmune diseases MS, IDDM and RA:

None of the synthetic genes exemplified in the present description and drawings include a portion encoding two adjacent IEC's, either fused in contiguity or separated by a synthetic spacer, that together form a contiguous natural sequence within a native autoantigen.

TABLE 1

| Autoimmune disease | Autoantigen | Location of immunogenic cluster |
|---|---|---|
| Multiple sclerosis (MS) | MOG | 34-56, 67-114, 3-27, 205-215 |
| | MBP | 84-111, 141-168, 12-42 |
| | OSP | 42-73, 98-109, 183-203, 21-34, 130-146 |
| | MOBP | 15-33, 55-90, 156-172 |
| | PLP | 103-150, 177-203, 218-240, 38-52, 264-276 |
| Diabetes mellitus (IDDM) | Preproinsulin | 5-24, 33-59, 73-88 |
| | Gad67 | 30-60, 121-135 |
| | Gad65 | 206-236, 247-282, 503-545, 553-572 |
| | ICA69 | 34-49, 119-214, 348-362 |
| | IA-2 | 789-819, 840-874 |
| | Imogen | 263-278 |
| | Hsp60 | 438-460, 469-484 |
| Rheumatoid arthritis (RA) | Collagen type II | 73-98, 253-275, 285-303, 442-456, 606-622, 924-943 |
| | Aggrecan | 89-103, 1053-1092, 201-213, 298-312, 623-635, 1804-1820 |
| | HCgP-39 | 79-95, 236-254, 303-319 |
| | Link protein | 207-219, 281-305 |
| | Hsp60 | 266-308, 197-225 |
| | hsp65* | 1-15 |
| | EcoDNAJ* | 60-75 |

*Sequences cross-reactive to human homologs known to be associated with rheumatoid arthritis E. The Synthetic Genes of the Invention According to the present invention, the synthetic human target autoantigen gene comprises nucleotide sequences coding for at least two immunogenic epitopic clusters (hereinafter IEC) of autoantigen(s) related to a specific autoimmune disease.

In one embodiment, the synthetic gene comprises nucleotide sequences coding for at least two IECs of a sole autoantigen related to said autoimmune disease, and these genes are herein in the specification and claims designated shTAGs.

In another embodiment, the synthetic gene is a multitarget autoantigen gene comprising nucleotide sequences coding for at least one IEC of at least two, but also 3, 4, 5 or more, different autoantigens related to said autoimmune disease, and these genes are herein in the specification and claims designated shMultiTAGs.

The autoimmune disease is selected from multiple sclerosis (MS), insulin-dependent diabetes mellitus (IDDM), rheumatoid arthritis (RA), myasthenia gravis (MG) and uveitis.

The IECs may be randomly organized in the shTAGs and shMultiTAGs. In the Figures and Examples, the designation of the shTAGs includes the abbreviation of the autoantigen followed by a capital E, e.g. shMOG/E, for the "pilot generation" of shTAGs, or followed by the abbreviation of the autoimmune disease for the "second generation" of shTAGs, e.g. shMOG/MS. The shMultiTAGs are indicated by an initial capital Y followed by the abbreviation of the autoimmune disease and a small letter: in the shMultiTAGs of the "pilot generation" used for preliminary experiments in mice the letters are "a" or "b", e.g. Y-MSPa, Y-DMPa, Y-RAPb, and in the "second generation" of shMultiTAGs comprising a higher number of IECs, the letters are "c' or "d", e.g. Y-MSPc, Y-RAPd, those marked by the letter "d" containing the preferred IECs of the selected autoantigens related to the autoimmune disease.

The invention further encompasses synthetic genes with variations in the nucleotide sequence, particularly in the sequences encoding the IECs, provided that the immunogenicity, or more preferably, the immunomodulatory activity, of the expressed IEC is retained.

In one embodiment, the nucleotide variation from the wild type coding sequence is within the scope of the genetic code.

In another embodiment, the variation includes homologous sequences which term covers a certain degree of identity with respect to structure and/or function provided that the expression product of the resultant nucleotide sequence has the desired activity. The discussion in Section H below is based upon sequence identity (homology) of the nucleotide sequences of the IEC coding regions taken individually. With respect to sequence identity (i.e. similarity), preferably there is at least 75%, more preferably at least 85%, more preferably at least 90% sequence identity with each IEC coding region. More preferably there is at least 95%, more preferably at least 98%, sequence identity. These terms also encompass allelic variations of the sequences.

The present invention also encompasses nucleotide sequences that are complementary to the sequences of the synthetic genes of the invention as well as nucleotide sequences that are capable of hybridizing to the nucleotide sequences of the invention or to the complementary sequences under conditions of intermediate to maximal stringency. Hybridization conditions are based on the melting temperature (Tm) of the nucleic acid binding complex and confer a defined "stringency". Thus, maximum stringency typically occurs at about Tm−5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridization can be used to identify or detect identical nucleotide sequences while an intermediate (or low) stringency hybridization can be used to identify or detect similar or related nucleotide sequences. In a preferred embodiment, the nucleotide sequences hybridize to the nucleotide sequences of the present invention under stringent conditions such as 65° C. and 0.1×SSC (1×SSC=0.15 M NaCl, 0.015 sodium citrate pH 7.0}.

E.1 The Synthetic Genes for Multiple Sclerosis (MS)

The sgTAGs and shMultiTAGs for MS, herein referred to as shTAG/MS and shMultiTAG/MS, respectively, comprise nucleotide sequences coding for IECs of autoantigen(s) related to MS, said autoantigen being selected from the group consisting of myelin-associated glycoprotein (MAG), myelin basic protein (MBP), myelin oligodendrocyte glycoprotein (MOG), myelin-oligodendrocytic basic protein (MOBP), oligodendrocyte-specific protein (OSP) and proteolipid protein (PLP).

Figure 1:
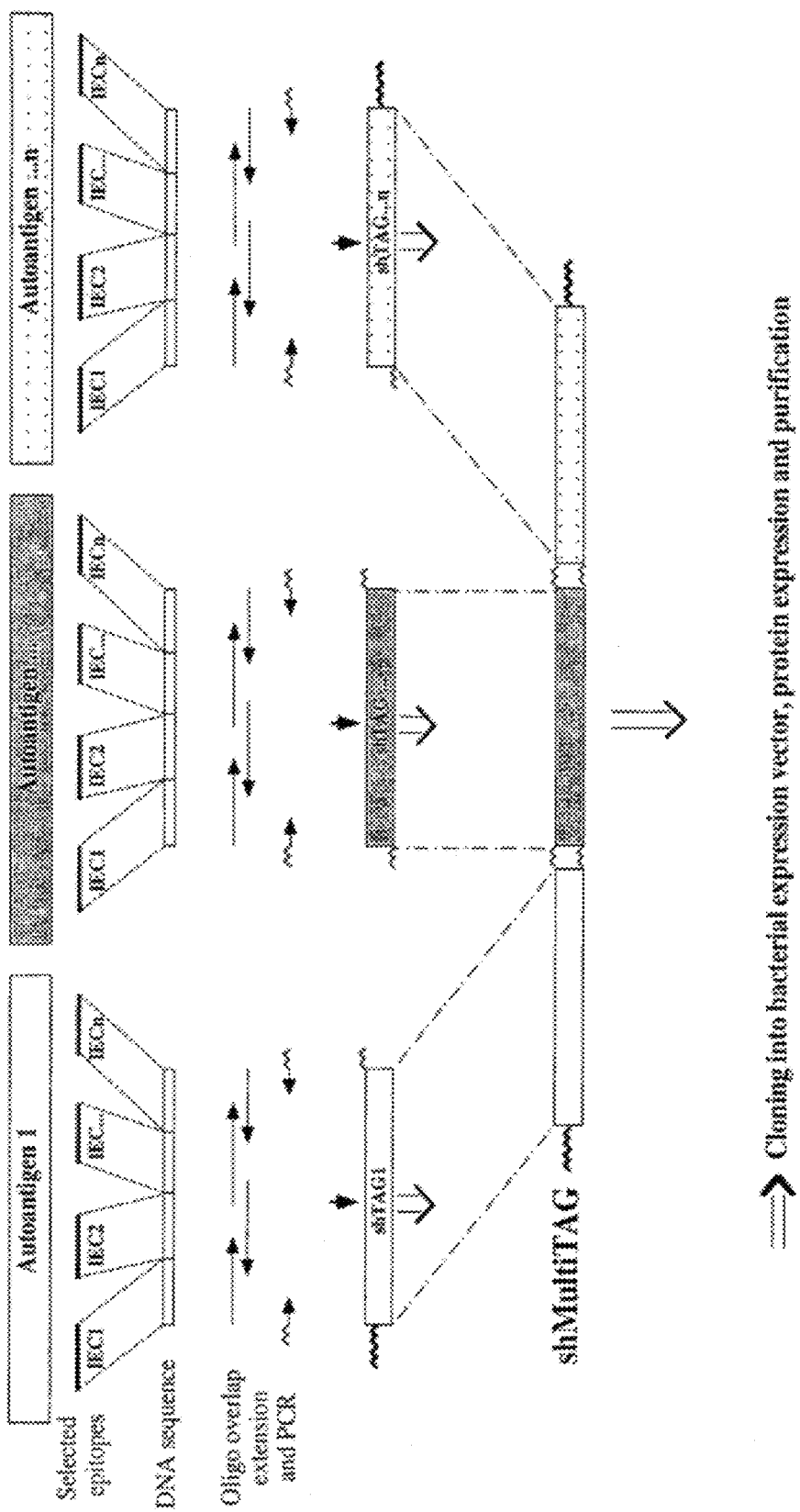
FIG. 1 depicts a general scheme for construction of a synthetic human target autoantigen gene (shTAG and shMultiTAG) of the invention for a given autoimmune disease.
Figure 2:
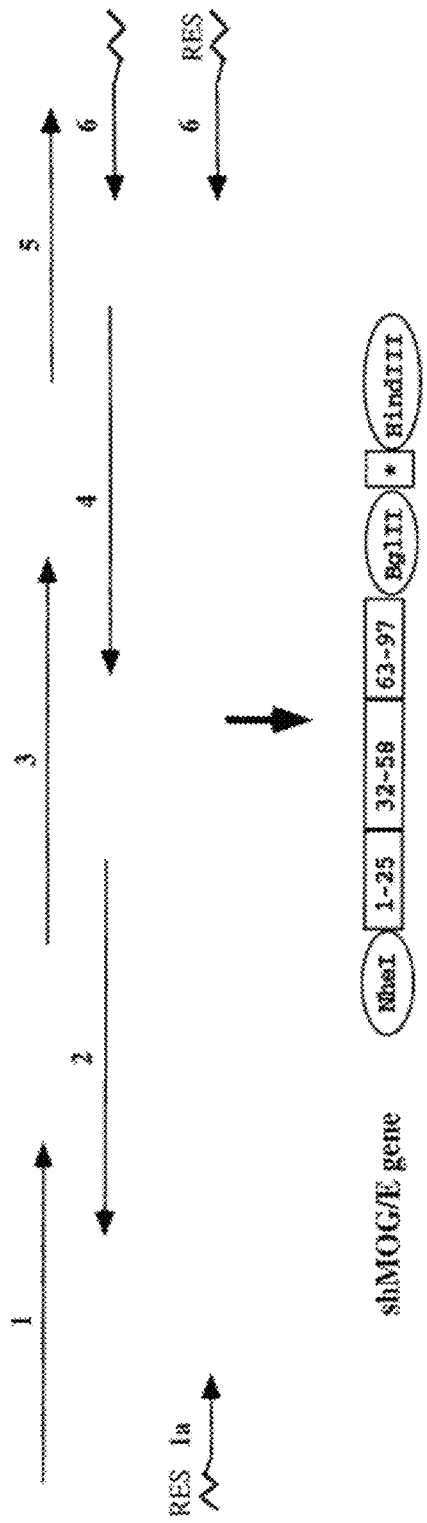
FIG. 2 depicts a scheme for construction of the shTAG/MS (shTAG related to multiple sclerosis) herein designated shMOG/E gene. The MOG peptides 1-25 (SEQ ID NO:135), 32-58 (SEQ ID NO:136), and 63-97 (SEQ ID NO:137) are presented at the top. The arrows below indicate the position and orientation of the oligonucleotides listed, which were used to generate and to amplify the DNA template. The oligonucleotides for template synthesis and PCR amplification are shown below the gene construct as follows: shMOG 1a (SEQ ID NO:3); shMOG1 (nucleotides 7-75 of SEQ ID NO:1); shMOG 2 (3'rev) (SEQ ID NO:4); shMOG 3 (nucleotides 110-177 of SEQ ID NO:1); shMOG 4 (3'rev) (SEQ ID NO:5); shMOG 5 (nucleotides 211-276 of SEQ ID NO:1); and shMOG 6 (3'rev) (SEQ ID NO:6).
Figure 5:
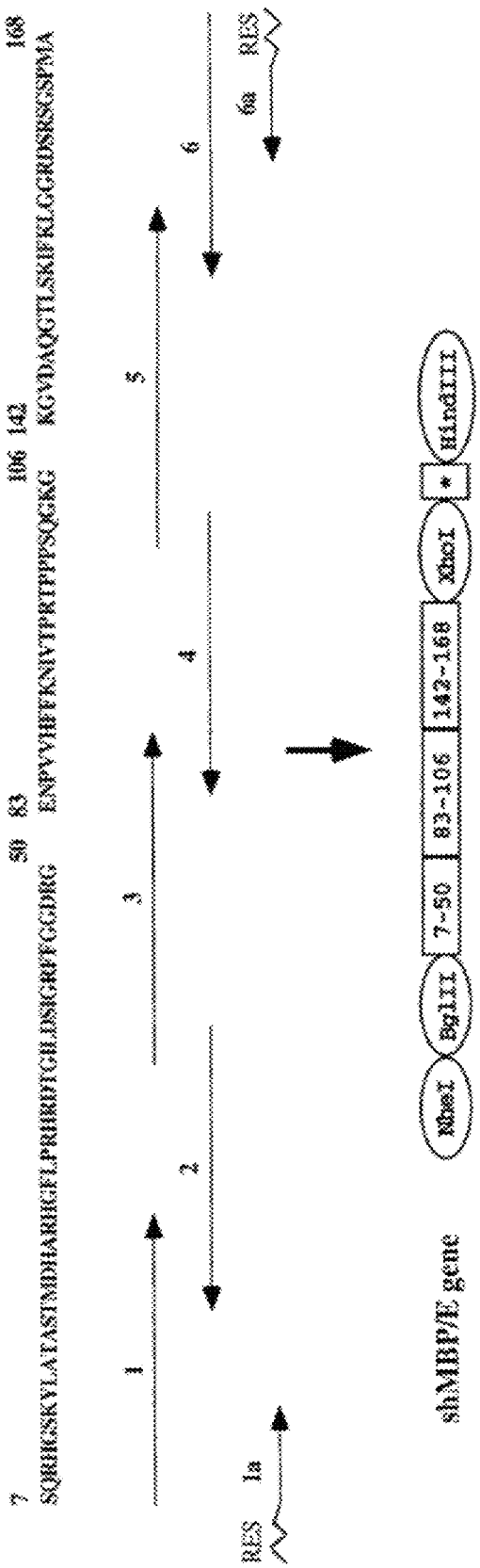
FIG. 5 depicts a scheme for construction of the shTAG/MS herein designated shMBP/E gene. The MBP peptides 7-50 (SEQ ID NO:138), 83-106 (SEQ ID NO:139), and 142-168 (SEQ ID NO:140) are presented at the top. The arrows below indicate the position and orientation of the oligonucleotides listed, which are used to generate and to amplify the DNA template. The oligonucleotides for template synthesis and PCR amplification are shown below the gene construct as follows: shMBP 1a (SEQ ID NO:9); shMBP 1 (nucleotides 13-75 of SEQ ID NO:7); shMBP 2 (3'rev) (SEQ ID NO:10); shMBP 3 (nucleotides 103-165 of SEQ ID NO:7); shMBP 4 (3'rev) (SEQ ID NO:11); shMBP 5 (nucleotides 196-255 of SEQ ID NO:7); shMBP 6 (3'rev) (SEQ ID NO:12); and shMBP 6a (3'rev) (SEQ ID NO:13).
Figure 7:
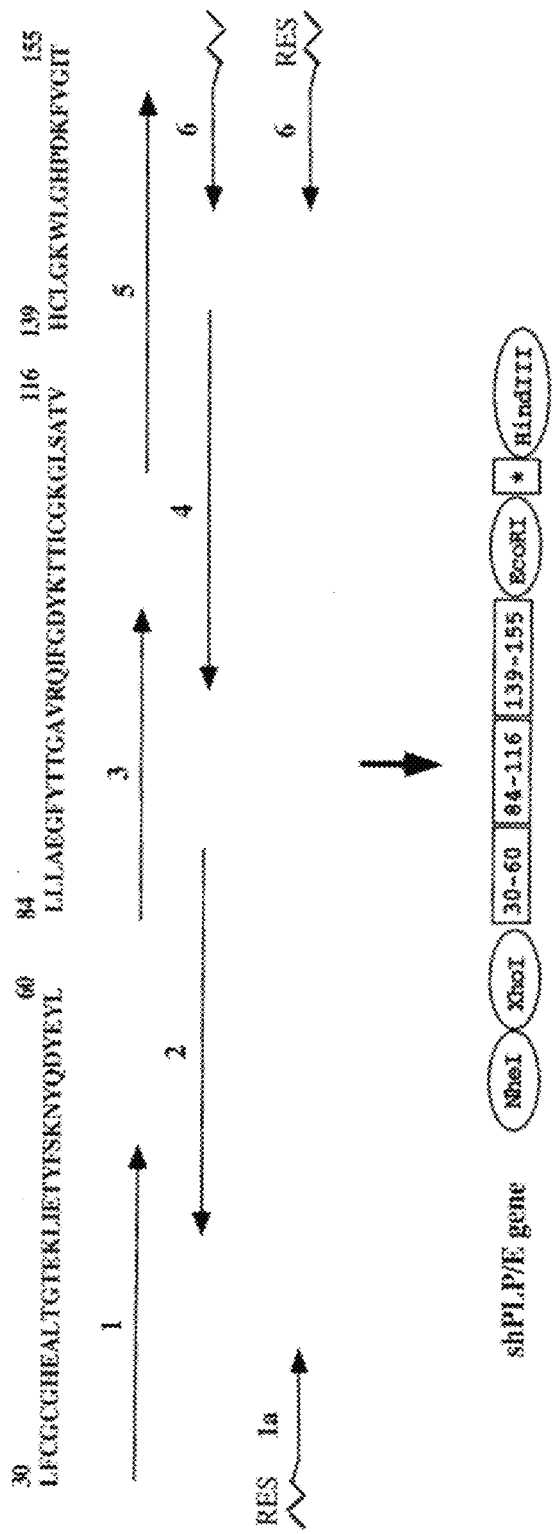
FIG. 7 depicts a scheme for construction of the shTAG/MS herein designated shPLP/E gene. The PLP peptides 30-60 (SEQ ID NO:141), 84-116 (SEQ ID NO:142), and 139-155 (SEQ ID NO:143) are presented at the top. The arrows below indicate the position and orientation of the oligonucleotides listed, which are used to generate and to amplify the DNA template. The oligonucleotides for template synthesis and PCR amplification are shown below the gene construct as follows: shPLP 1a (SEQ ID NO:16); shPLP 1 (nucleotides 1-75 of SEQ ID NO:14); shPLP 2 (3'rev) (SEQ ID NO:17); shPLP 3 (nucleotides 103-165 of SEQ ID NO:14); shPLP 4 (3'rev) (SEQ ID NO:18); shPLP 5 (nucleotides 193-255 of SEQ ID NO:14); and shPLP 6 (3'rev) (SEQ ID NO:19).
Figure 9:
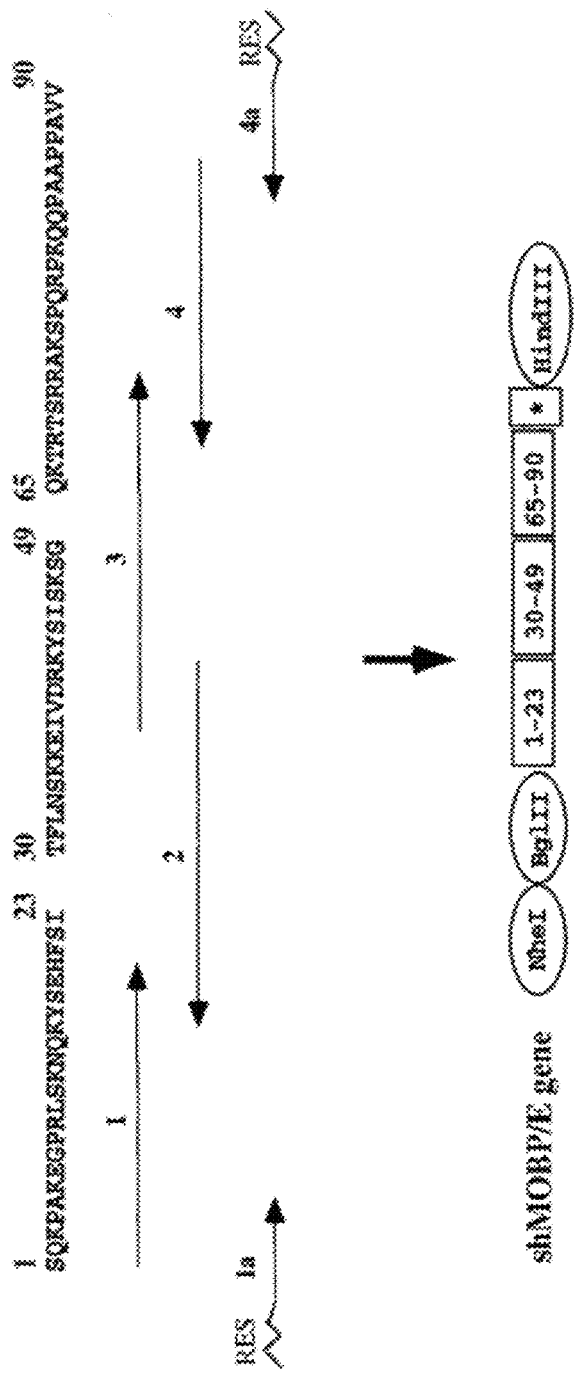
FIG. 9 depicts a scheme for construction of the shTAG/MS herein designated shMOBP/E gene. The MOBP peptides 1-23 (SEQ ID NO:144), 30-49 (SEQ ID NO:145) and 65-90 (SEQ ID NO:146) are presented at the top. The arrows below indicate the position and orientation of the oligonucleotides listed, which are used to generate and to amplify the DNA template. The oligonucleotides for template synthesis and PCR amplification are shown below the gene construct as follows: shMOBP 1a (SEQ ID NO:22), shMOBP 1 (nucleotides 1-75 of SEQ ID NO:20), shMOBP 2 (3'rev) (SEQ ID NO:23), shMOBP 3 (nucleotides 109-177 of SEQ ID NO:20), shMOBP4 (3'rev) (SEQ ID NO:24) and shMOBP 4a (3'rev) (SEQ ID NO:25).
Figure 20:
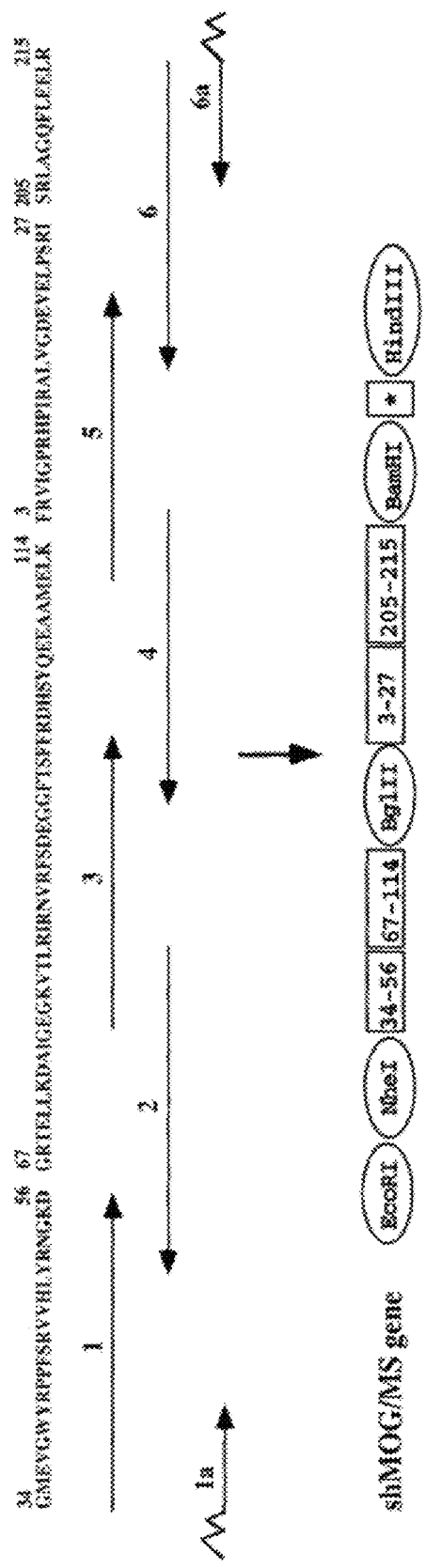
FIG. 20 depicts a scheme for construction of the shTAG/MS herein designated shMOG/MS gene. The MOG peptides 34-56 (SEQ ID NO:147), 67-114 (SEQ ID NO:148), 3-27 (SEQ ID NO:149), and 205-215 (SEQ ID NO:150) are presented at the top. The arrows below indicate the position and orientation of the oligonucleotides listed, which are used to generate and to amplify the DNA template. The oligonucleotides for template synthesis and PCR amplification are shown below the gene construct as follows: shMOG 1a (nucleotides 1-33 of SEQ ID NO:36), shMOG 1 (nucleotides 13-81 of SEQ ID NO:36), shMOG 2 (3'reverse) (SEQ ID NO:32), shMOG 3 (nucleotides 115-183 of SEQ ID NO:30), shMOG 4 (3'reverse) (SEQ ID NO:33), shMOG 5 (nucleotides 217-285 of SEQ ID NO:30), shMOG 6 (3'reverse) (SEQ ID NO:34) and shMOG 6a (3'reverse) (SEQ ID NO:35).
Figure 22:
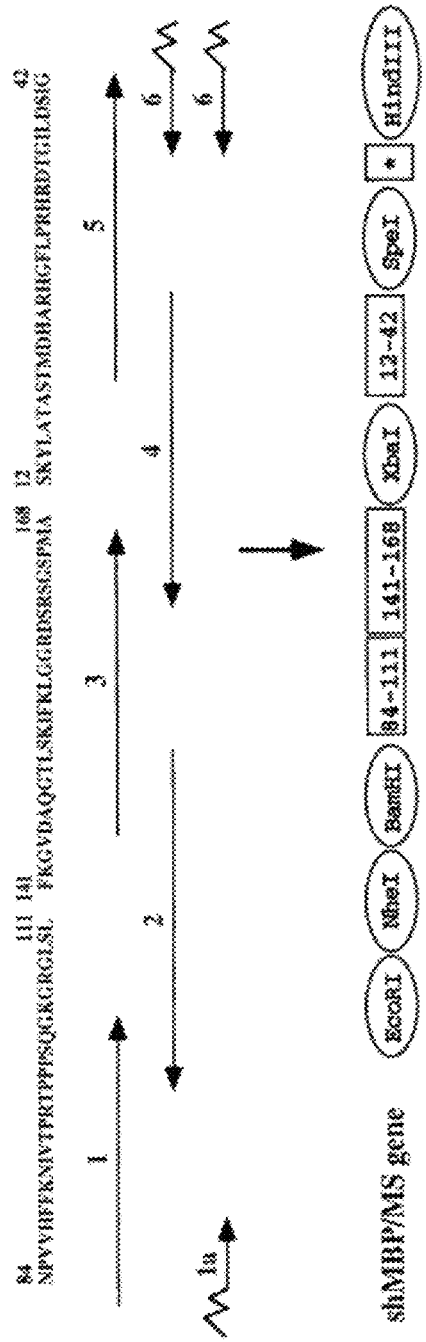
FIG. 22 depicts a scheme for construction of the shTAG/MS herein designated shMBP/MS gene. The MBP peptides 84-111 (SEQ ID NO:151), 141-168 (SEQ ID NO:152) and 12-42 (SEQ ID NO:153) are presented at the top. The arrows below indicate the position and orientation of the oligonucleotides listed, which are used to generate and to amplify the DNA template. The oligonucleotides for template synthesis and PCR amplification are shown below the gene construct as follows: shMBP 1a (nucleotides 1-33 of SEQ ID NO:36), shMBP 1 (nucleotides 13-81 of SEQ ID NO:36), shMBP 2 (3'reverse) (SEQ ID NO:38), shMBP 3 (nucleotides 115-183 of SEQ ID NO:36), shMBP 4 (3'reverse) (SEQ ID NO:39), shMBP 5 (nucleotides 217-285 of SEQ ID NO:36) and shMBP 6 (3'reverse) (SEQ ID NO:40).
Figure 24:
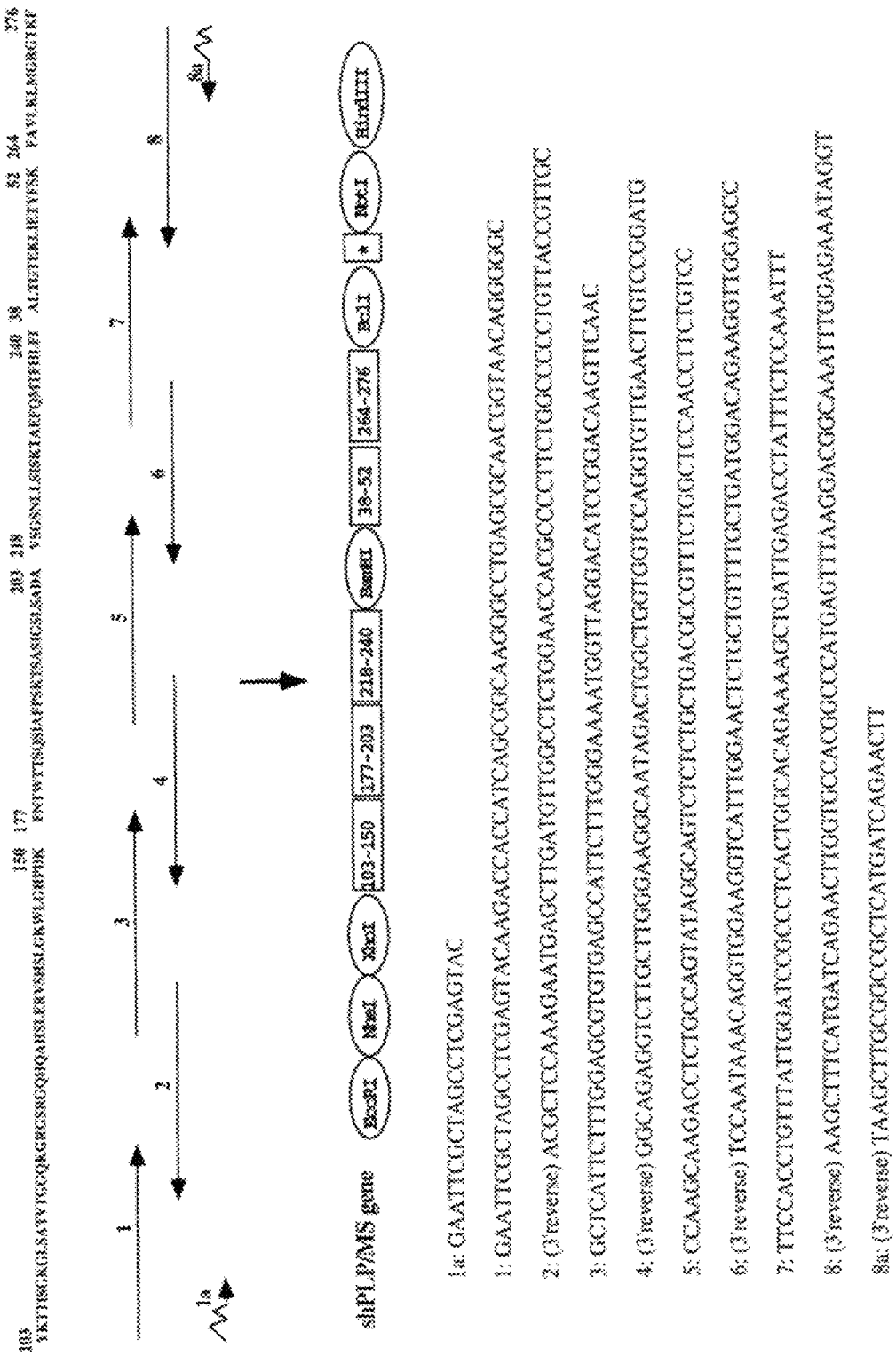
FIG. 24 depicts a scheme for construction of the shTAG/MS herein designated shPLP/MS gene. The PLP peptides 103-150 (SEQ ID NO:154), 177-203 (SEQ ID NO:155), 218-240 (SEQ ID NO:156), 38-52 (SEQ ID NO:157) and 264-276

Examples of shTAG/MS according to the invention include:

(i) a shTAG/MS comprising nucleotide sequences encoding at least two of the amino acid sequences 1-25, 32-58, and 63-97 of MOG, preferably containing the three sequences, more preferably the shMOG/E gene depicted by the construct of FIG. 2 and having the nucleotide sequence depicted in FIG. 3;

(ii) a shTAG/MS comprising nucleotide sequences encoding at least two of the amino acid sequences 7-50, 83-106, and 142-168 of MBP, preferably containing the three sequences, more preferably the shMBP/E gene depicted by the construct of FIG. 5 and having the nucleotide sequence depicted in FIG. 6;

(iii) a shTAG/MS comprising nucleotide sequences encoding at least two of the amino acid sequences 30-60, 84-116, and 139-155 of PLP, preferably comprising the three sequences, more preferably the shPLP/E gene depicted by the construct of FIG. 7 and having the nucleotide sequence depicted in FIG. 8;

(iv) a shTAG/MS comprising nucleotide sequences encoding at least two of the amino acid sequences 1-23, 30-49, and 65-90 of MOBP, preferably comprising the three sequences, more preferably the shMOBP/E gene depicted by the construct of FIG. 9 and having the nucleotide sequence depicted in FIG. 10;

(v) a shTAG/MS comprising nucleotide sequences encoding at least two of the amino acid sequences 3-27, 34-56, 67-114, and 205-215 of MOG, preferably comprising the four sequences, more preferably the shMOG/MS gene depicted by the construct of FIG. 20 and having the nucleotide sequence depicted in FIG. 21;

(vi) a shTAG/MS comprising nucleotide sequences encoding at least two of the amino acid sequences 12-42, 84-111, and 141-168 of MBP, preferably comprising the three sequences, more preferably the shMBP/MS gene depicted by the construct of FIG. 22 and having the nucleotide sequence depicted in FIG. 23;

(vii) a shTAG/MS comprising nucleotide sequences encoding at least two of the amino acid sequences 38-52, 103-150, 177-203, 218-240, and 264-276 of PLP, preferably comprising the five sequences, more preferably the shPLP/MS gene depicted by the construct of FIG. 24 and having the nucleotide sequence depicted in FIG. 25;

(viii) a shTAG/MS comprising nucleotide sequences encoding at least two of the amino acid sequences 15-33, 55-90, and 156-172 of MOBP, preferably comprising the three sequences, more preferably the shMOBP/MS gene depicted by the construct of FIG. 26 and having the nucleotide sequence depicted in FIG. 27; and (ix) a shTAG/MS comprising nucleotide sequences encoding at least two of the amino acid sequences 21-34, 42-73, 98-109, 130-146, and 183-203 of OSP; preferably comprising the five sequences, more preferably the shOSP/MS gene depicted by the construct of FIG. 28 and having the nucleotide sequence depicted in FIG. 29.

The shMultiTAG/MS according to the invention preferably comprise nucleotide sequences coding for at least two IECs specific for each of at least three of the autoantigens MAG, MBP, MOG, MOBP, OSP and PLP, and include:

(a) a shMultiTAG/MS comprising nucleotide sequences coding for: (i) at least two of the amino acid sequences 1-25, 32-58 and 63-97 of MOG; (ii) at least two of the amino acid sequences 7-50, 83-106, and 142-168 of MBP; and (iii) at least two of the amino acid sequences 30-60, 84-116 and 139-155 of PLP, preferably comprising all said sequences, more preferably the "pilot generation" Y-MSPa gene comprising the shMOG/E, shMBP/E and shPLP/E genes, depicted by the construct of FIG. 11 and having the nucleotide sequence depicted in FIG. 12;

(b) a shMultiTAG/MS comprising nucleotide sequences coding for: (i) at least two of the amino acid sequences 1-25, 32-58 and 63-97 of MOG; (ii) at least two of the amino acid sequences 7-50, 83-106, and 142-168 of MBP; (iii) at least two of the amino acid sequences 30-60, 84-116 and 139-155 of PLP; and (iv) at least two of the amino acid sequences 1-23, 30-49 and 65-90 of MOPB, preferably comprising all said sequences, more preferably the "pilot generation" Y-MSPb gene comprising the shMOG/E, shMBP/E, shPLP/E and shMOBP/E genes, depicted by the construct of FIG. 14 and having the nucleotide sequence depicted in FIG. 15;

(c) a shMultiTAG/MS comprising nucleotide sequences coding for: (i) at least two of the amino acid sequences 3-27, 34-56, 67-114 and 205-215 of MOG; (ii) at least two of the amino acid sequences 12-42, 84-111 and 141-168 of MBP; (iii) at least two of the amino acid sequences 38-52, 103-150, 177-203, 218-240 and 264-276 of PLP; (iv) at least two of the amino acid sequences 21-34, 42-73, 98-109, 130-146 and 183-203 of OSP; and (v) at least two of the amino acid sequences 15-33, 55-90 and 156-172 of MOBP, preferably comprising all said sequences, more preferably the "second generation" Y-MSPc gene comprising the shMOG/MS, shMBP/MS, shOSP/MS, shMOBP/E and shPLP/MS genes, depicted by the construct of FIG. 30 and having the nucleotide sequence depicted in FIG. 31; and (d) the truncated form of (c), comprising nucleotide sequences coding for the amino acid sequences 34-56 and 67-114 of MOG; 84-111 and 141-168 of MBP; 103-150, 177-203 and 218-240 of PLP; 42-73, 98-109 and 183-203 of OSP; and 15-33 and 55-90 of MOBP, preferably comprising all said sequences, most preferably the "second generation" Y-MSPd gene comprising the shMOG/MS, shMBP/MS, shOSP/MS, shMOBP/E and shPLP/MS genes, depicted by the construct of FIG. 32 and having the nucleotide sequence depicted in FIG. 33.

E.2 The Synthetic Genes for Insulin-Dependent Diabetes Mellitus (IDDM)

The sgTAGs and shMultiTAGs for IDDM, herein referred to as shTAG/DM and shMultiTAG/DM, respectively, comprise nucleotide sequences coding for IECs of autoantigen(s) related to IDDM, said autoantigen being selected from the group consisting of preproinsulin (PPI), 67 kDa glutamic acid decarboxylase (Gad67), 65 kDa glutamic acid decarboxylase (Gad65), islet cell antigen p69 (ICA69), tyrosine phosphatase islet antigen 2 (IA-2), imogen and 60 kDa human heat shock protein (Hsp60).

Examples of shTAG/DM according to the invention include:

(i) a shTAG/DM comprising nucleotide sequences coding for at least two of the amino acid sequences 206-236, 247-282, 503-545, and 553-572 of Gad65, preferably containing the four sequences, more preferably the shGad65/DM gene depicted by the construct of FIG. 36 and having the nucleotide sequence depicted in FIG. 37; and (ii) a shTAG/DM comprising nucleotide sequences coding for at least the two amino acid sequences 438-460 and 469-484 of Hsp60, preferably containing the two sequences, more preferably the shHSP/DM gene depicted by the construct of FIG. 40 and having the nucleotide sequence depicted in FIG. 41.

The shMultiTAG/DM according to the invention preferably comprises nucleotide sequences coding for at least one IEC of at least two of the autoantigens PPI, Gad67, Gad65, ICA69, IA-2, imogen and Hsp60, and include:

(a) a shMultiTAG/DM comprising nucleotide sequences coding for: (i) at least two of the amino acid sequences 5-24, 33-59 and 73-88 of PPI; and (ii) at least the two amino acid sequences 30-60 and 121-135 of Gad67, preferably comprising all said sequences, most preferably the shMultiTAG/DM depicted by the construct of FIG. 34 and having the nucleotide sequence depicted in FIG. 35;

(b) a shMultiTAG/DM comprising nucleotide sequences coding for: (i) at least two of the amino acid sequences 34-49, 199-214 and 348-362 of ICA69; (ii) at least the two amino acid sequences 789-819 and 840-874 of IA-2; and (iii) at least the amino acid sequence 263-278 of Imogen, preferably comprising all said sequences, more preferably the shMultiTAG/DM depicted by the construct of FIG. 38 and having the nucleotide sequence depicted in FIG. 39;

(c) a shMultiTAG/DM comprising nucleotide sequences coding for: (i) at least two of the amino acid sequences 5-24, 33-59, and 73-88 of PPI; (ii) at least the two amino acid sequences 30-60 and 121-135 of Gad67; (iii) at least two of the amino acid sequences 206-236, 247-282, 503-545, and 553-572 of Gad65; (iv) at least two of the amino acid sequences 34-49, 199-214 and 348-362 of ICA69; (v) at least the two amino acid sequences 789-819 and 840-874 of IA-2; and (vi) at least the amino acid sequence 263-278 of Imogen, preferably comprising all said sequences, more preferably the Y-DMPa gene depicted by the construct of FIG. 42 and having the nucleotide sequence depicted in FIG. 43, wherein shPPIG/DM comprises said sequences (i) and (ii) of PPI and Gad67, respectively, and shI3/DM comprises said sequences (iv), (v) and (vi) of ICA69, IA-2 and Imogen, respectively;

(d) a shMultiTAG/DM comprising nucleotide sequences coding for: (i) at least two of the amino acid sequences 5-24, 33-59, and 73-88 of PPI; (ii) at least the two amino acid sequences 30-60 and 121-135 of Gad67; (iii) at least two of the amino acid sequences 206-236, 247-282, 503-545, and 553-572 of Gad65; (iv) at least two of the amino acid sequences 34-49, 199-214 and 348-362 of ICA69; (v) at least the two amino acid sequences 789-819 and 840-874 of IA-2; and (vi) at least the amino acid sequence 263-278 of Imogen, preferably comprising all said sequences, more preferably the Y-DMPc gene depicted by the construct of FIG. 42e and having the nucleotide sequence depicted in FIG. 43a, wherein shPPI/DM comprises said sequences (i) of PPI, shGad67/65/DM comprises said sequences (ii) and (iii) of Gad67 and Gad 65, respectively, and shI3/DM comprises said sequences (iv), (v) and (vi) of ICA69, IA-2 and Imogen, respectively;

(e) a shMultiTAG/DM comprising nucleotide sequences coding for: (i) at least two of the amino acid sequences 5-24, 33-59, 73-88, of PPI; (ii) at least the two amino acid sequences 30-60 and 121-135 of Gad67; (iii) at least two of the amino acid sequences 206-236, 247-282, 503-545, and 553-572 of Gad65; (iv) at least two of the amino acid sequences 34-49, 199-214 and 348-362 of ICA69; (v) at least the two amino acid sequences 789-819 and 840-874 of IA-2; (vi) at least the amino acid sequence 263-278 of Imogen; and (vii) at least the two amino acid sequences 438-460 and 469-484 of Hsp60; preferably comprising all said sequences, more preferably the Y-DMPb gene depicted by the construct of FIG. 44 and having the nucleotide sequence depicted in FIG. 45, wherein shPPIG/DM comprises said sequences (i) and (ii) of PPI and Gad67, respectively, shGad65/DM corresponds to said sequences (iii) of Gad65, shI3/DM comprises said sequences (iv), (v) and (vi) of ICA69, IA-2 and Imogen, respectively, and shHSP/DM corresponds to said sequences (vii) of Hsp60; and (f) a shMultiTAG/DM comprising nucleotide sequences coding for: (i) at least two of the amino acid sequences 5-24, 33-59, 73-88, of PPI; (ii) at least the two amino acid sequences 30-60 and 121-135 of Gad67; (iii) at least two of the amino acid sequences 206-236, 247-282, 503-545, and 553-572 of Gad65; (iv) at least two of the amino acid sequences 34-49, 199-214 and 348-362 of ICA69; (v) at least the two amino acid sequences 789-819 and 840-874 of IA-2; (vi) at least the amino acid sequence 263-278 of Imogen; and (vii) at least the two amino acid sequences 438-460 and 469-484 of Hsp60; preferably comprising all said sequences, more preferably the Y-DMPg gene depicted by the construct of FIG. 44a and having the nucleotide sequence depicted in FIG. 45a, wherein shPPI/DM comprises said sequences (i) of PPI, shGad67/65/DM comprises said sequences (ii) and (iii) of Gad67 and Gad 65, respectively, shI3/DM comprises said sequences (iv), (v) and (vi) of ICA69, IA-2 and Imogen, respectively, and shHSP/DM corresponds to said sequences (vii) of Hsp60.

E.3 The Synthetic Genes for Rheumatoid Arthritis (RA)

The sgTAGs and shMultiTAGs for RA, herein referred to as shTAG/RA and shMultiTAG/RA, respectively, comprise nucleotide sequences coding for IECs of autoantigen(s) related to RA, said autoantigen being selected from the group consisting of collagen type II, aggrecan, human chondrocyte glycoprotein 69 (HCgp-39), cartilage link protein, human 60 kDa heat shock protein (Hsp60), *Mycobacterium tuberculosis* 65 kDa heat shock protein (hsp65) and *Escherichia coli* DNAJ protein (EcoDNAJ).

Examples of shTAG/RA according to the invention include:

(i) a shTAG/RA comprising nucleotide sequences coding for at least two of the amino acid sequences 73-98, 253-275, 285-303, 442-456, 606-622 and 924-943 of collagen type II, preferably comprising the six sequences, more preferably the shCollagen/RA gene depicted by the construct of FIG. 46 and having the nucleotide sequence depicted in FIG. 47; and (ii) a shTAG/RA comprising nucleotide sequences coding for at least two of the amino acid sequences 89-103, 201-213, 298-312, 623-635, 1053-1092 and 1804-1820 of aggrecan, preferably comprising the six sequences, more preferably the shAggrecan/RA gene depicted by the construct of FIG. 48 and having the nucleotide sequence depicted in FIG. 49.

Examples of shMultiTAG/RA genes according to the invention include:

(a) a shMultiTAG/RA comprising nucleotide sequences coding for: (i) at least two of the amino acid sequences 79-95, 236-254 and 303-319 of HCgP-39; and (ii) at least the two amino acid sequences 207-219 and 281-305 of cartilage link protein, preferably comprising all said sequences, more preferably the shGPL/RA gene depicted by the construct of FIG. 50 and having the nucleotide sequence depicted in FIG. 51;

(b) a shMultiTAG/RA comprising nucleotide sequences coding for: (i) at least the two amino acid sequences 197-225 and 266-308 of Hsp60; (ii) at least the amino acid sequence 1-15 of hsp65; and (iii) at least the amino acid sequence 60-75 of EcoDNAJ; preferably comprising all said sequences, more preferably the shHSP/RA gene depicted by the construct of FIG. 52 and having the nucleotide sequence depicted in FIG. 53;

(c) a shMultiTAG/RA comprising nucleotide sequences coding for: (i) at least two of the amino acid sequences 73-98, 253-275, 285-303, 442-456, 606-622 and 924-943 of collagen type II; (ii) at least two of the amino acid sequences 89-103, 201-213, 298-312, 623-635, 1053-1092 and 1804-1820 of aggrecan; (iii) at least two of the amino acid sequences 79-95, 236-254 and 303-319 of HCgP-39; and (iv) at least the two amino acid sequences 207-219 and 281-305 of cartilage link protein; preferably comprising all said sequences, more preferably the Y-RAPa gene depicted by the construct of FIG. 54 and having the nucleotide sequence depicted in FIG. 55, wherein shGPL/RA comprises said sequences (iii) of HCgP-39 and (iv) of cartilage link protein;

(d) a shMultiTAG/RA comprising nucleotide sequences coding for: (i) at least two of the amino acid sequences 73-98, 253-275, 285-303, 442-456, 606-622 and 924-943 of collagen type II; (ii) at least two of the amino acid sequences 89-103, 201-213, 298-312, 623-635, 1053-1092 and 1804-1820 of aggrecan; (iii) at least two of the amino acid sequences 79-95, 236-254 and 303-319 of HCgP-39; (iv) at least the two amino acid sequences 207-219 and 281-305 of cartilage link protein; (v) at least the two amino acid sequences 197-225 and 266-308 of Hsp60; (vi) at least the amino acid sequence 1-15 of hsp65; and (vii) at least the amino acid sequence 60-75 of EcoDNAJ; preferably comprising all said sequences, more preferably the Y-RAPb gene depicted by the construct of FIG. 56 and having the nucleotide sequence depicted in FIG. 57, wherein shGPL/RA comprises said sequences (iii) of HCgP-39 and (iv) of cartilage link protein, and shHSP/Ra comprises said sequences (v) of Hsp60, (vi) of hsp65 and (vii) of EcoDNAJ;

(e) a truncated form of (c), comprising nucleotide sequences coding for: (i) at least two of the amino acid sequences 73-98, 253-275 and 285-303 of collagen type II; (ii) at least two of the amino acid sequences 89-103, 201-213, 298-312, and 1053-1092 of aggrecan; and (iii) least two of the amino acid sequences 79-95, 236-254 and 303-319 of HCgP-39, preferably comprising all said sequences, most preferably the "second generation" Y-MSPc gene comprising the shCollagen/RA, shAggrecan/RA, and shGPL/RA genes, depicted by the construct of FIG. 58 and having the nucleotide sequence depicted in FIG. 59, wherein shGPL/RA comprises said sequences (iii) of HCgP-39; and (f) a truncated form of (d), comprising nucleotide sequences coding for: (i) at least two of the amino acid sequences 73-98, 253-275 and 285-303 of collagen type II; (ii) at least two of the amino acid sequences 89-103, 201-213, 298-312, and 1053-1092 of aggrecan; (iii) at least two of the amino acid sequences 79-95, 236-254 and 303-319 of HCgP-39; (iv) at least the amino acid sequence 266-308 of Hsp60; and (v) at least the amino acid sequence 1-15 of hsp65; preferably comprising all said sequences, most preferably the "second generation" Y-MSPd gene depicted by the construct of FIG. 60 and having the nucleotide sequence depicted in FIG. 61, comprising the shCollagen/RA, shAggrecan/RA, shGPL/RA and shHSP/RA genes, wherein shGPL/RA comprises said sequences (iii) of HCgP-39 and shHSP/RA comprises said sequences (v) of Hsp60 and (vi) of hsp65.

F. Preparation of the Synthetic Genes

With knowledge of the autoantigens and immunogenic epitopic clusters associated with the disease, the skilled person may prepare the synthetic genes encoding the IECs of the appropriate autoantigens. The synthetic genes may contain the coding sequences for the IECs in any particular order, for example, the coding regions for all the clusters from each autoantigen may be grouped together or, alternatively, IECs from different autoantigens may be organized randomly along the synthetic genes. Preferably, the former arrangement prevails and each cluster coding region may be separated from the next by 3, 6, 9 etc. nucleotides or possibly by a restriction site. Any spacing sequences may be inserted in between the coding regions provided that the single open reading frame for the totality of cluster coding regions is retained. In a preferred embodiment, the synthetic gene codes for at least one, preferably 2-3, immunogenic epitopic clusters specific for each of at least two autoantigens, though it may be more preferable to include 4 or 5 or possibly more clusters from each autoantigen.

The synthetic gene coding for the IECs of autoantigens related to an autoimmune disease is obtained stepwise. A shTAG for each autoantigen encoding the selected IECs arranged tandemly is prepared by PCR overlap extension using overlapping synthetic oligonucleotides encoding the IECs. A shMultiTAG encoding randomly organized IECs of several autoantigens is prepared by ligating together the resulting shTAGs in one open reading frame to form the desired shMultiTAG. Other available technologies of molecular biology can be used by a person skilled in the art to prepare the synthetic genes of the invention.

G. The Polypeptides of the Invention

The synthetic genes of the invention under appropriate conditions will express a polypeptide that will contain a multiplicity of IEC's. Such polypeptides form a further aspect of the present invention.

In this aspect, the present invention provides a synthetic polypeptide that comprises amino acid sequences of at least two immunogenic epitopic clusters (hereinafter IEC) of autoantigens related to a specific autoimmune disease, said synthetic polypeptide being selected from:

(i) a synthetic human polypeptide (hereinafter shPEP) comprising amino acid sequences of at least two IECs of a sole autoantigen related to said autoimmune disease; and (ii) a synthetic human multitarget polypeptide (hereinafter shMultiPEP) comprising amino acid sequences of at least one IEC of at least two different autoantigens related to said autoimmune disease.

None of the polypeptides exemplified in the present description and drawings include two adjacent IEC's, either fused in contiguity or separated by a synthetic spacer, that together form a contiguous natural sequence within a native autoantigen.

This aspect of the invention further includes analogs of the polypeptides of the invention obtained by substitution, variation, modification, replacement, deletion, or addition of one (or more) amino acid residues from or to the sequence of the polypeptide, provided that immunogenicity or more preferably, the immunomodulatory activity of the IEC is retained.

G.1 The Polypeptides for MS

The shPEPs and shMultiPEPs for MS, herein referred to as shPEP/MS and shMultiPEP/MS, respectively, comprise amino acid sequences of IECs of autoantigen(s) related to MS, said autoantigen being selected from the group consisting of myelin-associated glycoprotein (MAG), myelin basic protein (MBP), myelin oligodendrocyte glycoprotein (MOG), myelin-oligodendrocytic basic protein (MOBP), oligodendrocyte-specific protein (OSP) and proteolipid protein (PLP).

Examples of shPEP/MS according to the invention include:

(i) a shPEP/MS comprising at least two of the amino acid sequences 1-25, 32-58, and 63-97 of MOG, preferably comprising the three sequences, more preferably the shPEP/MS having the amino acid sequence depicted in FIG. 3;

(ii) a shPEP/MS comprising at least two of the amino acid sequences 3-27, 34-56, 67-114, and 205-215 of MOG, preferably comprising the four sequences, more preferably the shPEP/MS having the amino acid sequence depicted in FIG. 21;

(iii) a shPEP/MS comprising at least two of the amino acid sequences 7-50, 83-106, and 142-168 of MBP, preferably comprising the three sequences, more preferably the shPEP/MS having the amino acid sequence depicted in FIG. 6;

(iv) a shPEP/MS comprising at least two of the amino acid sequences 12-42, 84-111, and 141-168 of MBP, preferably comprising the three sequences, more preferably the shPEP/MS having the amino acid sequence depicted in FIG. 23;

(v) a shPEP/MS comprising at least two of the amino acid sequences 30-60, 84-116, and 139-155 of PLP, preferably comprising the three sequences, more preferably the shPEP/MS having the amino acid sequence depicted in FIG. 8;

(vi) a shPEP/MS comprising at least two of the amino acid sequences 38-52, 103-150, 177-203, 218-240, and 264-276 of PLP, preferably comprising the five sequences, more preferably the shPEP/MS having the amino acid sequence depicted in FIG. 25;

(vii) a shPEP/comprising at least two of the amino acid sequences 1-23, 30-49, and 65-90 of MOBP, preferably comprising the three sequences, more preferably the shPEP/MS having the amino acid sequence depicted in FIG. 10;

(viii) a shPEP/MS comprising at least two of the amino acid sequences 15-33, 55-90, and 156-172 of MOBP, preferably comprising the three sequences, more preferably the shPEP/MS having the amino acid sequence depicted in FIG. 27; and (ix) a shPEP/MS comprising at least two of the amino acid sequences 21-34, 42-73, 98-109, 130-146, and 183-203 of OSP, preferably comprising the five sequences, more preferably the shPEP/MS having the amino acid sequence depicted in FIG. 29.

The shMultiPEP/MS of the invention preferably comprise the amino acid sequences of at least two IECs specific for each of at least three of the autoantigens MAG, MBP, MOG, MOBP, OSP and PLP, and include:

(a) a shMultiPEP/MS comprising: (i) at least two of the amino acid sequences 1-25, 32-58 and 63-97 of MOG; (ii) at least two of the amino acid sequences 7-50, 83-106, and 142-168 of MBP; and (iii) at least two of the amino acid sequences 30-60, 84-116 and 139-155 of PLP, preferably all said sequences, more preferably the shMultiPEP/S of the amino acid sequence depicted in FIG. 12;

(b) a shMultiPEP/MS comprising: (i) at least two of the amino acid sequences 1-25, 32-58 and 63-97 of MOG; (ii) at least two of the amino acid sequences 7-50, 83-106, and 142-168 of MBP; (iii) at least two of the amino acid sequences 30-60, 84-116 and 139-155 of PLP; and (iv) at least two of the amino acid sequences 1-23. 30-49 and 65-90 of MOPB, preferably all said sequences, more preferably the shMultiPEP/S of the amino acid sequence depicted in FIG. 15;

(c) a shMultiPEP/MS comprising: (i) at least two of the amino acid sequences 3-27, 34-56, 67-114 and 205-215 of MOG; (ii) at least two of the amino acid sequences 12-42, 84-111 and 141-168 of MBP; (iii) at least two of the amino acid sequences 38-52, 103-150, 177-203, 218-240 and 264-276 of PLP; (iv) at least two of the amino acid sequences 21-34, 42-73, 98-109, 130-146 and 183-203 of OSP; and (v) at least two of the amino acid sequences 15-33, 55-90 and 156-172 of MOBP, preferably all said amino acid sequences, most preferably the amino acid sequence depicted in FIG. 31; and (d) the truncated form of (c), comprising the amino acid sequences 34-56 and 67-114 of MOG; 84-111 and 141-168 of MBP; 103-150, 177-203 and 218-240 of PLP; 42-73, 98-109 and 183-203 of OSP; and 15-33 and 55-90 of MOBP, most preferably the amino acid sequence depicted in FIG. 33.

G.2 The Polypeptides for IDDM

The shPEPs and shMultiPEPs for IDDM, herein referred to as shPEP/DM and shMultiPEP/DM, respectively, comprise amino acid sequences of IECs of autoantigen(s) related to IDDM, said autoantigen being selected from the group consisting of preproinsulin (PPI), 67 kDa glutamic acid decarboxylase (Gad67), 65 kDa glutamic acid decarboxylase (Gad65), islet cell antigen p69 (ICA69), tyrosine phosphatase islet antigen 2 (IA-2), imogen and 60 kDa human heat shock protein (Hsp60).

Examples of shPEP/DM according to the invention include:

(i) a shPEP/DM comprising at least two of the amino acid sequences 206-236, 247-282, 503-545, and 553-572 of Gad65, preferably the four sequences, more preferably the shPEP/DM having the amino acid sequence depicted in FIG. 37; and (ii) a shPEP/DM comprising at least the two amino acid sequences 438-460 and 469-484 of Hsp60, preferably the two sequences, more preferably the shPEP/DM having the amino acid sequence depicted in FIG. 41.

Examples of shMultiPEP/DM according to the invention include:

(a) a shMultiPEP/DM comprising: (i) at least two of the amino acid sequences 5-24, 33-59 and 73-88 of PPI; and (ii) at least the two amino acid sequences 30-60 and 121-135 of Gad67, preferably all said sequences, more preferably the shMultiPEP/DM having the amino acid sequence depicted in FIG. 35;

(b) a shMultiPEP/DM comprising: (i) at least two of the amino acid sequences 34-49, 199-214 and 348-362 of ICA69; (ii) at least the two amino acid sequences 789-819 and 840-874 of IA-2; and (iii) at least the amino acid sequence 263-278 of Imogen, preferably all said sequences, more preferably the shMultiPEP/DM having the amino acid sequence depicted in FIG. 39;

(c) a shMultiPEP/DM comprising: (i) at least two of the amino acid sequences 5-24, 33-59, and 73-88 of PPI; (ii) at least the two amino acid sequences 30-60 and 121-135 of Gad67; (iii) at least two of the amino acid sequences 206-236, 247-282, 503-545, and 553-572 of Gad65; (iv) at least two of the amino acid sequences 34-49, 199-214 and 348-362 of ICA69; (v) at least the two amino acid sequences 789-819 and 840-874 of IA-2; and (vi) at least the amino acid sequence 263-278 of Imogen, preferably all said sequences, more preferably the shMultiPEP/DM having the amino acid sequence depicted in FIG. 43;

(d) a shMultiPEP/DM comprising: (i) at least two of the amino acid sequences 5-24, 33-59, 73-88, of PPI; (ii) at least the two amino acid sequences 30-60 and 121-135 of Gad67; (iii) at least two of the amino acid sequences 206-236, 247-282, 503-545, and 553-572 of Gad65; (iv) at least two of the amino acid sequences 34-49, 199-214 and 348-362 of ICA69; (v) at least the two amino acid sequences 789-819 and 840-874 of IA-2; (vi) at least the amino acid sequence 263-278 of Imogen; and (vii) at least the two amino acid sequences 438-460 and 469-484 of Hsp60, preferably all said sequences, more preferably the shMultiPEP/DM having the amino acid sequence depicted in FIG. 45.

G.3 The Polypeptides for RA

The shPEPs and shMultiPEPs for RA, herein referred to as shPEP/RA and shMultiPEP/RA, respectively, comprise amino acid sequences of IECs of autoantigen(s) related to RA, said autoantigen being selected from the group consisting of collagen type II, aggrecan, human chondrocyte glycoprotein 69 (HCgp-39), cartilage link protein, human 60 kDa heat shock protein (Hsp60), *Mycobacterium tuberculosis* 65 kDa heat shock protein (hsp65) and *Escherichia coli* DNAJ protein (EcoDNAJ).

Examples of shPEP/RA according to the invention include:

(i) a shPEP/RA comprising at least two of the amino acid sequences 73-98, 253-275, 285-303, 442-456, 606-622 and 924-943 of collagen type II, preferably the six sequences, more preferably the shPEP/RA having the amino acid sequence depicted in FIG. 47; and (ii) a shPEP/RA comprising at least two of the amino acid sequences 89-103, 201-213, 298-312, 623-635, 1053-1092 and 1804-1820 of aggrecan; preferably the six sequences, more preferably the shPEP/RA of the amino acid sequence depicted in FIG. 49.

Examples of shMultiPEP/RA according to the invention include:

(a) a shMultiPEP/RA comprising: (i) at least two of the amino acid sequences 79-95, 236-254 and 303-319 of HCgP-39; and (ii) at least the two amino acid sequences 207-219 and 281-305 of cartilage link protein, preferably all said sequences, more preferably the shMultiPEP/RA of the amino acid sequence depicted in FIG. 51;

(b) a shMultiPEP/RA comprising: (i) at least the two amino acid sequences 197-225 and 266-308 of Hsp60; (ii) at least the amino acid sequence 1-15 of hsp65; and (iii) at least the amino acid sequence 60-75 of EcoDNAJ, preferably all said sequences, more preferably the shMultiPEP/RA of the amino acid sequence depicted in FIG. 53;

(c) a shMultiPEP/RA comprising: (i) at least two of the amino acid sequences 73-98, 253-275, 285-303, 442-456, 606-622 and 924-943 of collagen type II; (ii) at least two of the amino acid sequences 89-103, 201-213, 298-312, 623-635, 1053-1092 and 1804-1820 of aggrecan; (iii) at least two of the amino acid sequences 79-95, 236-254 and 303-319 of HCgP-39; and (iv) at least the two amino acid sequences 207-219 and 281-305 of cartilage link protein, preferably all said sequences, more preferably the shMultiPEP/RA of the amino acid sequence depicted in FIG. 55;

(d) a shMultiPEP/RA comprising: (i) at least two of the amino acid sequences 73-98, 253-275, 285-303, 442-456, 606-622 and 924-943 of collagen type II; (ii) at least two of the amino acid sequences 89-103, 201-213, 298-312, 623-635, 1053-1092 and 1804-1820 of aggrecan; (iii) at least two of the amino acid sequences 79-95, 236-254 and 303-319 of HCgP-39; (iv) at least the two amino acid sequences 207-219 and 281-305 of cartilage link protein; (v) at least the two amino acid sequences 197-225 and 266-308 of Hsp60; (ii) at least the amino acid sequence 1-15 of hsp65; and (iii) at least the amino acid sequence 60-75 of EcoDNAJ, preferably all said sequences, more preferably the shMultiPEP/RA of the amino acid sequence depicted in FIG. 57;

(e) a shMultiPEP/RA being a truncated form of (c) above and comprising: (i) at least two of the amino acid sequences 73-98, 253-275 and 285-303 of collagen type II; (ii) at least two of the amino acid sequences 89-103, 201-213, 298-312, and 1053-1092 of aggrecan; and (iii) at least two of the amino acid sequences 79-95, 236-254 and 303-319 of HCgP-39, preferably all said sequences, more preferably the shMulti-PEP/RA of the amino acid sequence depicted in FIG. 59; and (f) a shMultiPEP/RA being a truncated form of (d), and comprising: (i) at least two of the amino acid sequences 73-98, 253-275 and 285-303 of collagen type II; (ii) at least two of the amino acid sequences 89-103, 201-213, 298-312, and 1053-1092 of aggrecan; (iii) at least two of the amino acid sequences 79-95, 236-254 and 303-319 of HCgP-39; (iv) at least the amino acid sequence 266-308 of Hsp60; and (v) at least the amino acid sequence 1-15 of hsp65, preferably all said sequences, more preferably the shMultiPEP/RA of the amino acid sequence depicted in FIG. 61.

H. Testing Sequence Homology of the Synthetic Genes and Polypeptides

Sequence identity with respect to the sequences can be determined by a simple "eyeball" comparison (i.e. a strict comparison) of any one or more of the sequences with another sequence to see if that other sequence has, for example, at least 75% sequence identity to the sequence(s).

Relative sequence identity can also be determined by commercially available computer programs that can calculate % identity between two or more sequences using any suitable algorithm for determining identity, using for example default parameters. A typical example of such a computer program is CLUSTAL. For this purpose, the BLAST (Basic Local Alignment Search Tool) algorithm, described in detail at www.ncbi.nih.gov/BLAST/blast_help.html, incorporated herein by reference, can be employed, with parameters set to default values. The search parameters defined as follows, can be advantageously set to the defined default parameters. Advantageously, "substantial identity" when assessed by BLAST equates to sequences which match with an EXPECT value of at least about 7, preferably at least about 9 and most preferably 10 or more. The default threshold for EXPECT in BLAST searching is usually 10.

The BLAST programs were tailored for sequence similarity searching, for example to identify homologues to a query sequence. For a discussion of basic issues in similarity searching of sequence databases, see Altschul et al (1994) Nature Genetics 6:119-129. The five BLAST programs available at www.ncbi.nlm.nih.gov perform the following tasks: BLASTP compares an amino acid query sequence against a protein sequence database; BLASTN compares a nucleotide query sequence against a nucleotide sequence database; BLASTX compares the six-frame conceptual translation products of a nucleotide query sequence (both strands) against a protein sequence database; TBLASTN compares a protein query sequence against a nucleotide sequence database dynamically translated in all six reading frames (both strands); and TBLASTX compares the six-frame translations of a nucleotide query sequence against the six-frame translations of a nucleotide sequence database.

Most preferably, sequence comparisons are conducted using the simple BLAST search algorithm provided at www.ncbi.nlm.nih.gov/BLAST. However, other computer programs can be used to determine identify and similarity between the two sequences including, but not being limited to the GCG program package (Devereux et al 1984 Nucleic Acids Research 12: 387) and FASTA (Atschul et al 1990 J Molec Biol 403-410).

I. Expression Vectors, Host Cells, Protein Expression and Purification

The synthetic genes of the present invention can be incorporated into expression vector that may be, for example, plasmid or virus vectors provided with an origin of replication, optionally a promoter for the expression of the said synthetic gene and optionally a regulator of the promoter. The recombinant expression vector may then be used to transform or transfect suitable host cells such as bacterial cells, e.g. *E. coli* cells, or eukaryotic cells such as yeast, insect or preferably, mammalian cells, to provide for expression of a polypeptide of the invention. This process may comprise culturing a host cell transformed with an expression vector as described above under conditions to provide for expression of the polypeptide. The expressed polypeptide is then recovered by extraction from the host cells by a variety of techniques known in the art, including enzymatic, chemical and/or osmotic lysis and physical disruption, and isolated by protein purification methods known in the art, such as metal chelate chromatography, HPLC, antibody-affinity chromatography etc.

J. Pharmaceutical Compositions

The present invention also provides pharmaceutical compositions for the treatment of an autoimmune disease such as MS, IDDM and RA, comprising at least one synthetic gene according to the invention and a suitable gene delivery vehicle (GDV) for delivery of the synthetic gene to a target cell population ex vivo or in vivo.

The GDV can be designed by a person ordinarily skilled in the art of recombinant DNA technology and gene therapy to express the polypeptide at appropriate levels and with the cellular specificity demanded by a particular application. The vector comprising the synthetic gene can be delivered by viral or non-viral techniques. Non-viral delivery systems include, but are not limited to, DNA transfection methods using a non-viral vector to deliver a synthetic gene of the invention to a target mammalian cell. Viral delivery systems include, but are not limited to, adenovirus vector, an adeno-associated viral (AAV) vector, a herpes viral vector, a retroviral vector, a lentiviral vector or a baculoviral vector.

The present invention further provides pharmaceutical compositions for the treatment of an autoimmune disease such as MS, IDDM and RA, comprising at least one polypeptide according to the invention and a suitable pharmaceutically acceptable carrier.

The formulation will depend upon the route of administration but typically they can be formulated for topical, parenteral, intramuscular, intravenous, intra-peritoneal, intranasal inhalation, lung inhalation, intradermal or intra-articular administration. The polypeptide may be administered in an injectable form. It may therefore be mixed with any vehicle which is pharmaceutically acceptable for injectable formulation, preferably for a direct injection at the site to be treated, although it may be administered systemically.

The pharmaceutically acceptable carrier or diluent may be, for example, sterile isotonic saline solutions, or other isotonic solutions such as phosphate-buffered saline. Additional ingredients of the formulations include suitable binder(s), lubricant(s), suspending agent(s), coating agent(s), solubilising agent(s).

Typically, the physician will determine the actual dosage which will be most suitable for an individual patient and it will vary with the age, weight and response of the particular patient. There can, of course, be individual instances where higher or lower dosage ranges are merited, and such are within the scope of this invention.

Alternatively, the polypeptides can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin. They can also be incorporated, at a concentration of between 1 and 10% by weight, into an ointment consisting of a white wax or white soft paraffin base together with stabilisers and preservatives.

For some applications, preferably the compositions are administered orally in the form of tablets containing excipients such as starch or lactose, or in capsules or ovules either alone or in admixture with excipients, or in the form of elixirs, solutions or suspensions containing flavouring or colouring agents.

The compositions as well as the polypeptides alone can also be injected parenterally, for example intracavernosally, intravenously, intramuscularly or subcutaneously. In this case, the compositions will comprise a suitable carrier or diluent. For parenteral administration, the compositions are best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner. For oral, parenteral, buccal and sublingual administration to subjects (such as patients), the daily dosage level of the compounds of the present invention and their pharmaceutically acceptable salts and solvates may typically be from 10 to 500 mg (in single or divided doses). Thus, and by way of example, tablets or capsules may contain from 5 to 100 mg of active compound for administration singly, or two or more at a time, as appropriate. As indicated above, the physician will determine the actual dosage which will be most suitable for an individual patient and it will vary with the age, weight and response of the particular patient. It is to be noted that whilst the above-mentioned dosages are exemplary of the average case there can, of course, be individual instances where higher or lower dosage ranges are merited and such dose ranges are within the scope of this invention.

When injected in a soluble tolerogenic route (s.c., i.v. or i.p.) or administered by oral or nasal application, the gene consisting of the major immunodominant epitopes associated with MS, is expected to downregulate the potentially pathogenic autoimmune responses in MS. Alternatively, when administered as a naked DNA constructed into an appropriate mamalian expression vector, the synthetic gene can be effective in vaccinating against the disease. The construction of the synthetic gene encoding for the myelin-like protein, the expression, purification and refolding of the protein product is described in the Examples, and their potential protective and/or curative effect were tested on EAE induced with MBP, PLP, MOG, MOBP, or on EAE induced with the whole mouse spinal cord homogenate (MSCH).

As used herein the terms protein and polypeptide and peptide may be assumed to be synonymous, protein merely being used in a general sense to indicate a relatively longer amino acid sequence than that present in a polypeptide, and polypeptide merely being used in a general sense to indicate a relatively longer amino acid sequence than that present in a peptide. Generally for ease of reference only we will simply refer to the term polypeptide.

K. Diagnostic Compositions

ShTAGs and shMultiTAGs related to a given autoimmune disease can be used for diagnosis and/or monitoring the progression of said autoimmune disease by measuring the levels of immunoactivation of T- and B-cells specific for the autoantigen(s) associated with the disease. T- or B-cell responses to shTAGs or shMultiTAGs are likely to be higher in patients than in control individuals, and measurement of such responses by blood cells or serum can be used as a diagnostic/monitoring tool.

The levels of T-cell autoreactivity to the shTAGs and shMultiTAGs related to the disease are measured by incubating PBLs isolated from peripheral blood in the presence of the relevant shTAGs and shMultiTAGs, and monitoring the activation of the reactive T-cells by detection of T-cell proliferation, cytokine release and expression of cytokine receptors and other activation-associated cell surface markers. Such assays of T-cell activation are well known to those of skill in the art.

The levels of B-cell autoreactivity to the shTAGs and shMultiTAGs related to the disease are measured by reacting serum (or relevant body fluids such as CSF, synovial fluid and the like) with the shTAGs and shMultiTAGS in antibody detection assays such as enzyme-linked immunosorbent assays, radioimmunoassays, immunoradiometric assays and luminescence assays, including immunoblotting, all of which are assays well known to those of skill in the art.

EXAMPLES

Figure 4:
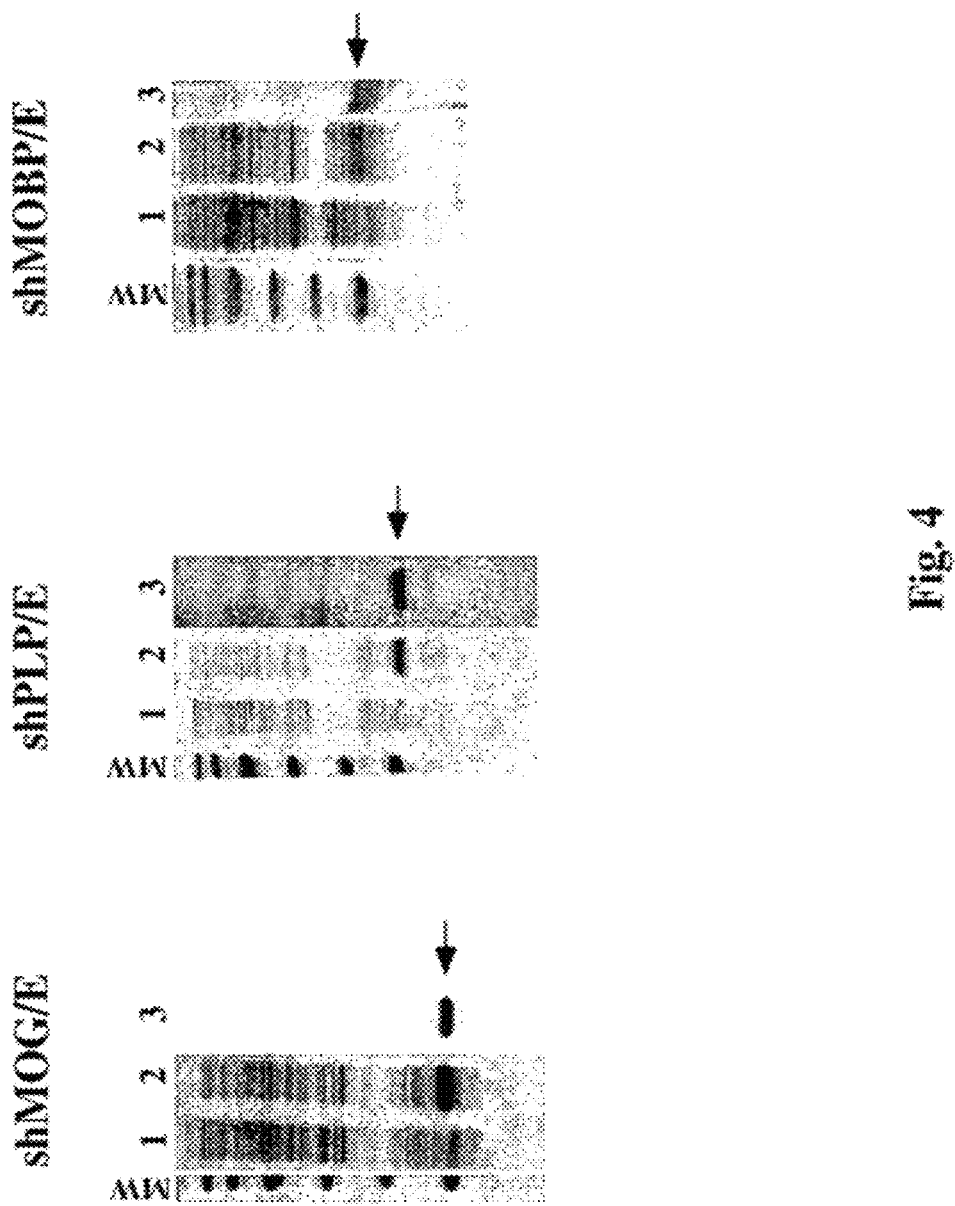
FIG. 4 are Coomassie Blue-stained SDS-PAGE pictures showing bacterial expression and purified polypeptide products of the following synthetic human target autoantigen genes related to MS (shTAG/MS): shMOG/E (left), shPLP/E (middle) and shMOBP/E (right).

The invention will now be described in further detail with reference to the following non-limiting examples.

Example 1

General Method for Construction of the Synthetic Genes

FIG. 1 shows a general scheme for the preparation of a shMultiTAG for a given autoimmune disease. For each target autoantigen, once the disease-relevant epitopes have been identified, the DNA sequences encoding the different IECs selected to compose the shTAG are organized in tandem and examined for potential problems at the DNA or expressed protein levels. When necessary, modifications of the DNA sequences include alterations not resulting in amino acid changes, to neutralize possibly problematic endonuclease restriction sites, to minimize formation of DNA secondary structures or to "bacterize" codons, as well as alterations leading to cysteine to serine substitution in order to increase the solubility of the expressed protein.

To prepare the shTAG, DNA sequences corresponding to endonuclease restriction sites are also added to facilitate cloning or, if needed, to enable construction of shMultiTAG with preferred IECs. The sequences are also engineereed to contain a stop codon enabling individual expression of each shTAG if desired. Complementary overlapping oligonucleotides spanning the desired sequence encoding the joined IECs are then synthesized to prepare the shTAG by PCR overlap extension and amplification. Each shTAG is then cloned in a bacterial expression vector and the expressed protein is purified and tested for its immunogenicity and potential immunomodulatory effect. The shTAGs are ligated together in one open reading frame via the designed restriction sites at their 5' and/or 3' end, to generate the shMultiTAG.

The following examples present the data obtained with "pilot preparations" of shTAGs and shMultiTAGs relevant for MS.

Example 2

Construction of Pilot shTAGs and shMultiTAGs for MS

The shMultiTAGs related to MS are designated Y-MSP genes coding for MS-related Proteins (Y-MSP). The Y-MSPa gene was constructed by sequentially ligating the following shTAGs: shMOG/E, shMBP/E and shPLP/E genes. Following our finding that MOBP may also be a highly relevant target antigen for MS, Y-MSPb gene was then constructed in which shMOBP/E gene was ligated to the Y-MSPa gene.

2.1. Construction of the shMOG/E Gene (FIG. 2)

Studies from our laboratory (Kerlero de Rosbo et al., 1997) have indicated that the autoimmune reactivity against MOG by MS PBLs is predominantly directed against three epitope clusters located within amino acids 1-22, 34-56, and 64-96 of the human MOG molecule. The shMOG/E gene was designed to encode a polypeptide comprising the amino acids encompassed by these regions of MOG, in tandem. Thus, 60-70 nucleotide-long oligonucleotides representing codons of the amino acid residues in these regions of the human MOG were synthesized. The oligonucleotides 1 to 6 in FIG. 2 overlap at their 5' and/or 3' ends by 15-18 nucleotides which are complementary to their neighboring oligonucleotides. Specific restriction endonuclease sites were included in the first and the last oligonucleotide to facilitate cloning, as well as to enable in frame ligation to neighboring shTAGs (see below for the construction of the Y-MSP genes). A template for the shMOG/E gene was prepared by mixing the oligonucleotides (75 pmoles) at 1:1 molar ratio (40 l final volume), denaturing at 94° C. for 1 min., and PCR overlap extension was carried out at 72° C. for 5 min in the presence of dNTPs and Taq polymerase, following annealing of the oligonucleotides through their complementary ends at 55° C. for 2 min. The resulting template (5 l) was amplified by PCR at standard conditions for 30 cycles, using oligonucleotides 1a and 6 as primers. The amplified PCR product of the expected size was eluted from agarose gel and subcloned into a T vector (pGEM-T). The constructed shMOG/E gene was cleaved out from the pGEM-T/shMOG/E plasmid and subcloned into the pRSET bacterial expression vector 3' to its 6×His tag, using standard molecular biology techniques. DNA sequence analysis was performed using the pRSET-specific primers to confirm the shMOG/E DNA sequence as an open reading frame with the ATG of the pRSET expression vector.

The pRSET/shMOG/E gene was transformed into *E. coli* BL21-DE3 cells where expression of shMOG/E polypeptide was induced by IPTG, and the polypeptide was purified as described below. The DNA sequence and derived amino acid sequence of shMOG/E are shown in FIG. 3; SDS-PAGE of bacterial expression of shMOG/E and of purified shMOG/E are shown in FIG. 4.

2.2. Construction of the shMBP/E Gene (FIG. 5)

Studies from our and other laboratories have indicated that PBLs of MS patients recognize epitopes of MBP mostly clustered within amino acids 7-50, 83-106 and 143-169 (reviewed in Kerlero de Rosbo and Ben-Nun, 1998). The shMBP/E gene encodes a polypeptide which comprises the amino acid residues encompassed by these regions of MBP sequentially, and in tandem. The shMBP/E gene was constructed using the strategy and the oligonucleotides shown in FIG. 5, according to the protocol detailed for the shMOG/E gene in Example 2.1 above. The DNA sequence and derived amino acid sequence of shMBP/E are shown in FIG. 6.

2.3. Construction of the shPLP/E Gene (FIG. 7)

Reports from several laboratories (reviewed in Tuohy, 1994) have indicated that the potentially pathogenic autoimmune reactivity to PLP by PBLs from MS patients is frequently directed against three major regions, encompassed by amino acids 40-60, 89-116 and 139-151 of PLP. The shPLP/E gene was designed to code for a protein which comprises the amino acid residues encompassed by these regions of PLP sequentially, and in tandem. The shPLP/E gene was constructed using the strategy and the oligonucleotides shown in FIG. 7 and expressed according to the protocol detailed for the shMOG/E gene in Example 2.1 above. The DNA sequence and derived amino acid sequence of shPLP/E are shown in FIG. 8; SDS-PAGE of bacterial expression of shPLP/E and of purified shPLP/E is shown in FIG. 4.

2.4. Construction of the shMOBP/E Gene (FIG. 9)

We have recently demonstrated epitopes of MOBP recognized by PBLs of MS patients, which are located within amino acids 1-22, 30-50, and 65-88 (Kaye et al., 2000). The shMOBP/E gene was designed to code for a protein which comprises the amino acids of these regions, in tandem. The shMOBP/E gene was constructed using the strategy and the oligonucleotides shown in FIG. 9 and expressed according to the protocol detailed for the shMOG/E gene in Example 2.1 above. The DNA sequence and derived amino acid sequence of shMOBP/E are shown in FIG. 10; SDS-PAGE of bacterial expression of shMOBP/E and of purified shMOBP/E is shown in FIG. 4.

2.5. Construction of the Y-MSPa Gene (FIG. 11)

Figure 11:
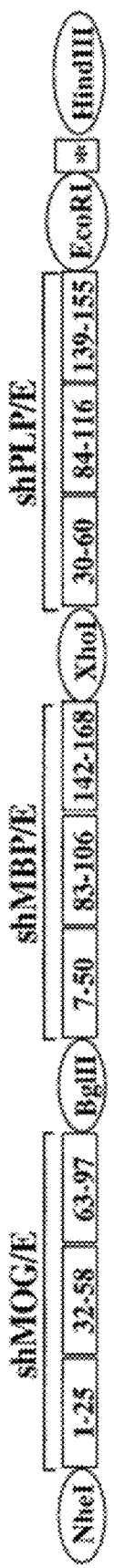
FIG. 11 depicts the construct of the shMultiTAG/MS (shMultiTAG related to multiple sclerosis) herein designated Y-MSPa gene.

For construction of the Y-MSPa gene, the shMOG/E, shMBP/E and shPLP/E genes were ligated sequentially via specific endonuclease restriction sites which had been incorporated to allow their ligation in one open reading frame as shown in the scheme (FIG. 11). To this end, the shPLP/E gene was excised from pGEM-T/shPLP/E with XhoI and HindIII, the shMBP/E gene was excised from pGEM-T/shMBP/E with BglII and XhoI, and pGEM-T/shMOG/E was cleaved at the BglII and HindIII sites. The relevant electrophoresed DNA fragments were eluted from the gels, cleaned and subjected to triple ligation to make the pGEM-T/Y-MSPa. The Y-MSPa DNA was then cleaved out using NheI and HindIII and subcloned into the pRSET bacterial expression vector, 3' to its 6×His tag. DNA sequence analysis was performed using the pRSET-specific primers to confirm the Y-MSPa DNA sequence as an open reading frame with the ATG of the pRSET expression vector. The pRSET/Y-MSPa was transformed into *E. coli* BL21-DE3. The DNA sequence and derived amino acid sequence of Y-MSPa are shown in FIG. 12; SDS-PAGE of bacterial expression of Y-MSPa and of purified Y-MSPa is shown in FIG. 13.

2.6. Construction of the Y-MSPb Gene (FIG. 14)

Figure 14:
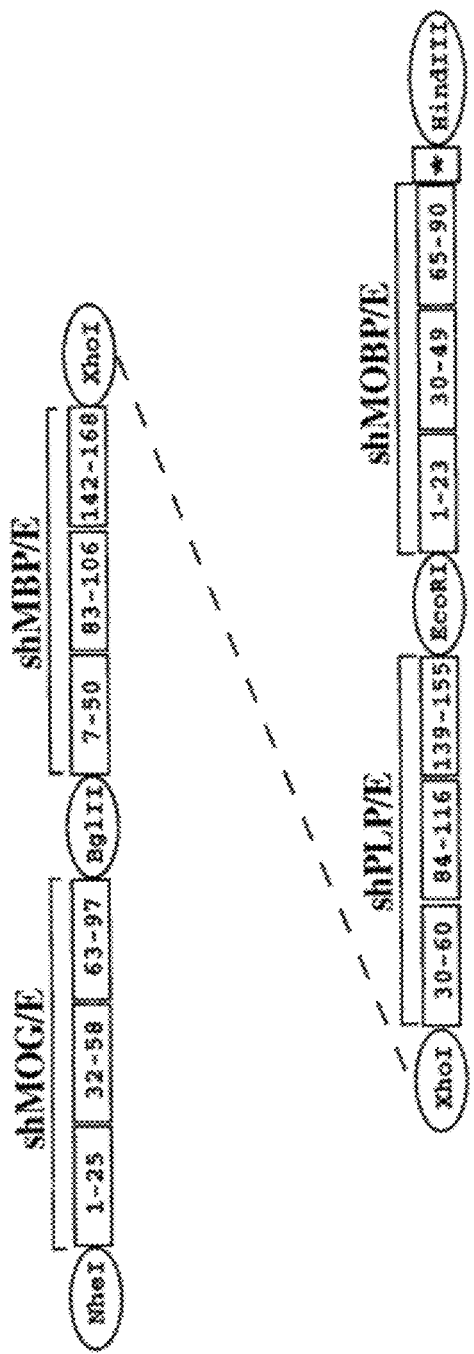
FIG. 14 depicts the construct of the shMultiTAG/MS (shMultiTAG related to multiple sclerosis) herein designated Y-MSPb gene.

To construct the Y-MSPb gene, the shMOBP/E gene was excised from pGEM-T/shMOBP/E with EcoRI and HindIII and ligated into the EcoRI/HindIII sites of the pRSET/Y-MSPa in one open reading frame (FIG. 14). After confirmation of Y-MSPb DNA sequence, the pRSET/Y-MSPb was transformed into *E. coli* BL21-DE3. The DNA sequence and derived amino acid sequence of Y-MSPb are shown in FIG. 15; SDS-PAGE of bacterial expression of Y-MSPb and of purified Y-MSPb is shown in FIG. 13.

Example 3

Purification and Refolding of the Synthetic Gene Products

For each of the pRSET/shMOG/E, pRSET/shMBP/E, pRSET/shPLP/E, pRSET/shMOBP/E, pRSET/Y-MSPa or pRSET/Y-MSPb *E. coli* transformants, a colony exhibiting the highest level of expression of the relevant recombinant protein was selected for large-scale induction of protein expression and preparation of inclusion bodies. The expressed protein was purified under denaturing conditions (8 M urea) by metal chelate chromatography, as per the manufacturer's instructions. Fractions containing purified protein, as evidenced by SDS-PAGE, were pooled and subjected to reducing conditions with -mercaptoethanol. The protein was then diluted to 50-100 g/ml in 8 M urea and allowed to refold by dialysis against gradually decreasing concentrations of urea (8 M to 0 M). Aggregated protein was removed by centrifugation and the soluble protein was lyophilized after estimating the protein concentration by Bradford reaction. Samples were analyzed by SDS-PAGE for their purity and to confirm their concentration (FIGS. 4 and 13).

Example 4

Biological Activity of the Polypeptides Related to MS

The polypeptides expressed by the constructed synthetic genes of Example 2 above were tested for their biological activity in relevance to MS, using EAE as a model system. Thus, the proteins were tested in vitro by standard well-known methods for their ability to stimulate T-cells specific for defined epitopes, thereby indicating their appropriate processing by antigen-presenting cells (APCs), and in vivo for their ability to immunomodulate EAE induced in mice.

4.1. Line of T-Cells Specific for Encephalitogenic Epitopes Recognize their Relevant Epitopes on Y-MSPa PLP139-151-specific line T-cells ($2\times10^4$), selected from SJL/J mice immunized with a synthetic peptide corresponding to the sequence PLP 139-151, were cultured in 96-well microtiter plates with $5\times10^5$ irradiated APC, in the presence of PLP 139-151 (0.5 g), shPLP/E (2 g) or Y-MSPa (5 g). MOG 35-55-specific line T-cells ($1.5\times10^4$) selected from C3H.SW mice immunized with synthetic peptide corresponding to the sequence MOG 35-55 were cultured in 96-well plates with $5\times10^5$ irradiated APC, in the presence of MOG35-55 (0.5 g), shMOG/E (2 g) or Y-MSPa (5 g). After 48 hours at 37° C. in humidified air containing 7.5% $CO_2$, [$^3$H]-thymidine (1 Ci/well) was added for the last 16 hrs of the incubation and the cultures were then harvested and counted using a Matrix 96 Direct beta counter (Packard Instr., Meriden, Conn.). The proliferative response was measured as [$^3$H]-thymidine incorporation and expressed as mean cpm ±SD of triplicate cultures.

As shown in FIGS. 16A-b, the Y-MSPa gene can stimulate a line of T-cells specific for PLP139-151 (FIG. 16A) or for MOG35-55 (FIG. 16B) to the same extent as their specific epitope.

4.2. Y-MSPa and Y-MSPb can be Encephalitogenic

C3H.SW and SJL/J mice were injected s.c. at one site in the flank with 200 μl of emulsion containing 150 μg Y-MSPa in CFA supplemented with 400 μg *Mycobacterium tuberculosis* (Mt); an identical booster immunization was given at one site on the other flank one week later. Mice received 300 ng pertussis toxin (PT) in 500 μl PBS in the tail vein immediately and 48 hours after the first immunization. (C3H.SW×SJL/J) F1 mice received a similar encephalitogenic challenge except that the emulsion contained 400 μg Y-MSPa in CFA supplemented with 300 μg Mt. EAE induction in (C3H.SW×SJL/J) F1 mice with YMSPb was carried out in the same way, with 400 μg Y-MSPb in CFA supplemented with 400 μg Mt. Mice were scored daily for clinical signs on a scale of 0-6, as described previously (Mendel et al., 1995).

Figure 17:
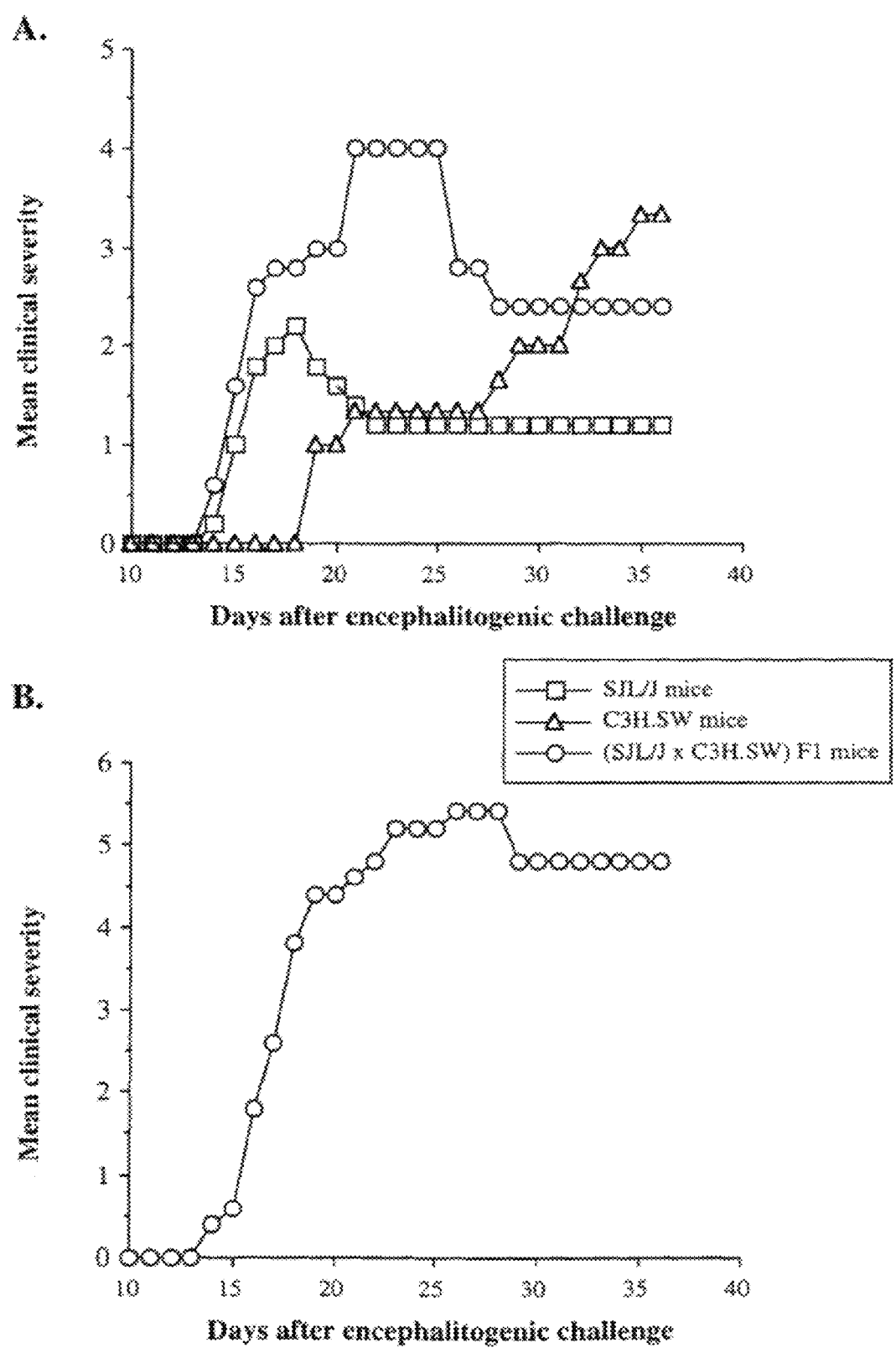
FIGS. 17A-B show the clinical course of EAE induced in mice by Y-MSPa (FIG. 17A) and Y-MSPb (FIG. 17B).

FIGS. 17A-B show the clinical course of EAE induced in mice by Y-MSPa and Y-MSPb. Immunization of mice with Y-MSPa or Y-MSPb as encephalitogenic inocula, resulted in a chronic type of EAE (FIG. 17), indicating that the epitopes comprised within these proteins can be recognized by and activate potentially pathogenic T-cells if administered in emulsion with complete Freund's adjuvant (CFA).

4.3. Y-MSPa and Y-MSPb can Modulate EAE in Mice

Figure 18:
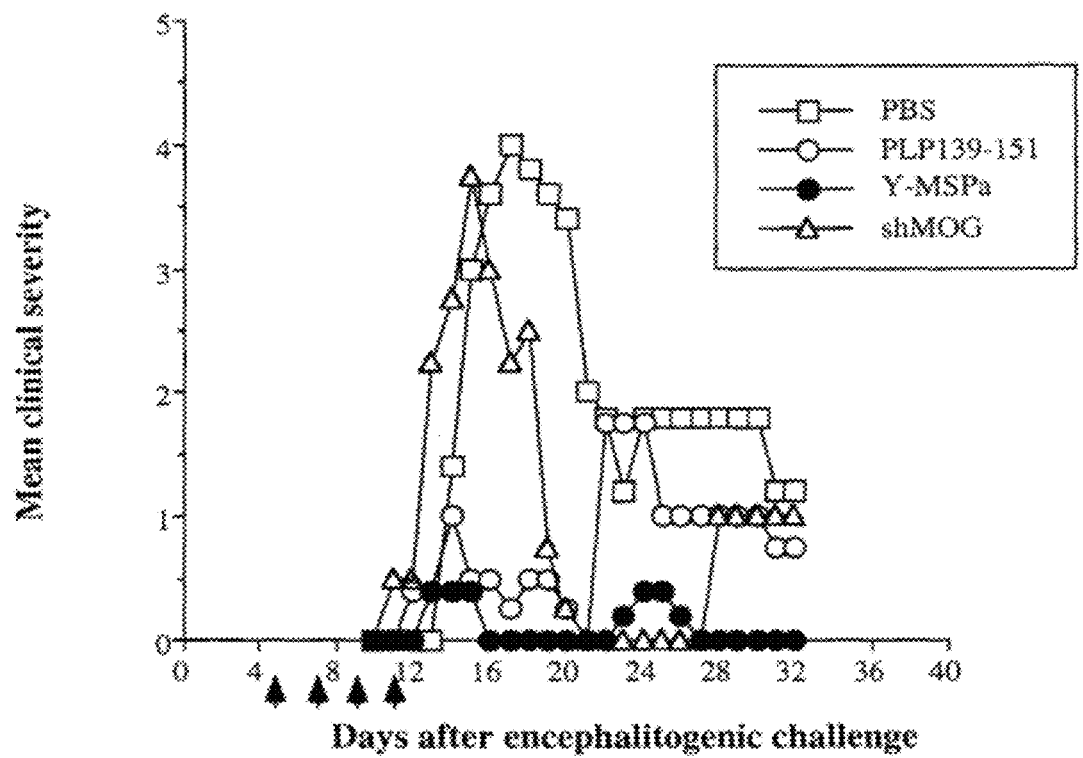
FIG. 18 show that intraperitoneal (IP) injections of Y-MSPa protect SJL/J mice against EAE induced with PLP139-151.

FIG. 18 shows that injections of Y-MSPa protect SJL/J mice against EAE induced with PLP139-151. SJL/J mice were injected s.c. at one site in the flank with 200 μl of emulsion containing 150 μg PLP139-151 in CFA supplemented with 200 μg *Mycobacterium tuberculosis*. On days 5, 7, 9 and 11 (indicated by arrowheads) after the encephalitogenic challenge, mice received IP injections of 500 μl PBS alone or PBS containing 200 μg PLP139-151, 200 μg Y-MSPa, or 200 μg shMOG/E. Mice were scored daily for clinical signs on a scale of 0-6 as described previously (Mendel et al., 1995).

Figure 19:
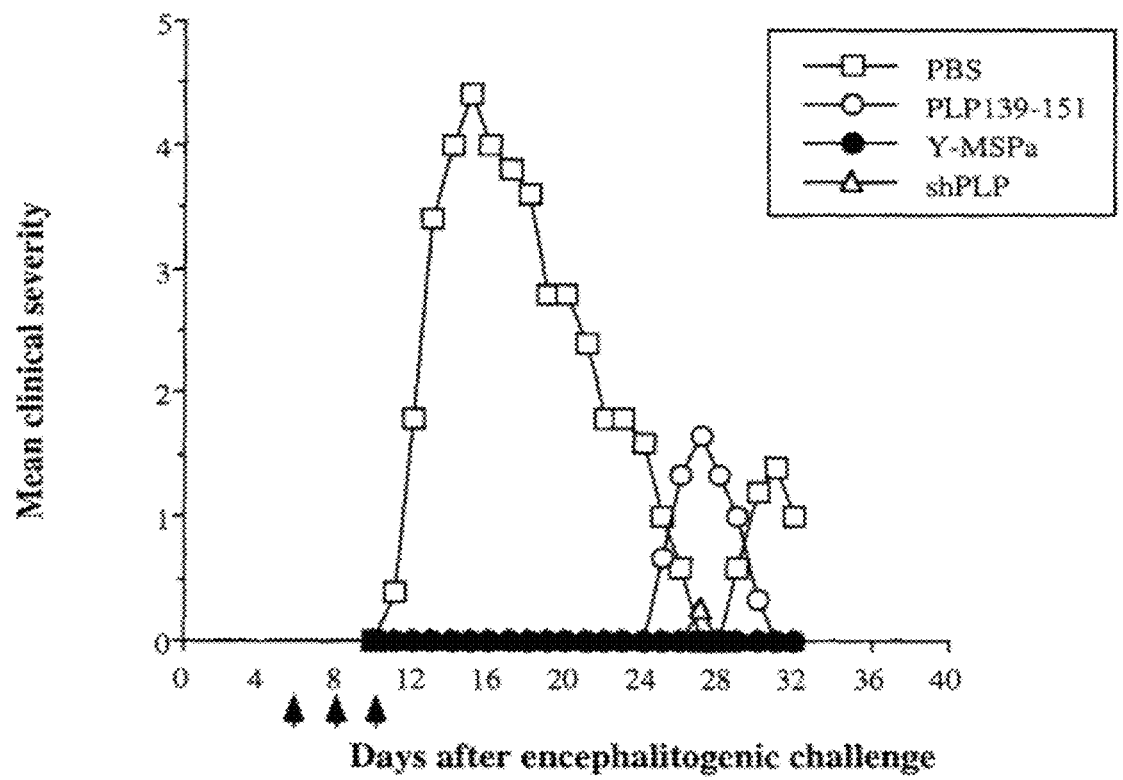
FIG. 19 show that intravenous (IV0 injections of Y-MSPa protect SJL/J mice against EAE induced with PLP139-151.

FIG. 19 shows that IV injections of Y-MSPa protect SJL/J mice against EAE induced with PLP139-151. SJL/J mice were injected s.c. at one site in the flank with 200 μl of emulsion containing 150 μg PLP139-151 in CFA supplemented with 200 μg *Mycobacterium tuberculosis*. On days 6, 8 and 10 (indicated by arrowheads) after the encephalitogenic challenge, mice were injected in the tail vein with 500 μl PBS alone or PBS containing 200 μg PLP139-151, 200 μg Y-MSPa, or 200 μg shPLP/E. Mice were scored daily for clinical signs on a scale of 0-6 as described previously (Mendel et al., 1995).

As shown in FIG. 18, i.v. administration of a soluble aqueous form of Y-MSPa on days 6, 8 and 10 after induction of EAE with PLP139-151 abrogated disease development in SJL/J mice. A similar effect was obtained with i.v. administration of shPLP/E. When Y-MSPa was administered i.p. on days 5, 7, 9 and 11 after induction of EAE with PLP139-151, disease development was almost fully abrogated (FIG. 19). In contrast, i.p. administration of soluble aqueous shMOG/E had no effect on disease development.

These data altogether indicate that administration of Y-MSP in a soluble form can be useful in immunomodulating potentially pathogenic autoreactive T-cells.

4.4. Vaccination Against EAE by Y-MSPb Naked DNA

The direct introduction of a plasmid DNA encoding an antigenic protein to be expressed within cells of the organism's tissue has become an acceptable approach to vaccination. The protein expressed in the tissue, following gene transfer, can trigger the immune system, and the nature of the immune response is much dependent on the immunogenicity of the protein, among other factors. This DNA-mediated immunization is known as naked-DNA vaccination or DNA vaccine.

To evaluate the vaccinogenic potential of the Y-MSPb gene, the translation initiation signal, ATG, was added in front of the coding nucleotide sequence of Y-MSPb. The ATG was added at the N-terminus of the shMOG/E in the pGEM-T/shMOG/E by PCR amplification, using a new 1a shMOG/E oligonucleotide comprising the ATG, and with the 6a oligonucleotide of shMOG/E (FIG. 2). The shMOG/E in the Y-MSPb gene was then replaced with the ATG-shMOG/E DNA fragment via NheI and BglII sites, and the appropriate sequence was confirmed by DNA sequencing. The pGEM-T/ATG-Y-MSPb was subcloned into the pCI mammalian expression vector via the NheI and NotI sites shared by pGEM-T and PcI vectors, to make the pCI/ATG-Y-MSPb to be used for DNA vaccination against EAE. SJL/J and C3H.SW mice were injected with cardiotoxin intramuscularly in the tibialis anterior muscle; 5 days later they were injected at the same site with 50 l PBS containing pCI/ATG-Y-MSPb DNA (50 g). The mice followed for 2-3 months did not show any sign of neurological impairment, indicating that immunization with pCI/ATG-Y-MSPb did not evoke encephalitogenic T cells. Studies are in progress to evaluate the anti-EAE vaccinogenic properties of the pCI/ATG-Y-MSPb in murine EAE models induced by different encephalitogens.

Example 5

Construction of the shMultiTAGs for MS Y-MSPc and Y-MSPd Genes

The strong immunomodulatory effect of the pilot Y-MSP on the notoriously severe EAE induced by PLP 139-151 indicated the potential effectiveness of a protein composed of multi-epitopes from different relevant target antigens, in immunomodulation of autoimmune disease. We therefore designed the construction of a new set of MS-related shTAGs in which a wider range of MS-related epitopes were included. Thus, in addition to epitopes demonstrated experimentally, these shTAGs also encompass potentially relevant epitopes predicted by computer modelling of MHC binding mode, preferably confirmed by HLA-binding assays and/or by their immunogenicity in transgenic mice expressing HLA associated to MS. The new set of MS-related shTAGs were designated shMOG/MS gene, shMBP/MS gene, shPLP/MS gene, shMOBP/MS gene, and shOSP/MS gene which includes epitopes of OSP potentially relevant to MS. As our and another laboratory recently demonstrated the encephalitogenic activity of OSP, this autoantigen is also likely to be of potential importance in MS. In this new set, each shTAG is composed of two main parts separated by an endonuclease restriction site which will allow excision of the epitopes which are likely to be less frequently recognized in disease, to obtain the shTAG in the construction of Y-MSPd (see below).

5.1. Construction of the shMOG/MS Gene (FIG. 20)

The construction of the shMOG/MS gene, schematically depicted in FIG. 20, is carried out using the oligonucleotides detailed in FIG. 20, according to the protocol described above for shMOG (Example 2.1 above). The resulting DNA sequence and derived amino acid sequence of shMOG/MS are shown in FIG. 21.

5.2. Construction of the shMBP/MS Gene (FIG. 22)

The construction of the shMBP/MS gene, schematically depicted in FIG. 22, is carried out using the oligonucleotides detailed in FIG. 22, according to the protocol described above for shMOG (Example 2.1 above). The resulting DNA sequence and derived amino acid sequence of shMBP/MS are shown in FIG. 23.

5.3. Construction of the shPLP/MS Gene (FIG. 24)

The construction of the shPLP/MS gene, schematically depicted in FIG. 24, is carried out using the oligonucleotides detailed in FIG. 24, according to the protocol described above for shMOG (Example 2.1). The resulting DNA sequence and derived amino acid sequence of shPLP/MS are shown in FIG. 25.

5.4. Construction of the shMOBP/MS Gene (FIG. 26)

The construction of the shMOBP/MS gene, schematically depicted in FIG. 26, is carried out using the oligonucleotides detailed in FIG. 26, according to the protocol described above for shMOG (Example 2.1). The resulting DNA sequence and derived amino acid sequence of shMOBP/MS are shown in FIG. 27.

5.5. Construction of the shOSP/MS Gene (FIG. 28)

The construction of the shOSP/MS gene, schematically depicted in FIG. 28, is carried out using the oligonucleotides detailed in FIG. 28, according to the protocol described above for shMOG (Example 2.1). The resulting DNA sequence and derived amino acid sequence of shOSP/MS are shown in FIG. 29.

5.6. Construction of the Y-MSPc Gene (FIG. 30)

The MS-related shMultiTAG constructed from this new set of shTAGs is designated Y-MSPc, and is generated by sequentially ligating the shMOG/MS gene, shMBP/MS gene, shOSP/MS gene, shMOBP/MS gene and shPLP/MS gene via specific endonuclease restriction sites which have been incorporated to allow their ligation in one open reading frame as shown in the scheme (FIG. 30). Thus, the pGEM-T/shMOG/MS is cleaved at the BamHI and HindIII sites, the shMBP/MS gene is cleaved out from the pGEM-T/shMBP/MS with BamHI and SpeI, the shOSP/MS gene is cleaved out from pGEM-T/shOSP/MS with SpeI and PstI, the shMOBP/MS gene is cleaved out from pGEM-T/shMOBP/MS with PstI and XhoI, and the shPLP/MS gene is cleaved out from pGEM-T/shPLP/MS with XhoI and HindIII. The DNA fragments of the right sizes are gel eluted, cleaned and sequential ligations are carried out to link the shMBP/MS gene to the shMOG/MS gene via their BamHI sites, the shOSP/MS gene to the shMBP/MS gene via their SpeI sites, the shMOBP/MS gene to the shOSP/MS gene via their PstI sites, and the shPLP/MS gene to the shMOBP/MS gene via their XhoI sites and to the pGEM-T/shMOG/MS via their HindIII sites, as depicted in FIG. 30. The resulting ligated DNA fragment comprising the shTAGs representing Y-MSPc is then subcloned into the pRSET bacterial expression vector, 3' to its 6×His tag, via the NheI and HindIII restriction sites. DNA sequence analysis is performed using the pRSET-specific primers to confirm the Y-MSPc DNA sequence as an open reading frame with the ATG of the pRSET expression vector. The Y-MSPc DNA sequence and derived amino acid sequence are presented in FIG. 31.

5.6.1. Expression and Purification of Y-MSPc (FIG. 31a)

The shTAGs/MS (shMOG/MS, shMBP/MS, shOSP/MS, shMOBP/MS and shPLP/MS) comprising the shMultiTAG/MS (Y-MSPc gene) were each cloned into the pRSET bacterial expression vectors described above, to ensure that the relevant protein could be expressed from each shTAG/MS (not shown). The pGEM-T/shMOG/MS, pGEM-T/shMBP/MS, pGEM-T/shOSP/MS, pGEM-T/shMOBP/MS and pGEM-T/shPLP/MS, were then ligated sequentially and the resulting Y-MSPc DNA was then cloned in the pRSET bacterial expression vector, as described above. Expression and purification of Y-MSPc are shown in FIG. 31a. As can be seen in FIG. 31a, the Y-MSPc eluted from the $Ni^{2+}$ affinity chromatography presents on SDS-PAGE as a major band of the expected molecular weight, as well as a number of faster migrating bands, all of which reacted in Western blotting analysis with an antibody specific for a MOG epitope present in Y-MSPc (amino acids 35-55), suggesting that the lower bands represent degradation and/or incomplete translation products. The protein representing the intact Y-MSPc was further purified by HPLC.

5.6.2. Mammalian Expression of Y-MSPc (FIG. 31b)

The Y-MSPc DNA was cleaved out from the pGEM-T/Y-MSPc with EcoRI and NotI and subcloned into the mammalian expression vector pcDNA 3.1. The ATG coding for the first methionine residue of Y-MSPc served as the signal for initiation of protein translation. The pcDNA 3.1/Y-MSPc was transfected into NIH3T3 mouse fibroblasts to ensure that the Y-MSPc can be expressed in mammalian cells, as a prerequisite for its application in DNA vaccination. Western blot analysis revealed an anti-MOG 35-55 antibody-reactive band of the expected molecular weight in the transfected NIH3T3 cells, which was not detected in the non-transfected NIH3T3 cells (FIG. 31b), demonstrating that Y-MSPc can be expressed in mammalian cells, and can be used in DNA vaccination.

5.7. Construction of the Y-MSPd Gene (FIG. 32)

The MS-related truncated shMultiTAG gene coding only for preferred epitopes likely to be more frequently recognized in disease on each of the autoantigens selected, and which is designated Y-MSPd, was prepared as follows: the pGEM-T/shPLP/MS was cleaved at BamHI and BclI and the small BamHI/BclI fragment was removed by gel electrophoresis. The pGEM-T/shPLP/MS was then religated via the compatible BamHI/BclI sites to generate the pGEM-T/shPLP/MS. The XhoI/HindIII DNA fragment comprising the shPLP/MS gene was excised out from the pGEM-T/shPLP/MS and ligated into the pRSET/Y-MSPc digested with XhoI and HindIII to replace the shPLP/MS gene. The resulting plasmid (prSET/Y-MSPc with shPLP/MS) was then digested with NheI and HindIII and the excised DNA fragment (Y-MSPc with shΔPLP/MS) was sequentially cleaved and religated via the compatible restriction sites BglII and BamHI, followed by XbaI and SpeI, followed by NsiI and PstI, followed by SalI and XhoI, as depicted in FIG. 32. The resulting DNA fragment comprising the shTAGs was cloned back into the pRSET vector via the NheI and HindIII sites. The resulting plasmid was the pRSET/shMultiTAG/MS (Y-MSPd). DNA sequence analysis was performed using the pRSET-specific primers to confirm the Y-MSPd DNA sequence as an open reading frame with the ATG of the pRSET expression vector. The Y-MSPd DNA sequence and derived amino acid sequence are presented in FIG. 33.

5.7.1. Expression and Purification of Y-MSPd (FIG. 33a)

The pRSET/shΔMultiTAG/MS (Y-MSPd) was transfected into *E. coli* BL21-D3. Induction of the expression of Y-MSPd and its purification were performed as described above. Expression and purification of Y-MSPc are shown in FIG. 33a. As can be seen in FIG. 33a, the Y-MSPd eluted from the $Ni^{2+}$ affinity chromatography also presents as a major band of the expected molecular weight, as well as a number of faster migrating bands, which reacted with the anti-MOG 35-55 antibody, suggesting that the lower bands also represent primarily degradation and/or incomplete translation products. The protein representing the intact Y-MSPd was further purified by HPLC.

Example 6

Construction of shTAGs and shMultiTAGs for IDDM

In a similar manner, using the rationale and strategy described above for designing the synthetic genes coding for MS-related proteins with immunomodulatory potential, shTAGs and shMultiTAGs can be constructed for other autoimmune diseases. The following are examples for designing the construction of shTAGs and shMultiTAGs for the autoimmune diseases IDDM and RA.

6.1. Construction of shMultiTAGs for IDDM

The shMultiTAGs related to IDDM are designated Y-DMP genes coding for IDDM-related proteins (Y-DMP). The Y-DMPa gene was constructed by sequentially ligating the following shTAGs: shPPIG/DM gene, shGad65/DM gene, and shI3/DM gene, encompassing DNA coding for selected disease-related epitopes on the potential target autoantigens (see Table 1 above), preproinsulin and Gad67 (shPPIG/DM gene), Gad65 (shGad65/DM gene) and ICA69, IA-2 and imogen (shI3/DM gene). The Y-DMPb gene was generated by inserting the DNA fragment representing the shHSP/DM gene encoding disease-related epitopes of HSP60 into the Y-DMPa gene.

6.1.1. Construction of the shPPIG/DM Gene (FIG. 34)

The shPPIG/DM gene was designed to code for a protein encompassing in tandem amino acids 5-24, 33-59 and 73-88 of preproinsulin (PPI) and amino acids 30-60 and 121-135 of Gad67, representing epitopes demonstrated to be recognized by patients with IDDM, as well as epitopes immunogenic in transgenic mice expressing HLA associated with IDDM. The shPPIG/DM gene was constructed according to the strategy and the oligonucleotides shown in FIG. 34, using the protocol detailed above for the shMOG gene (Example 2.1). The resulting DNA sequence and derived amino acid sequence of shPPIG/DM gene are shown in FIG. 35.

6.1.2. Construction of the shGad65/DM Gene (FIG. 36)

The shGad65/DM gene was designed to code for a protein encompassing in tandem amino acids 206-236, 247-282, 503-545 and 553-572, representing epitopes demonstrated to be recognized by patients with IDDM, as well as epitopes immunogenic in transgenic mice expressing HLA associated with IDDM. The shGad65/DM gene was constructed according to the strategy and the oligonucleotides shown in FIG. 36, using the protocol detailed above for the shMOG gene (Example 2.1). The resulting DNA sequence and derived amino acid sequence of shGad65/DM gene are shown in FIG. 37.

6.1.3. Construction of the shI3/DM Gene (FIG. 38)

The shI3/DM gene was designed to code for a protein encompassing in tandem amino acids 39-49, 119-214 and 348-362 of ICA69, amino acids 789-819 and 840-874 of IA-2 and amino acids 263-278 of imogen, representing epitopes demonstrated to be recognized by patients with IDDM, as well as epitopes immunogenic in transgenic mice expressing HLA associated with IDDM. The shI3/DM gene was constructed according to the strategy and the oligonucleotides shown in FIG. 38, using the protocol detailed above for the shMOG gene. The resulting DNA sequence and derived amino acid sequence of shI3/DM gene are shown in FIG. 39.

6.1.4. Construction of the shHSP/DM Gene (FIG. 40)

The shHSP/DM gene was designed to code for a protein encompassing in tandem amino acids 438-460 and 469-484 of Hsp60, representing epitopes demonstrated to be recognized by patients with DM, as well as epitopes immunogenic in transgenic mice expressing HLA associated with DM. The shHSP/DM gene was constructed according to the strategy and the oligonucleotides shown in FIG. 40, using the protocol detailed above for the shMOG gene. The resulting DNA sequence and derived amino acid sequence of shHSP/DM gene are shown in FIG. 41.

6.1.5. Construction of the Y-DMPa Gene (FIG. 42)

The DM-related shMultiTAG constructed from the shTAGs/DM is designated Y-DMPa and was generated by sequentially ligating the shPPIG/DM gene, shGad65/DM gene and shI3/DM gene via specific endonuclease restriction sites which have been incorporated to allow their ligation in one open reading frame as shown in the sheme (FIG. 42). Thus, the shPPIG/DM gene was cleaved out of the pGEM-T/shPPIG/DM at the NheI and BglII sites, the shGad65/DM gene was cleaved out from the pGEM-T/shGad65/DM with BglII and AvrII, and the shI3/DM gene was cleaved out from pGEM-T/shI3/DM with AvrII and EcoRI. The DNA fragments of the right sizes are gel eluted, cleaned and sequential ligations were carried out to link the shPPIG/DM gene to the shGad65/DM gene via their BglII sites, and the shI3/DM gene to the shGad65/DM gene via their AvrII sites as depicted in FIG. 42. The resulting ligated DNA fragment comprising the shTAGs representing the Y-DMPa gene was then cloned into the pRSET bacterial expression vector, 3' to its 6×His tag, via the NheI and EcoRI restriction sites. DNA sequence analysis was performed using the pRSET-specific primers to confirm the Y-DMPa DNA sequence as an open reading frame with the ATG of the pRSET expression vector. The Y-DMPa DNA sequence and derived amino acid sequence are presented in FIG. 43.

6.1.5.1. Construction of the Y-DMPc Gene (FIGS. 42a-42e)

Prior to generation of the DM-related shMultiTAG by sequential ligation of the shTAGs/DM, each of the shTAGs/DM comprising the shMultiTAG/DM (Y-DMPa) (shPPIG/DM, shGad65/DM and shI3/DM) was cloned into the pRSET bacterial expression vector as described above, and expression was induced in transformed $E.$ $coli$ BL21-D3, to ensure that the relevant protein could be expressed from each shTAG/DM. Although shGad65/DM and shI3/DM could each be expressed in $E.$ $coli$ transformed with pRSET/shGad65/DM and pRSET/shI3/DM, respectively (data not shown), shPPIG/DM could not be expressed in $E.$ $coli$ transformed with pRSET/shPPIG/DM. The attempt to drive protein expression of the shPPIG/DM gene by ligating together the shPPIG/DM gene with the expressible shGad65/DM gene, into a pRSET expression vector (pRSET/PPIG-Gad65, FIG. 42a) was unsuccessful. In fact, a complete construction of the Y-DMPa gene (FIG. 42) and ligation into the pRSET bacterial expression vector generating the pRSET/Y-DMPa, also resulted in failure of its expression in $E.$ $coli$ BL21-DE3. We therefore constructed a new Y-DMPa gene, designated Y-DMPc where the DNA sequence encoding PPI epitopes, which was believed to hinder protein expression, was shifted and inserted after the shGad 65 (see FIG. 42a), according to the following strategy (FIGS. 42a-42e): a shPPI/DM gene and a shGad67/65/DM gene were constructed by PCR amplification using the pRSET/PPIG-Gad65 plasmid DNA as a template, and relevant oligonucleotides (FIG. 42a). The confirmed DNA sequences and derived amino acid sequences of shPPI/DM and shGad67/65/DM are shown in FIGS. 42b and 42c, respectively. The shGad67/65/DM gene cloned into the pRSET vector via the NheI and BamHI sites was well expressed in the transformed $E.$ $coli$ BL21-DE3 (not shown). The construction of the shPPI/DM using oligonucleotides containing AvrII restriction sites before and after the DNA sequence coding for the selected PPI epitopes enabled its insertion in the pRSET/shGad67/65/DM at the AvrII site located 3' to the DNA sequence of the selected Gad65 epitopes (FIG. 42a). DNA sequence analysis of the resulting pRSET/shGad/PPI/DM, performed using the pRSET-specific primers, confirmed the shGad/PPI/DM DNA sequence as an open reading frame with the ATG of the pRSET expression vector. The pRSET/shGad/PPI/DM was transformed into $E.$ $coli$ BL21-DE3, where expression of shGad/PPI/DM was readily detected upon induction with IPTG (not shown). The DNA sequence and derived amino acid sequence of shGad/PPI/DM are shown in FIG. 42d. The pRSET/Y-DMPc (new pRSET/Y-DMPa) was then generated by inserting an AvrII/EcoRI DNA fragment containing the shI3/DM derived from the pRSET/shI3/DM, into the pRSET/shGad/PPI/DM digested with EcoRI and partially digested with AvrII (FIG. 42e). Screening of transformed $E.$ $coli$ by PCR analysis enabled the selection of a colony containing the DNA fragments of shGad67/65, shPPI and shI3 sequentially. DNA sequence analysis of the resulting pRSET/Y-DMPc, performed using the pRSET-specific primers, confirmed the Y-DMPc DNA sequence as an open reading frame with the ATG of the pRSET expression vector. The Y-DMPc (new Y-DMPa) DNA sequence and derived amino acid sequence are presented in FIG. 43a.

6.1.5.2. Expression and Purification of the Y-DMPc Gene (FIG. 43b)

Protein expression from the pRSET/Y-DMPc transformed into $E.$ $coli$ BL21-DE3 could be readily induced by IPTG, and the His-tagged recombinant protein was purified by $Ni^{2+}$ chelate chromatography as described above. SDS-PAGE of bacterial expression of the Y-DMPc and of purified Y-DMPc is shown in FIG. 43b.

6.1.6. Construction of the Y-DMPb Gene (FIG. 44)

Although Hsp60 is ubiquitous and not an organ-specific target antigen in IDDM, several studies have indicated the involvement of autoreactivity against Hsp60 in the initiation or progression of the disease. To prepare a Y-DMP which includes disease-relevant epitopes from the Hsp60, another IDDM-related shMultiTAG designated Y-DMPb was constructed by inserting the shHsp/DM gene into the Y-DMPa gene at the XbaI site in an appropriate orientation, as depicted in FIG. 44. DNA sequence analysis was performed using the pRSET-specific primers to confirm the Y-DMPb DNA sequence as an open reading frame with the ATG of the pRSET expression vector. The Y-DMPb DNA sequence and derived amino acid sequence are presented in FIG. 45.

6.1.6.1. Construction of the Y-DMPd Gene (New Y-DMPb Gene) (FIG. 44a)

For the construction of the pRSET/Y-DMPd gene (new pRSET/Y-DMPb), an XbaI/XbaI DNA fragment containing the shHSP/DM derived from pGEM-T/shHSP/DM (FIG. 40) was inserted into the pRSET/Y-DMPc at the XbaI site located downstream to the DNA sequence encoding the selected epitopes represented by the shI3 gene (FIG. 44a). PCR analysis was carried out to confirm that the shHSP/DM was inserted in the right orientation to generate the pRSET/Y-DMPd (FIG. 44a). DNA sequence analysis, performed using the pRSET-specific primers, confirmed the Y-DMPd DNA sequence as an open reading frame with the ATG of the pRSET expression vector. The Y-DMPd DNA sequence and derived amino acid sequence are presented in FIG. 45a.

6.1.6.2. Expression and Purification of the Y-DMPd (FIG. 45b)

The pRSET/Y-DMPd was transformed into *E. coli* BL21-DE3 where protein expression could be readily induced by IPTG, and the His-tagged recombinant protein was purified by $Ni^{2+}$ chelate chromatography as described above. SDS-PAGE of bacterial expression of the Y-DMPd and of purified Y-DMPd is shown in FIG. 45b.

Example 7

Construction of shTAGs and shMultiTAGs for RA 7.1. Construction of shMultiTAGs for RA The shMultiTAGS related to RA are designated Y-RAP genes coding for RA-related proteins (Y-RAP). The Y-RAPa gene was constructed by sequentially ligating the following shTAGs, shCollagen/RA gene, shAggrecan/RA gene and shGPL/RA gene, encompassing DNA coding for selected disease-related epitopes on the potential target autoantigens (see Table 1 above), collagen type II (shCollagen/RA gene), aggrecan (shAggrecan/RA gene), and HCgp-39 and cartilage link protein (shGPL/RA gene). The Y-RAPb gene was generated by inserting the shHSP/RA gene coding for disease-related epitopes on Hsp60, hsp65 and EcoDNAJ into the Y-RAPa gene.

7.1.1. Construction of the shCollagen/RA Gene (FIG. 46)

The shCollagen/RA gene was designed to code for a protein encompassing in tandem amino acids 73-98, 253-275, 285-303, 442-456, 606-622 and 924-943 of collagen type II, representing epitopes demonstrated to be recognized by patients with RA, as well as epitopes immunogenic in transgenic mice expressing HLA associated with RA. The shCollagen/RA gene was constructed according to the strategy and the oligonucleotides shown in FIG. 46, using the protocol detailed above for the shMOG gene. The resulting DNA sequence and derived amino acid sequence of shCollagen/RA gene are shown in FIG. 47.

7.1.2. Construction of the shAggrecan/RA Gene (FIG. 48)

The shAggrecan/RA gene was designed to code for a protein encompassing in tandem amino acids 89-103, 1053-1092, 201-213, 298-312, 623-635 and 1804-1820 of aggrecan, representing epitopes demonstrated to be recognized by patients with RA, as well as epitopes immunogenic in transgenic mice expressing HLA associated with RA. The shAggrecan/RA gene was constructed according to the strategy and the oligonucleotide shown in FIG. 48, using the protocol detailed above for the shMOG gene. The resulting DNA sequence and derived amino acid sequence of shAggrecan/RA gene are shown in FIG. 49.

7.1.3. Construction of the shGPL/RA Gene (FIG. 50)

The shGPL/RA gene was designed to code for a protein encompassing in tandem amino acids 79-95, 236-254 and 303-319 of HCgP-39 and amino acids 207-219 and 281-305 of link protein, representing epitopes demonstrated to be recognized by patients with RA, as well as epitopes immunogenic in transgenic mice expressing HLA associated with RA. The shGPL/RA gene gene was constructed according to the strategy and the oligonucleotides shown in FIG. 50, using the protocol detailed above for the shMOG gene. The resulting DNA sequence and derived amino acid sequence of shGPL/RA gene are shown in FIG. 51.

7.1.4. Construction of the shHSP/RA Gene (FIG. 52)

The shHSP/RA gene was designed to code for a protein encompassing in tandem amino acids 266-308 and 197-225 of Hsp60, amino acids 1-15 of hsp65 and amino acids 60-75 of EcoDNAJ, representing epitopes demonstrated to be recognized by patients with RA, as well as epitopes immunogenic in transgenic mice expressing HLA associated with RA. The shHSP/RA gene gene was constructed according to the strategy and the oligonucleotides shown in FIG. 52, using the protocol detailed above for the shMOG gene. The resulting DNA sequence and derived amino acid sequence of shHSP/RA gene are shown in FIG. 53.

7.1.5. Construction of the Y-RAPa Gene (FIG. 54)

The RA-related shMultiTAG constructed from the shTAGs/RA is designated Y-RAPa, and was generated by sequentially ligating the shCollagen/RA gene, shAggrecan/RA gene and shGPL/RA gene via specific endonuclease restriction sites which have been incorporated to allow their ligation in one open reading frame as shown in the scheme (FIG. 54). Thus, the pGEM-T/shCollagen/RA was cleaved at the BamHI and HindIII sites, the shAggrecan/RA gene was cleaved out from the pGEM-T/shAggrecan/RA with BamHI and SpeI, and the shGPL/RA gene was cleaved out from pGEM-T/shGPL/RA with SpeI and HindIII. The DNA fragments of the right sizes were gel eluted, cleaned and triple-ligated to link the shAggrecan/RA gene to the shCollagen/RA gene via their BamHI sites, and the shGPL/RA gene to the shAggrecan/RA gene via their SpeI sites and to the pGEM-T/shCollagen/RA via their HindIII sites, as depicted in FIG. 54. The NheI/HindIII DNA fragment of the resulting plasmid comprising the shTAGs representing the Y-RAPa gene was then cloned into the pRSET bacterial expression vector, 3' to its 6×His tag, via the NheI and HindIII restriction sites. DNA sequence analysis was performed using the pRSET-specific primers to confirm the Y-RAPa DNA sequence as an open reading frame with the ATG of the pRSET expression vector. The Y-RAPa DNA sequence and derived amino acid sequence are presented in FIG. 55.

7.1.6. Construction of the Y-RAPb Gene (FIG. 56)

Heat shock proteins are ubiquitous and not organ-specific target antigens in RA; however, several studies have indicated the involvement of the autoimmune response against bacterial Hsps cross-reactive with human counterpart Hsps in the initiation or progression of the disease. To prepare another Y-RAP which includes human HSP60 epitopes, as well as HSP epitopes derived from cross-reactive bacterial HSPs (HSP65 and EcoDNAJ) which have been implicated in disease, a RA-related shMultiTAG, designated Y-RAPb, was constructed by inserting the shHSP/RA gene into the pRSET/Y-RAPa via the XhoI and HindIII sites, as depicted in FIG. 56. DNA sequence analysis was performed using the pRSET-specific primers to confirm the Y-RAPb DNA sequence as an open reading frame with the ATG of the pRSET expression vector. The Y-RAPb DNA sequence and derived amino acid sequence are presented in FIG. 57.

7.1.7. Construction of Y-RAP Genes Coding for Preferred Epitopes: Y-RAPc (FIG. 58) and Y-RAPd (FIG. 60)

RA-related truncated shMultiTAG genes coding only for preferred epitopes likely to be more frequently recognized in disease on each of the autoantigens selected are designated herein Y-RAPc gene and Y-RAPd gene.

The Y-RAPc gene was constructed as follows: the pRSET/Y-RAPa was digested with NheI and HindIII and the excised Y-RAPa DNA fragment was sequentially cleaved and re-ligated at BglII and BamHI, followed by XbaI and SpeI, followed by SalI and XhoI, as depicted in FIG. 58. The resulting DNA fragment comprising the shTAGS was then cloned back into the pRSET vector via the NheI and HindIII sites. DNA sequence analysis was performed using the pRSET-specific primers to confirm the Y-RAPc DNA sequence as an open reading frame with the ATG of the pRSET expression vector. The Y-RAPc DNA sequence and derived amino acid sequence are presented in FIG. 59.

The Y-RAPd gene was prepared as follows: the pGEM-T/shHSP/RA was cleaved at BamHI and BclI and the small BamHI/BclI fragment was removed by gel electrophoresis. The pGEM-T/shHSP/RA was then religated via the compatible BamHI/BclI sites to generate the pGEM-T/shHSP/RA. The XhoI/HindIII DNA fragment comprising the shHSP/RA gene was excised out from the pGEM-T/shHSP/RA and ligated into the pRSET/Y-RAPa, via the XhoI and HindIII sites. The resulting plasmid (pRSET/Y-RAPa with shHSP/RA) was then digested with NheI and HindIII and the excised DNA fragment (Y-RAPa with shHSP/RA) was sequentially cleaved and religated via the compatible BglII and BamHI followed by XbaI and SpeI, followed by SalI and XhoI, as depicted in FIG. 60. The resulting DNA fragment comprising the shTAGS was cloned back into the pRSET vector via the NheI and HindIII sites. The resulting plasmid was the pRSET/shHSP/RA (Y-RAPd). DNA sequence analysis was performed using the pRSET-specific primers to confirm the Y-RAPd DNA sequence as an open reading frame with the ATG of the pRSET expression vector. The Y-RAPd DNA sequence and derived amino acid sequence are presented in FIG. 61.

References

Bach, J.-F. (1999) The immunology of diabetes: Revolution of concepts over a decade. In Shoenfeld, Y. (Ed.) The decade of autoimmunity 1987-1997. Elsevier Science, Amsterdam, pp 149-156.

Bronstein, J. M., Micevych, P. E. and Chen, K. (1997) Oligodendrocyte-specific protein (OSP) is a major component of CNS myelin. J. Neurosci. Res. 50, 713-20.

Cope, A. P. and Sonderstrup, G. (1998) Evaluating candidate autoantigens in rheumatoid arthritis. Springer Semin. Immunopathol. 20, 23-39.

Gardinier, M. V., Amiguet, P., Linington, C., and Matthieu, J.-M. (1992). Myelin/oligodendrocyte glycoprotein is a unique member of the immunoglobulin superfamily. J. Neurosci. Res. 33, 177-187.

Guerassimov, A., Duffy, C., Zhang, Y., Banerjee, S., Leroux, J.-Y., Reimann, A., Webber, C., Delaunay, N., Vipparti, V., Ronbeck, L., Cartman, A., Arsenault, L., Rosenberg, L. C. and Poole, A. R. (1996) Immunity to cartilage link protein in patients with juvenile rheumatoid arthritis. J. Rheumatol. 24, 959-964.

Kaye, J. F., Kerlero de Rosbo, N., Mendel, I., Flechter, S., Hoffman, M., Yust, I. and Ben-Nun, A. (2000) The central nervous system-specific myelin oligodendrocytic basic protein (MOBP) is encephalitogenic and a potential target antigen in multiple sclerosis (MS). J. Neuroimmunol. 102, 189-198.

Kerlero de Rosbo, N. and Ben-Nun, A. (1998) T-cell responses to myelin antigens in multiple sclerosis. Relevance of the predominant autoimmune reactivity to myelin oligodeglycoprotein. J. Autoimmun. 11, 287-299.

Kerlero de Rosbo, N. and Ben-Nun, A. (1999) Experimental autoimmune encephalomyelitis induced by various antigens of the central nervous system. Overview and relevance to multiple sclerosis. In Shoenfeld, Y. (Ed.) The decade of autoimmunity 1987-1997. Elsevier Science, Amsterdam, pp 169-177.

Kerlero de Rosbo, N., Hoffman, M., Mendel, I., Yust, I., Kaye, J., Bakimer, R., Flechter, S., Abramsky, O., Milo, R., Karni, A., and Ben-Nun, A. (1997). Predominance of the autoimmune response to myelin oligodendrocyte glycoprotein (MOG) in multiple sclerosis: reactivity to the extracellular domain of MOG is directed against three main regions. Eur. J. Immunol. 27, 3059-3069.

Kumar, V. (1998) Determinant spreading during experimental autoimmune encephalomyelitis: is it potentiating, protecting or participating in the disease? Immunol. Rev. 164, 73-80.

Maatta, J. A., Kaldman, M. S., Sakoda, S., Salmi, A. A., and Hinkkanen, A. E. (1998) Encephalitogenicity of myelin-associated oligodendrocytic basic protein and 2',3'-cyclic nucleotide 3'-phosphodiesterase for BALB/c and SJL mice. Immunology 95, 383-388. Mendel, I., Kerlero de Rosbo, N. and Ben-Nun, A. (1995) A myelin-oligodendrocyte glycoprotein (MOG) peptide induces typical chronic experimental autoimmune encephalomyelitis in H-2b mice. Fine specificity and T-cell receptor V? expression of encephalitogenic T-cells. Eur. J. Immunol. 25, 1951-1959.

Roep, B. O. (1996) T-cell responses to autoantigens in IDDM. The search for the Holy Grail. Diabetes 45, 1147-1156.

Stevens, D. B., Chen, K., Seitz, R. S., Sercarz, E. E. and Bronstein, J. M. (1999) Oligodendrocyte-specific protein peptides induce experimental autoimmune encephalomyelitis in SJL/J mice. J. Immunol. 162, 7501-7509.

Tuohy, V. K., Yu, M., Yin, L., Kawczak, J. A., Johnson, J. M., Mathisen, P. M., Weinstock-Guttman, B. and Kinkel, R. P. (1998) The epitope spreading cascade during progression of experimental autoimmune encephalomyelitis and multiple sclerosis. Immunol. Rev. 164, 93-100.

Tuohy, V. K. (1994) Peptide determinants of myelin proteolipid protein (PLP) in autoimmune disease: A review. Neurochem. Res. 19, 935-944.

Yamamoto, Y., Mizuno, R., Nishimura, T., Ogawa, Y., Yoshikawa, H., Fujimura, H., Adachi, E., Kishimoto, T., Yanagihara, T., and Sakoda, S. (1994). Cloning and expression of myelin-associated oligodendrocytic basic protein. J. Biol. Chem. 269, 31725-31730.

Zhong, M. C., Cohen, L., Meshorer, A., Kerlero de Rosbo, N. and Ben-Nun, A. (2000) T-cells specific for soluble recombinant oligodendrocyte-specific protein induce severe experimental autoimmune encephalomyelitis in H-2b and H-2s mice. J. Neuroimmunol. 105, 39-45.

SEQUENCE LISTING

<160> NUMBER OF SEQ ID NOS: 204

<210> SEQ ID NO 1
<211> LENGTH: 282
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(282)

<400> SEQUENCE: 1

```
gct agc ggg cag ttc aga gtg ata gga cca aga cac cct atc cgg gct      48
Ala Ser Gly Gln Phe Arg Val Ile Gly Pro Arg His Pro Ile Arg Ala
1               5                   10                  15 ctg gtc ggg gat gaa gtg gaa ttg cca tgt cgc gct aca ggc atg gag      96
Leu Val Gly Asp Glu Val Glu Leu Pro Cys Arg Ala Thr Gly Met Glu
            20                  25                  30 gtg ggg tgg tac cgc ccc ccc ttc tct agg gtg gtt cat ctc tac aga     144
Val Gly Trp Tyr Arg Pro Pro Phe Ser Arg Val Val His Leu Tyr Arg
        35                  40                  45 aat ggc aag gac caa gat cct gaa tat cgg ggc cgg aca gag ctg ctg     192
Asn Gly Lys Asp Gln Asp Pro Glu Tyr Arg Gly Arg Thr Glu Leu Leu
    50                  55                  60 aaa gat gct att ggt gag gga aag gtg act ctc agg atc cgg aat gta     240
Lys Asp Ala Ile Gly Glu Gly Lys Val Thr Leu Arg Ile Arg Asn Val
65                  70                  75                  80 agg ttc tca gat gaa gga ggt ttc acc aga tct tag aag ctt             282
Arg Phe Ser Asp Glu Gly Gly Phe Thr Arg Ser     Lys Leu
                85                  90
```

<210> SEQ ID NO 2
<211> LENGTH: 91
<212> TYPE: PRT
<213> ORGANISM: Artificial Sequence
<220> FEATURE:
<223> OTHER INFORMATION: Synthetic

<400> SEQUENCE: 2

```
Ala Ser Gly Gln Phe Arg Val Ile Gly Pro Arg His Pro Ile Arg Ala
1               5                   10                  15

Leu Val Gly Asp Glu Val Glu Leu Pro Cys Arg Ala Thr Gly Met Glu
            20                  25                  30

Val Gly Trp Tyr Arg Pro Pro Phe Ser Arg Val Val His Leu Tyr Arg
        35                  40                  45

Asn Gly Lys Asp Gln Asp Pro Glu Tyr Arg Gly Arg Thr Glu Leu Leu
    50                  55                  60

Lys Asp Ala Ile Gly Glu Gly Lys Val Thr Leu Arg Ile Arg Asn Val
65                  70                  75                  80

Arg Phe Ser Asp Glu Gly Gly Phe Thr Arg Ser
                85                  90
```

<210> SEQ ID NO 3
<211> LENGTH: 29
<212> TYPE: DNA
<213> ORGANISM: Artificial Sequence
<220> FEATURE:
<223> OTHER INFORMATION: Synthetic

<400> SEQUENCE: 3
gagctagcgg gcagttcaga gtgatagga                                     29

<210> SEQ ID NO 4
<211> LENGTH: 69
<212> TYPE: DNA
<213> ORGANISM: Artificial Sequence
<220> FEATURE:
<223> OTHER INFORMATION: Synthetic

<400> SEQUENCE: 4
cctagagaag gggggggcggt accaccccac ctccatgcct gtagcgcgac atggcaattc    60
cacttcatc                                                             69

<210> SEQ ID NO 5
<211> LENGTH: 69
<212> TYPE: DNA
<213> ORGANISM: Artificial Sequence
<220> FEATURE:
<223> OTHER INFORMATION: Synthetic

<400> SEQUENCE: 5
cctgagagtc acctttccct caccaatagc atctttcagc agctctgtcc ggccccgata    60
ttcaggatc                                                             69

<210> SEQ ID NO 6
<211> LENGTH: 35
<212> TYPE: DNA
<213> ORGANISM: Artificial Sequence
<220> FEATURE:
<223> OTHER INFORMATION: synthetic

<400> SEQUENCE: 6
cgaagcttct aagatctggt gaaacctcct tcatc                                35

<210> SEQ ID NO 7
<211> LENGTH: 309
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(309)

<400> SEQUENCE: 7 gct agc aga tct tcc cag agg cac gga tcc aag tac ctg gcc aca gca      48
Ala Ser Arg Ser Ser Gln Arg His Gly Ser Lys Tyr Leu Ala Thr Ala
1               5                   10                  15 agt acc atg gac cat gcc agg cat ggc ttc ctc cca agg cac aga gac      96
Ser Thr Met Asp His Ala Arg His Gly Phe Leu Pro Arg His Arg Asp
            20                  25                  30 acg ggc atc ctt gac tcc atc ggg cgc ttc ttt ggc ggt gac agg ggt     144
Thr Gly Ile Leu Asp Ser Ile Gly Arg Phe Phe Gly Gly Asp Arg Gly
        35                  40                  45 gaa aac ccc gta gtc cac ttc ttc aag aac att gtg acg cct cgc aca     192
Glu Asn Pro Val Val His Phe Phe Lys Asn Ile Val Thr Pro Arg Thr
    50                  55                  60 cca ccc ccg tcg cag gga aag ggg aag gga gtc gat gcc cag ggc acg     240
Pro Pro Pro Ser Gln Gly Lys Gly Lys Gly Val Asp Ala Gln Gly Thr
65                  70                  75                  80 ctt tcc aaa att ttt aag ctg gga gga aga gat agt cgc tct gga tca     288
Leu Ser Lys Ile Phe Lys Leu Gly Gly Arg Asp Ser Arg Ser Gly Ser
                85                  90                  95 ccc atg ctc gag tag aag ctt                                          309
Pro Met Leu Glu     Lys Leu <210> SEQ ID NO 8
<211> LENGTH: 100
<212> TYPE: PRT
<213> ORGANISM: Artificial Sequence
<220> FEATURE:
<223> OTHER INFORMATION: Synthetic

<400> SEQUENCE: 8

Ala Ser Arg Ser Ser Gln Arg His Gly Ser Lys Tyr Leu Ala Thr Ala
1               5                   10                  15
Ser Thr Met Asp His Ala Arg His Gly Phe Leu Pro Arg His Arg Asp
            20                  25                  30
Thr Gly Ile Leu Asp Ser Ile Gly Arg Phe Phe Gly Gly Asp Arg Gly
        35                  40                  45
Glu Asn Pro Val Val His Phe Phe Lys Asn Ile Val Thr Pro Arg Thr
    50                  55                  60
Pro Pro Pro Ser Gln Gly Lys Gly Lys Gly Val Asp Ala Gln Gly Thr
65                  70                  75                  80
Leu Ser Lys Ile Phe Lys Leu Gly Gly Arg Asp Ser Arg Ser Gly Ser
                85                  90                  95
Pro Met Leu Glu
            100

<210> SEQ ID NO 9
<211> LENGTH: 35
<212> TYPE: DNA
<213> ORGANISM: Artificial Sequence
<220> FEATURE:
<223> OTHER INFORMATION: Synthetic

<400> SEQUENCE: 9
gagctagcag atcttcccag aggcacggat ccaag                               35

<210> SEQ ID NO 10
<211> LENGTH: 63
<212> TYPE: DNA
<213> ORGANISM: Artificial Sequence
<220> FEATURE:
<223> OTHER INFORMATION: Synthetic

<400> SEQUENCE: 10
cccgatggag tcaaggatgc ccgtgtctct gtgccttggg aggaagccat gcctggcatg    60
gtc                                                                  63

<210> SEQ ID NO 11
<211> LENGTH: 63
<212> TYPE: DNA
<213> ORGANISM: Artificial Sequence
<220> FEATURE:
<223> OTHER INFORMATION: Synthetic

<400> SEQUENCE: 11
tccctgcgac gggggtggtg tgcgaggcgt cacaatgttc ttgaagaagt ggactacggg    60
gtt                                                                  63

<210> SEQ ID NO 12
<211> LENGTH: 63
<212> TYPE: DNA
<213> ORGANISM: Artificial Sequence
<220> FEATURE:
<223> OTHER INFORMATION: Synthetic -continued

<400> SEQUENCE: 12

```
ctactcgagc atgggtgatc cagagcgact atctcttcct cccagcttaa aaatttggga    60
aag                                                                 63
```

<210> SEQ ID NO 13
<211> LENGTH: 35
<212> TYPE: DNA
<213> ORGANISM: Artificial Sequence
<220> FEATURE:
<223> OTHER INFORMATION: Synthetic

<400> SEQUENCE: 13

```
cgaagcttct actcgagcat gggtgatcca gagcg                              35
```

<210> SEQ ID NO 14
<211> LENGTH: 270
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(270)

<400> SEQUENCE: 14

```
gct agc ctc gag ctg ttc tgt ggc tgt gga cat gaa gcc ctc act ggc    48
Ala Ser Leu Glu Leu Phe Cys Gly Cys Gly His Glu Ala Leu Thr Gly
 1               5                  10                  15 aca gaa aag cta att gag acc tat ttc tcc aaa aac tac caa gac tat    96
Thr Glu Lys Leu Ile Glu Thr Tyr Phe Ser Lys Asn Tyr Gln Asp Tyr
             20                  25                  30 gag tat ctc ctc ctg ctg gct gag ggc ttc tac acc acc ggc gca gtc   144
Glu Tyr Leu Leu Leu Leu Ala Glu Gly Phe Tyr Thr Thr Gly Ala Val
         35                  40                  45 agg cag ata ttt ggc gac tac aag acc acc atc tgc ggc aag ggc ctg   192
Arg Gln Ile Phe Gly Asp Tyr Lys Thr Thr Ile Cys Gly Lys Gly Leu
     50                  55                  60 agc gca acg gta cat tgt ttg gga aaa tgg cta gga cat ccc gac aag   240
Ser Ala Thr Val His Cys Leu Gly Lys Trp Leu Gly His Pro Asp Lys
 65                  70                  75                  80 ttt gtg ggc atc acc gaa ttc tag aag ctt                           270
Phe Val Gly Ile Thr Glu Phe     Lys Leu
                 85
```

<210> SEQ ID NO 15
<211> LENGTH: 87
<212> TYPE: PRT
<213> ORGANISM: Artificial Sequence
<220> FEATURE:
<223> OTHER INFORMATION: Synthetic

<400> SEQUENCE: 15

```
Ala Ser Leu Glu Leu Phe Cys Gly Cys Gly His Glu Ala Leu Thr Gly
 1               5                  10                  15

Thr Glu Lys Leu Ile Glu Thr Tyr Phe Ser Lys Asn Tyr Gln Asp Tyr
             20                  25                  30

Glu Tyr Leu Leu Leu Leu Ala Glu Gly Phe Tyr Thr Thr Gly Ala Val
         35                  40                  45

Arg Gln Ile Phe Gly Asp Tyr Lys Thr Thr Ile Cys Gly Lys Gly Leu
     50                  55                  60

Ser Ala Thr Val His Cys Leu Gly Lys Trp Leu Gly His Pro Asp Lys
 65                  70                  75                  80
```

```
Phe Val Gly Ile Thr Glu Phe
            85

<210> SEQ ID NO 16
<211> LENGTH: 35
<212> TYPE: DNA
<213> ORGANISM: Artificial Sequence
<220> FEATURE:
<223> OTHER INFORMATION: Synthetic

<400> SEQUENCE: 16
gagctagcct cgagctgttc tgtggctgtg gacat                              35

<210> SEQ ID NO 17
<211> LENGTH: 63
<212> TYPE: DNA
<213> ORGANISM: Artificial Sequence
<220> FEATURE:
<223> OTHER INFORMATION: Synthetic

<400> SEQUENCE: 17
ctcagccagc aggaggagat actcatagtc ttggtagttt ttggagaaat aggtctcatt   60
tag                                                                63

<210> SEQ ID NO 18
<211> LENGTH: 63
<212> TYPE: DNA
<213> ORGANISM: Artificial Sequence
<220> FEATURE:
<223> OTHER INFORMATION: Synthetic

<400> SEQUENCE: 18
acaatgtacc gttgcgctca ggcccttgcc gcagatggtg ttcttgtagt cgccaaatat   60
ctg                                                                63

<210> SEQ ID NO 19
<211> LENGTH: 44
<212> TYPE: DNA
<213> ORGANISM: Artificial Sequence
<220> FEATURE:
<223> OTHER INFORMATION: Synthetic

<400> SEQUENCE: 19
cgaagcttct agaattcggt gatgcccaca aacttgtcgg gatg                    44

<210> SEQ ID NO 20
<211> LENGTH: 228
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(228)

<400> SEQUENCE: 20 gct agc gaa ttc agt cag aaa ccg gcc aag gag ggt ccc aga ctc tcc    48
Ala Ser Glu Phe Ser Gln Lys Pro Ala Lys Glu Gly Pro Arg Leu Ser
1               5                   10                  15 aag aac cag aag tac tcc gaa cac ttc agc ata acc ttc ctc aat tcc    96
Lys Asn Gln Lys Tyr Ser Glu His Phe Ser Ile Thr Phe Leu Asn Ser
            20                  25                  30 aag aag gag ata gtg gat cgg aaa tac agc atc agt aag agc ggc cag   144
Lys Lys Glu Ile Val Asp Arg Lys Tyr Ser Ile Ser Lys Ser Gly Gln
        35                  40                  45
```

```
aag acc aga acc agc cgc cgt gcc aag tcc cct cag agg ccc aag caa      192
Lys Thr Arg Thr Ser Arg Arg Ala Lys Ser Pro Gln Arg Pro Lys Gln
 50                  55                  60 cag cca gct gcg cct cca gcg gtg gtc tag aag ctt                      228
Gln Pro Ala Ala Pro Pro Ala Val Val     Lys Leu
 65                  70                  75
```

<210> SEQ ID NO 21
<211> LENGTH: 73
<212> TYPE: PRT
<213> ORGANISM: Artificial Sequence
<220> FEATURE:
<223> OTHER INFORMATION: Synthetic

<400> SEQUENCE: 21

```
Ala Ser Glu Phe Ser Gln Lys Pro Ala Lys Glu Gly Pro Arg Leu Ser
 1               5                  10                  15

Lys Asn Gln Lys Tyr Ser Glu His Phe Ser Ile Thr Phe Leu Asn Ser
                 20                  25                  30

Lys Lys Glu Ile Val Asp Arg Lys Tyr Ser Ile Ser Lys Ser Gly Gln
             35                  40                  45

Lys Thr Arg Thr Ser Arg Arg Ala Lys Ser Pro Gln Arg Pro Lys Gln
 50                  55                  60

Gln Pro Ala Ala Pro Pro Ala Val Val
 65                  70
```

<210> SEQ ID NO 22
<211> LENGTH: 29
<212> TYPE: DNA
<213> ORGANISM: Artificial Sequence
<220> FEATURE:
<223> OTHER INFORMATION: Synthetic

<400> SEQUENCE: 22
gagctagcga attcagtcag aaaccggcc                                       29

<210> SEQ ID NO 23
<211> LENGTH: 69
<212> TYPE: DNA
<213> ORGANISM: Artificial Sequence
<220> FEATURE:
<223> OTHER INFORMATION: Synthetic

<400> SEQUENCE: 23
gctgtatttc cgatccacta tctccttctt ggaattgagg aaggttatgc tgaagtgttc     60
ggagtactt                                                             69

<210> SEQ ID NO 24
<211> LENGTH: 69
<212> TYPE: DNA
<213> ORGANISM: Artificial Sequence
<220> FEATURE:
<223> OTHER INFORMATION: Synthetic

<400> SEQUENCE: 24
aagcttctag accaccgctg gaggcgcagc tggctgttgc ttgggcctct gaggggactt     60
ggcacggcg                                                             69

<210> SEQ ID NO 25
<211> LENGTH: 23
<212> TYPE: DNA
<213> ORGANISM: Artificial Sequence
<220> FEATURE:

<223> OTHER INFORMATION: Synthetic

<400> SEQUENCE: 25
cgaagcttct agaccaccgc tgg     23

<210> SEQ ID NO 26
<211> LENGTH: 819
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(819)

<400> SEQUENCE: 26

| gct | agc | ggg | cag | ttc | aga | gtg | ata | gga | cca | aga | cac | cct | atc | cgg | gct | 48 |
|---|---|---|---|---|---|---|---|---|---|---|---|---|---|---|---|---|
| Ala | Ser | Gly | Gln | Phe | Arg | Val | Ile | Gly | Pro | Arg | His | Pro | Ile | Arg | Ala | |
| 1 | | | | 5 | | | | | 10 | | | | | 15 | | |

| ctg | gtc | ggg | gat | gaa | gtg | gaa | ttg | cca | tgt | cgc | gct | aca | ggc | atg | gag | 96 |
|---|---|---|---|---|---|---|---|---|---|---|---|---|---|---|---|---|
| Leu | Val | Gly | Asp | Glu | Val | Glu | Leu | Pro | Cys | Arg | Ala | Thr | Gly | Met | Glu | |
| | | | 20 | | | | | 25 | | | | | 30 | | | |

| gtg | ggg | tgg | tac | cgc | ccc | ccc | ttc | tct | agg | gtg | gtt | cat | ctc | tac | aga | 144 |
|---|---|---|---|---|---|---|---|---|---|---|---|---|---|---|---|---|
| Val | Gly | Trp | Tyr | Arg | Pro | Pro | Phe | Ser | Arg | Val | Val | His | Leu | Tyr | Arg | |
| | 35 | | | | | 40 | | | | | 45 | | | | | |

| aat | ggc | aag | gac | caa | gat | cct | gaa | tat | cgg | ggc | cgg | aca | gag | ctg | ctg | 192 |
|---|---|---|---|---|---|---|---|---|---|---|---|---|---|---|---|---|
| Asn | Gly | Lys | Asp | Gln | Asp | Pro | Glu | Tyr | Arg | Gly | Arg | Thr | Glu | Leu | Leu | |
| 50 | | | | | 55 | | | | | 60 | | | | | | |

| aaa | gat | gct | att | ggt | gag | gga | aag | gtg | act | ctc | agg | atc | cgg | aat | gta | 240 |
|---|---|---|---|---|---|---|---|---|---|---|---|---|---|---|---|---|
| Lys | Asp | Ala | Ile | Gly | Glu | Gly | Lys | Val | Thr | Leu | Arg | Ile | Arg | Asn | Val | |
| 65 | | | | 70 | | | | | 75 | | | | | 80 | | |

| agg | ttc | tca | gat | gaa | gga | ggt | ttc | acc | aga | tct | tcc | cag | agg | cac | gga | 288 |
|---|---|---|---|---|---|---|---|---|---|---|---|---|---|---|---|---|
| Arg | Phe | Ser | Asp | Glu | Gly | Gly | Phe | Thr | Arg | Ser | Ser | Gln | Arg | His | Gly | |
| | | | | 85 | | | | | 90 | | | | | 95 | | |

| tcc | aag | tac | ctg | gcc | aca | gca | agt | acc | atg | gac | cat | gcc | agg | cat | ggc | 336 |
|---|---|---|---|---|---|---|---|---|---|---|---|---|---|---|---|---|
| Ser | Lys | Tyr | Leu | Ala | Thr | Ala | Ser | Thr | Met | Asp | His | Ala | Arg | His | Gly | |
| | | | 100 | | | | | 105 | | | | | 110 | | | |

| ttc | ctc | cca | agg | cac | aga | gac | acg | ggc | atc | ctt | gac | tcc | atc | ggg | cgc | 384 |
|---|---|---|---|---|---|---|---|---|---|---|---|---|---|---|---|---|
| Phe | Leu | Pro | Arg | His | Arg | Asp | Thr | Gly | Ile | Leu | Asp | Ser | Ile | Gly | Arg | |
| | | 115 | | | | | 120 | | | | | 125 | | | | |

| ttc | ttt | ggc | ggt | gac | agg | ggt | gaa | aac | ccc | gta | gtc | cac | ttc | ttc | aag | 432 |
|---|---|---|---|---|---|---|---|---|---|---|---|---|---|---|---|---|
| Phe | Phe | Gly | Gly | Asp | Arg | Gly | Glu | Asn | Pro | Val | Val | His | Phe | Phe | Lys | |
| 130 | | | | | 135 | | | | | 140 | | | | | | |

| aac | att | gtg | acg | cct | cgc | aca | cca | ccc | ccg | tcg | cag | gga | aag | ggg | aag | 480 |
|---|---|---|---|---|---|---|---|---|---|---|---|---|---|---|---|---|
| Asn | Ile | Val | Thr | Pro | Arg | Thr | Pro | Pro | Pro | Ser | Gln | Gly | Lys | Gly | Lys | |
| 145 | | | | 150 | | | | | 155 | | | | | 160 | | |

| gga | gtc | gat | gcc | cag | ggc | acg | ctt | tcc | aaa | att | ttt | aag | ctg | gga | gga | 528 |
|---|---|---|---|---|---|---|---|---|---|---|---|---|---|---|---|---|
| Gly | Val | Asp | Ala | Gln | Gly | Thr | Leu | Ser | Lys | Ile | Phe | Lys | Leu | Gly | Gly | |
| | | | | 165 | | | | | 170 | | | | | 175 | | |

| aga | gat | agt | cgc | tct | gga | tca | ccc | atg | ctc | gag | ctg | ttc | tgt | ggc | tgt | 576 |
|---|---|---|---|---|---|---|---|---|---|---|---|---|---|---|---|---|
| Arg | Asp | Ser | Arg | Ser | Gly | Ser | Pro | Met | Leu | Glu | Leu | Phe | Cys | Gly | Cys | |
| | | | 180 | | | | | 185 | | | | | 190 | | | |

| gga | cat | gaa | gcc | ctc | act | ggc | aca | gaa | aag | cta | att | gag | acc | tat | ttc | 624 |
|---|---|---|---|---|---|---|---|---|---|---|---|---|---|---|---|---|
| Gly | His | Glu | Ala | Leu | Thr | Gly | Thr | Glu | Lys | Leu | Ile | Glu | Thr | Tyr | Phe | |
| | | 195 | | | | | 200 | | | | | 205 | | | | |

| tcc | aaa | aac | tac | caa | gac | tat | gag | tat | ctc | ctc | ctg | ctg | gct | gag | ggc | 672 |
|---|---|---|---|---|---|---|---|---|---|---|---|---|---|---|---|---|
| Ser | Lys | Asn | Tyr | Gln | Asp | Tyr | Glu | Tyr | Leu | Leu | Leu | Leu | Ala | Glu | Gly | |
| 210 | | | | | 215 | | | | | 220 | | | | | | |

| ttc | tac | acc | acc | ggc | gca | gtc | agg | cag | ata | ttt | ggc | gac | tac | aag | acc | 720 |
|---|---|---|---|---|---|---|---|---|---|---|---|---|---|---|---|---|
| Phe | Tyr | Thr | Thr | Gly | Ala | Val | Arg | Gln | Ile | Phe | Gly | Asp | Tyr | Lys | Thr | |
| 225 | | | | | 230 | | | | | 235 | | | | | 240 | |

| acc | atc | tgc | ggc | aag | ggc | ctg | agc | gca | acg | gta | cat | tgt | ttg | gga | aaa | 768 |

```
Thr Ile Cys Gly Lys Gly Leu Ser Ala Thr Val His Cys Leu Gly Lys
                245                 250                 255 tgg cta gga cat ccc gac aag ttt gtg ggc atc acc gaa ttc tag aag      816
Trp Leu Gly His Pro Asp Lys Phe Val Gly Ile Thr Glu Phe     Lys
            260                 265                 270 ctt                                                                   819
Leu
```

<210> SEQ ID NO 27
<211> LENGTH: 270
<212> TYPE: PRT
<213> ORGANISM: Artificial Sequence
<220> FEATURE:
<223> OTHER INFORMATION: Synthetic

<400> SEQUENCE: 27

```
Ala Ser Gly Gln Phe Arg Val Ile Gly Pro Arg His Pro Ile Arg Ala
1               5                   10                  15

Leu Val Gly Asp Glu Val Glu Leu Pro Cys Arg Ala Thr Gly Met Glu
            20                  25                  30

Val Gly Trp Tyr Arg Pro Pro Phe Ser Arg Val Val His Leu Tyr Arg
        35                  40                  45

Asn Gly Lys Asp Gln Asp Pro Glu Tyr Arg Gly Arg Thr Glu Leu Leu
    50                  55                  60

Lys Asp Ala Ile Gly Glu Gly Lys Val Thr Leu Arg Ile Arg Asn Val
65                  70                  75                  80

Arg Phe Ser Asp Glu Gly Gly Phe Thr Arg Ser Ser Gln Arg His Gly
                85                  90                  95

Ser Lys Tyr Leu Ala Thr Ala Ser Thr Met Asp His Ala Arg His Gly
            100                 105                 110

Phe Leu Pro Arg His Arg Asp Thr Gly Ile Leu Asp Ser Ile Gly Arg
        115                 120                 125

Phe Phe Gly Gly Asp Arg Gly Glu Asn Pro Val Val His Phe Lys
    130                 135                 140

Asn Ile Val Thr Pro Arg Thr Pro Pro Ser Gln Gly Lys Gly Lys
145                 150                 155                 160

Gly Val Asp Ala Gln Gly Thr Leu Ser Lys Ile Phe Lys Leu Gly Gly
                165                 170                 175

Arg Asp Ser Arg Ser Gly Ser Pro Met Leu Glu Leu Phe Cys Gly Cys
            180                 185                 190

Gly His Glu Ala Leu Thr Gly Thr Glu Lys Leu Ile Glu Thr Tyr Phe
        195                 200                 205

Ser Lys Asn Tyr Gln Asp Tyr Glu Tyr Leu Leu Leu Ala Glu Gly
    210                 215                 220

Phe Tyr Thr Thr Gly Ala Val Arg Gln Ile Phe Gly Asp Tyr Lys Thr
225                 230                 235                 240

Thr Ile Cys Gly Lys Gly Leu Ser Ala Thr Val His Cys Leu Gly Lys
                245                 250                 255

Trp Leu Gly His Pro Asp Lys Phe Val Gly Ile Thr Glu Phe
            260                 265                 270
```

<210> SEQ ID NO 28
<211> LENGTH: 1026
<212> TYPE: DNA
<213> ORGANISM: Artificial Sequence
<220> FEATURE:
<223> OTHER INFORMATION: Synthetic
<220> FEATURE:
<221> NAME/KEY: CDS

<222> LOCATION: (1)..(1026)

<400> SEQUENCE: 28

| | | | | | | | | | | | | | | | | |
|---|---|---|---|---|---|---|---|---|---|---|---|---|---|---|---|---|
| gct | agc | ggg | cag | ttc | aga | gtg | ata | gga | cca | aga | cac | cct | atc | cgg | gct | 48 |
| Ala | Ser | Gly | Gln | Phe | Arg | Val | Ile | Gly | Pro | Arg | His | Pro | Ile | Arg | Ala | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ctg | gtc | ggg | gat | gaa | gtg | gaa | ttg | cca | tgt | cgc | gct | aca | ggc | atg | gag | 96 |
| Leu | Val | Gly | Asp | Glu | Val | Glu | Leu | Pro | Cys | Arg | Ala | Thr | Gly | Met | Glu | |
| | | 20 | | | | | 25 | | | | | 30 | | | | |

| | | | | | | | | | | | | | | | | |
|---|---|---|---|---|---|---|---|---|---|---|---|---|---|---|---|---|
| gtg | ggg | tgg | tac | cgc | ccc | ccc | ttc | tct | agg | gtg | gtt | cat | ctc | tac | aga | 144 |
| Val | Gly | Trp | Tyr | Arg | Pro | Pro | Phe | Ser | Arg | Val | Val | His | Leu | Tyr | Arg | |
| | | | 35 | | | | | 40 | | | | | 45 | | | |

| | | | | | | | | | | | | | | | | |
|---|---|---|---|---|---|---|---|---|---|---|---|---|---|---|---|---|
| aat | ggc | aag | gac | caa | gat | cct | gaa | tat | cgg | ggc | cgg | aca | gag | ctg | ctg | 192 |
| Asn | Gly | Lys | Asp | Gln | Asp | Pro | Glu | Tyr | Arg | Gly | Arg | Thr | Glu | Leu | Leu | |
| 50 | | | | | 55 | | | | | 60 | | | | | | |

| | | | | | | | | | | | | | | | | |
|---|---|---|---|---|---|---|---|---|---|---|---|---|---|---|---|---|
| aaa | gat | gct | att | ggt | gag | gga | aag | gtg | act | ctc | agg | atc | cgg | aat | gta | 240 |
| Lys | Asp | Ala | Ile | Gly | Glu | Gly | Lys | Val | Thr | Leu | Arg | Ile | Arg | Asn | Val | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| agg | ttc | tca | gat | gaa | gga | ggt | ttc | acc | aga | tct | tcc | cag | agg | cac | gga | 288 |
| Arg | Phe | Ser | Asp | Glu | Gly | Gly | Phe | Thr | Arg | Ser | Ser | Gln | Arg | His | Gly | |
| | | | | 85 | | | | | 90 | | | | | 95 | | |

| | | | | | | | | | | | | | | | | |
|---|---|---|---|---|---|---|---|---|---|---|---|---|---|---|---|---|
| tcc | aag | tac | ctg | gcc | aca | gca | agt | acc | atg | gac | cat | gcc | agg | cat | ggc | 336 |
| Ser | Lys | Tyr | Leu | Ala | Thr | Ala | Ser | Thr | Met | Asp | His | Ala | Arg | His | Gly | |
| | | | 100 | | | | | 105 | | | | | 110 | | | |

| | | | | | | | | | | | | | | | | |
|---|---|---|---|---|---|---|---|---|---|---|---|---|---|---|---|---|
| ttc | ctc | cca | agg | cac | aga | gac | acg | ggc | atc | ctt | gac | tcc | atc | ggg | cgc | 384 |
| Phe | Leu | Pro | Arg | His | Arg | Asp | Thr | Gly | Ile | Leu | Asp | Ser | Ile | Gly | Arg | |
| | | 115 | | | | | 120 | | | | | 125 | | | | |

| | | | | | | | | | | | | | | | | |
|---|---|---|---|---|---|---|---|---|---|---|---|---|---|---|---|---|
| ttc | ttt | ggc | ggt | gac | agg | ggt | gaa | aac | ccc | gta | gtc | cac | ttc | ttc | aag | 432 |
| Phe | Phe | Gly | Gly | Asp | Arg | Gly | Glu | Asn | Pro | Val | Val | His | Phe | Phe | Lys | |
| | 130 | | | | | 135 | | | | | 140 | | | | | |

| | | | | | | | | | | | | | | | | |
|---|---|---|---|---|---|---|---|---|---|---|---|---|---|---|---|---|
| aac | att | gtg | acg | cct | cgc | aca | cca | ccc | ccg | tcg | cag | gga | aag | ggg | aag | 480 |
| Asn | Ile | Val | Thr | Pro | Arg | Thr | Pro | Pro | Pro | Ser | Gln | Gly | Lys | Gly | Lys | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| gga | gtc | gat | gcc | cag | ggc | acg | ctt | tcc | aaa | att | ttt | aag | ctg | gga | gga | 528 |
| Gly | Val | Asp | Ala | Gln | Gly | Thr | Leu | Ser | Lys | Ile | Phe | Lys | Leu | Gly | Gly | |
| | | | | 165 | | | | | 170 | | | | | 175 | | |

| | | | | | | | | | | | | | | | | |
|---|---|---|---|---|---|---|---|---|---|---|---|---|---|---|---|---|
| aga | gat | agt | cgc | tct | gga | tca | ccc | atg | ctc | gag | ctg | ttc | tgt | ggc | tgt | 576 |
| Arg | Asp | Ser | Arg | Ser | Gly | Ser | Pro | Met | Leu | Glu | Leu | Phe | Cys | Gly | Cys | |
| | | | 180 | | | | | 185 | | | | | 190 | | | |

| | | | | | | | | | | | | | | | | |
|---|---|---|---|---|---|---|---|---|---|---|---|---|---|---|---|---|
| gga | cat | gaa | gcc | ctc | act | ggc | aca | gaa | aag | cta | att | gag | acc | tat | ttc | 624 |
| Gly | His | Glu | Ala | Leu | Thr | Gly | Thr | Glu | Lys | Leu | Ile | Glu | Thr | Tyr | Phe | |
| | | 195 | | | | | 200 | | | | | 205 | | | | |

| | | | | | | | | | | | | | | | | |
|---|---|---|---|---|---|---|---|---|---|---|---|---|---|---|---|---|
| tcc | aaa | aac | tac | caa | gac | tat | gag | tat | ctc | ctg | ctg | gct | gag | ggc | | 672 |
| Ser | Lys | Asn | Tyr | Gln | Asp | Tyr | Glu | Tyr | Leu | Leu | Leu | Ala | Glu | Gly | | |
| | 210 | | | | | 215 | | | | | 220 | | | | | |

| | | | | | | | | | | | | | | | | |
|---|---|---|---|---|---|---|---|---|---|---|---|---|---|---|---|---|
| ttc | tac | acc | acc | ggc | gca | gtc | agg | cag | ata | ttt | ggc | gac | tac | aag | acc | 720 |
| Phe | Tyr | Thr | Thr | Gly | Ala | Val | Arg | Gln | Ile | Phe | Gly | Asp | Tyr | Lys | Thr | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| acc | atc | tgc | ggc | aag | ggc | ctg | agc | gca | acg | gta | cat | tgt | ttg | gga | aaa | 768 |
| Thr | Ile | Cys | Gly | Lys | Gly | Leu | Ser | Ala | Thr | Val | His | Cys | Leu | Gly | Lys | |
| | | | | 245 | | | | | 250 | | | | | 255 | | |

| | | | | | | | | | | | | | | | | |
|---|---|---|---|---|---|---|---|---|---|---|---|---|---|---|---|---|
| tgg | cta | gga | cat | ccc | gac | aag | ttt | gtg | ggc | atc | acc | gaa | ttc | agt | cag | 816 |
| Trp | Leu | Gly | His | Pro | Asp | Lys | Phe | Val | Gly | Ile | Thr | Glu | Phe | Ser | Gln | |
| | | | 260 | | | | | 265 | | | | | 270 | | | |

| | | | | | | | | | | | | | | | | |
|---|---|---|---|---|---|---|---|---|---|---|---|---|---|---|---|---|
| aaa | ccg | gcc | aag | gag | ggt | ccc | aga | ctc | tcc | aag | aac | cag | aag | tac | tcc | 864 |
| Lys | Pro | Ala | Lys | Glu | Gly | Pro | Arg | Leu | Ser | Lys | Asn | Gln | Lys | Tyr | Ser | |
| | | 275 | | | | | 280 | | | | | 285 | | | | |

| | | | | | | | | | | | | | | | | |
|---|---|---|---|---|---|---|---|---|---|---|---|---|---|---|---|---|
| gaa | cac | ttc | agc | ata | acc | ttc | ctc | aat | tcc | aag | aag | gag | ata | gtg | gat | 912 |
| Glu | His | Phe | Ser | Ile | Thr | Phe | Leu | Asn | Ser | Lys | Lys | Glu | Ile | Val | Asp | |
| | 290 | | | | | 295 | | | | | 300 | | | | | |

```
cgg aaa tac agc atc agt aag agc ggc cag aag acc aga acc agc cgc      960
Arg Lys Tyr Ser Ile Ser Lys Ser Gly Gln Lys Thr Arg Thr Ser Arg
305                 310                 315                 320 cgt gcc aag tcc cct cag agg ccc aag caa cag cca gct gcg cct cca     1008
Arg Ala Lys Ser Pro Gln Arg Pro Lys Gln Gln Pro Ala Ala Pro Pro
                325                 330                 335 gcg gtg gtc tag aag ctt                                             1026
Ala Val Val     Lys Leu
                340
```

<210> SEQ ID NO 29
<211> LENGTH: 339
<212> TYPE: PRT
<213> ORGANISM: Artificial Sequence
<220> FEATURE:
<223> OTHER INFORMATION: Synthetic

<400> SEQUENCE: 29

```
Ala Ser Gly Gln Phe Arg Val Ile Gly Pro Arg His Pro Ile Arg Ala
1               5                   10                  15

Leu Val Gly Asp Glu Val Glu Leu Pro Cys Arg Ala Thr Gly Met Glu
            20                  25                  30

Val Gly Trp Tyr Arg Pro Pro Phe Ser Arg Val Val His Leu Tyr Arg
        35                  40                  45

Asn Gly Lys Asp Gln Asp Pro Glu Tyr Arg Gly Arg Thr Glu Leu Leu
    50                  55                  60

Lys Asp Ala Ile Gly Glu Gly Lys Val Thr Leu Arg Ile Arg Asn Val
65                  70                  75                  80

Arg Phe Ser Asp Glu Gly Gly Phe Thr Arg Ser Ser Gln Arg His Gly
                85                  90                  95

Ser Lys Tyr Leu Ala Thr Ala Ser Thr Met Asp His Ala Arg His Gly
            100                 105                 110

Phe Leu Pro Arg His Arg Asp Thr Gly Ile Leu Asp Ser Ile Gly Arg
        115                 120                 125

Phe Phe Gly Gly Asp Arg Gly Glu Asn Pro Val Val His Phe Phe Lys
    130                 135                 140

Asn Ile Val Thr Pro Arg Thr Pro Pro Ser Gln Gly Lys Gly Lys
145                 150                 155                 160

Gly Val Asp Ala Gln Gly Thr Leu Ser Lys Ile Phe Lys Leu Gly Gly
                165                 170                 175

Arg Asp Ser Arg Ser Gly Ser Pro Met Leu Glu Leu Phe Cys Gly Cys
            180                 185                 190

Gly His Glu Ala Leu Thr Gly Thr Glu Lys Leu Ile Glu Thr Tyr Phe
        195                 200                 205

Ser Lys Asn Tyr Gln Asp Tyr Glu Tyr Leu Leu Leu Ala Glu Gly
    210                 215                 220

Phe Tyr Thr Thr Gly Ala Val Arg Gln Ile Phe Gly Asp Tyr Lys Thr
225                 230                 235                 240

Thr Ile Cys Gly Lys Gly Leu Ser Ala Thr Val His Cys Leu Gly Lys
                245                 250                 255

Trp Leu Gly His Pro Asp Lys Phe Val Gly Ile Thr Glu Phe Ser Gln
            260                 265                 270

Lys Pro Ala Lys Glu Gly Pro Arg Leu Ser Lys Asn Gln Lys Tyr Ser
        275                 280                 285

Glu His Phe Ser Ile Thr Phe Leu Asn Ser Lys Glu Ile Val Asp
    290                 295                 300

Arg Lys Tyr Ser Ile Ser Lys Ser Gly Gln Lys Thr Arg Thr Ser Arg
```

```
                    305                 310                 315                 320
Arg Ala Lys Ser Pro Gln Arg Pro Lys Gln Gln Pro Ala Ala Pro Pro
                325                 330                 335

Ala Val Val

<210> SEQ ID NO 30
<211> LENGTH: 354
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(354)

<400> SEQUENCE: 30 gaa ttc gct agc ggc atg gag gtg ggg tgg tat cgc cca cca ttc tct    48
Glu Phe Ala Ser Gly Met Glu Val Gly Trp Tyr Arg Pro Pro Phe Ser
1               5                   10                  15 agg gtg gtt cat ctc tac cgt aat ggc aag gac ggc cgt aca gag ctg    96
Arg Val Val His Leu Tyr Arg Asn Gly Lys Asp Gly Arg Thr Glu Leu
                20                  25                  30 ctg aaa gat gct att ggt gag gga aag gtg act ctc agg att cgg aat   144
Leu Lys Asp Ala Ile Gly Glu Gly Lys Val Thr Leu Arg Ile Arg Asn
            35                  40                  45 gta cgc ttc tct gat gaa gga ggt ttc acc agc ttc ttc cgt gac cat   192
Val Arg Phe Ser Asp Glu Gly Gly Phe Thr Ser Phe Phe Arg Asp His
        50                  55                  60 tct tac caa gag gag gca gca atg gaa ttg aaa aga tct ttc aga gtg   240
Ser Tyr Gln Glu Glu Ala Ala Met Glu Leu Lys Arg Ser Phe Arg Val
65                  70                  75                  80 ata gga cca aga cac cca atc cgt gct ctg gtc ggg gat gaa gtg gaa   288
Ile Gly Pro Arg His Pro Ile Arg Ala Leu Val Gly Asp Glu Val Glu
                85                  90                  95 ttg cca tct cgc ata tcg aga ctt gca ggg caa ttc ctt gaa gag ctg   336
Leu Pro Ser Arg Ile Ser Arg Leu Ala Gly Gln Phe Leu Glu Glu Leu
                100                 105                 110 cgt gga tcc tga aag ctt                                           354
Arg Gly Ser     Lys Leu
        115

<210> SEQ ID NO 31
<211> LENGTH: 115
<212> TYPE: PRT
<213> ORGANISM: Artificial Sequence
<220> FEATURE:
<223> OTHER INFORMATION: Synthetic

<400> SEQUENCE: 31

Glu Phe Ala Ser Gly Met Glu Val Gly Trp Tyr Arg Pro Pro Phe Ser
1               5                   10                  15

Arg Val Val His Leu Tyr Arg Asn Gly Lys Asp Gly Arg Thr Glu Leu
                20                  25                  30

Leu Lys Asp Ala Ile Gly Glu Gly Lys Val Thr Leu Arg Ile Arg Asn
            35                  40                  45

Val Arg Phe Ser Asp Glu Gly Gly Phe Thr Ser Phe Phe Arg Asp His
        50                  55                  60

Ser Tyr Gln Glu Glu Ala Ala Met Glu Leu Lys Arg Ser Phe Arg Val
65                  70                  75                  80

Ile Gly Pro Arg His Pro Ile Arg Ala Leu Val Gly Asp Glu Val Glu
                85                  90                  95
```

```
Leu Pro Ser Arg Ile Ser Arg Leu Ala Gly Gln Phe Leu Glu Glu Leu
                100                 105                 110
Arg Gly Ser
        115

<210> SEQ ID NO 32
<211> LENGTH: 69
<212> TYPE: DNA
<213> ORGANISM: Artificial Sequence
<220> FEATURE:
<223> OTHER INFORMATION: Synthetic

<400> SEQUENCE: 32
gagagtcacc tttccctcac caatagcatc tttcagcagc tctgtacggc cgtccttgcc    60
attacggta                                                           69

<210> SEQ ID NO 33
<211> LENGTH: 69
<212> TYPE: DNA
<213> ORGANISM: Artificial Sequence
<220> FEATURE:
<223> OTHER INFORMATION: Synthetic

<400> SEQUENCE: 33
gaaagatctt tcaattcca ttgctgcctc ctcttggtaa gaatggtcac ggaagaagct    60
ggtgaaacc                                                           69

<210> SEQ ID NO 34
<211> LENGTH: 69
<212> TYPE: DNA
<213> ORGANISM: Artificial Sequence
<220> FEATURE:
<223> OTHER INFORMATION: Synthetic

<400> SEQUENCE: 34
cagctcttca aggaattgcc ctgcaagtct cgatatgcga gatggcaatt ccacttcatc    60
cccgaccag                                                           69

<210> SEQ ID NO 35
<211> LENGTH: 39
<212> TYPE: DNA
<213> ORGANISM: Artificial Sequence
<220> FEATURE:
<223> OTHER INFORMATION: Synthetic

<400> SEQUENCE: 35
aagctttcag gatccacgca gctcttcaag gaattgccc                          39

<210> SEQ ID NO 36
<211> LENGTH: 300
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(300)

<400> SEQUENCE: 36 gaa ttc gct agc gga tcc aac cca gta gtc cac ttc ttc aag aac att    48
Glu Phe Ala Ser Gly Ser Asn Pro Val Val His Phe Phe Lys Asn Ile
1               5                   10                  15 gtg acg cca cgc aca cca cca ccg tcg cag gga aag ggg aga gga ctg    96
Val Thr Pro Arg Thr Pro Pro Pro Ser Gln Gly Lys Gly Arg Gly Leu
            20                  25                  30
```

```
tcc ctg ttc aag gga gtc gat gcc cag ggc acg ctt tcc aaa att ttt      144
Ser Leu Phe Lys Gly Val Asp Ala Gln Gly Thr Leu Ser Lys Ile Phe
        35                  40                  45 aag ctg gga gga cgt gat agt cgc tct gga tct ccg atg gct tct aga      192
Lys Leu Gly Gly Arg Asp Ser Arg Ser Gly Ser Pro Met Ala Ser Arg
 50                  55                  60 tcc aag tac ctg gcc aca gca agt acg atg gat cat gcc cgt cat ggc      240
Ser Lys Tyr Leu Ala Thr Ala Ser Thr Met Asp His Ala Arg His Gly
 65                  70                  75                  80 ttc ctc cca cgt cac cgc gac acg ggc atc ctt gac tcc atc ggg act      288
Phe Leu Pro Arg His Arg Asp Thr Gly Ile Leu Asp Ser Ile Gly Thr
                 85                  90                  95 agt tga aag ctt                                                      300
Ser     Lys Leu <210> SEQ ID NO 37
<211> LENGTH: 97
<212> TYPE: PRT
<213> ORGANISM: Artificial Sequence
<220> FEATURE:
<223> OTHER INFORMATION: Synthetic

<400> SEQUENCE: 37

Glu Phe Ala Ser Gly Ser Asn Pro Val Val His Phe Phe Lys Asn Ile
 1               5                  10                  15

Val Thr Pro Arg Thr Pro Pro Ser Gln Gly Lys Gly Arg Gly Leu
                 20                  25                  30

Ser Leu Phe Lys Gly Val Asp Ala Gln Gly Thr Leu Ser Lys Ile Phe
        35                  40                  45

Lys Leu Gly Gly Arg Asp Ser Arg Ser Gly Ser Pro Met Ala Ser Arg
 50                  55                  60

Ser Lys Tyr Leu Ala Thr Ala Ser Thr Met Asp His Ala Arg His Gly
 65                  70                  75                  80

Phe Leu Pro Arg His Arg Asp Thr Gly Ile Leu Asp Ser Ile Gly Thr
                 85                  90                  95

Ser

<210> SEQ ID NO 38
<211> LENGTH: 69
<212> TYPE: DNA
<213> ORGANISM: Artificial Sequence
<220> FEATURE:
<223> OTHER INFORMATION: Synthetic

<400> SEQUENCE: 38
aagcgtgccc tgggcatcga ctccttgaa cagggacagt cctctcccct ttccctgcga     60
cggtggtgg                                                            69

<210> SEQ ID NO 39
<211> LENGTH: 69
<212> TYPE: DNA
<213> ORGANISM: Artificial Sequence
<220> FEATURE:
<223> OTHER INFORMATION: Synthetic

<400> SEQUENCE: 39
acgggcatga tccatcgtac ttgctgtggc caggtacttg gatctagaag ccatcggaga     60
tccagagcg                                                            69

<210> SEQ ID NO 40
```

```
<211> LENGTH: 36
<212> TYPE: DNA
<213> ORGANISM: Artificial Sequence
<220> FEATURE:
<223> OTHER INFORMATION: Synthetic

<400> SEQUENCE: 40
aagctttcaa ctagtcccga tggagtcaag gatgcc                                36

<210> SEQ ID NO 41
<211> LENGTH: 426
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(402)

<400> SEQUENCE: 41 gaa ttc gct agc ctc gag tac aag acc acc atc agc ggc aag ggc ctg     48
Glu Phe Ala Ser Leu Glu Tyr Lys Thr Thr Ile Ser Gly Lys Gly Leu
1               5                   10                  15 agc gca acg gta aca ggg ggc cag aag ggg cgt ggt tcc aga ggc caa     96
Ser Ala Thr Val Thr Gly Gly Gln Lys Gly Arg Gly Ser Arg Gly Gln
            20                  25                  30 cat caa gct cat tct ttg gag cgt gtg agc cat tct ttg gga aaa tgg    144
His Gln Ala His Ser Leu Glu Arg Val Ser His Ser Leu Gly Lys Trp
        35                  40                  45 tta gga cat ccg gac aag ttc aac acc tgg acc acc agc cag tct att    192
Leu Gly His Pro Asp Lys Phe Asn Thr Trp Thr Thr Ser Gln Ser Ile
    50                  55                  60 gcc ttc cca agc aag acc tct gcc agt ata ggc agt ctc tct gct gac    240
Ala Phe Pro Ser Lys Thr Ser Ala Ser Ile Gly Ser Leu Ser Ala Asp
65                  70                  75                  80 gcc gtt tct ggc tcc aac ctt ctg tcc atc agc aaa aca gca gag ttc    288
Ala Val Ser Gly Ser Asn Leu Leu Ser Ile Ser Lys Thr Ala Glu Phe
                85                  90                  95 caa atg acc ttc cac ctg ttt att gga tcc gcc ctc act ggc aca gaa    336
Gln Met Thr Phe His Leu Phe Ile Gly Ser Ala Leu Thr Gly Thr Glu
            100                 105                 110 aag ctg att gag acc tat ttc tcc aaa ttt gcc gtc ctt aaa ctc atg    384
Lys Leu Ile Glu Thr Tyr Phe Ser Lys Phe Ala Val Leu Lys Leu Met
        115                 120                 125 ggc cgt ggc acc aag ttc tgatcatgag cggccgcaag ctta                 426
Gly Arg Gly Thr Lys Phe
    130

<210> SEQ ID NO 42
<211> LENGTH: 134
<212> TYPE: PRT
<213> ORGANISM: Artificial Sequence
<220> FEATURE:
<223> OTHER INFORMATION: Synthetic

<400> SEQUENCE: 42

Glu Phe Ala Ser Leu Glu Tyr Lys Thr Thr Ile Ser Gly Lys Gly Leu
1               5                   10                  15

Ser Ala Thr Val Thr Gly Gly Gln Lys Gly Arg Gly Ser Arg Gly Gln
            20                  25                  30

His Gln Ala His Ser Leu Glu Arg Val Ser His Ser Leu Gly Lys Trp
        35                  40                  45

Leu Gly His Pro Asp Lys Phe Asn Thr Trp Thr Thr Ser Gln Ser Ile
    50                  55                  60
```

Ala Phe Pro Ser Lys Thr Ser Ala Ser Ile Gly Ser Leu Ser Ala Asp
 65                  70                  75                  80

Ala Val Ser Gly Ser Asn Leu Leu Ser Ile Ser Lys Thr Ala Glu Phe
                 85                  90                  95

Gln Met Thr Phe His Leu Phe Ile Gly Ser Ala Leu Thr Gly Thr Glu
            100                 105                 110

Lys Leu Ile Glu Thr Tyr Phe Ser Lys Phe Ala Val Leu Lys Leu Met
        115                 120                 125

Gly Arg Gly Thr Lys Phe
    130

<210> SEQ ID NO 43
<211> LENGTH: 69
<212> TYPE: DNA
<213> ORGANISM: Artificial Sequence
<220> FEATURE:
<223> OTHER INFORMATION: Synthetic

<400> SEQUENCE: 43
acgctccaaa gaatgagctt gatgttggcc tctggaacca cgccccttct ggccccctgt      60
taccgttgc                                                             69

<210> SEQ ID NO 44
<211> LENGTH: 66
<212> TYPE: DNA
<213> ORGANISM: Artificial Sequence
<220> FEATURE:
<223> OTHER INFORMATION: Synthetic

<400> SEQUENCE: 44
ggcagaggtc ttgcttggga aggcaataga ctggctggtg gtccaggtgt tgaacttgtc      60
cggatg                                                                66

<210> SEQ ID NO 45
<211> LENGTH: 66
<212> TYPE: DNA
<213> ORGANISM: Artificial Sequence
<220> FEATURE:
<223> OTHER INFORMATION: Synthetic

<400> SEQUENCE: 45
tccaataaac aggtggaagg tcatttggaa ctctgctgtt ttgctgatgg acagaaggtt      60
ggagcc                                                                66

<210> SEQ ID NO 46
<211> LENGTH: 69
<212> TYPE: DNA
<213> ORGANISM: Artificial Sequence
<220> FEATURE:
<223> OTHER INFORMATION: Synthetic

<400> SEQUENCE: 46
aagctttcat gatcagaact tggtgccacg gcccatgagt ttaaggacgg caaatttgga      60
gaaataggt                                                             69

<210> SEQ ID NO 47
<211> LENGTH: 30
<212> TYPE: DNA
<213> ORGANISM: Artificial Sequence
<220> FEATURE:
<223> OTHER INFORMATION: Synthetic

<400> SEQUENCE: 47
taagcttgcg gccgctcatg atcagaactt                               30

<210> SEQ ID NO 48
<211> LENGTH: 255
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(255)

<400> SEQUENCE: 48

```
gaa ttc gct agc ctg cag cag aag tat tcc gaa cac ttc agc ata cac    48
Glu Phe Ala Ser Leu Gln Gln Lys Tyr Ser Glu His Phe Ser Ile His
1               5                   10                  15 agc agc cca ccg ttc acc ttc ctc aat aaa gag gag gac tgg atc agc    96
Ser Ser Pro Pro Phe Thr Phe Leu Asn Lys Glu Glu Asp Trp Ile Ser
            20                  25                  30 tct gcc agc cag aag acc cgt acc agc cgc cgt gcc aag tcc cca cag   144
Ser Ala Ser Gln Lys Thr Arg Thr Ser Arg Arg Ala Lys Ser Pro Gln
        35                  40                  45 cgt ccg aag caa cag cca gct gcg ccg cca gcg gtc gtc gtc gac aag   192
Arg Pro Lys Gln Gln Pro Ala Ala Pro Pro Ala Val Val Val Asp Lys
    50                  55                  60 caa cag ccg cgc agc agc ccg ctc cgt ggg cca ggt gcc agc cgt ggg   240
Gln Gln Pro Arg Ser Ser Pro Leu Arg Gly Pro Gly Ala Ser Arg Gly
65                  70                  75                  80 ctc gag tga aag ctt                                               255
Leu Glu     Lys Leu
```

<210> SEQ ID NO 49
<211> LENGTH: 82
<212> TYPE: PRT
<213> ORGANISM: Artificial Sequence
<220> FEATURE:
<223> OTHER INFORMATION: Synthetic

<400> SEQUENCE: 49

```
Glu Phe Ala Ser Leu Gln Gln Lys Tyr Ser Glu His Phe Ser Ile His
1               5                   10                  15

Ser Ser Pro Pro Phe Thr Phe Leu Asn Lys Glu Glu Asp Trp Ile Ser
            20                  25                  30

Ser Ala Ser Gln Lys Thr Arg Thr Ser Arg Arg Ala Lys Ser Pro Gln
        35                  40                  45

Arg Pro Lys Gln Gln Pro Ala Ala Pro Pro Ala Val Val Val Asp Lys
    50                  55                  60

Gln Gln Pro Arg Ser Ser Pro Leu Arg Gly Pro Gly Ala Ser Arg Gly
65                  70                  75                  80

Leu Glu
```

<210> SEQ ID NO 50
<211> LENGTH: 66
<212> TYPE: DNA
<213> ORGANISM: Artificial Sequence
<220> FEATURE:
<223> OTHER INFORMATION: Synthetic

<400> SEQUENCE: 50
ggtcttctgg ctggcagagc tgatccagtc ctcctcttta ttgaggaagg tgaacggtgg    60
gctgct                                                               66

<210> SEQ ID NO 51
<211> LENGTH: 66
<212> TYPE: DNA
<213> ORGANISM: Artificial Sequence
<220> FEATURE:
<223> OTHER INFORMATION: Synthetic

<400> SEQUENCE: 51
gctgctgcgc ggctgttgct tgtcgacgac caccgctggc ggcgcagctg gctgttgctt    60
cggacg                                                               66

<210> SEQ ID NO 52
<211> LENGTH: 24
<212> TYPE: DNA
<213> ORGANISM: Artificial Sequence
<220> FEATURE:
<223> OTHER INFORMATION: Synthetic

<400> SEQUENCE: 52
aagctttcac tcgagcccac ggct                                            24

<210> SEQ ID NO 53
<211> LENGTH: 321
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(321)

<400> SEQUENCE: 53 gaa ttc act agt aag ctg gat gag ctg ggc tcc aag ggg ctg tgg gcc      48
Glu Phe Thr Ser Lys Leu Asp Glu Leu Gly Ser Lys Gly Leu Trp Ala
1               5                   10                  15 gac agc gtc atg gca acg ggg ctg tac cac agc aag cca ctg gtg gac      96
Asp Ser Val Met Ala Thr Gly Leu Tyr His Ser Lys Pro Leu Val Asp
            20                  25                  30 atc ctc atc ctg ctg ctg act gtt ctt ccg tct atc cgt atg ggc cag     144
Ile Leu Ile Leu Leu Leu Thr Val Leu Pro Ser Ile Arg Met Gly Gln
        35                  40                  45 cag gca ttt ggt gaa aac gtt tct act aca ctg cgt gct ctg gct ccg     192
Gln Ala Phe Gly Glu Asn Val Ser Thr Thr Leu Arg Ala Leu Ala Pro
    50                  55                  60 cgt ctc atg cga aga atg cat gtc atc gtg acc acc tcc acc aat gac     240
Arg Leu Met Arg Arg Met His Val Ile Val Thr Thr Ser Thr Asn Asp
65                  70                  75                  80 tgg gtg gtg acc agc ctg gct ctc agc gcc ctt gtt gcc acc atc tgg     288
Trp Val Val Thr Ser Leu Ala Leu Ser Ala Leu Val Ala Thr Ile Trp
                85                  90                  95 ttc cca gtg agc gcc cac ctg cag tga aag ctt                         321
Phe Pro Val Ser Ala His Leu Gln     Lys Leu
                100                 105

<210> SEQ ID NO 54
<211> LENGTH: 104
<212> TYPE: PRT
<213> ORGANISM: Artificial Sequence
<220> FEATURE:
<223> OTHER INFORMATION: Synthetic

<400> SEQUENCE: 54

Glu Phe Thr Ser Lys Leu Asp Glu Leu Gly Ser Lys Gly Leu Trp Ala
1               5                   10                  15

Asp Ser Val Met Ala Thr Gly Leu Tyr His Ser Lys Pro Leu Val Asp
            20                  25                  30

Ile Leu Ile Leu Leu Leu Thr Val Leu Pro Ser Ile Arg Met Gly Gln
        35                  40                  45

Gln Ala Phe Gly Glu Asn Val Ser Thr Thr Leu Arg Ala Leu Ala Pro
    50                  55                  60

Arg Leu Met Arg Arg Met His Val Ile Val Thr Thr Ser Thr Asn Asp
65                  70                  75                  80

Trp Val Val Thr Ser Leu Ala Leu Ser Ala Leu Val Ala Thr Ile Trp
                85                  90                  95

Phe Pro Val Ser Ala His Leu Gln
            100

<210> SEQ ID NO 55
<211> LENGTH: 69
<212> TYPE: DNA
<213> ORGANISM: Artificial Sequence
<220> FEATURE:
<223> OTHER INFORMATION: Synthetic

<400> SEQUENCE: 55
gatagacgga agaacagtca gcagcaggat gaggatgtcc accagtggct tgctgtggta    60
cagccccgt                                                           69

<210> SEQ ID NO 56
<211> LENGTH: 69
<212> TYPE: DNA
<213> ORGANISM: Artificial Sequence
<220> FEATURE:
<223> OTHER INFORMATION: Synthetic

<400> SEQUENCE: 56
ggtggaggtg gtcacgatga catgcattct tcgcatgaga cgcggagcca gagcacgcag    60
tgtagtaga                                                           69

<210> SEQ ID NO 57
<211> LENGTH: 54
<212> TYPE: DNA
<213> ORGANISM: Artificial Sequence
<220> FEATURE:
<223> OTHER INFORMATION: Synthetic

<400> SEQUENCE: 57
aagctttcac tgcaggtggg cgctcactgg gaaccagatg gtggcaacaa gggc          54

<210> SEQ ID NO 58
<211> LENGTH: 21
<212> TYPE: DNA
<213> ORGANISM: Artificial Sequence
<220> FEATURE:
<223> OTHER INFORMATION: Synthetic

<400> SEQUENCE: 58
aagctttcac tgcaggtggg c                                             21

<210> SEQ ID NO 59
<211> LENGTH: 1554
<212> TYPE: DNA
<213> ORGANISM: Artificial Sequence
<220> FEATURE:
<223> OTHER INFORMATION: Synthetic
<220> FEATURE:
<221> NAME/KEY: CDS

<222> LOCATION: (1)..(1530)

<400> SEQUENCE: 59

```
gaa ttc gct agc ggc atg gag gtg ggg tgg tat cgc cca cca ttc tct      48
Glu Phe Ala Ser Gly Met Glu Val Gly Trp Tyr Arg Pro Pro Phe Ser
1               5                   10                  15 agg gtg gtt cat ctc tac cgt aat ggc aag gac ggc cgt aca gag ctg      96
Arg Val Val His Leu Tyr Arg Asn Gly Lys Asp Gly Arg Thr Glu Leu
            20                  25                  30 ctg aaa gat gct att ggt gag gga aag gtg act ctc agg att cgg aat     144
Leu Lys Asp Ala Ile Gly Glu Gly Lys Val Thr Leu Arg Ile Arg Asn
        35                  40                  45 gta cgc ttc tct gat gaa gga ggt ttc acc agc ttc ttc cgt gac cat     192
Val Arg Phe Ser Asp Glu Gly Gly Phe Thr Ser Phe Phe Arg Asp His
50                  55                  60 tct tac caa gag gag gca gca atg gaa ttg aaa aga tct ttc aga gtg     240
Ser Tyr Gln Glu Glu Ala Ala Met Glu Leu Lys Arg Ser Phe Arg Val
65                  70                  75                  80 ata gga cca aga cac cca atc cgt gct ctg gtc ggg gat gaa gtg gaa     288
Ile Gly Pro Arg His Pro Ile Arg Ala Leu Val Gly Asp Glu Val Glu
                85                  90                  95 ttg cca tct cgc ata tcg aga ctt gca ggg caa ttc ctt gaa gag ctg     336
Leu Pro Ser Arg Ile Ser Arg Leu Ala Gly Gln Phe Leu Glu Glu Leu
            100                 105                 110 cgt gga tcc aac cca gta gtc cac ttc ttc aag aac att gtg acg cca     384
Arg Gly Ser Asn Pro Val Val His Phe Phe Lys Asn Ile Val Thr Pro
        115                 120                 125 cgc aca cca cca ccg tcg cag gga aag ggg aga gga ctg tcc ctg ttc     432
Arg Thr Pro Pro Pro Ser Gln Gly Lys Gly Arg Gly Leu Ser Leu Phe
    130                 135                 140 aag gga gtc gat gcc cag ggc acg ctt tcc aaa att ttt aag ctg gga     480
Lys Gly Val Asp Ala Gln Gly Thr Leu Ser Lys Ile Phe Lys Leu Gly
145                 150                 155                 160 gga cgt gat agt cgc tct gga tct ccg atg gct tct aga tcc aag tac     528
Gly Arg Asp Ser Arg Ser Gly Ser Pro Met Ala Ser Arg Ser Lys Tyr
                165                 170                 175 ctg gcc aca gca agt acg atg gat cat gcc cgt cat ggc ttc ctc cca     576
Leu Ala Thr Ala Ser Thr Met Asp His Ala Arg His Gly Phe Leu Pro
            180                 185                 190 cgt cac cgc gac acg ggc atc ctt gac tcc atc ggg act agt aag ctg     624
Arg His Arg Asp Thr Gly Ile Leu Asp Ser Ile Gly Thr Ser Lys Leu
        195                 200                 205 gat gag ctg ggc tcc aag ggg ctg tgg gcc gac agc gtc atg gca acg     672
Asp Glu Leu Gly Ser Lys Gly Leu Trp Ala Asp Ser Val Met Ala Thr
    210                 215                 220 ggg ctg tac cac agc aag cca ctg gtg gac atc ctc atc ctg ctg         720
Gly Leu Tyr His Ser Lys Pro Leu Val Asp Ile Leu Ile Leu Leu
225                 230                 235                 240 act gtt ctt ccg tct atc cgt atg ggc cag cag gca ttt ggt gaa aac     768
Thr Val Leu Pro Ser Ile Arg Met Gly Gln Gln Ala Phe Gly Glu Asn
                245                 250                 255 gtt tct act aca ctg cgt gct ctg gct ccg cgt ctc atg cga aga atg     816
Val Ser Thr Thr Leu Arg Ala Leu Ala Pro Arg Leu Met Arg Arg Met
            260                 265                 270 cat gtc atc gtg acc acc tcc acc aat gac tgg gtg gtg acc agc ctg     864
His Val Ile Val Thr Thr Ser Thr Asn Asp Trp Val Val Thr Ser Leu
        275                 280                 285 gct ctc agc gcc ctt gtt gcc acc atc tgg ttc cca gtg agc gcc cac     912
Ala Leu Ser Ala Leu Val Ala Thr Ile Trp Phe Pro Val Ser Ala His
    290                 295                 300
```

```
ctg cag cag aag tat tcc gaa cac ttc agc ata cac agc agc cca ccg      960
Leu Gln Gln Lys Tyr Ser Glu His Phe Ser Ile His Ser Ser Pro Pro
305                 310                 315                 320 ttc acc ttc ctc aat aaa gag gag gac tgg atc agc tct gcc agc cag     1008
Phe Thr Phe Leu Asn Lys Glu Glu Asp Trp Ile Ser Ser Ala Ser Gln
                325                 330                 335 aag acc cgt acc agc cgc cgt gcc aag tcc cca cag cgt ccg aag caa     1056
Lys Thr Arg Thr Ser Arg Arg Ala Lys Ser Pro Gln Arg Pro Lys Gln
            340                 345                 350 cag cca gct gcg ccg cca gcg gtg gtc gtc gac aag caa cag ccg cgc     1104
Gln Pro Ala Ala Pro Pro Ala Val Val Val Asp Lys Gln Gln Pro Arg
        355                 360                 365 agc agc ccg ctc cgt ggg cca ggt gcc agc cgt ggg ctc gag tac aag     1152
Ser Ser Pro Leu Arg Gly Pro Gly Ala Ser Arg Gly Leu Glu Tyr Lys
    370                 375                 380 acc acc atc agc ggc aag ggc ctg agc gca acg gta aca ggg ggc cag     1200
Thr Thr Ile Ser Gly Lys Gly Leu Ser Ala Thr Val Thr Gly Gly Gln
385                 390                 395                 400 aag ggg cgt ggt tcc aga ggc caa cat caa gct cat tct ttg gag cgt     1248
Lys Gly Arg Gly Ser Arg Gly Gln His Gln Ala His Ser Leu Glu Arg
                405                 410                 415 gtg agc cat tct ttg gga aaa tgg tta gga cat ccg gac aag ttc aac     1296
Val Ser His Ser Leu Gly Lys Trp Leu Gly His Pro Asp Lys Phe Asn
            420                 425                 430 acc tgg acc acc agc cag tct att gcc ttc cca agc aag acc tct gcc     1344
Thr Trp Thr Thr Ser Gln Ser Ile Ala Phe Pro Ser Lys Thr Ser Ala
        435                 440                 445 agt ata ggc agt ctc tct gct gac gcc gtt tct ggc tcc aac ctt ctg     1392
Ser Ile Gly Ser Leu Ser Ala Asp Ala Val Ser Gly Ser Asn Leu Leu
    450                 455                 460 tcc atc agc aaa aca gca gag ttc caa atg acc ttc cac ctg ttt att     1440
Ser Ile Ser Lys Thr Ala Glu Phe Gln Met Thr Phe His Leu Phe Ile
465                 470                 475                 480 gga tcc gcc ctc act ggc aca gaa aag ctg att gag acc tat ttc tcc     1488
Gly Ser Ala Leu Thr Gly Thr Glu Lys Leu Ile Glu Thr Tyr Phe Ser
                485                 490                 495 aaa ttt gcc gtc ctt aaa ctc atg ggc cgt ggc acc aag ttc              1530
Lys Phe Ala Val Leu Lys Leu Met Gly Arg Gly Thr Lys Phe
            500                 505                 510 tgatcatgag cggccgcaag ctta                                          1554

<210> SEQ ID NO 60
<211> LENGTH: 510
<212> TYPE: PRT
<213> ORGANISM: Artificial Sequence
<220> FEATURE:
<223> OTHER INFORMATION: Synthetic

<400> SEQUENCE: 60

Glu Phe Ala Ser Gly Met Glu Val Gly Trp Tyr Arg Pro Pro Phe Ser
1               5                   10                  15

Arg Val Val His Leu Tyr Arg Asn Gly Lys Asp Gly Arg Thr Glu Leu
            20                  25                  30

Leu Lys Asp Ala Ile Gly Glu Gly Lys Val Thr Leu Arg Ile Arg Asn
        35                  40                  45

Val Arg Phe Ser Asp Glu Gly Gly Phe Thr Ser Phe Arg Asp His
    50                  55                  60

Ser Tyr Gln Glu Glu Ala Ala Met Glu Leu Lys Arg Ser Phe Arg Val
65                  70                  75                  80

Ile Gly Pro Arg His Pro Ile Arg Ala Leu Val Gly Asp Glu Val Glu
```

```
                85                  90                  95
Leu Pro Ser Arg Ile Ser Arg Leu Ala Gly Gln Phe Leu Glu Glu Leu
            100                 105                 110

Arg Gly Ser Asn Pro Val Val His Phe Phe Lys Asn Ile Val Thr Pro
            115                 120                 125

Arg Thr Pro Pro Pro Ser Gln Gly Lys Gly Arg Gly Leu Ser Leu Phe
            130                 135                 140

Lys Gly Val Asp Ala Gln Gly Thr Leu Ser Lys Ile Phe Lys Leu Gly
145                 150                 155                 160

Gly Arg Asp Ser Arg Ser Gly Ser Pro Met Ala Ser Arg Ser Lys Tyr
                165                 170                 175

Leu Ala Thr Ala Ser Thr Met Asp His Ala Arg His Gly Phe Leu Pro
            180                 185                 190

Arg His Arg Asp Thr Gly Ile Leu Asp Ser Ile Gly Thr Ser Lys Leu
            195                 200                 205

Asp Glu Leu Gly Ser Lys Gly Leu Trp Ala Asp Ser Val Met Ala Thr
            210                 215                 220

Gly Leu Tyr His Ser Lys Pro Leu Val Asp Ile Leu Ile Leu Leu Leu
225                 230                 235                 240

Thr Val Leu Pro Ser Ile Arg Met Gly Gln Gln Ala Phe Gly Glu Asn
                245                 250                 255

Val Ser Thr Thr Leu Arg Ala Leu Ala Pro Arg Leu Met Arg Arg Met
                260                 265                 270

His Val Ile Val Thr Thr Ser Thr Asn Asp Trp Val Val Thr Ser Leu
                275                 280                 285

Ala Leu Ser Ala Leu Val Ala Thr Ile Trp Phe Pro Val Ser Ala His
            290                 295                 300

Leu Gln Gln Lys Tyr Ser Glu His Phe Ser Ile His Ser Ser Pro Pro
305                 310                 315                 320

Phe Thr Phe Leu Asn Lys Glu Glu Asp Trp Ile Ser Ser Ala Ser Gln
                325                 330                 335

Lys Thr Arg Thr Ser Arg Arg Ala Lys Ser Pro Gln Arg Pro Lys Gln
            340                 345                 350

Gln Pro Ala Ala Pro Pro Ala Val Val Asp Lys Gln Gln Pro Arg
            355                 360                 365

Ser Ser Pro Leu Arg Gly Pro Gly Ala Ser Arg Gly Leu Glu Tyr Lys
            370                 375                 380

Thr Thr Ile Ser Gly Lys Gly Leu Ser Ala Thr Val Thr Gly Gly Gln
385                 390                 395                 400

Lys Gly Arg Gly Ser Arg Gly Gln His Gln Ala His Ser Leu Glu Arg
                405                 410                 415

Val Ser His Ser Leu Gly Lys Trp Leu Gly His Pro Asp Lys Phe Asn
            420                 425                 430

Thr Trp Thr Thr Ser Gln Ser Ile Ala Phe Pro Ser Lys Thr Ser Ala
            435                 440                 445

Ser Ile Gly Ser Leu Ser Ala Asp Ala Val Ser Gly Ser Asn Leu Leu
450                 455                 460

Ser Ile Ser Lys Thr Ala Glu Phe Gln Met Thr Phe His Leu Phe Ile
465                 470                 475                 480

Gly Ser Ala Leu Thr Gly Thr Glu Lys Leu Ile Glu Thr Tyr Phe Ser
                485                 490                 495

Lys Phe Ala Val Leu Lys Leu Met Gly Arg Gly Thr Lys Phe
            500                 505                 510
```

<210> SEQ ID NO 61
<211> LENGTH: 1095
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(1077)

<400> SEQUENCE: 61

```
gaa ttc gct agc ggc atg gag gtg ggg tgg tat cgc cca cca ttc tct      48
Glu Phe Ala Ser Gly Met Glu Val Gly Trp Tyr Arg Pro Pro Phe Ser
1               5                   10                  15 agg gtg gtt cat ctc tac cgt aat ggc aag gac ggc cgt aca gag ctg      96
Arg Val Val His Leu Tyr Arg Asn Gly Lys Asp Gly Arg Thr Glu Leu
            20                  25                  30 ctg aaa gat gct att ggt gag gga aag gtg act ctc agg att cgg aat     144
Leu Lys Asp Ala Ile Gly Glu Gly Lys Val Thr Leu Arg Ile Arg Asn
        35                  40                  45 gta cgc ttc tct gat gaa gga ggt ttc acc agc ttc ttc cgt gac cat     192
Val Arg Phe Ser Asp Glu Gly Gly Phe Thr Ser Phe Phe Arg Asp His
    50                  55                  60 tct tac caa gag gag gca gca atg gaa ttg aaa aga tcc aac cca gta     240
Ser Tyr Gln Glu Glu Ala Ala Met Glu Leu Lys Arg Ser Asn Pro Val
65                  70                  75                  80 gtc cac ttc ttc aag aac att gtg acg cca cgc aca cca cca ccg tcg     288
Val His Phe Phe Lys Asn Ile Val Thr Pro Arg Thr Pro Pro Pro Ser
                85                  90                  95 cag gga aag ggg aga gga ctg tcc ctg ttc aag gga gtc gat gcc cag     336
Gln Gly Lys Gly Arg Gly Leu Ser Leu Phe Lys Gly Val Asp Ala Gln
            100                 105                 110 ggc acg ctt tcc aaa att ttt aag ctg gga gga cgt gat agt cgc tct     384
Gly Thr Leu Ser Lys Ile Phe Lys Leu Gly Gly Arg Asp Ser Arg Ser
        115                 120                 125 gga tct ccg atg gct tct agt aag ctg gat gag ctg ggc tcc aag ggg     432
Gly Ser Pro Met Ala Ser Ser Lys Leu Asp Glu Leu Gly Ser Lys Gly
    130                 135                 140 ctg tgg gcc gac agc gtc atg gca acg ggg ctg tac cac agc aag cca     480
Leu Trp Ala Asp Ser Val Met Ala Thr Gly Leu Tyr His Ser Lys Pro
145                 150                 155                 160 ctg gtg gac atc ctc atc ctg ctg act gtt ctt ccg tct atc cgt         528
Leu Val Asp Ile Leu Ile Leu Leu Thr Val Leu Pro Ser Ile Arg
                165                 170                 175 atg ggc cag cag gca ttt ggt gaa aac gtt tct act aca ctg cgt gct     576
Met Gly Gln Gln Ala Phe Gly Glu Asn Val Ser Thr Thr Leu Arg Ala
            180                 185                 190 ctg gct ccg cgt ctc atg cga aga atg cag cag aag tat tcc gaa cac     624
Leu Ala Pro Arg Leu Met Arg Arg Met Gln Gln Lys Tyr Ser Glu His
        195                 200                 205 ttc agc ata cac agc agc cca ccg ttc acc ttc ctc aat aaa gag gag     672
Phe Ser Ile His Ser Ser Pro Pro Phe Thr Phe Leu Asn Lys Glu Glu
    210                 215                 220 gac tgg atc agc tct gcc agc cag aag acc cgt acc agc cgc cgt gcc     720
Asp Trp Ile Ser Ser Ala Ser Gln Lys Thr Arg Thr Ser Arg Arg Ala
225                 230                 235                 240 aag tcc cca cag cgt ccg aag caa cag cca gct gcg ccg cca gcg gtg     768
Lys Ser Pro Gln Arg Pro Lys Gln Gln Pro Ala Ala Pro Pro Ala Val
                245                 250                 255 gtc gtc gag tac aag acc acc atc agc ggc aag ggc ctg agc gca acg     816
Val Val Glu Tyr Lys Thr Thr Ile Ser Gly Lys Gly Leu Ser Ala Thr
            260                 265                 270
```

```
gta aca ggg ggc cag aag ggg cgt ggt tcc aga ggc caa cat caa gct        864
Val Thr Gly Gly Gln Lys Gly Arg Gly Ser Arg Gly Gln His Gln Ala
        275                 280                 285 cat tct ttg gag cgt gtg agc cat tct ttg gga aaa tgg tta gga cat        912
His Ser Leu Glu Arg Val Ser His Ser Leu Gly Lys Trp Leu Gly His
    290                 295                 300 ccg gac aag ttc aac acc tgg acc acc agc cag tct att gcc ttc cca        960
Pro Asp Lys Phe Asn Thr Trp Thr Thr Ser Gln Ser Ile Ala Phe Pro
305                 310                 315                 320 agc aag acc tct gcc agt ata ggc agt ctc tct gct gac gcc gtt tct       1008
Ser Lys Thr Ser Ala Ser Ile Gly Ser Leu Ser Ala Asp Ala Val Ser
                325                 330                 335 ggc tcc aac ctt ctg tcc atc agc aaa aca gca gag ttc caa atg acc       1056
Gly Ser Asn Leu Leu Ser Ile Ser Lys Thr Ala Glu Phe Gln Met Thr
            340                 345                 350 ttc cac ctg ttt att gga tcc tgagcggccg caagctta                        1095
Phe His Leu Phe Ile Gly Ser
            355

<210> SEQ ID NO 62
<211> LENGTH: 359
<212> TYPE: PRT
<213> ORGANISM: Artificial Sequence
<220> FEATURE:
<223> OTHER INFORMATION: Synthetic

<400> SEQUENCE: 62

Glu Phe Ala Ser Gly Met Glu Val Gly Trp Tyr Arg Pro Pro Phe Ser
1               5                   10                  15

Arg Val Val His Leu Tyr Arg Asn Gly Lys Asp Gly Arg Thr Glu Leu
            20                  25                  30

Leu Lys Asp Ala Ile Gly Glu Gly Lys Val Thr Leu Arg Ile Arg Asn
        35                  40                  45

Val Arg Phe Ser Asp Glu Gly Gly Phe Thr Ser Phe Arg Asp His
    50                  55                  60

Ser Tyr Gln Glu Glu Ala Ala Met Glu Leu Lys Arg Ser Asn Pro Val
65                  70                  75                  80

Val His Phe Phe Lys Asn Ile Val Thr Pro Arg Thr Pro Pro Ser
            85                  90                  95

Gln Gly Lys Gly Arg Gly Leu Ser Leu Phe Lys Gly Val Asp Ala Gln
            100                 105                 110

Gly Thr Leu Ser Lys Ile Phe Lys Leu Gly Gly Arg Asp Ser Arg Ser
            115                 120                 125

Gly Ser Pro Met Ala Ser Ser Lys Leu Asp Glu Leu Gly Ser Lys Gly
        130                 135                 140

Leu Trp Ala Asp Ser Val Met Ala Thr Gly Leu Tyr His Ser Lys Pro
145                 150                 155                 160

Leu Val Asp Ile Leu Ile Leu Leu Thr Val Leu Pro Ser Ile Arg
                165                 170                 175

Met Gly Gln Gln Ala Phe Gly Glu Asn Val Ser Thr Thr Leu Arg Ala
            180                 185                 190

Leu Ala Pro Arg Leu Met Arg Arg Met Gln Gln Lys Tyr Ser Glu His
        195                 200                 205

Phe Ser Ile His Ser Ser Pro Pro Phe Thr Phe Leu Asn Lys Glu Glu
    210                 215                 220

Asp Trp Ile Ser Ser Ala Ser Gln Lys Thr Arg Thr Ser Arg Arg Ala
225                 230                 235                 240
```

```
Lys Ser Pro Gln Arg Pro Lys Gln Gln Pro Ala Ala Pro Ala Val
            245                 250                 255

Val Val Glu Tyr Lys Thr Thr Ile Ser Gly Lys Gly Leu Ser Ala Thr
            260                 265                 270

Val Thr Gly Gly Gln Lys Gly Arg Gly Ser Arg Gly Gln His Gln Ala
            275                 280                 285

His Ser Leu Glu Arg Val Ser His Ser Leu Gly Lys Trp Leu Gly His
            290                 295                 300

Pro Asp Lys Phe Asn Thr Trp Thr Thr Ser Gln Ser Ile Ala Phe Pro
305                 310                 315                 320

Ser Lys Thr Ser Ala Ser Ile Gly Ser Leu Ser Ala Asp Ala Val Ser
            325                 330                 335

Gly Ser Asn Leu Leu Ser Ile Ser Lys Thr Ala Glu Phe Gln Met Thr
            340                 345                 350

Phe His Leu Phe Ile Gly Ser
            355

<210> SEQ ID NO 63
<211> LENGTH: 360
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(360)

<400> SEQUENCE: 63 atg gct agc atg cgc ctc ctg ccg ctg ctg gcg ctg ctg gcc ctc tgg     48
Met Ala Ser Met Arg Leu Leu Pro Leu Leu Ala Leu Leu Ala Leu Trp
1               5                   10                  15 gga cct gac cca gcc gca tca cac ctg gtg gaa gct ctc tac ctg gtg     96
Gly Pro Asp Pro Ala Ala Ser His Leu Val Glu Ala Leu Tyr Leu Val
            20                  25                  30 agc ggg gaa cgt ggc ttc ttc tac aca ccg aag acc cgc att gag gca    144
Ser Gly Glu Arg Gly Phe Phe Tyr Thr Pro Lys Thr Arg Ile Glu Ala
        35                  40                  45 gag gcg ggt gca ggc agc ctg caa ccg ttg gcc ctg gag ggg tcc ctg    192
Glu Ala Gly Ala Gly Ser Leu Gln Pro Leu Ala Leu Glu Gly Ser Leu
    50                  55                  60 caa aag ata cta gtc gat acc tgg agc ggc gtg gca cat gga agc acc    240
Gln Lys Ile Leu Val Asp Thr Trp Ser Gly Val Ala His Gly Ser Thr
65                  70                  75                  80 cgt aaa ctg ggg ctc aag atc agc ggc ttc ttg caa cgt acc aac agc    288
Arg Lys Leu Gly Leu Lys Ile Ser Gly Phe Leu Gln Arg Thr Asn Ser
                85                  90                  95 ctg gaa gag aag gcg gtg gac ata ctc ctc aac tat gtc cgc aag aca    336
Leu Glu Glu Lys Ala Val Asp Ile Leu Leu Asn Tyr Val Arg Lys Thr
            100                 105                 110 ttt gat aga tct tag ctc gag gcg                                    360
Phe Asp Arg Ser     Leu Glu Ala
        115

<210> SEQ ID NO 64
<211> LENGTH: 116
<212> TYPE: PRT
<213> ORGANISM: Artificial Sequence
<220> FEATURE:
<223> OTHER INFORMATION: Synthetic

<400> SEQUENCE: 64

Met Ala Ser Met Arg Leu Leu Pro Leu Leu Ala Leu Leu Ala Leu Trp
```

```
            1               5                  10                  15
Gly Pro Asp Pro Ala Ala Ser His Leu Val Glu Ala Leu Tyr Leu Val
                20                  25                  30

Ser Gly Glu Arg Gly Phe Phe Tyr Thr Pro Lys Thr Arg Ile Glu Ala
            35                  40                  45

Glu Ala Gly Ala Gly Ser Leu Gln Pro Leu Ala Leu Glu Gly Ser Leu
        50                  55                  60

Gln Lys Ile Leu Val Asp Thr Trp Ser Gly Val Ala His Gly Ser Thr
65                  70                  75                  80

Arg Lys Leu Gly Leu Lys Ile Ser Gly Phe Leu Gln Arg Thr Asn Ser
                85                  90                  95

Leu Glu Glu Lys Ala Val Asp Ile Leu Leu Asn Tyr Val Arg Lys Thr
            100                 105                 110

Phe Asp Arg Ser
        115

<210> SEQ ID NO 65
<211> LENGTH: 66
<212> TYPE: DNA
<213> ORGANISM: Artificial Sequence
<220> FEATURE:
<223> OTHER INFORMATION: Synthetic

<400> SEQUENCE: 65
caggtagaga gcttccacca ggtgtgatgc ggctgggtca ggtccccaga gggccagcag    60
cgccag                                                              66

<210> SEQ ID NO 66
<211> LENGTH: 66
<212> TYPE: DNA
<213> ORGANISM: Artificial Sequence
<220> FEATURE:
<223> OTHER INFORMATION: Synthetic

<400> SEQUENCE: 66
ggacccctcc agggccaacg gttgcaggct gcctgcaccc gcctctgcct caatgcgggt    60
cttcgg                                                              66

<210> SEQ ID NO 67
<211> LENGTH: 66
<212> TYPE: DNA
<213> ORGANISM: Artificial Sequence
<220> FEATURE:
<223> OTHER INFORMATION: Synthetic

<400> SEQUENCE: 67
gttggtacgt tgcaagaagc cgctgatctt gagccccagt ttacgggtgc ttccatgtgc    60
cacgcc                                                              66

<210> SEQ ID NO 68
<211> LENGTH: 48
<212> TYPE: DNA
<213> ORGANISM: Artificial Sequence
<220> FEATURE:
<223> OTHER INFORMATION: Synthetic

<400> SEQUENCE: 68
cgcctcgagc taagatctat caaatgtctt gcggacatag ttgaggag                48

<210> SEQ ID NO 69
<211> LENGTH: 429
```

<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(429)

<400> SEQUENCE: 69

```
gat aga tct gcg acc tat gaa att gct cca gta ttt gtg ctt ttg gaa      48
Asp Arg Ser Ala Thr Tyr Glu Ile Ala Pro Val Phe Val Leu Leu Glu
1               5                   10                  15 tat gtc aca ctg aag aaa atg cgt gaa atc att ggc tgg cca ggg ggc      96
Tyr Val Thr Leu Lys Lys Met Arg Glu Ile Ile Gly Trp Pro Gly Gly
            20                  25                  30 tct ggc gat gcg aac atg tat gcc atg atg atc gca cgc ttt aag atg    144
Ser Gly Asp Ala Asn Met Tyr Ala Met Met Ile Ala Arg Phe Lys Met
        35                  40                  45 ttc cca gaa gtc aag gag aaa gga atg gct gct ctt ccg cgt ctc att    192
Phe Pro Glu Val Lys Glu Lys Gly Met Ala Ala Leu Pro Arg Leu Ile
    50                  55                  60 gcc ttc acg tct gaa cat agt cat gcg aat gtc agc ttc tgg tac att    240
Ala Phe Thr Ser Glu His Ser His Ala Asn Val Ser Phe Trp Tyr Ile
65                  70                  75                  80 ccg ccg agc ttg cgt act ctg gaa gac aat gaa gag cgc atg agt cgc    288
Pro Pro Ser Leu Arg Thr Leu Glu Asp Asn Glu Glu Arg Met Ser Arg
                85                  90                  95 ctc tcg aag gtg gct cca gtg att aaa gcc cgt atg atg gag tat gga    336
Leu Ser Lys Val Ala Pro Val Ile Lys Ala Arg Met Met Glu Tyr Gly
            100                 105                 110 acc aca atg gtc gcg aag gtc aat ttc ttc cgc atg gtc atc tca aac    384
Thr Thr Met Val Ala Lys Val Asn Phe Phe Arg Met Val Ile Ser Asn
        115                 120                 125 cca gcg gca act cac caa gac att gac cct agg tag gga tcc gcg        429
Pro Ala Ala Thr His Gln Asp Ile Asp Pro Arg     Gly Ser Ala
    130                 135                 140
```

<210> SEQ ID NO 70
<211> LENGTH: 139
<212> TYPE: PRT
<213> ORGANISM: Artificial Sequence
<220> FEATURE:
<223> OTHER INFORMATION: Synthetic

<400> SEQUENCE: 70

```
Asp Arg Ser Ala Thr Tyr Glu Ile Ala Pro Val Phe Val Leu Leu Glu
1               5                   10                  15

Tyr Val Thr Leu Lys Lys Met Arg Glu Ile Ile Gly Trp Pro Gly Gly
            20                  25                  30

Ser Gly Asp Ala Asn Met Tyr Ala Met Met Ile Ala Arg Phe Lys Met
        35                  40                  45

Phe Pro Glu Val Lys Glu Lys Gly Met Ala Ala Leu Pro Arg Leu Ile
    50                  55                  60

Ala Phe Thr Ser Glu His Ser His Ala Asn Val Ser Phe Trp Tyr Ile
65                  70                  75                  80

Pro Pro Ser Leu Arg Thr Leu Glu Asp Asn Glu Glu Arg Met Ser Arg
                85                  90                  95

Leu Ser Lys Val Ala Pro Val Ile Lys Ala Arg Met Met Glu Tyr Gly
            100                 105                 110

Thr Thr Met Val Ala Lys Val Asn Phe Phe Arg Met Val Ile Ser Asn
        115                 120                 125
```

Pro Ala Ala Thr His Gln Asp Ile Asp Pro Arg
            130                 135

<210> SEQ ID NO 71
<211> LENGTH: 66
<212> TYPE: DNA
<213> ORGANISM: Artificial Sequence
<220> FEATURE:
<223> OTHER INFORMATION: Synthetic

<400> SEQUENCE: 71
ccagccaatg atttcacgca ttttcttcag tgtgacatat tccaaaagca caaatactgg    60
agcaat                                                                66

<210> SEQ ID NO 72
<211> LENGTH: 63
<212> TYPE: DNA
<213> ORGANISM: Artificial Sequence
<220> FEATURE:
<223> OTHER INFORMATION: Synthetic

<400> SEQUENCE: 72
agcagccatt cctttctcct tgacttctgg gaacatctta aagcgtgcga tcatcatggc    60
ata                                                                   63

<210> SEQ ID NO 73
<211> LENGTH: 60
<212> TYPE: DNA
<213> ORGANISM: Artificial Sequence
<220> FEATURE:
<223> OTHER INFORMATION: Synthetic

<400> SEQUENCE: 73
agtacgcaag ctcggcggaa tgtaccagaa gctgacattc gcatgactat gttcagacgt    60

<210> SEQ ID NO 74
<211> LENGTH: 57
<212> TYPE: DNA
<213> ORGANISM: Artificial Sequence
<220> FEATURE:
<223> OTHER INFORMATION: Synthetic

<400> SEQUENCE: 74
tccatactcc atcatacggg ctttaatcac tggagccacc ttcgagaggc gactcat       57

<210> SEQ ID NO 75
<211> LENGTH: 63
<212> TYPE: DNA
<213> ORGANISM: Artificial Sequence
<220> FEATURE:
<223> OTHER INFORMATION: Synthetic

<400> SEQUENCE: 75
cgcggatccc tacctagggt caatgtcttg gtgagttgcc gctgggtttg agatgaccat    60
gcg                                                                   63

<210> SEQ ID NO 76
<211> LENGTH: 429
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(429)

```
<400> SEQUENCE: 76 gat cct agg aag cag gcg ttt att aaa gcc aca ggg aag aag gaa gat    48
Asp Pro Arg Lys Gln Ala Phe Ile Lys Ala Thr Gly Lys Lys Glu Asp
1               5                   10                  15 gaa cat gtt gcg cgc ctt gca aag aag aac ttt gac aaa ttg aag atg    96
Glu His Val Ala Arg Leu Ala Lys Lys Asn Phe Asp Lys Leu Lys Met
            20                  25                  30 gat gtg agc caa gcg atg aaa tct gag gaa ggt gca agc ctg gga ccg   144
Asp Val Ser Gln Ala Met Lys Ser Glu Glu Gly Ala Ser Leu Gly Pro
        35                  40                  45 gtg gca ggg acc gcg cat acc atc gca gac ttc tgg cag atg gtg tgg   192
Val Ala Gly Thr Ala His Thr Ile Ala Asp Phe Trp Gln Met Val Trp
    50                  55                  60 gag agc ggc tct acc gtc atc gtc atg ctg act ccg ctg gtg gag gat   240
Glu Ser Gly Ser Thr Val Ile Val Met Leu Thr Pro Leu Val Glu Asp
65                  70                  75                  80 ggt gtc aag cag gcg gtg agc gag cac atc tgg agc gag gac ttt ctg   288
Gly Val Lys Gln Ala Val Ser Glu His Ile Trp Ser Glu Asp Phe Leu
                85                  90                  95 gtg cgt agc ttc tac ctg aag aac gtg cag acc cag gag acg cgt acg   336
Val Arg Ser Phe Tyr Leu Lys Asn Val Gln Thr Gln Glu Thr Arg Thr
            100                 105                 110 ctg acg cag ttc cac ttc ctg agc gcg agc ccg tct ctg tgg gag ata   384
Leu Thr Gln Phe His Phe Leu Ser Ala Ser Pro Ser Leu Trp Glu Ile
        115                 120                 125 gag ttt gct aag cag tta gcc agc gta tct aga tag gaa ttc gcg       429
Glu Phe Ala Lys Gln Leu Ala Ser Val Ser Arg     Glu Phe Ala
    130                 135                 140

<210> SEQ ID NO 77
<211> LENGTH: 139
<212> TYPE: PRT
<213> ORGANISM: Artificial Sequence
<220> FEATURE:
<223> OTHER INFORMATION: Synthetic

<400> SEQUENCE: 77

Asp Pro Arg Lys Gln Ala Phe Ile Lys Ala Thr Gly Lys Lys Glu Asp
1               5                   10                  15

Glu His Val Ala Arg Leu Ala Lys Lys Asn Phe Asp Lys Leu Lys Met
            20                  25                  30

Asp Val Ser Gln Ala Met Lys Ser Glu Glu Gly Ala Ser Leu Gly Pro
        35                  40                  45

Val Ala Gly Thr Ala His Thr Ile Ala Asp Phe Trp Gln Met Val Trp
    50                  55                  60

Glu Ser Gly Ser Thr Val Ile Val Met Leu Thr Pro Leu Val Glu Asp
65                  70                  75                  80

Gly Val Lys Gln Ala Val Ser Glu His Ile Trp Ser Glu Asp Phe Leu
                85                  90                  95

Val Arg Ser Phe Tyr Leu Lys Asn Val Gln Thr Gln Glu Thr Arg Thr
            100                 105                 110

Leu Thr Gln Phe His Phe Leu Ser Ala Ser Pro Ser Leu Trp Glu Ile
        115                 120                 125

Glu Phe Ala Lys Gln Leu Ala Ser Val Ser Arg
    130                 135

<210> SEQ ID NO 78
<211> LENGTH: 69
<212> TYPE: DNA
<213> ORGANISM: Artificial Sequence
```

```
-continued

<220> FEATURE:
<223> OTHER INFORMATION: Synthetic

<400> SEQUENCE: 78
tttcatcgct tggctcacat ccatcttcaa tttgtcaaag ttcttctttg caaggcgcgc    60
aacatgttc                                                           69

<210> SEQ ID NO 79
<211> LENGTH: 72
<212> TYPE: DNA
<213> ORGANISM: Artificial Sequence
<220> FEATURE:
<223> OTHER INFORMATION: Synthetic

<400> SEQUENCE: 79
cagcatgacg atgacggtag agccgctctc ccacaccatc tgccagaagt ctgcgatggt    60
atgcgcggtc cc                                                       72

<210> SEQ ID NO 80
<211> LENGTH: 69
<212> TYPE: DNA
<213> ORGANISM: Artificial Sequence
<220> FEATURE:
<223> OTHER INFORMATION: Synthetic

<400> SEQUENCE: 80
ctgggtctgc acgttcttca ggtagaagct acgcaccaga aagtcctcgc tccagatgtg    60
ctcgctcac                                                           69

<210> SEQ ID NO 81
<211> LENGTH: 69
<212> TYPE: DNA
<213> ORGANISM: Artificial Sequence
<220> FEATURE:
<223> OTHER INFORMATION: Synthetic

<400> SEQUENCE: 81
gaattcctat ctagatacgc tggctaactg cttagcaaac tctatctccc acagagacgg    60
gctcgcgct                                                           69

<210> SEQ ID NO 82
<211> LENGTH: 24
<212> TYPE: DNA
<213> ORGANISM: Artificial Sequence
<220> FEATURE:
<223> OTHER INFORMATION: Synthetic

<400> SEQUENCE: 82
cgcgaattcc tatctagata cgct                                          24

<210> SEQ ID NO 83
<211> LENGTH: 147
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(147)

<400> SEQUENCE: 83 tct aga ttg gga gga ggt tct gcc ctg ctt cgt agc att ccg gcc ttg    48
Ser Arg Leu Gly Gly Gly Ser Ala Leu Leu Arg Ser Ile Pro Ala Leu
 1               5                  10                  15
```

```
gac tct ttg act ccg gct aat gaa gat gcg aaa cgt aca ctg aaa att      96
Asp Ser Leu Thr Pro Ala Asn Glu Asp Ala Lys Arg Thr Leu Lys Ile
            20                  25                  30 ccg gca atg acc att gct aag aat gca ggt gtt tct aga tag gaa ttc     144
Pro Ala Met Thr Ile Ala Lys Asn Ala Gly Val Ser Arg     Glu Phe
        35                  40                  45 gcg                                                                  147
Ala

<210> SEQ ID NO 84
<211> LENGTH: 45
<212> TYPE: PRT
<213> ORGANISM: Artificial Sequence
<220> FEATURE:
<223> OTHER INFORMATION: Synthetic

<400> SEQUENCE: 84

Ser Arg Leu Gly Gly Gly Ser Ala Leu Leu Arg Ser Ile Pro Ala Leu
1               5                   10                  15

Asp Ser Leu Thr Pro Ala Asn Glu Asp Ala Lys Arg Thr Leu Lys Ile
            20                  25                  30

Pro Ala Met Thr Ile Ala Lys Asn Ala Gly Val Ser Arg
        35                  40                  45

<210> SEQ ID NO 85
<211> LENGTH: 69
<212> TYPE: DNA
<213> ORGANISM: Artificial Sequence
<220> FEATURE:
<223> OTHER INFORMATION: Synthetic

<400> SEQUENCE: 85
agaaacacct gcattcttag caatggtcat tgccggaatt ttcagtgtac gtttcgcatc   60
ttcattagc                                                           69

<210> SEQ ID NO 86
<211> LENGTH: 30
<212> TYPE: DNA
<213> ORGANISM: Artificial Sequence
<220> FEATURE:
<223> OTHER INFORMATION: Synthetic

<400> SEQUENCE: 86
cgcgaattcc tatctagaaa cacctgcatt                                    30

<210> SEQ ID NO 87
<211> LENGTH: 216
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(216)

<400> SEQUENCE: 87 atg cct agg cgc ctc ctg ccg ctg ctg gcg ctg ctg gcc ctc tgg gga     48
Met Pro Arg Arg Leu Leu Pro Leu Leu Ala Leu Leu Ala Leu Trp Gly
1               5                   10                  15 cct gac cca gcc gca tca cac ctg gtg gaa gct ctc tac ctg gtg agc     96
Pro Asp Pro Ala Ala Ser His Leu Val Glu Ala Leu Tyr Leu Val Ser
            20                  25                  30 ggg gaa cgt ggc ttc ttc tac aca ccg aag acc cgc att gag gca gag    144
Gly Glu Arg Gly Phe Phe Tyr Thr Pro Lys Thr Arg Ile Glu Ala Glu
        35                  40                  45
```

```
gcg ggt gca ggc agc ctg caa ccg ttg gcc ctg gag ggg tcc ctg caa    192
Ala Gly Ala Gly Ser Leu Gln Pro Leu Ala Leu Glu Gly Ser Leu Gln
    50                  55                  60 aag ata cct agg tag gaa ttc gcg                                    216
Lys Ile Pro Arg     Glu Phe Ala
65                      70

<210> SEQ ID NO 88
<211> LENGTH: 68
<212> TYPE: PRT
<213> ORGANISM: Artificial Sequence
<220> FEATURE:
<223> OTHER INFORMATION: Synthetic

<400> SEQUENCE: 88

Met Pro Arg Arg Leu Leu Pro Leu Leu Ala Leu Leu Ala Leu Trp Gly
1               5                   10                  15

Pro Asp Pro Ala Ala Ser His Leu Val Glu Ala Leu Tyr Leu Val Ser
            20                  25                  30

Gly Glu Arg Gly Phe Phe Tyr Thr Pro Lys Thr Arg Ile Glu Ala Glu
        35                  40                  45

Ala Gly Ala Gly Ser Leu Gln Pro Leu Ala Leu Glu Gly Ser Leu Gln
    50                  55                  60

Lys Ile Pro Arg
65

<210> SEQ ID NO 89
<211> LENGTH: 36
<212> TYPE: DNA
<213> ORGANISM: Artificial Sequence
<220> FEATURE:
<223> OTHER INFORMATION: Synthetic

<400> SEQUENCE: 89
gaattctcac ctaggtatct tttgcaggga cccctc                            36

<210> SEQ ID NO 90
<211> LENGTH: 63
<212> TYPE: DNA
<213> ORGANISM: Artificial Sequence
<220> FEATURE:
<223> OTHER INFORMATION: Synthetic

<400> SEQUENCE: 90
cgcggatccc tacctagggt caatgtcttg gtgagttgcc gctgggtttg agatgaccat    60
gcg                                                                63

<210> SEQ ID NO 91
<211> LENGTH: 765
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(765)

<400> SEQUENCE: 91 atg gct agc gat acc tgg agc ggc gtg gca cat gga agc acc cgt aaa    48
Met Ala Ser Asp Thr Trp Ser Gly Val Ala His Gly Ser Thr Arg Lys
1               5                   10                  15 ctg ggg ctc aag atc agc ggc ttc ttg caa cgt acc aac agc ctg gaa    96
Leu Gly Leu Lys Ile Ser Gly Phe Leu Gln Arg Thr Asn Ser Leu Glu
            20                  25                  30
```

```
gag aag gcg gtg gac ata ctc ctc aac tat gtc cgc aag aca ttt gat    144
Glu Lys Ala Val Asp Ile Leu Leu Asn Tyr Val Arg Lys Thr Phe Asp
            35                  40                  45 aga tct gcg acc tat gaa att gct cca gta ttt gtg ctt ttg gaa tat    192
Arg Ser Ala Thr Tyr Glu Ile Ala Pro Val Phe Val Leu Leu Glu Tyr
 50                  55                  60 gtc aca ctg aag aaa atg cgt gaa atc att ggc tgg cca ggg ggc tct    240
Val Thr Leu Lys Lys Met Arg Glu Ile Ile Gly Trp Pro Gly Gly Ser
 65                  70                  75                  80 ggc gat gcg aac atg tat gcc atg atg atc gca cgc ttt aag atg ttc    288
Gly Asp Ala Asn Met Tyr Ala Met Met Ile Ala Arg Phe Lys Met Phe
                 85                  90                  95 cca gaa gtc aag gag aaa gga atg gct gct ctt ccg cgt ctc att gcc    336
Pro Glu Val Lys Glu Lys Gly Met Ala Ala Leu Pro Arg Leu Ile Ala
            100                 105                 110 ttc acg tct gaa cat agt cat gcg aat gtc agc ttc tgg tac att ccg    384
Phe Thr Ser Glu His Ser His Ala Asn Val Ser Phe Trp Tyr Ile Pro
        115                 120                 125 ccg agc ttg cgt act ctg gaa gac aat gaa gag cgc atg agt cgc ctc    432
Pro Ser Leu Arg Thr Leu Glu Asp Asn Glu Glu Arg Met Ser Arg Leu
    130                 135                 140 tcg aag gtg gct cca gtg att aaa gcc cgt atg atg gag tat gga acc    480
Ser Lys Val Ala Pro Val Ile Lys Ala Arg Met Met Glu Tyr Gly Thr
145                 150                 155                 160 aca atg gtc gcg aag gtc aat ttc ttc cgc atg gtc atc tca aac cca    528
Thr Met Val Ala Lys Val Asn Phe Phe Arg Met Val Ile Ser Asn Pro
                165                 170                 175 gcg gca act cac caa gac att gac cct agg cgc ctc ctg ccg ctg ctg    576
Ala Ala Thr His Gln Asp Ile Asp Pro Arg Arg Leu Leu Pro Leu Leu
            180                 185                 190 gcg ctg ctg gcc ctc tgg gga cct gac cca gcc gca tca cac ctg gtg    624
Ala Leu Leu Ala Leu Trp Gly Pro Asp Pro Ala Ala Ser His Leu Val
        195                 200                 205 gaa gct ctc tac ctg gtg agc ggg gaa cgt ggc ttc ttc tac aca ccg    672
Glu Ala Leu Tyr Leu Val Ser Gly Glu Arg Gly Phe Phe Tyr Thr Pro
    210                 215                 220 aag acc cgc att gag gca gag gcg ggt gca ggc agc ctg caa ccg ttg    720
Lys Thr Arg Ile Glu Ala Glu Ala Gly Ala Gly Ser Leu Gln Pro Leu
225                 230                 235                 240 gcc ctg gag ggg tcc ctg caa aag ata cct agg tag gaa ttc gcg        765
Ala Leu Glu Gly Ser Leu Gln Lys Ile Pro Arg     Glu Phe Ala
                245                 250

<210> SEQ ID NO 92
<211> LENGTH: 251
<212> TYPE: PRT
<213> ORGANISM: Artificial Sequence
<220> FEATURE:
<223> OTHER INFORMATION: Synthetic

<400> SEQUENCE: 92

Met Ala Ser Asp Thr Trp Ser Gly Val Ala His Gly Ser Thr Arg Lys
 1               5                  10                  15

Leu Gly Leu Lys Ile Ser Gly Phe Leu Gln Arg Thr Asn Ser Leu Glu
            20                  25                  30

Glu Lys Ala Val Asp Ile Leu Leu Asn Tyr Val Arg Lys Thr Phe Asp
        35                  40                  45

Arg Ser Ala Thr Tyr Glu Ile Ala Pro Val Phe Val Leu Leu Glu Tyr
    50                  55                  60

Val Thr Leu Lys Lys Met Arg Glu Ile Ile Gly Trp Pro Gly Gly Ser
```

```
                65                  70                  75                  80
Gly Asp Ala Asn Met Tyr Ala Met Met Ile Arg Phe Lys Met Phe
                    85                  90                  95

Pro Glu Val Lys Glu Lys Gly Met Ala Ala Leu Pro Arg Leu Ile Ala
                100                 105                 110

Phe Thr Ser Glu His Ser His Ala Asn Val Ser Phe Trp Tyr Ile Pro
            115                 120                 125

Pro Ser Leu Arg Thr Leu Glu Asp Asn Glu Arg Met Ser Arg Leu
            130                 135                 140

Ser Lys Val Ala Pro Val Ile Lys Ala Arg Met Met Glu Tyr Gly Thr
145                 150                 155                 160

Thr Met Val Ala Lys Val Asn Phe Phe Arg Met Val Ile Ser Asn Pro
                165                 170                 175

Ala Ala Thr His Gln Asp Ile Asp Pro Arg Arg Leu Leu Pro Leu Leu
                180                 185                 190

Ala Leu Leu Ala Leu Trp Gly Pro Asp Pro Ala Ala Ser His Leu Val
            195                 200                 205

Glu Ala Leu Tyr Leu Val Ser Gly Glu Arg Gly Phe Phe Tyr Thr Pro
            210                 215                 220

Lys Thr Arg Ile Glu Ala Glu Ala Gly Ala Gly Ser Leu Gln Pro Leu
225                 230                 235                 240

Ala Leu Glu Gly Ser Leu Gln Lys Ile Pro Arg
                245                 250

<210> SEQ ID NO 93
<211> LENGTH: 1176
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(1176)

<400> SEQUENCE: 93 atg gct agc atg cgc ctc ctg ccg ctg ctg gcg ctg ctg gcc ctc tgg      48
Met Ala Ser Met Arg Leu Leu Pro Leu Leu Ala Leu Leu Ala Leu Trp
1               5                   10                  15 gga cct gac cca gcc gca tca cac ctg gtg gaa gct ctc tac ctg gtg      96
Gly Pro Asp Pro Ala Ala Ser His Leu Val Glu Ala Leu Tyr Leu Val
                20                  25                  30 agc ggg gaa cgt ggc ttc ttc tac aca ccg aag acc cgc att gag gca     144
Ser Gly Glu Arg Gly Phe Phe Tyr Thr Pro Lys Thr Arg Ile Glu Ala
            35                  40                  45 gag gcg ggt gca ggc agc ctg caa ccg ttg gcc ctg gag ggg tcc ctg     192
Glu Ala Gly Ala Gly Ser Leu Gln Pro Leu Ala Leu Glu Gly Ser Leu
        50                  55                  60 caa aag ata cta gtc gat acc tgg agc ggc gtg gca cat gga agc acc     240
Gln Lys Ile Leu Val Asp Thr Trp Ser Gly Val Ala His Gly Ser Thr
65                  70                  75                  80 cgt aaa ctg ggg ctc aag atc agc ggc ttc ttg caa cgt acc aac agc     288
Arg Lys Leu Gly Leu Lys Ile Ser Gly Phe Leu Gln Arg Thr Asn Ser
                85                  90                  95 ctg gaa gag aag gcg gtg gac ata ctc ctc aac tat gtc cgc aag aca     336
Leu Glu Glu Lys Ala Val Asp Ile Leu Leu Asn Tyr Val Arg Lys Thr
            100                 105                 110 ttt gat aga tct gcg acc tat gaa att gct cca gta ttt gtg ctt ttg     384
Phe Asp Arg Ser Ala Thr Tyr Glu Ile Ala Pro Val Phe Val Leu Leu
        115                 120                 125
```

```
gaa tat gtc aca ctg aag aaa atg cgt gaa atc att ggc tgg cca ggg    432
Glu Tyr Val Thr Leu Lys Lys Met Arg Glu Ile Ile Gly Trp Pro Gly
    130                 135                 140 ggc tct ggc gat gcg aac atg tat gcc atg atg atc gca cgc ttt aag    480
Gly Ser Gly Asp Ala Asn Met Tyr Ala Met Met Ile Ala Arg Phe Lys
145                 150                 155                 160 atg ttc cca gaa gtc aag gag aaa gga atg gct gct ctt ccg cgt ctc    528
Met Phe Pro Glu Val Lys Glu Lys Gly Met Ala Ala Leu Pro Arg Leu
                165                 170                 175 att gcc ttc acg tct gaa cat agt cat gcg aat gtc agc ttc tgg tac    576
Ile Ala Phe Thr Ser Glu His Ser His Ala Asn Val Ser Phe Trp Tyr
            180                 185                 190 att ccg ccg agc ttg cgt act ctg gaa gac aat gaa gag cgc atg agt    624
Ile Pro Pro Ser Leu Arg Thr Leu Glu Asp Asn Glu Glu Arg Met Ser
        195                 200                 205 cgc ctc tcg aag gtg gct cca gtg att aaa gcc cgt atg atg gag tat    672
Arg Leu Ser Lys Val Ala Pro Val Ile Lys Ala Arg Met Met Glu Tyr
    210                 215                 220 gga acc aca atg gtc gcg aag gtc aat ttc ttc cgc atg gtc atc tca    720
Gly Thr Thr Met Val Ala Lys Val Asn Phe Phe Arg Met Val Ile Ser
225                 230                 235                 240 aac cca gcg gca act cac caa gac att gac cct agg aag cag gcg ttt    768
Asn Pro Ala Ala Thr His Gln Asp Ile Asp Pro Arg Lys Gln Ala Phe
                245                 250                 255 att aaa gcc aca ggg aag aag gaa gat gaa cat gtt gcg cgc ctt gca    816
Ile Lys Ala Thr Gly Lys Lys Glu Asp Glu His Val Ala Arg Leu Ala
            260                 265                 270 aag aag aac ttt gac aaa ttg aag atg gat gtg agc caa gcg atg aaa    864
Lys Lys Asn Phe Asp Lys Leu Lys Met Asp Val Ser Gln Ala Met Lys
        275                 280                 285 tct gag gaa ggt gca agc ctg gga ccg gtg gca ggg acc gcg cat acc    912
Ser Glu Glu Gly Ala Ser Leu Gly Pro Val Ala Gly Thr Ala His Thr
    290                 295                 300 atc gca gac ttc tgg cag atg gtg tgg gag agc ggc tct acc gtc atc    960
Ile Ala Asp Phe Trp Gln Met Val Trp Glu Ser Gly Ser Thr Val Ile
305                 310                 315                 320 gtc atg ctg act ccg ctg gtg gag gat ggt gtc aag cag gcg gtg agc   1008
Val Met Leu Thr Pro Leu Val Glu Asp Gly Val Lys Gln Ala Val Ser
                325                 330                 335 gag cac atc tgg agc gag gac ttt ctg gtg cgt agc ttc tac ctg aag   1056
Glu His Ile Trp Ser Glu Asp Phe Leu Val Arg Ser Phe Tyr Leu Lys
            340                 345                 350 aac gtg cag acc cag gag acg cgt acg ctg acg cag ttc cac ttc ctg   1104
Asn Val Gln Thr Gln Glu Thr Arg Thr Leu Thr Gln Phe His Phe Leu
        355                 360                 365 agc gcg agc ccg tct ctg tgg gag ata gag ttt gct aag cag tta gcc   1152
Ser Ala Ser Pro Ser Leu Trp Glu Ile Glu Phe Ala Lys Gln Leu Ala
    370                 375                 380 agc gta tct aga tag gaa ttc gcg                                    1176
Ser Val Ser Arg     Glu Phe Ala
385                     390

<210> SEQ ID NO 94
<211> LENGTH: 388
<212> TYPE: PRT
<213> ORGANISM: Artificial Sequence
<220> FEATURE:
<223> OTHER INFORMATION: Synthetic

<400> SEQUENCE: 94

Met Ala Ser Met Arg Leu Leu Pro Leu Leu Ala Leu Leu Ala Leu Trp
1               5                   10                  15
```

Gly Pro Asp Pro Ala Ala Ser His Leu Val Glu Ala Leu Tyr Leu Val
            20                  25                  30

Ser Gly Glu Arg Gly Phe Phe Tyr Thr Pro Lys Thr Arg Ile Glu Ala
         35                  40                  45

Glu Ala Gly Ala Gly Ser Leu Gln Pro Leu Ala Leu Glu Gly Ser Leu
     50                  55                  60

Gln Lys Ile Leu Val Asp Thr Trp Ser Gly Val Ala His Gly Ser Thr
 65                  70                  75                  80

Arg Lys Leu Gly Leu Lys Ile Ser Gly Phe Leu Gln Arg Thr Asn Ser
                 85                  90                  95

Leu Glu Glu Lys Ala Val Asp Ile Leu Leu Asn Tyr Val Arg Lys Thr
            100                 105                 110

Phe Asp Arg Ser Ala Thr Tyr Glu Ile Ala Pro Val Phe Val Leu Leu
            115                 120                 125

Glu Tyr Val Thr Leu Lys Lys Met Arg Glu Ile Ile Gly Trp Pro Gly
        130                 135                 140

Gly Ser Gly Asp Ala Asn Met Tyr Ala Met Met Ile Ala Arg Phe Lys
145                 150                 155                 160

Met Phe Pro Glu Val Lys Glu Lys Gly Met Ala Ala Leu Pro Arg Leu
                165                 170                 175

Ile Ala Phe Thr Ser Glu His Ser His Ala Asn Val Ser Phe Trp Tyr
            180                 185                 190

Ile Pro Pro Ser Leu Arg Thr Leu Glu Asp Asn Glu Arg Met Ser
        195                 200                 205

Arg Leu Ser Lys Val Ala Pro Val Ile Lys Ala Arg Met Met Glu Tyr
    210                 215                 220

Gly Thr Thr Met Val Ala Lys Val Asn Phe Phe Arg Met Val Ile Ser
225                 230                 235                 240

Asn Pro Ala Ala Thr His Gln Asp Ile Asp Pro Arg Lys Gln Ala Phe
                245                 250                 255

Ile Lys Ala Thr Gly Lys Lys Glu Asp Glu His Val Ala Arg Leu Ala
            260                 265                 270

Lys Lys Asn Phe Asp Lys Leu Lys Met Asp Val Ser Gln Ala Met Lys
        275                 280                 285

Ser Glu Glu Gly Ala Ser Leu Gly Pro Val Ala Gly Thr Ala His Thr
    290                 295                 300

Ile Ala Asp Phe Trp Gln Met Val Trp Glu Ser Gly Ser Thr Val Ile
305                 310                 315                 320

Val Met Leu Thr Pro Leu Val Glu Asp Gly Val Lys Gln Ala Val Ser
                325                 330                 335

Glu His Ile Trp Ser Glu Asp Phe Leu Val Arg Ser Pro Tyr Leu Lys
            340                 345                 350

Asn Val Gln Thr Gln Glu Thr Arg Thr Leu Thr Gln Phe His Phe Leu
        355                 360                 365

Ser Ala Ser Pro Ser Leu Trp Glu Ile Glu Phe Ala Lys Gln Leu Ala
    370                 375                 380

Ser Val Ser Arg
385

<210> SEQ ID NO 95
<211> LENGTH: 1173
<212> TYPE: DNA
<213> ORGANISM: Artificial Sequence
<220> FEATURE:
<223> OTHER INFORMATION: Synthetic -continued

```
<220> FEATURE:
<221> NAME/KEY: CDS
<222> LOCATION: (1)..(1173)

<400> SEQUENCE: 95 atg gct agc gat acc tgg agc ggc gtg gca cat gga agc acc cgt aaa     48
Met Ala Ser Asp Thr Trp Ser Gly Val Ala His Gly Ser Thr Arg Lys
1               5                   10                  15 ctg ggg ctc aag atc agc ggc ttc ttg caa cgt acc aac agc ctg gaa     96
Leu Gly Leu Lys Ile Ser Gly Phe Leu Gln Arg Thr Asn Ser Leu Glu
                20                  25                  30 gag aag gcg gtg gac ata ctc ctc aac tat gtc cgc aag aca ttt gat    144
Glu Lys Ala Val Asp Ile Leu Leu Asn Tyr Val Arg Lys Thr Phe Asp
            35                  40                  45 aga tct gcg acc tat gaa att gct cca gta ttt gtg ctt ttg gaa tat    192
Arg Ser Ala Thr Tyr Glu Ile Ala Pro Val Phe Val Leu Leu Glu Tyr
        50                  55                  60 gtc aca ctg aag aaa atg cgt gaa atc att ggc tgg cca ggg ggc tct    240
Val Thr Leu Lys Lys Met Arg Glu Ile Ile Gly Trp Pro Gly Gly Ser
65                  70                  75                  80 ggc gat gcg aac atg tat gcc atg atg atc gca cgc ttt aag atg ttc    288
Gly Asp Ala Asn Met Tyr Ala Met Met Ile Ala Arg Phe Lys Met Phe
                85                  90                  95 cca gaa gtc aag gag aaa gga atg gct gct ctt ccg cgt ctc att gcc    336
Pro Glu Val Lys Glu Lys Gly Met Ala Ala Leu Pro Arg Leu Ile Ala
                100                 105                 110 ttc acg tct gaa cat agt cat gcg aat gtc agc ttc tgg tac att ccg    384
Phe Thr Ser Glu His Ser His Ala Asn Val Ser Phe Trp Tyr Ile Pro
            115                 120                 125 ccg agc ttg cgt act ctg gaa gac aat gaa gag cgc atg agt cgc ctc    432
Pro Ser Leu Arg Thr Leu Glu Asp Asn Glu Glu Arg Met Ser Arg Leu
        130                 135                 140 tcg aag gtg gct cca gtg att aaa gcc cgt atg atg gag tat gga acc    480
Ser Lys Val Ala Pro Val Ile Lys Ala Arg Met Met Glu Tyr Gly Thr
145                 150                 155                 160 aca atg gtc gcg aag gtc aat ttc ttc cgc atg gtc atc tca aac cca    528
Thr Met Val Ala Lys Val Asn Phe Phe Arg Met Val Ile Ser Asn Pro
                165                 170                 175 gcg gca act cac caa gac att gac cct agg cgc ctc ctg ccg ctg ctg    576
Ala Ala Thr His Gln Asp Ile Asp Pro Arg Arg Leu Leu Pro Leu Leu
                180                 185                 190 gcg ctg ctg gcc ctc tgg gga cct gac cca gcc gca tca cac ctg gtg    624
Ala Leu Leu Ala Leu Trp Gly Pro Asp Pro Ala Ala Ser His Leu Val
            195                 200                 205 gaa gct ctc tac ctg gtg agc ggg gaa cgt ggc ttc ttc tac aca ccg    672
Glu Ala Leu Tyr Leu Val Ser Gly Glu Arg Gly Phe Phe Tyr Thr Pro
        210                 215                 220 aag acc cgc att gag gca gag gcg ggt gca ggc agc ctg caa ccg ttg    720
Lys Thr Arg Ile Glu Ala Glu Ala Gly Ala Gly Ser Leu Gln Pro Leu
225                 230                 235                 240 gcc ctg gag ggg tcc ctg caa aag ata cct agg aag cag gcg ttt att    768
Ala Leu Glu Gly Ser Leu Gln Lys Ile Pro Arg Lys Gln Ala Phe Ile
                245                 250                 255 aaa gcc aca ggg aag aag gaa gat gaa cat gtt gcg cgc ctt gca aag    816
Lys Ala Thr Gly Lys Lys Glu Asp Glu His Val Ala Arg Leu Ala Lys
                260                 265                 270 aag aac ttt gac aaa ttg aag atg gat gtg agc caa gcg atg aaa tct    864
Lys Asn Phe Asp Lys Leu Lys Met Asp Val Ser Gln Ala Met Lys Ser
            275                 280                 285 gag gaa ggt gca agc ctg gga ccg gtg gca ggg acc gcg cat acc atc    912
Glu Glu Gly Ala Ser Leu Gly Pro Val Ala Gly Thr Ala His Thr Ile
```

```
              290                 295                 300
gca gac ttc tgg cag atg gtg tgg gag agc ggc tct acc gtc atc gtc        960
Ala Asp Phe Trp Gln Met Val Trp Glu Ser Gly Ser Thr Val Ile Val
305                 310                 315                 320 atg ctg act ccg ctg gtg gag gat ggt gtc aag cag gcg gtg agc gag       1008
Met Leu Thr Pro Leu Val Glu Asp Gly Val Lys Gln Ala Val Ser Glu
                325                 330                 335 cac atc tgg agc gag gac ttt ctg gtg cgt agc ttc tac ctg aag aac       1056
His Ile Trp Ser Glu Asp Phe Leu Val Arg Ser Phe Tyr Leu Lys Asn
                340                 345                 350 gtg cag acc cag gag acg cgt acg ctg acg cag ttc cac ttc ctg agc       1104
Val Gln Thr Gln Glu Thr Arg Thr Leu Thr Gln Phe His Phe Leu Ser
                355                 360                 365 gcg agc ccg tct ctg tgg gag ata gag ttt gct aag cag tta gcc agc       1152
Ala Ser Pro Ser Leu Trp Glu Ile Glu Phe Ala Lys Gln Leu Ala Ser
370                 375                 380 gta tct aga tag gaa ttc gcg                                           1173
Val Ser Arg     Glu Phe Ala
385                 390

<210> SEQ ID NO 96
<211> LENGTH: 387
<212> TYPE: PRT
<213> ORGANISM: Artificial Sequence
<220> FEATURE:
<223> OTHER INFORMATION: Synthetic

<400> SEQUENCE: 96

Met Ala Ser Asp Thr Trp Ser Gly Val Ala His Gly Ser Thr Arg Lys
1               5                   10                  15

Leu Gly Leu Lys Ile Ser Gly Phe Leu Gln Arg Thr Asn Ser Leu Glu
            20                  25                  30

Glu Lys Ala Val Asp Ile Leu Leu Asn Tyr Val Arg Lys Thr Phe Asp
        35                  40                  45

Arg Ser Ala Thr Tyr Glu Ile Ala Pro Val Phe Val Leu Leu Glu Tyr
    50                  55                  60

Val Thr Leu Lys Lys Met Arg Glu Ile Ile Gly Trp Pro Gly Gly Ser
65                  70                  75                  80

Gly Asp Ala Asn Met Tyr Ala Met Met Ile Ala Arg Phe Lys Met Phe
                85                  90                  95

Pro Glu Val Lys Glu Lys Gly Met Ala Ala Leu Pro Arg Leu Ile Ala
            100                 105                 110

Phe Thr Ser Glu His Ser His Ala Asn Val Ser Phe Trp Tyr Ile Pro
        115                 120                 125

Pro Ser Leu Arg Thr Leu Glu Asp Asn Glu Arg Met Ser Arg Leu
    130                 135                 140

Ser Lys Val Ala Pro Val Ile Lys Ala Arg Met Met Glu Tyr Gly Thr
145                 150                 155                 160

Thr Met Val Ala Lys Val Asn Phe Phe Arg Met Val Ile Ser Asn Pro
                165                 170                 175

Ala Ala Thr His Gln Asp Ile Asp Pro Arg Arg Leu Leu Pro Leu Leu
            180                 185                 190

Ala Leu Leu Ala Leu Trp Gly Pro Asp Pro Ala Ser His Leu Val
        195                 200                 205

Glu Ala Leu Tyr Leu Val Ser Gly Glu Arg Gly Phe Phe Tyr Thr Pro
    210                 215                 220

Lys Thr Arg Ile Glu Ala Glu Ala Gly Ala Gly Ser Leu Gln Pro Leu
225                 230                 235                 240
```

```
Ala Leu Glu Gly Ser Leu Gln Lys Ile Pro Arg Lys Gln Ala Phe Ile
                245                 250                 255

Lys Ala Thr Gly Lys Lys Glu Asp Glu His Val Ala Arg Leu Ala Lys
            260                 265                 270

Lys Asn Phe Asp Lys Leu Lys Met Asp Val Ser Gln Ala Met Lys Ser
        275                 280                 285

Glu Glu Gly Ala Ser Leu Gly Pro Val Ala Gly Thr Ala His Thr Ile
    290                 295                 300

Ala Asp Phe Trp Gln Met Val Trp Glu Ser Gly Ser Thr Val Ile Val
305                 310                 315                 320

Met Leu Thr Pro Leu Val Glu Asp Gly Val Lys Gln Ala Val Ser Glu
                325                 330                 335

His Ile Trp Ser Glu Asp Phe Leu Val Arg Ser Phe Tyr Leu Lys Asn
            340                 345                 350

Val Gln Thr Gln Glu Thr Arg Thr Leu Thr Gln Phe His Phe Leu Ser
        355                 360                 365

Ala Ser Pro Ser Leu Trp Glu Ile Glu Phe Ala Lys Gln Leu Ala Ser
    370                 375                 380

Val Ser Arg
385

<210> SEQ ID NO 97
<211> LENGTH: 1305
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(1305)

<400> SEQUENCE: 97 atg gct agc atg cgc ctc ctg ccg ctg ctg gcg ctg ctg gcc ctc tgg      48
Met Ala Ser Met Arg Leu Leu Pro Leu Leu Ala Leu Leu Ala Leu Trp
1               5                   10                  15 gga cct gac cca gcc gca tca cac ctg gtg gaa gct ctc tac ctg gtg      96
Gly Pro Asp Pro Ala Ala Ser His Leu Val Glu Ala Leu Tyr Leu Val
                20                  25                  30 agc ggg gaa cgt ggc ttc ttc tac aca ccg aag acc cgc att gag gca     144
Ser Gly Glu Arg Gly Phe Phe Tyr Thr Pro Lys Thr Arg Ile Glu Ala
            35                  40                  45 gag gcg ggt gca ggc agc ctg caa ccg ttg gcc ctg gag ggg tcc ctg     192
Glu Ala Gly Ala Gly Ser Leu Gln Pro Leu Ala Leu Glu Gly Ser Leu
        50                  55                  60 caa aag ata cta gtc gat acc tgg agc ggc gtg gca cat gga agc acc     240
Gln Lys Ile Leu Val Asp Thr Trp Ser Gly Val Ala His Gly Ser Thr
65                  70                  75                  80 cgt aaa ctg ggg ctc aag atc agc ggc ttc ttg caa cgt acc aac agc     288
Arg Lys Leu Gly Leu Lys Ile Ser Gly Phe Leu Gln Arg Thr Asn Ser
                85                  90                  95 ctg gaa gag aag gcg gtg gac ata ctc ctc aac tat gtc cgc aag aca     336
Leu Glu Glu Lys Ala Val Asp Ile Leu Leu Asn Tyr Val Arg Lys Thr
            100                 105                 110 ttt gat aga tct gcg acc tat gaa att gct cca gta ttt gtg ctt ttg     384
Phe Asp Arg Ser Ala Thr Tyr Glu Ile Ala Pro Val Phe Val Leu Leu
        115                 120                 125 gaa tat gtc aca ctg aag aaa atg cgt gaa atc att ggc tgg cca ggg     432
Glu Tyr Val Thr Leu Lys Lys Met Arg Glu Ile Ile Gly Trp Pro Gly
    130                 135                 140
```

```
ggc tct ggc gat gcg aac atg tat gcc atg atg atc gca cgc ttt aag      480
Gly Ser Gly Asp Ala Asn Met Tyr Ala Met Met Ile Ala Arg Phe Lys
145                 150                 155                 160 atg ttc cca gaa gtc aag gag aaa gga atg gct gct ctt ccg cgt ctc      528
Met Phe Pro Glu Val Lys Glu Lys Gly Met Ala Ala Leu Pro Arg Leu
                165                 170                 175 att gcc ttc acg tct gaa cat agt cat gcg aat gtc agc ttc tgg tac      576
Ile Ala Phe Thr Ser Glu His Ser His Ala Asn Val Ser Phe Trp Tyr
            180                 185                 190 att ccg ccg agc ttg cgt act ctg gaa gac aat gaa gag cgc atg agt      624
Ile Pro Pro Ser Leu Arg Thr Leu Glu Asp Asn Glu Glu Arg Met Ser
        195                 200                 205 cgc ctc tcg aag gtg gct cca gtg att aaa gcc cgt atg atg gag tat      672
Arg Leu Ser Lys Val Ala Pro Val Ile Lys Ala Arg Met Met Glu Tyr
    210                 215                 220 gga acc aca atg gtc gcg aag gtc aat ttc ttc cgc atg gtc atc tca      720
Gly Thr Thr Met Val Ala Lys Val Asn Phe Phe Arg Met Val Ile Ser
225                 230                 235                 240 aac cca gcg gca act cac caa gac att gac cct agg aag cag gcg ttt      768
Asn Pro Ala Ala Thr His Gln Asp Ile Asp Pro Arg Lys Gln Ala Phe
                245                 250                 255 att aaa gcc aca ggg aag aag gaa gat gaa cat gtt gcg cgc ctt gca      816
Ile Lys Ala Thr Gly Lys Lys Glu Asp Glu His Val Ala Arg Leu Ala
            260                 265                 270 aag aag aac ttt gac aaa ttg aag atg gat gtg agc caa gcg atg aaa      864
Lys Lys Asn Phe Asp Lys Leu Lys Met Asp Val Ser Gln Ala Met Lys
        275                 280                 285 tct gag gaa ggt gca agc ctg gga ccg gtg gca ggg acc gcg cat acc      912
Ser Glu Glu Gly Ala Ser Leu Gly Pro Val Ala Gly Thr Ala His Thr
    290                 295                 300 atc gca gac ttc tgg cag atg gtg tgg gag agc ggc tct acc gtc atc      960
Ile Ala Asp Phe Trp Gln Met Val Trp Glu Ser Gly Ser Thr Val Ile
305                 310                 315                 320 gtc atg ctg act ccg ctg gtg gag gat ggt gtc aag cag gcg gtg agc     1008
Val Met Leu Thr Pro Leu Val Glu Asp Gly Val Lys Gln Ala Val Ser
                325                 330                 335 gag cac atc tgg agc gag gac ttt ctg gtg cgt agc ttc tac ctg aag     1056
Glu His Ile Trp Ser Glu Asp Phe Leu Val Arg Ser Phe Tyr Leu Lys
            340                 345                 350 aac gtg cag acc cag gag acg cgt acg ctg acg cag ttc cac ttc ctg     1104
Asn Val Gln Thr Gln Glu Thr Arg Thr Leu Thr Gln Phe His Phe Leu
        355                 360                 365 agc gcg agc ccg tct ctg tgg gag ata gag ttt gct aag cag tta gcc     1152
Ser Ala Ser Pro Ser Leu Trp Glu Ile Glu Phe Ala Lys Gln Leu Ala
    370                 375                 380 agc gta tct aga ttg gga gga ggt tct gcc ctg ctt cgt agc att ccg     1200
Ser Val Ser Arg Leu Gly Gly Gly Ser Ala Leu Leu Arg Ser Ile Pro
385                 390                 395                 400 gcc ttg gac tct ttg act ccg gct aat gaa gat gcg aaa cgt aca ctg     1248
Ala Leu Asp Ser Leu Thr Pro Ala Asn Glu Asp Ala Lys Arg Thr Leu
                405                 410                 415 aaa att ccg gca atg acc att gct aag aat gca ggt gtt tct aga tag     1296
Lys Ile Pro Ala Met Thr Ile Ala Lys Asn Ala Gly Val Ser Arg
            420                 425                 430 gaa ttc gcg                                                         1305
Glu Phe Ala <210> SEQ ID NO 98
<211> LENGTH: 431
<212> TYPE: PRT
<213> ORGANISM: Artificial Sequence
```

<220> FEATURE:
<223> OTHER INFORMATION: Synthetic

<400> SEQUENCE: 98

Met Ala Ser Met Arg Leu Leu Pro Leu Leu Ala Leu Ala Leu Trp
1               5                   10                  15

Gly Pro Asp Pro Ala Ala Ser His Leu Val Glu Ala Leu Tyr Leu Val
            20                  25                  30

Ser Gly Glu Arg Gly Phe Phe Tyr Thr Pro Lys Thr Arg Ile Glu Ala
        35                  40                  45

Glu Ala Gly Ala Gly Ser Leu Gln Pro Leu Ala Leu Glu Gly Ser Leu
    50                  55                  60

Gln Lys Ile Leu Val Asp Thr Trp Ser Gly Val Ala His Gly Ser Thr
65                  70                  75                  80

Arg Lys Leu Gly Leu Lys Ile Ser Gly Phe Leu Gln Arg Thr Asn Ser
                85                  90                  95

Leu Glu Glu Lys Ala Val Asp Ile Leu Leu Asn Tyr Val Arg Lys Thr
            100                 105                 110

Phe Asp Arg Ser Ala Thr Tyr Glu Ile Ala Pro Val Phe Val Leu Leu
        115                 120                 125

Glu Tyr Val Thr Leu Lys Lys Met Arg Glu Ile Ile Gly Trp Pro Gly
    130                 135                 140

Gly Ser Gly Asp Ala Asn Met Tyr Ala Met Met Ile Ala Arg Phe Lys
145                 150                 155                 160

Met Phe Pro Glu Val Lys Glu Lys Gly Met Ala Ala Leu Pro Arg Leu
                165                 170                 175

Ile Ala Phe Thr Ser Glu His Ser His Ala Asn Val Ser Phe Trp Tyr
            180                 185                 190

Ile Pro Pro Ser Leu Arg Thr Leu Glu Asp Asn Glu Glu Arg Met Ser
        195                 200                 205

Arg Leu Ser Lys Val Ala Pro Val Ile Lys Ala Arg Met Met Glu Tyr
    210                 215                 220

Gly Thr Thr Met Val Ala Lys Val Asn Phe Phe Arg Met Val Ile Ser
225                 230                 235                 240

Asn Pro Ala Ala Thr His Gln Asp Ile Asp Pro Arg Lys Gln Ala Phe
                245                 250                 255

Ile Lys Ala Thr Gly Lys Lys Glu Asp His Val Ala Arg Leu Ala
            260                 265                 270

Lys Lys Asn Phe Asp Lys Leu Lys Met Asp Val Ser Gln Ala Met Lys
        275                 280                 285

Ser Glu Glu Gly Ala Ser Leu Gly Pro Val Ala Gly Thr Ala His Thr
    290                 295                 300

Ile Ala Asp Phe Trp Gln Met Val Trp Glu Ser Gly Ser Thr Val Ile
305                 310                 315                 320

Val Met Leu Thr Pro Leu Val Glu Asp Gly Val Lys Gln Ala Val Ser
                325                 330                 335

Glu His Ile Trp Ser Glu Asp Phe Leu Val Arg Ser Phe Tyr Leu Lys
            340                 345                 350

Asn Val Gln Thr Gln Glu Thr Arg Thr Leu Thr Gln Phe His Phe Leu
        355                 360                 365

Ser Ala Ser Pro Ser Leu Trp Glu Ile Glu Phe Ala Lys Gln Leu Ala
    370                 375                 380

Ser Val Ser Arg Leu Gly Gly Gly Ser Ala Leu Leu Arg Ser Ile Pro
385                 390                 395                 400

-continued

```
Ala Leu Asp Ser Leu Thr Pro Ala Asn Glu Asp Ala Lys Arg Thr Leu
            405                 410                 415
Lys Ile Pro Ala Met Thr Ile Ala Lys Asn Ala Gly Val Ser Arg
        420                 425                 430

<210> SEQ ID NO 99
<211> LENGTH: 1302
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(1302)

<400> SEQUENCE: 99 atg gct agc gat acc tgg agc ggc gtg gca cat gga agc acc cgt aaa      48
Met Ala Ser Asp Thr Trp Ser Gly Val Ala His Gly Ser Thr Arg Lys
1               5                  10                  15 ctg ggg ctc aag atc agc ggc ttc ttg caa cgt acc aac agc ctg gaa      96
Leu Gly Leu Lys Ile Ser Gly Phe Leu Gln Arg Thr Asn Ser Leu Glu
            20                  25                  30 gag aag gcg gtg gac ata ctc ctc aac tat gtc cgc aag aca ttt gat     144
Glu Lys Ala Val Asp Ile Leu Leu Asn Tyr Val Arg Lys Thr Phe Asp
        35                  40                  45 aga tct gcg acc tat gaa att gct cca gta ttt gtg ctt ttg gaa tat     192
Arg Ser Ala Thr Tyr Glu Ile Ala Pro Val Phe Val Leu Leu Glu Tyr
    50                  55                  60 gtc aca ctg aag aaa atg cgt gaa atc att ggc tgg cca ggg ggc tct     240
Val Thr Leu Lys Lys Met Arg Glu Ile Ile Gly Trp Pro Gly Gly Ser
65                  70                  75                  80 ggc gat gcg aac atg tat gcc atg atg atc gca cgc ttt aag atg ttc     288
Gly Asp Ala Asn Met Tyr Ala Met Met Ile Ala Arg Phe Lys Met Phe
                85                  90                  95 cca gaa gtc aag gag aaa gga atg gct gct ctt ccg cgt ctc att gcc     336
Pro Glu Val Lys Glu Lys Gly Met Ala Ala Leu Pro Arg Leu Ile Ala
            100                 105                 110 ttc acg tct gaa cat agt cat gcg aat gtc agc ttc tgg tac att ccg     384
Phe Thr Ser Glu His Ser His Ala Asn Val Ser Phe Trp Tyr Ile Pro
        115                 120                 125 ccg agc ttg cgt act ctg gaa gac aat gaa gag cgc atg agt cgc ctc     432
Pro Ser Leu Arg Thr Leu Glu Asp Asn Glu Glu Arg Met Ser Arg Leu
    130                 135                 140 tcg aag gtg gct cca gtg att aaa gcc cgt atg atg gag tat gga acc     480
Ser Lys Val Ala Pro Val Ile Lys Ala Arg Met Met Glu Tyr Gly Thr
145                 150                 155                 160 aca atg gtc gcg aag gtc aat ttc ttc cgc atg gtc atc tca aac cca     528
Thr Met Val Ala Lys Val Asn Phe Phe Arg Met Val Ile Ser Asn Pro
                165                 170                 175 gcg gca act cac caa gac att gac cct agg cgc ctc ctg ccg ctg ctg     576
Ala Ala Thr His Gln Asp Ile Asp Pro Arg Arg Leu Leu Pro Leu Leu
            180                 185                 190 gcg ctg ctg gcc ctc tgg gga cct gac cca gcc gca tca cac ctg gtg     624
Ala Leu Leu Ala Leu Trp Gly Pro Asp Pro Ala Ala Ser His Leu Val
        195                 200                 205 gaa gct ctc tac ctg gtg agc ggg gaa cgt ggc ttc ttc tac aca ccg     672
Glu Ala Leu Tyr Leu Val Ser Gly Glu Arg Gly Phe Phe Tyr Thr Pro
    210                 215                 220 aag acc cgc att gag gca gag gcg ggt gca ggc agc ctg caa ccg ttg     720
Lys Thr Arg Ile Glu Ala Glu Ala Gly Ala Gly Ser Leu Gln Pro Leu
225                 230                 235                 240 gcc ctg gag ggg tcc ctg caa aag ata cct agg aag cag gcg ttt att     768
```

```
Ala Leu Glu Gly Ser Leu Gln Lys Ile Pro Arg Lys Gln Ala Phe Ile
                245                 250                 255 aaa gcc aca ggg aag aag gaa gat gaa cat gtt gcg cgc ctt gca aag        816
Lys Ala Thr Gly Lys Lys Glu Asp Glu His Val Ala Arg Leu Ala Lys
                260                 265                 270 aag aac ttt gac aaa ttg aag atg gat gtg agc caa gcg atg aaa tct        864
Lys Asn Phe Asp Lys Leu Lys Met Asp Val Ser Gln Ala Met Lys Ser
                275                 280                 285 gag gaa ggt gca agc ctg gga ccg gtg gca ggg acc gcg cat acc atc        912
Glu Glu Gly Ala Ser Leu Gly Pro Val Ala Gly Thr Ala His Thr Ile
        290                 295                 300 gca gac ttc tgg cag atg gtg tgg gag agc ggc tct acc gtc atc gtc        960
Ala Asp Phe Trp Gln Met Val Trp Glu Ser Gly Ser Thr Val Ile Val
305                 310                 315                 320 atg ctg act ccg ctg gtg gag gat ggt gtc aag cag gcg gtg agc gag       1008
Met Leu Thr Pro Leu Val Glu Asp Gly Val Lys Gln Ala Val Ser Glu
                325                 330                 335 cac atc tgg agc gag gac ttt ctg gtg cgt agc ttc tac ctg aag aac       1056
His Ile Trp Ser Glu Asp Phe Leu Val Arg Ser Phe Tyr Leu Lys Asn
                340                 345                 350 gtg cag acc cag gag acg cgt acg ctg acg cag ttc cac ttc ctg agc       1104
Val Gln Thr Gln Glu Thr Arg Thr Leu Thr Gln Phe His Phe Leu Ser
        355                 360                 365 gcg agc ccg tct ctg tgg gag ata gag ttt gct aag cag tta gcc agc       1152
Ala Ser Pro Ser Leu Trp Glu Ile Glu Phe Ala Lys Gln Leu Ala Ser
370                 375                 380 gta tct aga ttg gga gga ggt tct gcc ctg ctt cgt agc att ccg gcc       1200
Val Ser Arg Leu Gly Gly Gly Ser Ala Leu Leu Arg Ser Ile Pro Ala
385                 390                 395                 400 ttg gac tct ttg act ccg gct aat gaa gat gcg aaa cgt aca ctg aaa       1248
Leu Asp Ser Leu Thr Pro Ala Asn Glu Asp Ala Lys Arg Thr Leu Lys
                405                 410                 415 att ccg gca atg acc att gct aag aat gca ggt gtt tct aga tag gaa       1296
Ile Pro Ala Met Thr Ile Ala Lys Asn Ala Gly Val Ser Arg     Glu
                420                 425                 430 ttc gcg                                                                1302
Phe Ala <210> SEQ ID NO 100
<211> LENGTH: 430
<212> TYPE: PRT
<213> ORGANISM: Artificial Sequence
<220> FEATURE:
<223> OTHER INFORMATION: Synthetic

<400> SEQUENCE: 100

Met Ala Ser Asp Thr Trp Ser Gly Val Ala His Gly Ser Thr Arg Lys
1               5                   10                  15

Leu Gly Leu Lys Ile Ser Gly Phe Leu Gln Arg Thr Asn Ser Leu Glu
            20                  25                  30

Glu Lys Ala Val Asp Ile Leu Leu Asn Tyr Val Arg Lys Thr Phe Asp
        35                  40                  45

Arg Ser Ala Thr Tyr Glu Ile Ala Pro Val Phe Val Leu Leu Glu Tyr
    50                  55                  60

Val Thr Leu Lys Lys Met Arg Glu Ile Ile Gly Trp Pro Gly Gly Ser
65                  70                  75                  80

Gly Asp Ala Asn Met Tyr Ala Met Met Ile Ala Arg Phe Lys Met Phe
                85                  90                  95

Pro Glu Val Lys Glu Lys Gly Met Ala Ala Leu Pro Arg Leu Ile Ala
            100                 105                 110
```

Phe Thr Ser Glu His Ser His Ala Asn Val Ser Phe Trp Tyr Ile Pro
            115                 120                 125

Pro Ser Leu Arg Thr Leu Glu Asp Asn Glu Glu Arg Met Ser Arg Leu
        130                 135                 140

Ser Lys Val Ala Pro Val Ile Lys Ala Arg Met Met Glu Tyr Gly Thr
145                 150                 155                 160

Thr Met Val Ala Lys Val Asn Phe Phe Arg Met Val Ile Ser Asn Pro
                165                 170                 175

Ala Ala Thr His Gln Asp Ile Asp Pro Arg Arg Leu Leu Pro Leu Leu
            180                 185                 190

Ala Leu Leu Ala Leu Trp Gly Pro Asp Pro Ala Ala Ser His Leu Val
        195                 200                 205

Glu Ala Leu Tyr Leu Val Ser Gly Glu Arg Gly Phe Phe Tyr Thr Pro
    210                 215                 220

Lys Thr Arg Ile Glu Ala Glu Ala Gly Ala Gly Ser Leu Gln Pro Leu
225                 230                 235                 240

Ala Leu Glu Gly Ser Leu Gln Lys Ile Pro Arg Lys Gln Ala Phe Ile
                245                 250                 255

Lys Ala Thr Gly Lys Lys Glu Asp Glu His Val Ala Arg Leu Ala Lys
            260                 265                 270

Lys Asn Phe Asp Lys Leu Lys Met Asp Val Ser Gln Ala Met Lys Ser
        275                 280                 285

Glu Glu Gly Ala Ser Leu Gly Pro Val Ala Gly Thr Ala His Thr Ile
    290                 295                 300

Ala Asp Phe Trp Gln Met Val Trp Glu Ser Gly Ser Thr Val Ile Val
305                 310                 315                 320

Met Leu Thr Pro Leu Val Glu Asp Gly Val Lys Gln Ala Val Ser Glu
                325                 330                 335

His Ile Trp Ser Glu Asp Phe Leu Val Arg Ser Phe Tyr Leu Lys Asn
            340                 345                 350

Val Gln Thr Gln Glu Thr Arg Thr Leu Thr Gln Phe His Phe Leu Ser
        355                 360                 365

Ala Ser Pro Ser Leu Trp Glu Ile Glu Phe Ala Lys Gln Leu Ala Ser
    370                 375                 380

Val Ser Arg Leu Gly Gly Gly Ser Ala Leu Leu Arg Ser Ile Pro Ala
385                 390                 395                 400

Leu Asp Ser Leu Thr Pro Ala Asn Glu Asp Ala Lys Arg Thr Leu Lys
                405                 410                 415

Ile Pro Ala Met Thr Ile Ala Lys Asn Ala Gly Val Ser Arg
            420                 425                 430

<210> SEQ ID NO 101
<211> LENGTH: 399
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(399)

<400> SEQUENCE: 101 gaa ttc gct agc ggt gct cgt ggt ttc cca gga acc cca ggt ctt ccg     48
Glu Phe Ala Ser Gly Ala Arg Gly Phe Pro Gly Thr Pro Gly Leu Pro
1               5                   10                  15 ggt gtc aaa ggt cac cgt ggt tat ccg ggc ctg gac ggt gct ggt cag     96
Gly Val Lys Gly His Arg Gly Tyr Pro Gly Leu Asp Gly Ala Gly Gln

```
                    20                  25                  30
acg ggt aaa cca ggt att gct ggc ttc aaa ggt gaa caa ggc ccg aag     144
Thr Gly Lys Pro Gly Ile Ala Gly Phe Lys Gly Glu Gln Gly Pro Lys
             35                  40                  45 gga gaa ccg ggc cca gca ggt gaa gaa ggc aag cgt ggt gcc cgt gga     192
Gly Glu Pro Gly Pro Ala Gly Glu Glu Gly Lys Arg Gly Ala Arg Gly
 50                  55                  60 gag ccg ggt ggc gtt ggg ccg atc aga tct ggc cca cca ggc ccg gct     240
Glu Pro Gly Gly Val Gly Pro Ile Arg Ser Gly Pro Pro Gly Pro Ala
 65                  70                  75                  80 gga cca gct ggt gaa cgt ggc gag cag gcg gtt gga ccg cca ggt ccg     288
Gly Pro Ala Gly Glu Arg Gly Glu Gln Ala Val Gly Pro Pro Gly Pro
                 85                  90                  95 gca gga agc gct ggt gct cgt ggc gct ccg ggt gcg cca ggc gag cgt     336
Ala Gly Ser Ala Gly Ala Arg Gly Ala Pro Gly Ala Pro Gly Glu Arg
            100                 105                 110 ggc ctg aag gga cac cgt ggc ttc act ggt ctg caa ggt ctg cca ggc     384
Gly Leu Lys Gly His Arg Gly Phe Thr Gly Leu Gln Gly Leu Pro Gly
        115                 120                 125 gga tcc tag aag ctt                                                 399
Gly Ser     Lys Leu
    130

<210> SEQ ID NO 102
<211> LENGTH: 130
<212> TYPE: PRT
<213> ORGANISM: Artificial Sequence
<220> FEATURE:
<223> OTHER INFORMATION: Synthetic

<400> SEQUENCE: 102

Glu Phe Ala Ser Gly Ala Arg Gly Phe Pro Gly Thr Pro Gly Leu Pro
 1               5                  10                  15

Gly Val Lys Gly His Arg Gly Tyr Pro Gly Leu Asp Gly Ala Gly Gln
                 20                  25                  30

Thr Gly Lys Pro Gly Ile Ala Gly Phe Lys Gly Glu Gln Gly Pro Lys
             35                  40                  45

Gly Glu Pro Gly Pro Ala Gly Glu Glu Gly Lys Arg Gly Ala Arg Gly
 50                  55                  60

Glu Pro Gly Gly Val Gly Pro Ile Arg Ser Gly Pro Pro Gly Pro Ala
 65                  70                  75                  80

Gly Pro Ala Gly Glu Arg Gly Glu Gln Ala Val Gly Pro Pro Gly Pro
                 85                  90                  95

Ala Gly Ser Ala Gly Ala Arg Gly Ala Pro Gly Ala Pro Gly Glu Arg
            100                 105                 110

Gly Leu Lys Gly His Arg Gly Phe Thr Gly Leu Gln Gly Leu Pro Gly
        115                 120                 125

Gly Ser
    130

<210> SEQ ID NO 103
<211> LENGTH: 69
<212> TYPE: DNA
<213> ORGANISM: Artificial Sequence
<220> FEATURE:
<223> OTHER INFORMATION: Synthetic

<400> SEQUENCE: 103
acctttgaag ccagcaatac ctggtttacc cgtctgacca gcaccgtcca ggcccggata      60
accacggtg                                                             69
```

<210> SEQ ID NO 104
<211> LENGTH: 66
<212> TYPE: DNA
<213> ORGANISM: Artificial Sequence
<220> FEATURE:
<223> OTHER INFORMATION: Synthetic

<400> SEQUENCE: 104
gccagatctg atcggcccaa cgccacccgg ctctccacgg gcaccacgct tgccttcttc    60
acctgc                                                              66

<210> SEQ ID NO 105
<211> LENGTH: 69
<212> TYPE: DNA
<213> ORGANISM: Artificial Sequence
<220> FEATURE:
<223> OTHER INFORMATION: Synthetic

<400> SEQUENCE: 105
tggcgcaccc ggagcgccac gagcaccagc gcttcctgcc ggacctggcg gtccaaccgc    60
ctgctcgcc                                                           69

<210> SEQ ID NO 106
<211> LENGTH: 45
<212> TYPE: DNA
<213> ORGANISM: Artificial Sequence
<220> FEATURE:
<223> OTHER INFORMATION: Synthetic

<400> SEQUENCE: 106
aagcttctag gatccgcctg gcagaccttg cagaccagtg aagcc                   45

<210> SEQ ID NO 107
<211> LENGTH: 381
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(381)

<400> SEQUENCE: 107 gaa ttc cta gga tcc gcc act gaa ggg cgc gtg cgt gtc aac agc gcc     48
Glu Phe Leu Gly Ser Ala Thr Glu Gly Arg Val Arg Val Asn Ser Ala
1               5                   10                  15 tat cag gac aag gcg tct gga gaa gtt ctg gag acc act gcc cca gga     96
Tyr Gln Asp Lys Ala Ser Gly Glu Val Leu Glu Thr Thr Ala Pro Gly
            20                  25                  30 gta gag gac atc agc ggg ctt ccg tct gga gaa gtt ctg gag acc gct    144
Val Glu Asp Ile Ser Gly Leu Pro Ser Gly Glu Val Leu Glu Thr Ala
        35                  40                  45 gcc cca gga gta gag gac atc agc ggg ctt ccg tct gga gcc ggc tgg    192
Ala Pro Gly Val Glu Asp Ile Ser Gly Leu Pro Ser Gly Ala Gly Trp
    50                  55                  60 ctg gct gac cag act gtc cgt tac ccg atc agc gcc ggc tgg ctg gcc    240
Leu Ala Asp Gln Thr Val Arg Tyr Pro Ile Ser Ala Gly Trp Leu Ala
65                  70                  75                  80 gac cgc agc gtg cgc tac ccg atc tct tct aga gcc ggc tgg ctg gcc    288
Asp Arg Ser Val Arg Tyr Pro Ile Ser Ser Arg Ala Gly Trp Leu Ala
                85                  90                  95 gac ggc agc ctg cgc tac ccg atc gcg tct gga gca tat tat ggc agc    336
Asp Gly Ser Leu Arg Tyr Pro Ile Ala Ser Gly Ala Tyr Tyr Gly Ser

```
                            100                 105                 110
gga act ccg tct agc ttc ccg acg gtc tct act agt tag aag ctt         381
Gly Thr Pro Ser Ser Phe Pro Thr Val Ser Thr Ser     Lys Leu
        115                 120                     125

<210> SEQ ID NO 108
<211> LENGTH: 124
<212> TYPE: PRT
<213> ORGANISM: Artificial Sequence
<220> FEATURE:
<223> OTHER INFORMATION: Synthetic

<400> SEQUENCE: 108

Glu Phe Leu Gly Ser Ala Thr Glu Gly Arg Val Arg Val Asn Ser Ala
1               5                   10                  15

Tyr Gln Asp Lys Ala Ser Gly Glu Val Leu Glu Thr Thr Ala Pro Gly
            20                  25                  30

Val Glu Asp Ile Ser Gly Leu Pro Ser Gly Glu Val Leu Glu Thr Ala
        35                  40                  45

Ala Pro Gly Val Glu Asp Ile Ser Gly Leu Pro Ser Gly Ala Gly Trp
    50                  55                  60

Leu Ala Asp Gln Thr Val Arg Tyr Pro Ile Ser Ala Gly Trp Leu Ala
65                  70                  75                  80

Asp Arg Ser Val Arg Tyr Pro Ile Ser Ser Arg Ala Gly Trp Leu Ala
                85                  90                  95

Asp Gly Ser Leu Arg Tyr Pro Ile Ala Ser Gly Ala Tyr Tyr Gly Ser
            100                 105                 110

Gly Thr Pro Ser Ser Phe Pro Thr Val Ser Thr Ser
        115                 120

<210> SEQ ID NO 109
<211> LENGTH: 69
<212> TYPE: DNA
<213> ORGANISM: Artificial Sequence
<220> FEATURE:
<223> OTHER INFORMATION: Synthetic

<400> SEQUENCE: 109
tcctggggca gtggtctcca gaacttctcc agacgccttg tcctgatagg cgctgttgac      60
acgcacgcg                                                              69

<210> SEQ ID NO 110
<211> LENGTH: 69
<212> TYPE: DNA
<213> ORGANISM: Artificial Sequence
<220> FEATURE:
<223> OTHER INFORMATION: Synthetic

<400> SEQUENCE: 110
agccagccag ccggctccag acggaagccc gctgatgtcc tctactcctg ggcagcggt       60 ctccagaac                                                              69

<210> SEQ ID NO 111
<211> LENGTH: 69
<212> TYPE: DNA
<213> ORGANISM: Artificial Sequence
<220> FEATURE:
<223> OTHER INFORMATION: Synthetic

<400> SEQUENCE: 111
caggctgccg tcggccagcc agccggctct agaagagatc gggtagcgca cgctgcggtc      60
``` ggccagcca                                                          69

<210> SEQ ID NO 112
<211> LENGTH: 48
<212> TYPE: DNA
<213> ORGANISM: Artificial Sequence
<220> FEATURE:
<223> OTHER INFORMATION: Synthetic

<400> SEQUENCE: 112
aagcttctaa ctagtagaga ccgtcgggaa gctagacgga gttccgct              48

<210> SEQ ID NO 113
<211> LENGTH: 315
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(315)

<400> SEQUENCE: 113 gaa ttc act agt aac ttt ggg tct caa cgc ttt tct aag ata gcc tcc     48
Glu Phe Thr Ser Asn Phe Gly Ser Gln Arg Phe Ser Lys Ile Ala Ser
1               5                   10                  15 aac acc cag agc cgc gcg ggc atc ccg acc ttc ggg cgt agc ttc act     96
Asn Thr Gln Ser Arg Ala Gly Ile Pro Thr Phe Gly Arg Ser Phe Thr
            20                  25                  30 ctg gct tct tct gag act ggt gtt gga gcg cag tgg gta gga tac gac    144
Leu Ala Ser Ser Glu Thr Gly Val Gly Ala Gln Trp Val Gly Tyr Asp
        35                  40                  45 gac cag gaa agc gtc aaa agc aag gtg cag tac gtc gac gcc ggc tgg    192
Asp Gln Glu Ser Val Lys Ser Lys Val Gln Tyr Val Asp Ala Gly Trp
    50                  55                  60 ctg agc gat ggc tct gtg caa tat ccg att gcg aat gat ggt gct cag    240
Leu Ser Asp Gly Ser Val Gln Tyr Pro Ile Ala Asn Asp Gly Ala Gln
65                  70                  75                  80 att gca aaa gtg ggc cag ata ttt gct gcc tgg aaa att ctg gga tat    288
Ile Ala Lys Val Gly Gln Ile Phe Ala Ala Trp Lys Ile Leu Gly Tyr
                85                  90                  95 gac cgc tct gat ctc gag tag aag ctt                                315
Asp Arg Ser Asp Leu Glu     Lys Leu
            100

<210> SEQ ID NO 114
<211> LENGTH: 102
<212> TYPE: PRT
<213> ORGANISM: Artificial Sequence
<220> FEATURE:
<223> OTHER INFORMATION: Synthetic

<400> SEQUENCE: 114

Glu Phe Thr Ser Asn Phe Gly Ser Gln Arg Phe Ser Lys Ile Ala Ser
1               5                   10                  15

Asn Thr Gln Ser Arg Ala Gly Ile Pro Thr Phe Gly Arg Ser Phe Thr
            20                  25                  30

Leu Ala Ser Ser Glu Thr Gly Val Gly Ala Gln Trp Val Gly Tyr Asp
        35                  40                  45

Asp Gln Glu Ser Val Lys Ser Lys Val Gln Tyr Val Asp Ala Gly Trp
    50                  55                  60

Leu Ser Asp Gly Ser Val Gln Tyr Pro Ile Ala Asn Asp Gly Ala Gln
65                  70                  75                  80

```
Ile Ala Lys Val Gly Gln Ile Phe Ala Ala Trp Lys Ile Leu Gly Tyr
                85                  90                  95

Asp Arg Ser Asp Leu Glu
            100

<210> SEQ ID NO 115
<211> LENGTH: 66
<212> TYPE: DNA
<213> ORGANISM: Artificial Sequence
<220> FEATURE:
<223> OTHER INFORMATION: Synthetic

<400> SEQUENCE: 115
agtctcagaa gaagccagag tgaagctacg cccgaaggtc gggatgcccg cgcggctctg      60
ggtgtt                                                                66

<210> SEQ ID NO 116
<211> LENGTH: 66
<212> TYPE: DNA
<213> ORGANISM: Artificial Sequence
<220> FEATURE:
<223> OTHER INFORMATION: Synthetic

<400> SEQUENCE: 116
cacagagcca tcgctcagcc agccggcgtc gacgtactgc accttgcttt tgacgctttc      60
ctggtc                                                                66

<210> SEQ ID NO 117
<211> LENGTH: 66
<212> TYPE: DNA
<213> ORGANISM: Artificial Sequence
<220> FEATURE:
<223> OTHER INFORMATION: Synthetic

<400> SEQUENCE: 117
ctcgagatca gagcggtcat atcccagaat tttccaggca gcaaatatct ggcccacttt      60
tgcaat                                                                66

<210> SEQ ID NO 118
<211> LENGTH: 30
<212> TYPE: DNA
<213> ORGANISM: Artificial Sequence
<220> FEATURE:
<223> OTHER INFORMATION: Synthetic

<400> SEQUENCE: 118
aagcttctac tcgagatcag agcggtcata                                      30

<210> SEQ ID NO 119
<211> LENGTH: 354
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(354)

<400> SEQUENCE: 119 gaa ttc gct agc ctc gag gct cac cgt aag ccg ttg gtc ata atc gct      48
Glu Phe Ala Ser Leu Glu Ala His Arg Lys Pro Leu Val Ile Ile Ala
1               5                   10                  15 gaa gat gtt gat gga gaa gct ctg agc aca ctg gtc ttg aat cgt ctt      96
Glu Asp Val Asp Gly Glu Ala Leu Ser Thr Leu Val Leu Asn Arg Leu
            20                  25                  30
```

```
aag gtt ggt ctt cag gtt gtg gca gtc aag gct cca ggg ttt ggt gac    144
Lys Val Gly Leu Gln Val Val Ala Val Lys Ala Pro Gly Phe Gly Asp
         35                  40                  45 aat gcg atg gcc aag aca att gcg tac gac gaa gag gcc cgt cgc ggc    192
Asn Ala Met Ala Lys Thr Ile Ala Tyr Asp Glu Glu Ala Arg Arg Gly
 50                  55                  60 ctc gga tcc ggt gtc atc aca gta aag gat gga aaa aca ctg aat gat    240
Leu Gly Ser Gly Val Ile Thr Val Lys Asp Gly Lys Thr Leu Asn Asp
 65                  70                  75                  80 gaa tta gaa att att gaa ggc atg aag ttt gat cgt ggc tat att tct    288
Glu Leu Glu Ile Ile Glu Gly Met Lys Phe Asp Arg Gly Tyr Ile Ser
                 85                  90                  95 gcg tct caa aaa cgt gcg gca tac gat cag tat ggt cat gct gcg ttt    336
Ala Ser Gln Lys Arg Ala Ala Tyr Asp Gln Tyr Gly His Ala Ala Phe
             100                 105                 110 gag tga tca tag aag ctt                                            354
Glu     Ser     Lys Leu
                115
```

<210> SEQ ID NO 120
<211> LENGTH: 113
<212> TYPE: PRT
<213> ORGANISM: Artificial Sequence
<220> FEATURE:
<223> OTHER INFORMATION: Synthetic

<400> SEQUENCE: 120

```
Glu Phe Ala Ser Leu Glu Ala His Arg Lys Pro Leu Val Ile Ile Ala
 1               5                  10                  15

Glu Asp Val Asp Gly Glu Ala Leu Ser Thr Leu Val Leu Asn Arg Leu
             20                  25                  30

Lys Val Gly Leu Gln Val Val Ala Val Lys Ala Pro Gly Phe Gly Asp
         35                  40                  45

Asn Ala Met Ala Lys Thr Ile Ala Tyr Asp Glu Glu Ala Arg Arg Gly
 50                  55                  60

Leu Gly Ser Gly Val Ile Thr Val Lys Asp Gly Lys Thr Leu Asn Asp
 65                  70                  75                  80

Glu Leu Glu Ile Ile Glu Gly Met Lys Phe Asp Arg Gly Tyr Ile Ser
                 85                  90                  95

Ala Ser Gln Lys Arg Ala Ala Tyr Asp Gln Tyr Gly His Ala Ala Phe
             100                 105                 110

Glu
```

<210> SEQ ID NO 121
<211> LENGTH: 69
<212> TYPE: DNA
<213> ORGANISM: Artificial Sequence
<220> FEATURE:
<223> OTHER INFORMATION: Synthetic

<400> SEQUENCE: 121
tggagccttg actgccacaa cctgaagacc aaccttaaga cgattcaaga ccagtgtgct    60
cagagcttc                                                            69

<210> SEQ ID NO 122
<211> LENGTH: 69
<212> TYPE: DNA
<213> ORGANISM: Artificial Sequence
<220> FEATURE:
<223> OTHER INFORMATION: Synthetic
<210> SEQ ID NO 122 [continued]

<400> SEQUENCE: 122

```
cagtgttttt ccatccttta ctgtgatgac accggatccg aggccgcgac gggcctcttc    60
gtcgtacgc                                                            69
```

<210> SEQ ID NO 123
<211> LENGTH: 69
<212> TYPE: DNA
<213> ORGANISM: Artificial Sequence
<220> FEATURE:
<223> OTHER INFORMATION: Synthetic

<400> SEQUENCE: 123

```
aaacgcagca tgaccatact gatcgtatgc cgcacgtttt tgagacgcag aaatatagcc    60
acgatcaaa                                                            69
```

<210> SEQ ID NO 124
<211> LENGTH: 39
<212> TYPE: DNA
<213> ORGANISM: Artificial Sequence
<220> FEATURE:
<223> OTHER INFORMATION: Synthetic

<400> SEQUENCE: 124

```
aagcttctat gatcactcaa acgcagcatg accatactg                           39
```

<210> SEQ ID NO 125
<211> LENGTH: 1050
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(1050)

<400> SEQUENCE: 125

```
gaa ttc gct agc ggt gct cgt ggt ttc cca gga acc cca ggt ctt ccg       48
Glu Phe Ala Ser Gly Ala Arg Gly Phe Pro Gly Thr Pro Gly Leu Pro
1               5                   10                  15 ggt gtc aaa ggt cac cgt ggt tat ccg ggc ctg gac ggt gct ggt cag       96
Gly Val Lys Gly His Arg Gly Tyr Pro Gly Leu Asp Gly Ala Gly Gln
            20                  25                  30 acg ggt aaa cca ggt att gct ggc ttc aaa ggt gaa caa ggc ccg aag      144
Thr Gly Lys Pro Gly Ile Ala Gly Phe Lys Gly Glu Gln Gly Pro Lys
        35                  40                  45 gga gaa ccg ggc cca gca ggt gaa gaa ggc aag cgt ggt gcc cgt gga      192
Gly Glu Pro Gly Pro Ala Gly Glu Glu Gly Lys Arg Gly Ala Arg Gly
    50                  55                  60 gag ccg ggt ggc gtt ggg ccg atc aga tct ggc cca cca ggc ccg gct      240
Glu Pro Gly Gly Val Gly Pro Ile Arg Ser Gly Pro Pro Gly Pro Ala
65                  70                  75                  80 gga cca gct ggt gaa cgt ggc gag cag gcg gtt gga ccg cca ggt ccg      288
Gly Pro Ala Gly Glu Arg Gly Glu Gln Ala Val Gly Pro Pro Gly Pro
                85                  90                  95 gca gga agc gct ggt gct cgt ggc gct ccg ggt gcg cca ggc gag cgt      336
Ala Gly Ser Ala Gly Ala Arg Gly Ala Pro Gly Ala Pro Gly Glu Arg
            100                 105                 110 ggc ctg aag gga cac cgt ggc ttc act ggt ctg caa ggt ctg cca ggc      384
Gly Leu Lys Gly His Arg Gly Phe Thr Gly Leu Gln Gly Leu Pro Gly
        115                 120                 125 gga tcc gcc act gaa ggg cgc gtg cgt gtc aac agc gcc tat cag gac      432
Gly Ser Ala Thr Glu Gly Arg Val Arg Val Asn Ser Ala Tyr Gln Asp
    130                 135                 140
```

```
aag gcg tct gga gaa gtt ctg gag acc act gcc cca gga gta gag gac      480
Lys Ala Ser Gly Glu Val Leu Glu Thr Thr Ala Pro Gly Val Glu Asp
145                 150                 155                 160 atc agc ggg ctt ccg tct gga gaa gtt ctg gag acc gct gcc cca gga      528
Ile Ser Gly Leu Pro Ser Gly Glu Val Leu Glu Thr Ala Ala Pro Gly
                165                 170                 175 gta gag gac atc agc ggg ctt ccg tct gga gcc ggc tgg ctg gct gac      576
Val Glu Asp Ile Ser Gly Leu Pro Ser Gly Ala Gly Trp Leu Ala Asp
            180                 185                 190 cag act gtc cgt tac ccg atc agc gcc ggc tgg ctg gcc gac cgc agc      624
Gln Thr Val Arg Tyr Pro Ile Ser Ala Gly Trp Leu Ala Asp Arg Ser
        195                 200                 205 gtg cgc tac ccg atc tct tct aga gcc ggc tgg ctg gcc gac ggc agc      672
Val Arg Tyr Pro Ile Ser Ser Arg Ala Gly Trp Leu Ala Asp Gly Ser
    210                 215                 220 ctg cgc tac ccg att gcg tct gga gca tat tat ggc agc gga act ccg      720
Leu Arg Tyr Pro Ile Ala Ser Gly Ala Tyr Tyr Gly Ser Gly Thr Pro
225                 230                 235                 240 tct agc ttc ccg acg gtc tct act agt aac ttt ggg tct caa cgc ttt      768
Ser Ser Phe Pro Thr Val Ser Thr Ser Asn Phe Gly Ser Gln Arg Phe
                245                 250                 255 tct aag ata gcc tcc aac acc cag agc cgc gcg ggc atc ccg acc ttc      816
Ser Lys Ile Ala Ser Asn Thr Gln Ser Arg Ala Gly Ile Pro Thr Phe
            260                 265                 270 ggg cgt agc ttc act ctg gct tct tct gag act ggt gtt gga gcg cag      864
Gly Arg Ser Phe Thr Leu Ala Ser Ser Glu Thr Gly Val Gly Ala Gln
        275                 280                 285 tgg gta gga tac gac gac cag gaa agc gtc aaa agc aag gtg cag tac      912
Trp Val Gly Tyr Asp Asp Gln Glu Ser Val Lys Ser Lys Val Gln Tyr
    290                 295                 300 gtc gac gcc ggc tgg ctg agc gat ggc tct gtg caa tat ccg att gcg      960
Val Asp Ala Gly Trp Leu Ser Asp Gly Ser Val Gln Tyr Pro Ile Ala
305                 310                 315                 320 aat gat ggt gct cag att gca aaa gtg ggc cag ata ttt gct gcc tgg     1008
Asn Asp Gly Ala Gln Ile Ala Lys Val Gly Gln Ile Phe Ala Ala Trp
                325                 330                 335 aaa att ctg gga tat gac cgc tct gat ctc gag tag aag ctt             1050
Lys Ile Leu Gly Tyr Asp Arg Ser Asp Leu Glu     Lys Leu
                340                 345

<210> SEQ ID NO 126
<211> LENGTH: 347
<212> TYPE: PRT
<213> ORGANISM: Artificial Sequence
<220> FEATURE:
<223> OTHER INFORMATION: Synthetic

<400> SEQUENCE: 126

Glu Phe Ala Ser Gly Ala Arg Gly Phe Pro Gly Thr Pro Gly Leu Pro
1               5                   10                  15

Gly Val Lys Gly His Arg Gly Tyr Pro Gly Leu Asp Gly Ala Gly Gln
            20                  25                  30

Thr Gly Lys Pro Gly Ile Ala Gly Phe Lys Gly Glu Gln Gly Pro Lys
        35                  40                  45

Gly Glu Pro Gly Pro Ala Gly Glu Glu Gly Lys Arg Gly Ala Arg Gly
    50                  55                  60

Glu Pro Gly Gly Val Gly Pro Ile Arg Ser Gly Pro Pro Gly Pro Ala
65                  70                  75                  80

Gly Pro Ala Gly Glu Arg Gly Glu Gln Ala Val Gly Pro Pro Gly Pro
                85                  90                  95
```

```
Ala Gly Ser Ala Gly Ala Arg Gly Ala Pro Gly Ala Pro Gly Glu Arg
                100                 105                 110

Gly Leu Lys Gly His Arg Gly Phe Thr Gly Leu Gln Gly Leu Pro Gly
            115                 120                 125

Gly Ser Ala Thr Glu Gly Arg Val Arg Val Asn Ser Ala Tyr Gln Asp
        130                 135                 140

Lys Ala Ser Gly Glu Val Leu Glu Thr Thr Ala Pro Gly Val Glu Asp
145                 150                 155                 160

Ile Ser Gly Leu Pro Ser Gly Glu Val Leu Glu Thr Ala Ala Pro Gly
                165                 170                 175

Val Glu Asp Ile Ser Gly Leu Pro Ser Gly Ala Gly Trp Leu Ala Asp
            180                 185                 190

Gln Thr Val Arg Tyr Pro Ile Ser Ala Gly Trp Leu Ala Asp Arg Ser
        195                 200                 205

Val Arg Tyr Pro Ile Ser Ser Arg Ala Gly Trp Leu Ala Asp Gly Ser
    210                 215                 220

Leu Arg Tyr Pro Ile Ala Ser Gly Ala Tyr Tyr Gly Ser Gly Thr Pro
225                 230                 235                 240

Ser Ser Phe Pro Thr Val Ser Thr Ser Asn Phe Gly Ser Gln Arg Phe
                245                 250                 255

Ser Lys Ile Ala Ser Asn Thr Gln Ser Arg Ala Gly Ile Pro Thr Phe
            260                 265                 270

Gly Arg Ser Phe Thr Leu Ala Ser Ser Glu Thr Gly Val Gly Ala Gln
        275                 280                 285

Trp Val Gly Tyr Asp Asp Gln Glu Ser Val Lys Ser Lys Val Gln Tyr
    290                 295                 300

Val Asp Ala Gly Trp Leu Ser Asp Gly Ser Val Gln Tyr Pro Ile Ala
305                 310                 315                 320

Asn Asp Gly Ala Gln Ile Ala Lys Val Gly Gln Ile Phe Ala Ala Trp
                325                 330                 335

Lys Ile Leu Gly Tyr Asp Arg Ser Asp Leu Glu
            340                 345

<210> SEQ ID NO 127
<211> LENGTH: 1377
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(1377)

<400> SEQUENCE: 127 gaa ttc gct agc ggt gct cgt ggt ttc cca gga acc cca ggt ctt ccg      48
Glu Phe Ala Ser Gly Ala Arg Gly Phe Pro Gly Thr Pro Gly Leu Pro
1               5                   10                  15 ggt gtc aaa ggt cac cgt ggt tat ccg ggc ctg gac ggt gct ggt cag      96
Gly Val Lys Gly His Arg Gly Tyr Pro Gly Leu Asp Gly Ala Gly Gln
            20                  25                  30 acg ggt aaa cca ggt att gct ggc ttc aaa ggt gaa caa ggc ccg aag     144
Thr Gly Lys Pro Gly Ile Ala Gly Phe Lys Gly Glu Gln Gly Pro Lys
        35                  40                  45 gga gaa ccg ggc cca gca ggt gaa gaa ggc aag cgt ggt gcc cgt gga     192
Gly Glu Pro Gly Pro Ala Gly Glu Glu Gly Lys Arg Gly Ala Arg Gly
    50                  55                  60 gag ccg ggt ggc gtt ggg ccg atc aga tct ggc cca cca ggc ccg gct     240
Glu Pro Gly Gly Val Gly Pro Ile Arg Ser Gly Pro Pro Gly Pro Ala
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     | 65  |     |     |     | 70  |     |     |     | 75  |     |     |     | 80  |     |      |
| gga | cca | gct | ggt | gaa | cgt | ggc | gag | cag | gcg | gtt | gga | ccg | cca | ggt | ccg | 288  |
| Gly | Pro | Ala | Gly | Glu | Arg | Gly | Glu | Gln | Ala | Val | Gly | Pro | Pro | Gly | Pro |      |
|     |     |     |     |     | 85  |     |     |     |     | 90  |     |     |     |     | 95  |      |
| gca | gga | agc | gct | ggt | gct | cgt | ggc | gct | ccg | ggt | gcg | cca | ggc | gag | cgt | 336  |
| Ala | Gly | Ser | Ala | Gly | Ala | Arg | Gly | Ala | Pro | Gly | Ala | Pro | Gly | Glu | Arg |      |
|     |     |     | 100 |     |     |     |     | 105 |     |     |     |     | 110 |     |     |      |
| ggc | ctg | aag | gga | cac | cgt | ggc | ttc | act | ggt | ctg | caa | ggt | ctg | cca | ggc | 384  |
| Gly | Leu | Lys | Gly | His | Arg | Gly | Phe | Thr | Gly | Leu | Gln | Gly | Leu | Pro | Gly |      |
|     |     | 115 |     |     |     |     | 120 |     |     |     |     | 125 |     |     |     |      |
| gga | tcc | gcc | act | gaa | ggg | cgt | gtg | cgt | gtc | aac | agc | gcc | tat | cag | gac | 432  |
| Gly | Ser | Ala | Thr | Glu | Gly | Arg | Val | Arg | Val | Asn | Ser | Ala | Tyr | Gln | Asp |      |
|     | 130 |     |     |     |     | 135 |     |     |     |     | 140 |     |     |     |     |      |
| aag | gcg | tct | gga | gaa | gtt | ctg | gag | acc | act | gcc | cca | gga | gta | gag | gac | 480  |
| Lys | Ala | Ser | Gly | Glu | Val | Leu | Glu | Thr | Thr | Ala | Pro | Gly | Val | Glu | Asp |      |
| 145 |     |     |     |     | 150 |     |     |     |     | 155 |     |     |     |     | 160 |      |
| atc | agc | ggg | ctt | ccg | tct | gga | gaa | gtt | ctg | gag | acc | gct | gcc | cca | gga | 528  |
| Ile | Ser | Gly | Leu | Pro | Ser | Gly | Glu | Val | Leu | Glu | Thr | Ala | Ala | Pro | Gly |      |
|     |     |     |     | 165 |     |     |     |     | 170 |     |     |     |     | 175 |     |      |
| gta | gag | gac | atc | agc | ggg | ctt | ccg | tct | gga | gcc | ggc | tgg | ctg | gct | gac | 576  |
| Val | Glu | Asp | Ile | Ser | Gly | Leu | Pro | Ser | Gly | Ala | Gly | Trp | Leu | Ala | Asp |      |
|     |     |     | 180 |     |     |     |     | 185 |     |     |     |     | 190 |     |     |      |
| cag | act | gtc | cgt | tac | ccg | atc | agc | gcc | ggc | tgg | ctg | gcc | gac | cgc | agc | 624  |
| Gln | Thr | Val | Arg | Tyr | Pro | Ile | Ser | Ala | Gly | Trp | Leu | Ala | Asp | Arg | Ser |      |
|     |     | 195 |     |     |     |     | 200 |     |     |     |     | 205 |     |     |     |      |
| gtg | cgc | tac | ccg | atc | tct | tct | aga | gcc | ggc | tgg | ctg | gcc | gac | ggc | agc | 672  |
| Val | Arg | Tyr | Pro | Ile | Ser | Ser | Arg | Ala | Gly | Trp | Leu | Ala | Asp | Gly | Ser |      |
|     | 210 |     |     |     |     | 215 |     |     |     |     | 220 |     |     |     |     |      |
| ctg | cgc | tac | ccg | att | gcg | tct | gga | gca | tat | tat | ggc | agc | gga | act | ccg | 720  |
| Leu | Arg | Tyr | Pro | Ile | Ala | Ser | Gly | Ala | Tyr | Tyr | Gly | Ser | Gly | Thr | Pro |      |
| 225 |     |     |     |     | 230 |     |     |     |     | 235 |     |     |     |     | 240 |      |
| tct | agc | ttc | ccg | acg | gtc | tct | act | agt | aac | ttt | ggg | tct | caa | cgc | ttt | 768  |
| Ser | Ser | Phe | Pro | Thr | Val | Ser | Thr | Ser | Asn | Phe | Gly | Ser | Gln | Arg | Phe |      |
|     |     |     |     | 245 |     |     |     |     | 250 |     |     |     |     | 255 |     |      |
| tct | aag | ata | gcc | tcc | aac | acc | cag | agc | cgc | gcg | ggc | atc | ccg | acc | ttc | 816  |
| Ser | Lys | Ile | Ala | Ser | Asn | Thr | Gln | Ser | Arg | Ala | Gly | Ile | Pro | Thr | Phe |      |
|     |     |     | 260 |     |     |     |     | 265 |     |     |     |     | 270 |     |     |      |
| ggg | cgt | agc | ttc | act | ctg | gct | tct | tct | gag | act | ggt | gtt | gga | gcg | cag | 864  |
| Gly | Arg | Ser | Phe | Thr | Leu | Ala | Ser | Ser | Glu | Thr | Gly | Val | Gly | Ala | Gln |      |
|     |     | 275 |     |     |     |     | 280 |     |     |     |     | 285 |     |     |     |      |
| tgg | gta | gga | tac | gac | gac | cag | gaa | agc | gtc | aaa | agc | aag | gtg | cag | tac | 912  |
| Trp | Val | Gly | Tyr | Asp | Asp | Gln | Glu | Ser | Val | Lys | Ser | Lys | Val | Gln | Tyr |      |
|     | 290 |     |     |     |     | 295 |     |     |     |     | 300 |     |     |     |     |      |
| gtc | gac | gcc | ggc | tgg | ctg | agc | gat | ggc | tct | gtg | caa | tat | ccg | att | gcg | 960  |
| Val | Asp | Ala | Gly | Trp | Leu | Ser | Asp | Gly | Ser | Val | Gln | Tyr | Pro | Ile | Ala |      |
| 305 |     |     |     |     | 310 |     |     |     |     | 315 |     |     |     |     | 320 |      |
| aat | gat | ggt | gct | cag | att | gca | aaa | gtg | ggc | cag | ata | ttt | gct | gcc | tgg | 1008 |
| Asn | Asp | Gly | Ala | Gln | Ile | Ala | Lys | Val | Gly | Gln | Ile | Phe | Ala | Ala | Trp |      |
|     |     |     |     | 325 |     |     |     |     | 330 |     |     |     |     | 335 |     |      |
| aaa | att | ctg | gga | tat | gac | cgc | tct | gat | ctc | gag | gct | cac | cgt | aag | ccg | 1056 |
| Lys | Ile | Leu | Gly | Tyr | Asp | Arg | Ser | Asp | Leu | Glu | Ala | His | Arg | Lys | Pro |      |
|     |     |     | 340 |     |     |     |     | 345 |     |     |     |     | 350 |     |     |      |
| ttg | gtc | ata | atc | gct | gaa | gat | gtt | gat | gga | gaa | gct | ctg | agc | aca | ctg | 1104 |
| Leu | Val | Ile | Ile | Ala | Glu | Asp | Val | Asp | Gly | Glu | Ala | Leu | Ser | Thr | Leu |      |
|     |     | 355 |     |     |     |     | 360 |     |     |     |     | 365 |     |     |     |      |
| gtc | ttg | aat | cgt | ctt | aag | gtt | ggt | ctt | cag | gtt | gtg | gca | gtc | aag | gct | 1152 |
| Val | Leu | Asn | Arg | Leu | Lys | Val | Gly | Leu | Gln | Val | Val | Ala | Val | Lys | Ala |      |
|     | 370 |     |     |     |     | 375 |     |     |     |     | 380 |     |     |     |     |      |
| cca | ggg | ttt | ggt | gac | aat | gcg | atg | gcc | aag | aca | att | gcg | tac | gac | gaa | 1200 |
| Pro | Gly | Phe | Gly | Asp | Asn | Ala | Met | Ala | Lys | Thr | Ile | Ala | Tyr | Asp | Glu |      |

```
                385                 390                 395                 400
gag gcc cgt cgc ggc ctc gga tcc ggt gtc atc aca gta aag gat gga    1248
Glu Ala Arg Arg Gly Leu Gly Ser Gly Val Ile Thr Val Lys Asp Gly
                405                 410                 415 aaa aca ctg aat gat gaa tta gaa att att gaa ggc atg aag ttt gat    1296
Lys Thr Leu Asn Asp Glu Leu Glu Ile Ile Glu Gly Met Lys Phe Asp
            420                 425                 430 cgt ggc tat att tct gcg tct caa aaa cgt gcg gca tac gat cag tat    1344
Arg Gly Tyr Ile Ser Ala Ser Gln Lys Arg Ala Ala Tyr Asp Gln Tyr
                435                 440                 445 ggt cat gct gcg ttt gag tga tca tag aag ctt                        1377
Gly His Ala Ala Phe Glu     Ser     Lys Leu
            450                 455

<210> SEQ ID NO 128
<211> LENGTH: 454
<212> TYPE: PRT
<213> ORGANISM: Artificial Sequence
<220> FEATURE:
<223> OTHER INFORMATION: Synthetic

<400> SEQUENCE: 128

Glu Phe Ala Ser Gly Ala Arg Gly Phe Pro Gly Thr Pro Gly Leu Pro
1               5                   10                  15

Gly Val Lys Gly His Arg Gly Tyr Pro Gly Leu Asp Gly Ala Gly Gln
            20                  25                  30

Thr Gly Lys Pro Gly Ile Ala Gly Phe Lys Gly Glu Gln Gly Pro Lys
        35                  40                  45

Gly Glu Pro Gly Pro Ala Gly Glu Glu Gly Lys Arg Gly Ala Arg Gly
    50                  55                  60

Glu Pro Gly Gly Val Gly Pro Ile Arg Ser Gly Pro Pro Gly Pro Ala
65                  70                  75                  80

Gly Pro Ala Gly Glu Arg Gly Glu Gln Ala Val Gly Pro Pro Gly Pro
                85                  90                  95

Ala Gly Ser Ala Gly Ala Arg Gly Ala Pro Gly Ala Pro Gly Glu Arg
            100                 105                 110

Gly Leu Lys Gly His Arg Gly Phe Thr Gly Leu Gln Gly Leu Pro Gly
        115                 120                 125

Gly Ser Ala Thr Glu Gly Arg Val Arg Val Asn Ser Ala Tyr Gln Asp
    130                 135                 140

Lys Ala Ser Gly Glu Val Leu Glu Thr Ala Pro Gly Val Glu Asp
145                 150                 155                 160

Ile Ser Gly Leu Pro Ser Gly Glu Val Leu Glu Thr Ala Pro Gly
                165                 170                 175

Val Glu Asp Ile Ser Gly Leu Pro Ser Gly Ala Gly Trp Leu Ala Asp
            180                 185                 190

Gln Thr Val Arg Tyr Pro Ile Ser Ala Gly Trp Leu Ala Asp Arg Ser
        195                 200                 205

Val Arg Tyr Pro Ile Ser Ser Arg Ala Gly Trp Leu Ala Asp Gly Ser
    210                 215                 220

Leu Arg Tyr Pro Ile Ala Ser Gly Ala Tyr Tyr Gly Ser Gly Thr Pro
225                 230                 235                 240

Ser Ser Phe Pro Thr Val Ser Ser Asn Phe Gly Ser Gln Arg Phe
                245                 250                 255

Ser Lys Ile Ala Ser Asn Thr Gln Ser Arg Ala Gly Ile Pro Thr Phe
            260                 265                 270

Gly Arg Ser Phe Thr Leu Ala Ser Ser Glu Thr Gly Val Gly Ala Gln
```

```
                       275                 280                 285
Trp Val Gly Tyr Asp Asp Gln Glu Ser Val Lys Ser Lys Val Gln Tyr
    290                 295                 300
Val Asp Ala Gly Trp Leu Ser Asp Gly Ser Val Gln Tyr Pro Ile Ala
305                 310                 315                 320
Asn Asp Gly Ala Gln Ile Ala Lys Val Gly Gln Ile Phe Ala Ala Trp
                325                 330                 335
Lys Ile Leu Gly Tyr Asp Arg Ser Asp Leu Glu Ala His Arg Lys Pro
            340                 345                 350
Leu Val Ile Ile Ala Glu Asp Val Asp Gly Glu Ala Leu Ser Thr Leu
        355                 360                 365
Val Leu Asn Arg Leu Lys Val Gly Leu Gln Val Val Ala Val Lys Ala
    370                 375                 380
Pro Gly Phe Gly Asp Asn Ala Met Ala Lys Thr Ile Ala Tyr Asp Glu
385                 390                 395                 400
Glu Ala Arg Arg Gly Leu Gly Ser Gly Val Ile Thr Val Lys Asp Gly
                405                 410                 415
Lys Thr Leu Asn Asp Glu Leu Glu Ile Ile Glu Gly Met Lys Phe Asp
            420                 425                 430
Arg Gly Tyr Ile Ser Ala Ser Gln Lys Arg Ala Ala Tyr Asp Gln Tyr
        435                 440                 445
Gly His Ala Ala Phe Glu
    450

<210> SEQ ID NO 129
<211> LENGTH: 660
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(660)

<400> SEQUENCE: 129 gaa ttc gct agc ggt gct cgt ggt ttc cca gga acc cca ggt ctt ccg      48
Glu Phe Ala Ser Gly Ala Arg Gly Phe Pro Gly Thr Pro Gly Leu Pro
1               5                   10                  15 ggt gtc aaa ggt cac cgt ggt tat ccg ggc ctg gac ggt gct ggt cag      96
Gly Val Lys Gly His Arg Gly Tyr Pro Gly Leu Asp Gly Ala Gly Gln
            20                  25                  30 acg ggt aaa cca ggt att gct ggc ttc aaa ggt gaa caa ggc ccg aag     144
Thr Gly Lys Pro Gly Ile Ala Gly Phe Lys Gly Glu Gln Gly Pro Lys
        35                  40                  45 gga gaa ccg ggc cca gca ggt gaa gaa ggc aag cgt ggt gcc cgt gga     192
Gly Glu Pro Gly Pro Ala Gly Glu Glu Gly Lys Arg Gly Ala Arg Gly
    50                  55                  60 gag ccg ggt ggc gtt ggg ccg atc aga tcc gcc act gaa ggg cgc gtg     240
Glu Pro Gly Gly Val Gly Pro Ile Arg Ser Ala Thr Glu Gly Arg Val
65                  70                  75                  80 cgt gtc aac agc gcc tat cag gac aag gcg tct gga gaa gtt ctg gag     288
Arg Val Asn Ser Ala Tyr Gln Asp Lys Ala Ser Gly Glu Val Leu Glu
                85                  90                  95 acc act gcc cca gga gta gag gac atc agc ggg ctt ccg tct gga gaa     336
Thr Thr Ala Pro Gly Val Glu Asp Ile Ser Gly Leu Pro Ser Gly Glu
            100                 105                 110 gtt ctg gag acc gct gcc cca gga gta gag gac atc agc ggg ctt ccg     384
Val Leu Glu Thr Ala Ala Pro Gly Val Glu Asp Ile Ser Gly Leu Pro
        115                 120                 125
```

```
tct gga gcc ggc tgg ctg gct gac cag act gtc cgt tac ccg atc agc    432
Ser Gly Ala Gly Trp Leu Ala Asp Gln Thr Val Arg Tyr Pro Ile Ser
    130                 135                 140 gcc ggc tgg ctg gcc gac cgc agc gtg cgc tac ccg atc tct tct agt    480
Ala Gly Trp Leu Ala Asp Arg Ser Val Arg Tyr Pro Ile Ser Ser Ser
145                 150                 155                 160 aac ttt ggg tct caa cgc ttt tct aag ata gcc tcc aac acc cag agc    528
Asn Phe Gly Ser Gln Arg Phe Ser Lys Ile Ala Ser Asn Thr Gln Ser
                165                 170                 175 cgc gcg ggc atc ccg acc ttc ggg cgt agc ttc act ctg gct tct tct    576
Arg Ala Gly Ile Pro Thr Phe Gly Arg Ser Phe Thr Leu Ala Ser Ser
            180                 185                 190 gag act ggt gtt gga gcg cag tgg gta gga tac gac gac cag gaa agc    624
Glu Thr Gly Val Gly Ala Gln Trp Val Gly Tyr Asp Asp Gln Glu Ser
        195                 200                 205 gtc aaa agc aag gtg cag tac gtc gag tag aag ctt                    660
Val Lys Ser Lys Val Gln Tyr Val Glu     Lys Leu
    210                 215
```

<210> SEQ ID NO 130
<211> LENGTH: 217
<212> TYPE: PRT
<213> ORGANISM: Artificial Sequence
<220> FEATURE:
<223> OTHER INFORMATION: Synthetic

<400> SEQUENCE: 130

```
Glu Phe Ala Ser Gly Ala Arg Gly Phe Pro Gly Thr Pro Gly Leu Pro
1               5                   10                  15

Gly Val Lys Gly His Arg Gly Tyr Pro Gly Leu Asp Gly Ala Gly Gln
            20                  25                  30

Thr Gly Lys Pro Gly Ile Ala Gly Phe Lys Gly Glu Gln Gly Pro Lys
        35                  40                  45

Gly Glu Pro Gly Pro Ala Gly Glu Gly Lys Arg Gly Ala Arg Gly
    50                  55                  60

Glu Pro Gly Gly Val Gly Pro Ile Arg Ser Ala Thr Glu Gly Arg Val
65                  70                  75                  80

Arg Val Asn Ser Ala Tyr Gln Asp Lys Ala Ser Gly Glu Val Leu Glu
                85                  90                  95

Thr Thr Ala Pro Gly Val Glu Asp Ile Ser Gly Leu Pro Ser Gly Glu
            100                 105                 110

Val Leu Glu Thr Ala Ala Pro Gly Val Glu Asp Ile Ser Gly Leu Pro
        115                 120                 125

Ser Gly Ala Gly Trp Leu Ala Asp Gln Thr Val Arg Tyr Pro Ile Ser
    130                 135                 140

Ala Gly Trp Leu Ala Asp Arg Ser Val Arg Tyr Pro Ile Ser Ser Ser
145                 150                 155                 160

Asn Phe Gly Ser Gln Arg Phe Ser Lys Ile Ala Ser Asn Thr Gln Ser
                165                 170                 175

Arg Ala Gly Ile Pro Thr Phe Gly Arg Ser Phe Thr Leu Ala Ser Ser
            180                 185                 190

Glu Thr Gly Val Gly Ala Gln Trp Val Gly Tyr Asp Asp Gln Glu Ser
        195                 200                 205

Val Lys Ser Lys Val Gln Tyr Val Glu
    210                 215
```

<210> SEQ ID NO 131
<211> LENGTH: 843
<212> TYPE: DNA

<213> ORGANISM: Artificial Sequence
<220> FEATURE:
<223> OTHER INFORMATION: Synthetic
<220> FEATURE:
<221> NAME/KEY: CDS
<222> LOCATION: (1)..(843)

<400> SEQUENCE: 131

```
gaa ttc gct agc ggt gct cgt ggt ttc cca gga acc cca ggt ctt ccg        48
Glu Phe Ala Ser Gly Ala Arg Gly Phe Pro Gly Thr Pro Gly Leu Pro
1               5                   10                  15 ggt gtc aaa ggt cac cgt ggt tat ccg ggc ctg gac ggt gct ggt cag        96
Gly Val Lys Gly His Arg Gly Tyr Pro Gly Leu Asp Gly Ala Gly Gln
            20                  25                  30 acg ggt aaa cca ggt att gct ggc ttc aaa ggt gaa caa ggc ccg aag       144
Thr Gly Lys Pro Gly Ile Ala Gly Phe Lys Gly Glu Gln Gly Pro Lys
        35                  40                  45 gga gaa ccg ggc cca gca ggt gaa gaa ggc aag cgt ggt gcc cgt gga       192
Gly Glu Pro Gly Pro Ala Gly Glu Glu Gly Lys Arg Gly Ala Arg Gly
    50                  55                  60 gag ccg ggt ggc gtt ggg ccg atc aga tcc gcc act gaa ggg cgc gtg       240
Glu Pro Gly Gly Val Gly Pro Ile Arg Ser Ala Thr Glu Gly Arg Val
65                  70                  75                  80 cgt gtc aac agc gcc tat cag gac aag gcg tct gga gaa gtt ctg gag       288
Arg Val Asn Ser Ala Tyr Gln Asp Lys Ala Ser Gly Glu Val Leu Glu
                85                  90                  95 acc act gcc cca gga gta gag gac atc agc ggg ctt ccg tct gga gaa       336
Thr Thr Ala Pro Gly Val Glu Asp Ile Ser Gly Leu Pro Ser Gly Glu
            100                 105                 110 gtt ctg gag acc gct gcc cca gga gta gag gac atc agc ggg ctt ccg       384
Val Leu Glu Thr Ala Ala Pro Gly Val Glu Asp Ile Ser Gly Leu Pro
        115                 120                 125 tct gga gcc ggc tgg ctg gct gac cag act gtc cgt tac ccg atc agc       432
Ser Gly Ala Gly Trp Leu Ala Asp Gln Thr Val Arg Tyr Pro Ile Ser
    130                 135                 140 gcc ggc tgg ctg gcc gac cgc agc gtg cgc tac ccg atc tct tct agt       480
Ala Gly Trp Leu Ala Asp Arg Ser Val Arg Tyr Pro Ile Ser Ser Ser
145                 150                 155                 160 aac ttt ggg tct caa cgc ttt tct aag ata gcc tcc aac acc cag agc       528
Asn Phe Gly Ser Gln Arg Phe Ser Lys Ile Ala Ser Asn Thr Gln Ser
                165                 170                 175 cgc gcg ggc atc ccg acc ttc ggg cgt agc ttc act ctg gct tct tct       576
Arg Ala Gly Ile Pro Thr Phe Gly Arg Ser Phe Thr Leu Ala Ser Ser
            180                 185                 190 gag act ggt gtt gga gcg cag tgg gta gga tac gac gac cag gaa agc       624
Glu Thr Gly Val Gly Ala Gln Trp Val Gly Tyr Asp Asp Gln Glu Ser
        195                 200                 205 gtc aaa agc aag gtg cag tac gtc gag gct cac cgt aag ccg ttg gtc       672
Val Lys Ser Lys Val Gln Tyr Val Glu Ala His Arg Lys Pro Leu Val
    210                 215                 220 ata atc gct gaa gat gtt gat gga gaa gct ctg agc aca ctg gtc ttg       720
Ile Ile Ala Glu Asp Val Asp Gly Glu Ala Leu Ser Thr Leu Val Leu
225                 230                 235                 240 aat cgt ctt aag gtt ggt ctt cag gtt gtg gca gtc aag gct cca ggg       768
Asn Arg Leu Lys Val Gly Leu Gln Val Val Ala Val Lys Ala Pro Gly
                245                 250                 255 ttt ggt gac aat gcg atg gcc aag aca att gcg tac gac gaa gag gcc       816
Phe Gly Asp Asn Ala Met Ala Lys Thr Ile Ala Tyr Asp Glu Glu Ala
            260                 265                 270 cgt cgc ggc ctc gga tca tag aag ctt                                   843
Arg Arg Gly Leu Gly Ser     Lys Leu
        275                 280
```

<210> SEQ ID NO 132
<211> LENGTH: 278
<212> TYPE: PRT
<213> ORGANISM: Artificial Sequence
<220> FEATURE:
<223> OTHER INFORMATION: Synthetic

<400> SEQUENCE: 132

Glu Phe Ala Ser Gly Ala Arg Gly Phe Pro Gly Thr Pro Gly Leu Pro
1               5                   10                  15

Gly Val Lys Gly His Arg Gly Tyr Pro Gly Leu Asp Gly Ala Gly Gln
            20                  25                  30

Thr Gly Lys Pro Gly Ile Ala Gly Phe Lys Gly Glu Gln Gly Pro Lys
        35                  40                  45

Gly Glu Pro Gly Pro Ala Gly Glu Glu Gly Lys Arg Gly Ala Arg Gly
    50                  55                  60

Glu Pro Gly Gly Val Gly Pro Ile Arg Ser Ala Thr Glu Gly Arg Val
65                  70                  75                  80

Arg Val Asn Ser Ala Tyr Gln Asp Lys Ala Ser Gly Glu Val Leu Glu
                85                  90                  95

Thr Thr Ala Pro Gly Val Glu Asp Ile Ser Gly Leu Pro Ser Gly Glu
            100                 105                 110

Val Leu Glu Thr Ala Ala Pro Gly Val Glu Asp Ile Ser Gly Leu Pro
        115                 120                 125

Ser Gly Ala Gly Trp Leu Ala Asp Gln Thr Val Arg Tyr Pro Ile Ser
    130                 135                 140

Ala Gly Trp Leu Ala Asp Arg Ser Val Arg Tyr Pro Ile Ser Ser
145                 150                 155                 160

Asn Phe Gly Ser Gln Arg Phe Ser Lys Ile Ala Ser Asn Thr Gln Ser
                165                 170                 175

Arg Ala Gly Ile Pro Thr Phe Gly Arg Ser Phe Thr Leu Ala Ser Ser
            180                 185                 190

Glu Thr Gly Val Gly Ala Gln Trp Val Gly Tyr Asp Asp Gln Glu Ser
        195                 200                 205

Val Lys Ser Lys Val Gln Tyr Val Glu Ala His Arg Lys Pro Leu Val
    210                 215                 220

Ile Ile Ala Glu Asp Val Asp Gly Glu Ala Leu Ser Thr Leu Val Leu
225                 230                 235                 240

Asn Arg Leu Lys Val Gly Leu Gln Val Val Ala Val Lys Ala Pro Gly
                245                 250                 255

Phe Gly Asp Asn Ala Met Ala Lys Thr Ile Ala Tyr Asp Glu Glu Ala
            260                 265                 270

Arg Arg Gly Leu Gly Ser
        275

<210> SEQ ID NO 133
<211> LENGTH: 570
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(558)

<400> SEQUENCE: 133 atg gct agc gat acc tgg agc ggc gtg gca cat gga agc acc cgt aaa      48
Met Ala Ser Asp Thr Trp Ser Gly Val Ala His Gly Ser Thr Arg Lys

| | | | | | | | | | | | | | | | | |
|---|---|---|---|---|---|---|---|---|---|---|---|---|---|---|---|---|
| 1 | | | | 5 | | | | | 10 | | | | | 15 | | |

```
ctg ggg ctc aag atc agc ggc ttc ttg caa cgt acc aac agc ctg gaa      96
Leu Gly Leu Lys Ile Ser Gly Phe Leu Gln Arg Thr Asn Ser Leu Glu
             20                  25                  30 gag aag gcg gtg gac ata ctc ctc aac tat gtc cgc aag aca ttt gat     144
Glu Lys Ala Val Asp Ile Leu Leu Asn Tyr Val Arg Lys Thr Phe Asp
         35                  40                  45 aga tct gcg acc tat gaa att gct cca gta ttt gtg ctt ttg gaa tat     192
Arg Ser Ala Thr Tyr Glu Ile Ala Pro Val Phe Val Leu Leu Glu Tyr
     50                  55                  60 gtc aca ctg aag aaa atg cgt gaa atc att ggc tgg cca ggg ggc tct     240
Val Thr Leu Lys Lys Met Arg Glu Ile Ile Gly Trp Pro Gly Gly Ser
 65                  70                  75                  80 ggc gat gcg aac atg tat gcc atg atg atc gca cgc ttt aag atg ttc     288
Gly Asp Ala Asn Met Tyr Ala Met Met Ile Ala Arg Phe Lys Met Phe
                 85                  90                  95 cca gaa gtc aag gag aaa gga atg gct gct ctt ccg cgt ctc att gcc     336
Pro Glu Val Lys Glu Lys Gly Met Ala Ala Leu Pro Arg Leu Ile Ala
             100                 105                 110 ttc acg tct gaa cat agt cat gcg aat gtc agc ttc tgg tac att ccg     384
Phe Thr Ser Glu His Ser His Ala Asn Val Ser Phe Trp Tyr Ile Pro
         115                 120                 125 ccg agc ttg cgt act ctg gaa gac aat gaa gag cgc atg agt cgc ctc     432
Pro Ser Leu Arg Thr Leu Glu Asp Asn Glu Glu Arg Met Ser Arg Leu
     130                 135                 140 tcg aag gtg gct cca gtg att aaa gcc cgt atg atg gag tat gga acc     480
Ser Lys Val Ala Pro Val Ile Lys Ala Arg Met Met Glu Tyr Gly Thr
145                 150                 155                 160 aca atg gtc gcg aag gtc aat ttc ttc cgc atg gtc atc tca aac cca     528
Thr Met Val Ala Lys Val Asn Phe Phe Arg Met Val Ile Ser Asn Pro
                 165                 170                 175 gcg gca act cac caa gac att gac cct agg tagggatccg cg              570
Ala Ala Thr His Gln Asp Ile Asp Pro Arg
             180                 185
```

<210> SEQ ID NO 134
<211> LENGTH: 186
<212> TYPE: PRT
<213> ORGANISM: Artificial Sequence
<220> FEATURE:
<223> OTHER INFORMATION: Synthetic

<400> SEQUENCE: 134

```
Met Ala Ser Asp Thr Trp Ser Gly Val Ala His Gly Ser Thr Arg Lys
 1               5                  10                  15

Leu Gly Leu Lys Ile Ser Gly Phe Leu Gln Arg Thr Asn Ser Leu Glu
             20                  25                  30

Glu Lys Ala Val Asp Ile Leu Leu Asn Tyr Val Arg Lys Thr Phe Asp
         35                  40                  45

Arg Ser Ala Thr Tyr Glu Ile Ala Pro Val Phe Val Leu Leu Glu Tyr
     50                  55                  60

Val Thr Leu Lys Lys Met Arg Glu Ile Ile Gly Trp Pro Gly Gly Ser
 65                  70                  75                  80

Gly Asp Ala Asn Met Tyr Ala Met Met Ile Ala Arg Phe Lys Met Phe
                 85                  90                  95

Pro Glu Val Lys Glu Lys Gly Met Ala Ala Leu Pro Arg Leu Ile Ala
             100                 105                 110

Phe Thr Ser Glu His Ser His Ala Asn Val Ser Phe Trp Tyr Ile Pro
         115                 120                 125
```

-continued

```
Pro Ser Leu Arg Thr Leu Glu Asp Asn Glu Glu Arg Met Ser Arg Leu
        130                 135                 140

Ser Lys Val Ala Pro Val Ile Lys Ala Arg Met Met Glu Tyr Gly Thr
145                 150                 155                 160

Thr Met Val Ala Lys Val Asn Phe Phe Arg Met Val Ile Ser Asn Pro
                165                 170                 175

Ala Ala Thr His Gln Asp Ile Asp Pro Arg
            180                 185

<210> SEQ ID NO 135
<211> LENGTH: 25
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Fig. 2 - MOG 1-25

<400> SEQUENCE: 135

Gly Gln Phe Arg Val Ile Gly Pro Arg His Pro Ile Arg Ala Leu Val
1               5                   10                  15

Gly Asp Glu Val Glu Leu Pro Cys Arg
            20                  25

<210> SEQ ID NO 136
<211> LENGTH: 27
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Fig. 2 - MOG 32-58

<400> SEQUENCE: 136

Ala Thr Gly Met Glu Val Gly Trp Tyr Arg Pro Pro Phe Ser Arg Val
1               5                   10                  15

Val His Leu Tyr Arg Asn Gly Lys Asp Gln Asp
            20                  25

<210> SEQ ID NO 137
<211> LENGTH: 35
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Fig. 2 - MOG 63-97

<400> SEQUENCE: 137

Pro Glu Tyr Arg Gly Arg Thr Glu Leu Leu Lys Asp Ala Ile Gly Glu
1               5                   10                  15

Gly Lys Val Thr Leu Arg Ile Arg Asn Val Arg Phe Ser Asp Glu Gly
            20                  25                  30

Gly Phe Thr
        35

<210> SEQ ID NO 138
<211> LENGTH: 44
<212> TYPE: PRT
<213> ORGANISM: Artificial Sequence
<220> FEATURE:
<223> OTHER INFORMATION: Synthetic
<220> FEATURE:
```

```
<221> NAME/KEY: misc_feature
<223> OTHER INFORMATION: Fig. 5 - MBP 7-50

<400> SEQUENCE: 138

Ser Gln Arg His Gly Ser Lys Tyr Leu Ala Thr Ala Ser Thr Met Asp
1               5                   10                  15

His Ala Arg His Gly Phe Leu Pro Arg His Arg Asp Thr Gly Ile Leu
            20                  25                  30

Asp Ser Ile Gly Arg Phe Phe Gly Gly Asp Arg Gly
            35                  40

<210> SEQ ID NO 139
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Fig. 5 - MBP 83-106

<400> SEQUENCE: 139

Glu Asn Pro Val Val His Phe Phe Lys Asn Ile Val Thr Pro Arg Thr
1               5                   10                  15

Pro Pro Pro Ser Gln Gly Lys Gly
            20

<210> SEQ ID NO 140
<211> LENGTH: 27
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Fig. 5 - MBP 142-168

<400> SEQUENCE: 140

Lys Gly Val Asp Ala Gln Gly Thr Leu Ser Lys Ile Phe Lys Leu Gly
1               5                   10                  15

Gly Arg Asp Ser Arg Ser Gly Ser Pro Met Leu
            20                  25

<210> SEQ ID NO 141
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Fig. 7 - PLP 30-60

<400> SEQUENCE: 141

Leu Phe Cys Gly Cys Gly His Glu Ala Leu Thr Gly Thr Glu Lys Leu
1               5                   10                  15

Ile Glu Thr Tyr Phe Ser Lys Asn Tyr Gln Asp Tyr Glu Tyr Leu
            20                  25                  30

<210> SEQ ID NO 142
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: misc_feature
```

-continued

<223> OTHER INFORMATION: Fig. 7 - PLP 84-116

<400> SEQUENCE: 142

Leu Leu Leu Ala Glu Gly Phe Tyr Thr Thr Gly Ala Val Arg Gln Ile
1               5                   10                  15
Phe Gly Asp Tyr Lys Thr Thr Ile Cys Gly Lys Gly Leu Ser Ala Thr
            20                  25                  30
Val

<210> SEQ ID NO 143
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Fig. 7 - PLP 139-155

<400> SEQUENCE: 143

His Cys Leu Gly Lys Trp Leu Gly His Pro Asp Lys Phe Val Gly Ile
1               5                   10                  15
Thr

<210> SEQ ID NO 144
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Fig. 9 - MOBP 1-23

<400> SEQUENCE: 144

Ser Gln Lys Pro Ala Lys Glu Gly Pro Arg Leu Ser Lys Asn Gln Lys
1               5                   10                  15
Tyr Ser Glu His Phe Ser Ile
            20

<210> SEQ ID NO 145
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Fig. 9 - MOBP 30-49

<400> SEQUENCE: 145

Thr Phe Leu Asn Ser Lys Lys Glu Ile Val Asp Arg Lys Tyr Ser Ile
1               5                   10                  15
Ser Lys Ser Gly
            20

<210> SEQ ID NO 146
<211> LENGTH: 26
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Fig. 9 - MOBP 65-90

<400> SEQUENCE: 146

Gln Lys Thr Arg Thr Ser Arg Arg Ala Lys Ser Pro Gln Arg Pro Lys
1               5                   10                  15

Gln Gln Pro Ala Ala Pro Pro Ala Val Val
            20                  25

<210> SEQ ID NO 147
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Fig. 20 - MOG/MS 34-56

<400> SEQUENCE: 147

Gly Met Glu Val Gly Trp Tyr Arg Pro Pro Phe Ser Arg Val Val His
1               5                   10                  15

Leu Tyr Arg Asn Gly Lys Asp
            20

<210> SEQ ID NO 148
<211> LENGTH: 48
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Fig. 20 - MOG/MS 67-114

<400> SEQUENCE: 148

Gly Arg Thr Glu Leu Leu Lys Asp Ala Ile Gly Glu Gly Lys Val Thr
1               5                   10                  15

Leu Arg Ile Arg Asn Val Arg Phe Ser Asp Glu Gly Gly Phe Thr Ser
            20                  25                  30

Phe Phe Arg Asp His Ser Tyr Gln Glu Glu Ala Ala Met Glu Leu Lys
        35                  40                  45

<210> SEQ ID NO 149
<211> LENGTH: 25
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Fig. 20 - MOG/MS 3-27

<400> SEQUENCE: 149

Phe Arg Val Ile Gly Pro Arg His Pro Ile Arg Ala Leu Val Gly Asp
1               5                   10                  15

Glu Val Glu Leu Pro Ser Arg Ile Ser
            20                  25

<210> SEQ ID NO 150
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Fig. 20 - MOG/MS 205-215

<400> SEQUENCE: 150

Arg Leu Ala Gly Gln Phe Leu Glu Glu Leu Arg
1               5                   10

<210> SEQ ID NO 151
<211> LENGTH: 28
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Fig. 22 - MBP/MS 84-111

<400> SEQUENCE: 151

Asn Pro Val Val His Phe Phe Lys Asn Ile Val Thr Pro Arg Thr Pro
1               5                   10                  15

Pro Pro Ser Gln Gly Lys Gly Arg Gly Leu Ser Leu
            20                  25

<210> SEQ ID NO 152
<211> LENGTH: 28
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Fig. 22 - MBP/MS 141-168

<400> SEQUENCE: 152

Phe Lys Gly Val Asp Ala Gln Gly Thr Leu Ser Lys Ile Phe Lys Leu
1               5                   10                  15

Gly Gly Arg Asp Ser Arg Ser Gly Ser Pro Met Ala
            20                  25

<210> SEQ ID NO 153
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Fig. 22 - MBP/MS 12-42

<400> SEQUENCE: 153

Ser Lys Tyr Leu Ala Thr Ala Ser Thr Met Asp His Ala Arg His Gly
1               5                   10                  15

Phe Leu Pro Arg His Arg Asp Thr Gly Ile Leu Asp Ser Ile Gly
            20                  25                  30

<210> SEQ ID NO 154
<211> LENGTH: 48
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Fig. 24 - PLP/MS 103-150

<400> SEQUENCE: 154

Tyr Lys Thr Thr Ile Ser Gly Lys Gly Leu Ser Ala Thr Val Thr Gly
1               5                   10                  15

Gly Gln Lys Gly Arg Gly Ser Arg Gly Gln His Gln Ala His Ser Leu
            20                  25                  30

Glu Arg Val Ser His Ser Leu Gly Lys Trp Leu Gly His Pro Asp Lys

-continued

```
<210> SEQ ID NO 155
<211> LENGTH: 27
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Fig. 24 - PLP/MS 177-203

<400> SEQUENCE: 155

Phe Asn Thr Trp Thr Thr Ser Gln Ser Ile Ala Phe Pro Ser Lys Thr
1               5                   10                  15

Ser Ala Ser Ile Gly Ser Leu Ser Ala Asp Ala
            20                  25

<210> SEQ ID NO 156
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Fig. 24 - PLP/MS 218-240

<400> SEQUENCE: 156

Val Ser Gly Ser Asn Leu Leu Ser Ile Ser Lys Thr Ala Glu Phe Gln
1               5                   10                  15

Met Thr Phe His Leu Phe Ile
            20

<210> SEQ ID NO 157
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Fig. 24 - PLP/MS 38-52

<400> SEQUENCE: 157

Ala Leu Thr Gly Thr Glu Lys Leu Ile Glu Thr Tyr Phe Ser Lys
1               5                   10                  15

<210> SEQ ID NO 158
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Fig. 24 - PLP/MS 264-276

<400> SEQUENCE: 158

Phe Ala Val Leu Lys Leu Met Gly Arg Gly Thr Lys Phe
1               5                   10

<210> SEQ ID NO 159
<211> LENGTH: 19
<212> TYPE: PRT
<213> ORGANISM: Artificial Sequence
<220> FEATURE:
<223> OTHER INFORMATION: Synthetic
<220> FEATURE:
```

```
<221> NAME/KEY: misc_feature
<223> OTHER INFORMATION: Fig. 26 - MOBP/MS 15-33

<400> SEQUENCE: 159

Gln Lys Tyr Ser Glu His Phe Ser Ile His Ser Ser Pro Pro Phe Thr
1               5                   10                  15

Phe Leu Asn

<210> SEQ ID NO 160
<211> LENGTH: 36
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Fig. 26 - MOBP/MS 55-90

<400> SEQUENCE: 160

Lys Glu Glu Asp Trp Ile Ser Ser Ala Ser Gln Lys Thr Arg Thr Ser
1               5                   10                  15

Arg Arg Ala Lys Ser Pro Gln Arg Pro Lys Gln Gln Pro Ala Ala Pro
                20                  25                  30

Pro Ala Val Val
        35

<210> SEQ ID NO 161
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Fig. 26 - MOBP/MS 156-172

<400> SEQUENCE: 161

Lys Gln Gln Pro Arg Ser Ser Pro Leu Arg Gly Pro Gly Ala Ser Arg
1               5                   10                  15

Gly

<210> SEQ ID NO 162
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Fig. 28 - OSP/MS 42-73

<400> SEQUENCE: 162

Lys Leu Asp Glu Leu Gly Ser Lys Gly Leu Trp Ala Asp Ser Val Met
1               5                   10                  15

Ala Thr Gly Leu Tyr His Ser Lys Pro Leu Val Asp Ile Leu Ile Leu
                20                  25                  30

<210> SEQ ID NO 163
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Fig. 28 - OSP/MS 98-109
```

```
<400> SEQUENCE: 163

Leu Leu Thr Val Leu Pro Ser Ile Arg Met Gly Gln
1               5                   10

<210> SEQ ID NO 164
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Fig. 28 - OSP/MS 183-203

<400> SEQUENCE: 164

Gln Ala Phe Gly Glu Asn Val Ser Thr Thr Leu Arg Ala Leu Ala Pro
1               5                   10                  15

Arg Leu Met Arg Arg
            20

<210> SEQ ID NO 165
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Fig. 28 - OSP/MS 21-34

<400> SEQUENCE: 165

Val Ile Val Thr Thr Ser Thr Asn Asp Trp Val Val Thr Ser
1               5                   10

<210> SEQ ID NO 166
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Fig. 28 - OSP/MS 130-146

<400> SEQUENCE: 166

Leu Ala Leu Ser Ala Leu Val Ala Thr Ile Trp Phe Pro Val Ser Ala
1               5                   10                  15

His

<210> SEQ ID NO 167
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Fig. 34 - Preproinsulin 5-24

<400> SEQUENCE: 167

Met Arg Leu Leu Pro Leu Leu Ala Leu Leu Ala Leu Trp Gly Pro Asp
1               5                   10                  15

Pro Ala Ala

<210> SEQ ID NO 168
<211> LENGTH: 27
<212> TYPE: PRT
```

```
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Fig. 34 - Preproinsulin 33-59

<400> SEQUENCE: 168

Ser His Leu Val Glu Ala Leu Tyr Leu Val Ser Gly Glu Arg Gly Phe
1               5                   10                  15

Phe Tyr Thr Pro Lys Thr Arg Ile Glu Ala Glu
            20                  25

<210> SEQ ID NO 169
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Fig. 34 - Preproinsulin 73-88

<400> SEQUENCE: 169

Gly Ala Gly Ser Leu Gln Pro Leu Ala Leu Glu Gly Ser Leu Gln Lys
1               5                   10                  15

<210> SEQ ID NO 170
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Fig. 34 - Gad67 30-60

<400> SEQUENCE: 170

Asp Thr Trp Ser Gly Val Ala His Gly Ser Thr Arg Lys Leu Gly Leu
1               5                   10                  15

Lys Ile Ser Gly Phe Leu Gln Arg Thr Asn Ser Leu Glu Glu Lys
            20                  25                  30

<210> SEQ ID NO 171
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Fig. 34 - Gad67 121-135

<400> SEQUENCE: 171

Val Asp Ile Leu Leu Asn Gln Val Arg Lys Thr Phe Asp Arg Ser
1               5                   10                  15

<210> SEQ ID NO 172
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Fig. 36 - Gad65 206-236

<400> SEQUENCE: 172

Thr Tyr Glu Ile Ala Pro Val Phe Val Leu Leu Glu Tyr Val Thr Leu
```

-continued

```
                1               5                  10                 15
Lys Lys Met Arg Glu Ile Ile Gly Trp Pro Gly Gly Ser Gly Asp
                20                 25                 30

<210> SEQ ID NO 173
<211> LENGTH: 36
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Fig. 36 - Gad65 247-282

<400> SEQUENCE: 173

Asn Met Tyr Ala Met Met Ile Ala Arg Phe Lys Met Phe Pro Glu Val
1               5                   10                  15

Lys Glu Lys Gly Met Ala Ala Leu Pro Arg Leu Ile Ala Phe Thr Ser
                20                  25                  30

Glu His Ser His
            35

<210> SEQ ID NO 174
<211> LENGTH: 43
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Fig. 36 - Gad65 503-545

<400> SEQUENCE: 174

Asn Val Ser Phe Trp Tyr Ile Pro Pro Ser Leu Arg Thr Leu Glu Asp
1               5                   10                  15

Asn Glu Glu Arg Met Ser Arg Leu Ser Lys Val Ala Pro Val Ile Lys
                20                  25                  30

Ala Arg Met Met Glu Tyr Gly Thr Thr Met Val
            35                  40

<210> SEQ ID NO 175
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Fig. 36 - Gad65 553-572

<400> SEQUENCE: 175

Lys Asn Val Phe Phe Arg Met Val Ile Ser Asn Pro Ala Ala Thr His
1               5                   10                  15

Gln Asp Ile Asp
            20

<210> SEQ ID NO 176
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Fig. 38 - ICA69 34-49

<400> SEQUENCE: 176
```

```
Lys Gln Ala Phe Ile Lys Ala Thr Gly Lys Lys Glu Asp Glu Ile Ile
1               5                  10                  15

Val

<210> SEQ ID NO 177
<211> LENGTH: 16
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Fig. 38 - ICA69 199-214

<400> SEQUENCE: 177

Arg Leu Ala Lys Lys Asn Phe Asp Lys Leu Lys Met Asp Val Ser Gln
1               5                  10                  15

<210> SEQ ID NO 178
<211> LENGTH: 15
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Fig. 38 - ICA69 348-362

<400> SEQUENCE: 178

Met Lys Ser Glu Glu Gly Ala Ser Leu Gly Pro Val Ala Gly Thr
1               5                  10                  15

<210> SEQ ID NO 179
<211> LENGTH: 31
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Fig. 38 - IA-2 789-819

<400> SEQUENCE: 179

His Thr Ile Ala Asp Phe Trp Gln Met Val Trp Glu Ser Gly Ser Thr
1               5                  10                  15

Val Ile Val Met Leu Thr Pro Leu Val Glu Asp Gly Val Lys Gln
                20                  25                  30

<210> SEQ ID NO 180
<211> LENGTH: 35
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Fig. 38 - IA-2 840-874

<400> SEQUENCE: 180

Val Ser Glu His Ile Trp Ser Glu Asp Phe Leu Val Arg Ser Phe Tyr
1               5                  10                  15

Leu Lys Asn Val Gln Thr Gln Glu Thr Arg Thr Leu Thr Gln Phe His
                20                  25                  30

Phe Leu Ser
        35
```

```
<210> SEQ ID NO 181
<211> LENGTH: 16
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Fig. 38 - Imogen 263-278

<400> SEQUENCE: 181

Ser Pro Ser Leu Trp Glu Ile Glu Phe Ala Lys Gln Leu Ala Ser Val
1               5                   10                  15

<210> SEQ ID NO 182
<211> LENGTH: 23
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Fig. 40 - Hsp60 438-460

<400> SEQUENCE: 182

Leu Gly Gly Gly Ser Ala Leu Leu Arg Ser Ile Pro Ala Leu Asp Ser
1               5                   10                  15

Leu Thr Pro Ala Asn Glu Asp
            20

<210> SEQ ID NO 183
<211> LENGTH: 16
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Fig. 40 - Hsp60 469-484

<400> SEQUENCE: 183

Lys Arg Thr Leu Lys Ile Pro Ala Met Thr Ile Ala Lys Asn Ala Gly
1               5                   10                  15

<210> SEQ ID NO 184
<211> LENGTH: 26
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Fig. 46 - Collagen 73-98

<400> SEQUENCE: 184

Gly Ala Arg Gly Phe Pro Gly Thr Pro Gly Leu Pro Gly Val Lys Gly
1               5                   10                  15

His Arg Gly Tyr Pro Gly Leu Asp Gly Ala
            20                  25

<210> SEQ ID NO 185
<211> LENGTH: 23
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Fig. 46 - Collagen 253-275
```

<400> SEQUENCE: 185

Gly Gln Thr Gly Lys Pro Gly Ile Ala Gly Phe Lys Gly Glu Gln Gly
1               5                   10                  15

Pro Lys Gly Glu Pro Gly Pro
            20

<210> SEQ ID NO 186
<211> LENGTH: 19
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Fig. 46 - Collagen 285-303

<400> SEQUENCE: 186

Ala Gly Glu Glu Gly Lys Arg Gly Ala Arg Gly Glu Pro Gly Gly Val
1               5                   10                  15

Gly Pro Ile

<210> SEQ ID NO 187
<211> LENGTH: 15
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Fig. 46 - Collagen 442-456

<400> SEQUENCE: 187

Gly Pro Pro Gly Pro Ala Gly Pro Ala Gly Glu Arg Gly Glu Gln
1               5                   10                  15

<210> SEQ ID NO 188
<211> LENGTH: 17
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Fig. 46 - Collagen 606-622

<400> SEQUENCE: 188

Val Gly Pro Pro Gly Pro Ala Gly Ser Ala Gly Ala Arg Gly Ala Pro
1               5                   10                  15

Gly

<210> SEQ ID NO 189
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Fig. 46 - Collagen 924-943

<400> SEQUENCE: 189

Pro Gly Glu Arg Gly Leu Lys Gly His Arg Gly Phe Thr Gly Leu Gln
1               5                   10                  15

Gly Leu Pro Gly
            20

```
<210> SEQ ID NO 190
<211> LENGTH: 16
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Fig. 48 - Aggrecan 89-103

<400> SEQUENCE: 190

Ala Thr Glu Gly Arg Val Arg Val Asn Ser Ala Tyr Gln Asp Lys Ala
1               5                   10                  15

<210> SEQ ID NO 191
<211> LENGTH: 40
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Fig. 48 - Aggrecan 1053-1092

<400> SEQUENCE: 191

Ser Gly Glu Val Leu Glu Thr Thr Ala Pro Gly Val Glu Asp Ile Ser
1               5                   10                  15

Gly Leu Pro Ser Gly Glu Val Leu Glu Thr Ala Ala Pro Gly Val Glu
            20                  25                  30

Asp Ile Ser Gly Leu Pro Ser Gly
        35                  40

<210> SEQ ID NO 192
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Fig. 48 - Aggrecan 201-213

<400> SEQUENCE: 192

Ala Gly Trp Leu Ala Asp Gln Thr Val Arg Tyr Pro Ile
1               5                   10

<210> SEQ ID NO 193
<211> LENGTH: 15
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Fig. 48 - Aggrecan 298-312

<400> SEQUENCE: 193

Ser Ala Gly Trp Leu Ala Asp Arg Ser Val Arg Tyr Pro Ile Ser
1               5                   10                  15

<210> SEQ ID NO 194
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Fig. 48 - Aggrecan 623-635
```

```
<400> SEQUENCE: 194

Ala Gly Trp Leu Ala Asp Gly Ser Leu Arg Tyr Pro Ile
1               5                   10

<210> SEQ ID NO 195
<211> LENGTH: 17
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Fig. 48 - Aggrecan 1804-1820

<400> SEQUENCE: 195

Ser Gly Ala Tyr Tyr Gly Ser Gly Thr Pro Ser Ser Phe Pro Thr Val
1               5                   10                  15

Ser

<210> SEQ ID NO 196
<211> LENGTH: 17
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Fig. 50 - HCgP-39 79-95

<400> SEQUENCE: 196

Asn Phe Gly Ser Gln Arg Phe Ser Lys Ile Ala Ser Asn Thr Gln Ser
1               5                   10                  15

Arg

<210> SEQ ID NO 197
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Fig. 50 - HCgP-39 236-254

<400> SEQUENCE: 197

Ala Gly Ile Pro Thr Phe Gly Arg Ser Phe Thr Leu Ala Ser Ser Glu
1               5                   10                  15

Thr Gly Val Gly
            20

<210> SEQ ID NO 198
<211> LENGTH: 17
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Fig. 50 - HCgP-39 303-319

<400> SEQUENCE: 198

Gln Trp Val Gly Tyr Asp Asp Gln Glu Ser Val Lys Ser Lys Val Gln
1               5                   10                  15

Tyr

<210> SEQ ID NO 199
```

```
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Fig. 50 - Link protein 207-219

<400> SEQUENCE: 199

Ala Gly Trp Leu Ser Asp Gly Ser Val Gln Tyr Pro Ile
1               5                   10

<210> SEQ ID NO 200
<211> LENGTH: 25
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Fig. 50 - Link protein 281-305

<400> SEQUENCE: 200

Asn Asp Gly Ala Gln Ile Ala Lys Val Gly Gln Ile Phe Ala Ala Trp
1               5                   10                  15

Lys Ile Leu Gly Tyr Asp Arg Ser Asp
            20                  25

<210> SEQ ID NO 201
<211> LENGTH: 43
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Fig. 52 - HSP60 266-308

<400> SEQUENCE: 201

Ala His Arg Lys Pro Leu Val Ile Ile Ala Glu Asp Val Asp Gly Glu
1               5                   10                  15

Ala Leu Ser Thr Leu Val Leu Asn Arg Leu Lys Val Gly Leu Gln Val
            20                  25                  30

Val Ala Val Lys Ala Pro Gly Phe Gly Asp Asn
        35                  40

<210> SEQ ID NO 202
<211> LENGTH: 15
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Fig. 52 - HSP65 1-15

<400> SEQUENCE: 202

Met Ala Lys Thr Ile Ala Tyr Asp Glu Glu Ala Arg Arg Gly Leu
1               5                   10                  15

<210> SEQ ID NO 203
<211> LENGTH: 29
<212> TYPE: PRT
<213> ORGANISM: Artificial Sequence
<220> FEATURE:
<223> OTHER INFORMATION: synthetic
<220> FEATURE:
<221> NAME/KEY: misc_feature
```

```
<223> OTHER INFORMATION: Fig. 52 - HSP60 197-225

<400> SEQUENCE: 203

Gly Val Ile Thr Val Lys Asp Gly Lys Thr Leu Asn Asp Glu Leu Glu
1               5                   10                  15

Ile Ile Glu Gly Met Lys Phe Asp Arg Gly Tyr Ile Ser
            20                  25

<210> SEQ ID NO 204
<211> LENGTH: 16
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Fig. 52 - EcoDNAJ 60-75

<400> SEQUENCE: 204

Ser Gln Lys Arg Ala Ala Tyr Asp Gln Tyr Gly His Ala Ala Phe Glu
1               5                   10                  15
```

The invention claimed is:

1. A synthetic human multitarget polypeptide comprising amino acid sequences of at least one immunogenic epitopic cluster (IEC) of at least four different autoantigens related to insulin-dependent diabetes mellitus (IDDM), said at least four autoantigens related to IDDM being selected from the group consisting of preproinsulin (PPI), 67kDa glutamic acid decarboxylase (Gad67), 65kDa glutamic acid decarboxylase (Gad65), islet cell antigen p69 (ICA69), tyrosine phosphatase islet antigen 2(IA-2), imogen and 60kDa human heat shock protein (Hsp60), wherein one or more cystein residue in a native IEC is optionally substituted by a serine residue, provided that any said Cys→Ser substituted IEC improves the solubility of the native IEC.

2. The synthetic human multitarget polypeptide according to claim 1, comprising: (i) at least two of the amino acid sequences 5-24(SEQ ID NO:167), 33-59 (SEQ ID NO:168), and 73-88 (SEQ ID NO:169) of PPI; (ii) at least the two amino acid sequences 30-60 (SEQ ID NO:170) and 121-135 (SEQ ID NO:171) of Gad67; (iii) at least two of the amino acid sequences 206-236 (SEQ ID NO:172), 247-282(SEQ ID NO:173), 503-545 (SEQ ID NO:174), and 553-572 (SEQ ID NO:175) of Gad65; (iv) at least two of the amino acid sequences 34-49 (SEQ ID NO:176), 199-214 (SEQ ID NO.:177) and 348-362 (SEQ ID NO:178) of ICA69; (v) at least the two amino acid sequences 789-819 (SEQ ID NO:179) and 840-874 (SEQ ID NO:180) of IA-2; and (vi) at least the amino acid sequence 263-278 (SEQ ID NO:181) of imogen.

3. The synthetic human multitarget polypeptide according to claim 1, comprising: (i) at least two of the amino acid sequences 5-24(SEQ ID NO:167), 33-59 (SEQ ID NO:168), 73-88 (SEQ ID NO:169), of PPI; (ii) at least the two amino acid sequences 30-60 (SEQ ID NO:170) and 121-135 (SEQ ID NO:171) of Gad67; (iii) at least two of the amino acid sequences 206-236 (SEQ ID NO:172), 247-282(SEQ ID NO:173), 503-545 (SEQ ID NO:174), and 553-572 (SEQ ID NO:175) of Gad65; (iv) at least two of the amino acid sequences 34-49 (SEQ ID NO:176), 199-214 (SEQ ID NO:177) and 348-362 (SEQ ID NO:178) of ICA69; (v) at least the two amino acid sequences 789-819 (SEQ ID NO:179) and 840-874 (SEQ ID NO:180) of IA-2; (vi) at least the amino acid sequence 263-278 (SEQ ID NO:181) of imogen; and (vii) at least the two amino acid sequences 438-460 (SEQ ID NO:182) and 469-484 (SEQ ID NO:183) of Hsp60.

4. A composition comprising at least one polypeptide according to claim 1 and a pharmaceutically acceptable carrier.

5. A diagnostic composition for the diagnosis and/or monitoring of progression of an insulin-dependent diabetes mellitus comprising at least one synthetic polypeptide according to claim 1.

6. A synthetic polypeptide consisting of
   (i) amino acid sequences of at least one immunogenic epitopic cluster (hereinafter IEC) of each of at least four different human autoantigens related to human insulin-dependent diabetes mellitus selected from the group consisting of preproinsulin (PPI), 67kDa glutamic acid decarboxylase (Gad67), 65kDa glutamic acid decarboxylase (Gad65), islet cell antigen p69 (ICA69), tyrosine phosphatase islet antigen 2 (IA-2), imogen and 60kDa human heat shock protein (Hsp60), each said IEC consisting of a region of a said autoantigen containing (a) an immunogenic epitope or (b) a collection of immunogenic epitopes, wherein at least four of the IECs of the polypeptide, including at least one IEC from each of four of said different human autoantigens, are selected from the group consisting of the amino acid sequences 5-24 (SEQ ID NO:167), 33-59 (SEQ ID NO:168), 73-88 (SEQ ID NO:169), of PPI; 30-60 (SEQ ID NO:170) and 121-135 (SEQ ID NO:171) of Gad67; 206-236 (SEQ ID NO:172), 247-282 (SEQ ID NO:173), 503-545 (SEQ ID NO:174), and 553-572 (SEQ ID NO:175) of Gad65; 34-49 (SEQ ID NO:176), 199-214 (SEQ ID NO:177) and 348-362 (SEQ ID NO:178) of ICA69; 789-819 (SEQ ID NO:179) and 840-874 (SEQ ID NO:180) of IA-2; 263-278 (SEQ ID NO:181) of imogen; and 438-460 (SEQ ID NO:182) and 469-484 (SEQ ID NO:183) of Hsp60, and
   (ii) optional synthetic spacers,
      wherein each said IEC is fused contiguously to, or separated by a synthetic spacer from, each adjacent IEC,
      wherein, no two adjacent IECs, either fused in contiguity or separated by a synthetic spacer, together form a contiguous sequence within any of said autoantigens, and wherein one or more cysteine residue in a native IEC is optionally substituted by a serine residue, provided that any said Cys→*Ser substituted IEC improves the solubility of the native IEC.

7. The synthetic polypeptide according to claim 6, wherein at least four of the IECs of the polypeptide, including at least one IEC from each of four of said different human autoantigens, comprise the amino acid sequences 5-24 (SEQ ID NO:167), 33-59 (SEQ ID NO:168), 73-88 (SEQ ID NO:169), of PPI; 30-60 (SEQ ID NO:170) and 121-135 (SEQ ID NO:171) of Gad67; 206-236 (SEQ ID NO:172), 247-282 (SEQ ID NO:173), 503-545 (SEQ ID NO:174), and 553-572 (SEQ ID NO:175) of Gad65; 34-49 (SEQ ID NO:176), 199-214 (SEQ ID NO:177) and 348-362 (SEQ ID NO:178) of ICA69; 789-819 (SEQ ID NO:179) and 840-874 (SEQ ID NO:180) of IA-2; and 263-278(SEQ ID NO:181) of imogen.

8. The synthetic polypeptide according to claim 7, wherein at least four of the IECs of the polypeptide, including at least one IEC from each of four of said different human autoantigens, further comprise the amino acid sequences 438-460 (SEQ ID NO:182) and 469-484 (SEQ ID NO:183) of Hsp60.

9. The synthetic polypeptide according to claim 6, consisting of the amino acid sequence of SEQ ID NO:94, 96, 98 or 100.

10. A composition comprising at least one polypeptide according to claim 6 and a pharmaceutically acceptable carrier.

11. A diagnostic composition for the diagnosis and/or monitoring of progression of insulin-dependent diabetes mellitus comprising at least one synthetic polypeptide according to claim 6.

12. The synthetic human multitarget polypeptide in accordance with claim 1, comprising amino acid sequences of at least one IEC of at least five different autoantigens related to IDDM.

13. The synthetic polypeptide of claim 6, wherein the amino acid sequences of (i) are amino acid sequences of at least one IEC of each of at least five different human autoantigens related to human insulin-dependent diabetes mellitus selected from the group consisting of PPI, Gad67, Gad65, ICA69, IA-2, imogen and Hsp60, each said IEC consisting of a region of a said autoantigen containing (a) an immunogenic epitope or (b) a collection of immunogenic epitopes, wherein at least five of the IECs of the polypeptide, including at least one IEC from each of five of said different human autoantigens, are selected from the group consisting of the amino acid sequences 5-24 (SEQ ID NO:167), 33-59 (SEQ ID NO:168), 73-88 (SEQ ID NO:169), of PPI; 30-60 (SEQ ID NO:170) and 121-135 (SEQ ID NO:171) of Gad67; 206-236 (SEQ ID NO:172), 247-282(SEQ ID NO:173), 503-545 (SEQ ID NO:174), and 553-572 (SEQ ID NO:175) of Gad65; 34-49 (SEQ ID NO:176), 199-214 (SEQ ID NO:177) and 348-362 (SEQ ID NO:178) of ICA69; 789-819 (SEQ ID NO:179) and 840-874 (SEQ ID NO:180) of IA-2; 263-278 (SEQ ID NO:181) of imogen; and 438-460 (SEQ ID NO:182) and 469-484 (SEQ ID NO:183) of Hsp60.

* * * * *